(12) United States Patent
Huang et al.

(10) Patent No.: US 9,856,245 B2
(45) Date of Patent: Jan. 2, 2018

(54) GPR40 AGONISTS FOR THE TREATMENT OF TYPE II DIABETES

(71) Applicant: Janssen Pharmaceutica NV, Beerse (BE)

(72) Inventors: Hui Huang, Blue Bell, PA (US); Sanath Meegalla, Garnet Valley, PA (US); Mark R. Player, Phoenixville, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/228,042

(22) Filed: Aug. 4, 2016

(65) Prior Publication Data

US 2017/0044148 A1 Feb. 16, 2017

Related U.S. Application Data

(60) Provisional application No. 62/203,977, filed on Aug. 12, 2015.

(51) Int. Cl.

| | |
|---|---|
| C07D 413/12 | (2006.01) |
| C07D 413/04 | (2006.01) |
| C07D 275/02 | (2006.01) |
| C07D 261/12 | (2006.01) |
| C07D 261/08 | (2006.01) |
| C07D 231/12 | (2006.01) |
| C07D 249/06 | (2006.01) |
| C07D 401/12 | (2006.01) |
| C07D 401/04 | (2006.01) |
| C07D 233/64 | (2006.01) |
| C07D 333/24 | (2006.01) |
| C07D 409/04 | (2006.01) |

(52) U.S. Cl.
CPC ......... C07D 413/12 (2013.01); C07D 231/12 (2013.01); C07D 233/64 (2013.01); C07D 249/06 (2013.01); C07D 261/08 (2013.01); C07D 261/12 (2013.01); C07D 275/02 (2013.01); C07D 333/24 (2013.01); C07D 401/04 (2013.01); C07D 401/12 (2013.01); C07D 409/04 (2013.01); C07D 413/04 (2013.01)

(58) Field of Classification Search
None
See application file for complete search history.

(56) References Cited

U.S. PATENT DOCUMENTS

| | | |
|---|---|---|
| 7,384,965 B2 | 6/2008 | Conner et al. |
| 7,598,266 B2 | 10/2009 | Conner et al. |
| 7,816,367 B2 | 10/2010 | Akerman et al. |
| 2003/0220373 A1 | 11/2003 | Jaye et al. |
| 2006/0205744 A1 | 9/2006 | Conner et al. |
| 2007/0093476 A1 | 4/2007 | Debnath et al. |
| 2014/0275179 A1 | 9/2014 | Sui et al. |
| 2017/0044146 A1 | 2/2017 | Huang et al. |
| 2017/0044147 A1 | 2/2017 | Huang et al. |

FOREIGN PATENT DOCUMENTS

| | | |
|---|---|---|
| EP | 1535915 A1 | 6/2005 |
| WO | WO 01/66098 A2 | 9/2001 |
| WO | WO 2004/063155 A1 | 7/2004 |
| WO | WO 2005/040127 A1 | 5/2005 |
| WO | WO 2005/086661 A2 | 9/2005 |
| WO | WO 2010/048207 A2 | 4/2010 |
| WO | WO 2015/119899 A1 | 8/2015 |

OTHER PUBLICATIONS

Database CAPLUS in STN, Acc. No. 2005:395278, Kim et al., WO 2005040127 A1 (May 6, 2005) (abstract).*
International Search Report relating to International Patent Application No. PCT/US2016/045523, filed Aug. 4, 2016. Date of Mailing of International Search Report: dated Oct. 7, 2016.
Written Opinion of the International Searching Authority relating to International Patent Application No. PCT/US2016/045523, filed Aug. 4, 2016. Date of Mailing of Written Opinion: dated Oct. 7, 2016.
International Search Report relating to International Patent Application No. PCT/US2016/045519, filed Aug. 4, 2016. Date of Mailing of International Search Report: dated Oct. 7, 2016.
Written Opinion of the International Searching Authority relating to International Patent Application No. PCT/US2016/045519, filed Aug. 4, 2016. Date of Mailing of Written Opinion: dated Oct. 7, 2016.
International Search Report relating to International Patent Application No. PCT/US2016/045517, filed Aug. 4, 2016. Date of Mailing of International Search Report: dated Oct. 7, 2016.

(Continued)

*Primary Examiner* — Brian J Davis

(57) ABSTRACT

Disclosed are compounds, compositions and methods for treating of disorders that are affected by the modulation of the GPR40 receptor. Such compounds are represented by Formula (III) as follows:

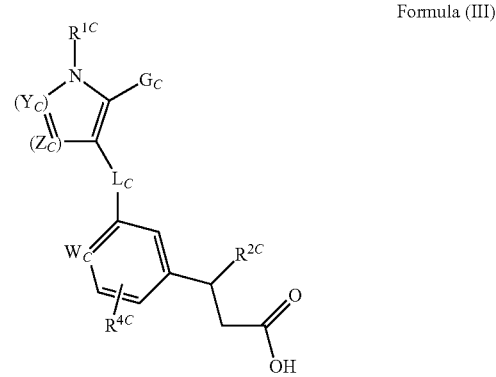

Formula (III)

wherein $R^{1C}$, $R^{2C}$, $R^{4C}$, $W_C$, $Y_C$, $Z_C$, and $G_C$, are defined herein.

31 Claims, No Drawings

(56) References Cited

OTHER PUBLICATIONS

Written Opinion of the International Searching Authority relating to International Patent Application No. PCT/US2016/045517, filed Aug. 4, 2016. Date of Mailing of Written Opinion: dated Oct. 7, 2016.
Briscoe et al., "The Orphan G Protein-coupled Receptor GPR40 Is Activated by Medium and Long Chain Fatty Acids.", J. Biol. Chem., 2003, pp. 11303-11311, vol. 278.
Edfalk et al., "Gpr40 is Expressed in Enteroendocrine Cells and Mediates Free Fatty Acid Stimulation of Incretin Secretion.", Diabetes, 2008, pp. 2280-2287, vol. 57.
Itoh et al., "Free fatty acids regulate insulin secretion from pancreatic β cells through GPR40", Nature, Mar. 13, 2003, pp. 173-176, vol. 422.
Kotarsky et al., "A human cell surface receptor activated by free fatty acids and thiazolidinedione drugs.", Biochem. Biophys. Res. Commun., 2003, pp. 406-410, vol. 301.

* cited by examiner

GPR40 AGONISTS FOR THE TREATMENT OF TYPE II DIABETES

CROSS-REFERENCE TO RELATED APPLICATIONS

This application claims priority to U.S. Provisional Patent Application No. 62/203,977, filed Aug. 12, 2015, which is hereby incorporated by reference in its entirety.

FIELD OF THE INVENTION

The present invention relates to novel compounds which are GPR40 agonists and are useful for the treatment of disorders that are affected by the modulation of the GPR40 receptor. The invention also relates to pharmaceutical compositions comprising one or more of such compounds, to processes to prepare such compounds and compositions, and to the use of such compounds or pharmaceutical compositions for the treatment of various diseases, syndromes and disorders, including Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, that are related to GPR40 modulation.

BACKGROUND OF THE INVENTION

Diabetes is a rapidly expanding, devastating disease that currently affects over 371 million people in the world, with associated healthcare costs exceeding 470 billion dollars in the USA alone. There are two main types of diabetes. Type 1 diabetes affects ~10% of the patients and is characterized by complete insulinopenia due to autoimmune destruction of the insulin-secreting pancreatic beta cells. Treatment of Type 1 diabetes requires insulin therapy. Type 2 diabetes affects ~90% of the patients and is a polygenic syndrome with not only a hereditary component but also a strong environmental influence. It is caused by insulin resistance and defective insulin secretion. In most individuals, the pancreatic beta cell compensates for obesity-associated insulin resistance by expanding its functional mass and secretion of insulin. In a subset of ~20% of obese subjects, beta cell compensation fails and Type 2 diabetes develops. Two major classes of type 2 diabetes drugs are insulin sensitizers (e.g. metformin, thiazolidinediones) and insulin secretagogues (e.g. sulfonylureas, glinides, glucagon-like peptide-1 (GLP-1)-based drugs). Most of the recently approved drugs belong to the latter category and are based on the GLP-1 mechanism, either by pharmacologically enhancing GLP-1 levels (GLP-1 agonists) or by inhibiting the degradation of endogenous GLP-1 (dipeptidyl-peptidase 4 inhibitors). One advantageous feature of these drugs is that they only stimulate insulin secretion when blood glucose levels are elevated (as opposed to sulfonylureas and glinides), thus minimizing the risk of iatrogenic hypoglycemia. A decade ago, the discovery of the G-protein-coupled receptor GPR40 as a fatty acid receptor specifically expressed in beta cells and which stimulates glucose-dependent insulin secretion, sparked interest in the pharmaceutical industry as a potential therapeutic target to enhance insulin secretion in type 2 diabetes, in a manner similar to GLP-1-based drugs. GPR40, also known as free fatty acid receptor 1 (FFAR1), is one of a family of G-protein coupled receptors that, through receptor deorphanization studies, was shown to be endogenously activated by medium- to long-chain saturated and unsaturated fatty acids (~$C_{12-20}$) (Brisco, et al., 2003, J. Biol. Chem., vol. 278: pgs 11303-11311; Itoh, et al., 2003, Nature, vol. 422, pgs 173-176; Kotarsky et al., 2003, Biochem. Biophys. Res. Commun., vol. 301, pgs 406-410). In humans and rodents, although present in brain and enteroendocrine cells, its expression is particularly high in pancreatic beta cells and enteroendocrine cells in the gut. Operating primarily through $G\alpha_{q/11}$ signaling, GPR40 activation of the beta cell leads to an increase in intracellular calcium levels, which in the presence of glucose, ultimately results in augmented insulin secretion. In enteroendocrine cells, GPR40 activation by fatty acids leads to stimulation of incretin secretion (Edfalk, et al., 2008, Diabetes, vol. 57, pgs 2280-2287). Thus, in addition to directly promoting GSIS from islet beta cells, GPR40 activation in enteroendocrine cells provides an indirect means of stimulating GSIS through the actions of released incretins.

Because of the glucose dependency of GPR40-mediated effects on insulin secretion, selective activation of this receptor provides a unique potential therapeutic mechanism by which to treat the diabetic state with minimal risk of hypoglycemic incidents. Given the relatively restricted tissue expression pattern of GPR40, selective GPR40 receptor agonists may offer the additional advantage of providing an improved safety profile relative to the aforementioned therapeutic agents.

Thus, GPR40 receptor agonists of the present invention may provide a therapeutic benefit for the treatment of diabetes, particularly Type 2 diabetes, as well as diseases, syndromes and disorders, including obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema.

SUMMARY OF THE INVENTION

The present invention is directed to compounds of Formula (III)

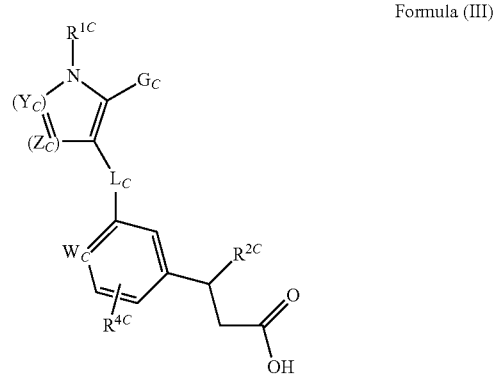

Formula (III)

wherein
$Y_C$ is N or CH;
$Z_C$ is N or CH;
$W_C$ is N or CH;
$L_C$ is —$CH_2O$—, —CH═CH—, or —$(CH_2)_{1-2}$—;
$R^{1C}$ is selected from the group consisting of phenyl, pyridin-4-yl, thienyl, benzothiophenyl, benzofuranyl, and indolyl; wherein said benzothiophenyl, benzofuranyl, and indolyl are attached to the core $(Y_Z)$—$(Z_C)$ containing ring via its benzo ring; and wherein $R^{1C}$ is optionally independently substituted with one or two substituents selected from $C_{1-4}$alkyl, methoxy, fluoro, cyano, di($C_{1-4}$alkyl)amino, or trifluoromethyl;

$R^{2C}$ is $C_{3-5}$cycloalkyl, $C_{1-6}$alkyl, or cyano;

$R^{4C}$ is hydrogen or chloro;

$G_C$ is selected from the group consisting of hydrogen, bromo, $C_{1-6}$alkyl, $C_{1-6}$alkoxy, unsubstituted $C_{3-7}$cycloalkyl, unsubstituted $C_{3-7}$cycloalkoxy, unsubstituted $C_{3-7}$cycloalkyl-methoxy, $C_{2-6}$alk-1-en-1-yl, 3,3,3-trifluoropropoxy, ($C_{1-6}$alkyl)thien-2-yl, difluorophenyl, dimethylphenyl, and a substituent selected from the group consisting of g1 to g9;

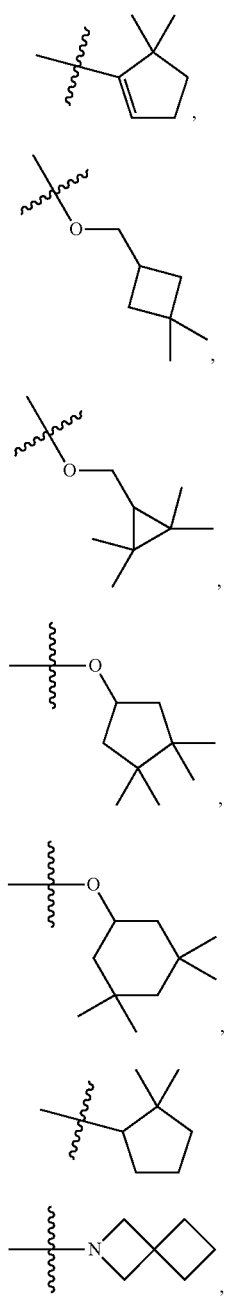
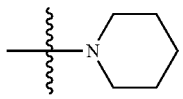
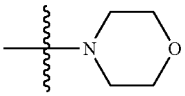

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (III) or a pharmaceutically acceptable salt form thereof.

Also provided are processes for making a pharmaceutical composition comprising, consisting of, and/or consisting essentially of admixing a compound of Formula (III), and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the agonism of the GPR40 receptor, such as Type II diabetes, using a compound of Formula (III).

The present invention also is also directed to the use of any of the compounds described herein in the preparation of a medicament wherein the medicament is prepared for treating a disease or condition that is affected by the agonism of the GPR40 receptor, selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders, in a subject in need thereof.

Exemplifying the invention are methods of treating a disorder modulated by the GPR40 receptor selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders, comprising administering to a subject in need thereof a therapeutically effective amount of any of the compounds or pharmaceutical compositions described above.

In another embodiment, the present invention is directed to a compound of Formula (III) for use in the treatment of a disorder affected by the agonism of the GPR40 receptor selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

In another embodiment, the present invention is directed to a composition comprising a compound of Formula (III) for the treatment of a disorder affected by the agonism of the GPR40 receptor selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2amino-$, the $C_{1-6}alkyl$ groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "formyl" refers to the group —C(=O)H.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

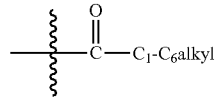

The substituent "—CH₂O—" is oriented such that the oxygen atom is covalently bound to the W-containing ring.

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Thus a compound of the present invention can be an S-enantiomer, an R-enantiomer, or a mixture of both an S-enantiomer and an R-enantiomer.

In one embodiment, the compound of the present invention is an S-enantiomer.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "GPR40 agonist" is intended to encompass a compound that interacts with the GPR40 receptor to substantially increase its catalytic activity, thereby increasing the concentrations of its substrate(s).

The term "GPR40-modulated" is used to refer to the condition of being affected by the modulation of the GPR40 receptor, including but not limited to, the state of being mediated by the GPR40 receptor, for the treatment of a disease or condition such as obesity or Type II diabetes.

The term "agonism of the GPR40 receptor" is used to refer to the state of interaction of a compound of the present invention with said receptor resulting in a substantial increase in intracellular signaling, thereby increasing the consequential biological effects.

As used herein, unless otherwise noted, the term "disorder modulated by the GPR40 receptor" shall mean any disease, disorder or condition characterized in that at least one of its characteristic symptoms is alleviated or eliminated upon treatment with a GPR40 receptor agonist. Suitable examples include, but are not limited to, obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus, dyslipidemia or metabolic syndrome X; more preferably, Type II diabetes mellitus or dyslipidemia.

As used herein unless otherwise noted, the term "obesity related cardiovascular disorders" shall mean any cardiovascular disease, disorder or condition in which obesity or diabetes (preferably, Type II Diabetes) has a role in the initiation or exacerbation of said disorder or condition. Suitable examples include, but are not limited to, hypertension, atherosclerosis and cardiac fibrosis.

As used herein, unless otherwise noted, the term "affect" or "affected" (when referring to a disease, syndrome, condition or disorder that is affected by agonism of the GPR40 receptor) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the agonism of the GPR40 receptor. Such methods comprise, consist of and/or consist essentially of administering to a subject, including an animal, a mammal, and a human in need of such treatment, amelioration and/or prevention, a therapeutically effective amount of a compound of Formula (III) or an enantiomer, diastereomer, solvate or pharmaceutically acceptable salt thereof.

In particular, the compounds of Formula (III), or an enantiomer, diastereomer, solvate or pharmaceutically acceptable salt thereof, are useful for treating or ameliorating diseases, syndromes, conditions, or disorders such as obesity and type II diabetes.

More particularly, the compounds of Formula (III) or an enantiomer, diastereomer, solvate or pharmaceutically acceptable salt thereof are useful for treating or ameliorating type II diabetes, comprising administering to a subject in need thereof a therapeutically effective amount of a compound of Formula (III), or an enantiomer, diastereomer, solvate or pharmaceutically acceptable salt thereof as herein defined.

Embodiments of the present invention include a compound of Formula (III)

Formula (III)

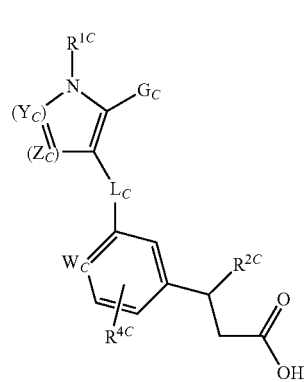

wherein
a) $Y_C$ is N;
b) $L_C$ is —CH$_2$O—;
c) $L_C$ is —CH$_2$O—, (E)-CH=CH—, —(CH$_2$)$_2$—
d) $R^{1C}$ is selected from the group consisting of phenyl, pyridin-4-yl, and thienyl; wherein $R^{1C}$ is optionally independently substituted with one or two substituents selected from C$_{1-4}$alkyl, methoxy, or fluoro;
e) $R^{1C}$ is selected from the group consisting of phenyl and pyridin-4-yl; wherein $R^{1C}$ is optionally independently substituted with one or two substituents selected from methoxy or fluoro;
f) $R^{1C}$ is 2-fluoro-5-methoxyphenyl or 5-fluoro-2-methoxy-4-pyridyl;
g) $R^{2C}$ is C$_{3-5}$cycloalkyl;
h) $R^{2C}$ is cyclopropyl;
i) $R^{4C}$ is hydrogen;
j) $R^{4C}$ is hydrogen or chloro;
k) $G_C$ is selected from the group consisting of hydrogen, bromo, C$_{1-4}$alkyl, C$_{1-4}$alkoxy, unsubstituted C$_{3-7}$cycloalkyl, unsubstituted C$_{3-7}$cycloalkoxy, C$_{2-4}$alk-1-en-1-yl, difluorophenyl, dimethylphenyl, (C$_{1-4}$alkyl)thien-2-yl, and a substituent selected from the group consisting of g1 to g9;

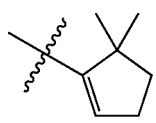
g1

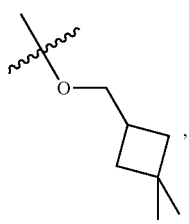
g2

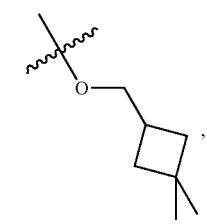
g3

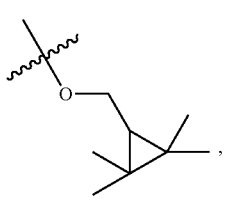
g4

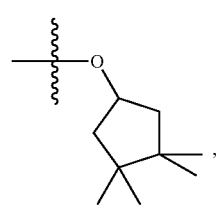
g5

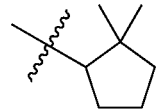
g6

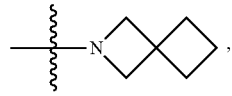
g7

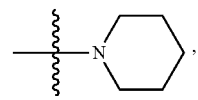
g8

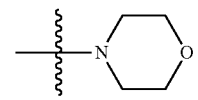
g9 l) $G_c$ is hydrogen, bromo, methyl, isobutyl, isopropyloxy, piperidin-1-yl, cyclopropyl, cyclopentyloxy, cyclohexyloxy, 2-fluoro-5-methoxy-phenyl, 5-methyl-thien-2-yl, 5-t-butyl-thien-2-yl, 2-methyl-prop-1-enyl, and a substituent selected from g1, g7, g8, or g9;

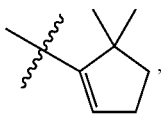
g1

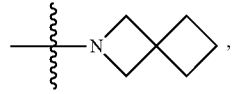
g7

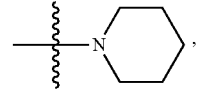
g8

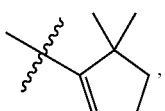
g9 m) $G_c$ is hydrogen, bromo, methyl, isobutyl, isopropyloxy, piperidin-1-yl, cyclopropyl, cyclopentyloxy, cyclohexyloxy, 5-methyl-thien-2-yl, 5-t-butyl-thien-2-yl, 2-methyl-prop-1-enyl, 2,4-difluorophenyl, 3,5-dimethylphenyl, and a substituent selected from g1, g7, or g9;

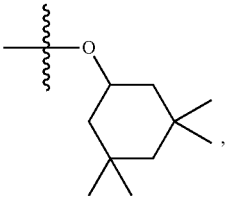
g1

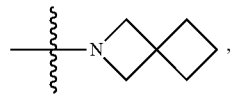
g7

-continued

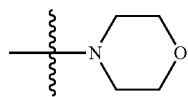
g9 and any combination of embodiments a) through m) above, provided that it is understood that combinations in which different embodiments of the same substituent would be combined are excluded;

or an enantiomer, diastereomer, or pharmaceutically acceptable salt form thereof.

An embodiment of the present invention includes a compound of Formula (III)

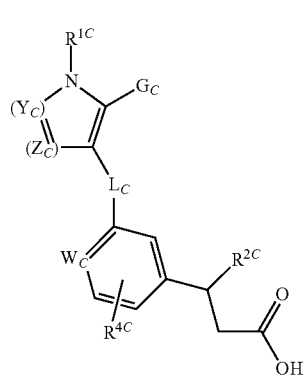
Formula (III)

wherein
$Y_C$ is N or CH;
$Z_C$ is N or CH;
$W_C$ is N or CH;
$L_C$ is —CH$_2$O—, —CH=CH—, or —(CH$_2$)$_2$—;
$R^{1C}$ is selected from the group consisting of phenyl, pyridin-4-yl, and thienyl; wherein $R^{1C}$ is optionally independently substituted with one or two substituents selected from C$_{1-4}$alkyl, methoxy, or fluoro;
$R^{2C}$ is C$_{3-5}$cycloalkyl;
$R^{4C}$ is hydrogen or chloro;
$G_C$ is selected from the group consisting of hydrogen, bromo, C$_{1-4}$alkyl, C$_{1-4}$alkoxy, unsubstituted C$_{3-7}$cycloalkyl, unsubstituted C$_{3-7}$cycloalkoxy, C$_{2-4}$alk-1-en-1-yl, difluorophenyl, dimethylphenyl, (C$_{1-4}$alkyl)thien-2-yl, and a substituent selected from the group consisting of g1 to g9;

g1

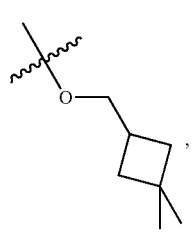
g2

-continued

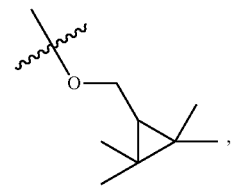
g3

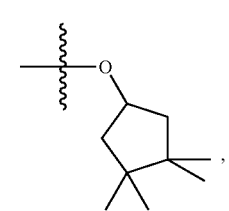
g4

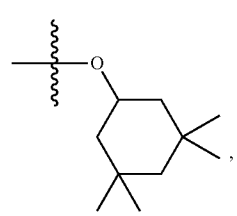
g5

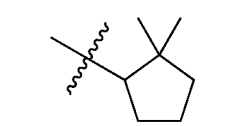
g6

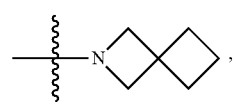
g7

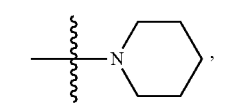
g8

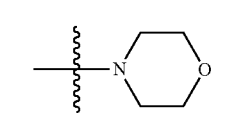
g9 or an enantiomer, diastereomer, or pharmaceutically acceptable salt form thereof.

An embodiment of the present invention includes a compound of Formula (III)

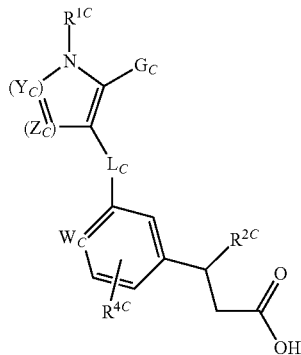
Formula (III)

wherein
Y$_C$ is N;
Z$_C$ is N or CH;
W$_C$ is N or CH;
L$_C$ is —CH$_2$O—, —CH=CH—, or —(CH$_2$)$_2$—;
R$^{1C}$ is selected from the group consisting of phenyl and pyridin-4-yl; wherein R$^{1C}$ is optionally independently substituted with one or two substituents selected from methoxy or fluoro;
R$^{2C}$ is C$_{3-5}$cycloalkyl;
R$^{4C}$ is hydrogen or chloro;
G$_C$ is selected from the group consisting of hydrogen, bromo, C$_{1-4}$alkyl, C$_{1-4}$alkoxy, unsubstituted C$_{3-7}$cycloalkyl, unsubstituted C$_{3-7}$cycloalkoxy, C$_{2-4}$alk-1-en-1-yl, difluorophenyl, dimethylphenyl, (C$_{1-4}$alkyl)thien-2-yl, and a substituent selected from the group consisting of g1 to g9;

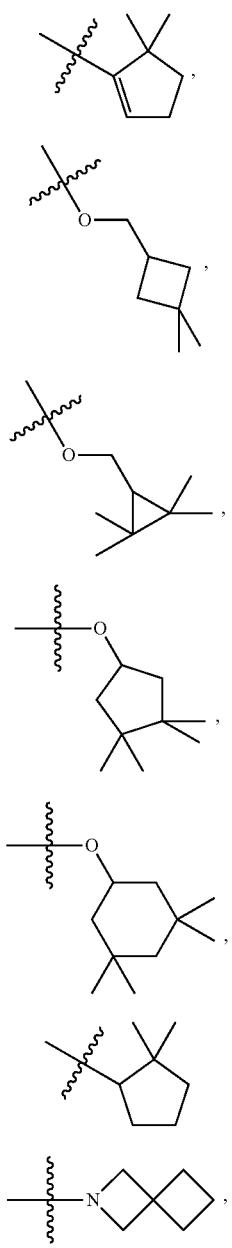

g1 g2 g3 g4 g5 g6 g7

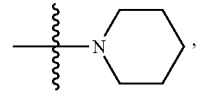

g8

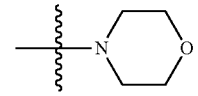

g9 or an enantiomer, diastereomer, or pharmaceutically acceptable salt form thereof.

An embodiment of the present invention includes a compound of Formula (III)

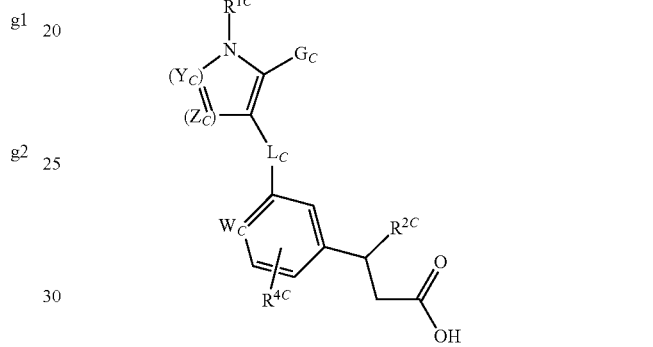

Formula (III)

wherein
Y$_C$ is N;
Z$_C$ is N or CH;
W$_C$ is N or CH;
L$_C$ is —CH$_2$O—, —CH=CH—, or —(CH$_2$)$_2$—;
R$^{1C}$ is selected from the group consisting of phenyl and pyridin-4-yl; wherein R$^{1C}$ is optionally independently substituted with one or two substituents selected from methoxy or fluoro;
R$^{2C}$ is C$_{3-5}$cycloalkyl;
R$^{4C}$ is hydrogen or chloro;
G$_C$ is selected from the group consisting of hydrogen, bromo, C$_{1-4}$alkyl, C$_{1-4}$alkoxy, unsubstituted C$_{3-7}$cycloalkyl, unsubstituted C$_{3-7}$cycloalkoxy, C$_{2-4}$alk-1-en-1-yl, difluorophenyl, dimethylphenyl, (C$_{1-4}$alkyl)thien-2-yl, and a substituent selected from the group consisting of g1, g7, g8, and g9;

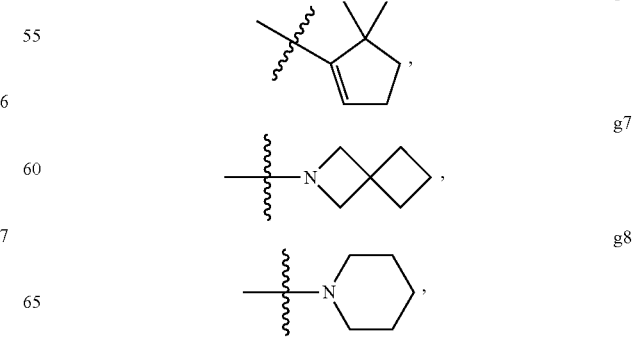

g1 g7 g8

-continued

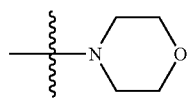
g9 or an enantiomer, diastereomer, or pharmaceutically acceptable salt form thereof.

An embodiment of the present invention includes a compound of Formula (III)

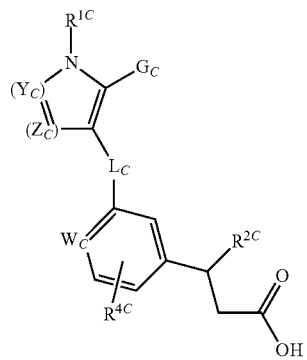
Formula (III)

wherein
$Y_C$ is N or CH;
$Z_C$ is N or CH;
$W_C$ is N or CH;
$L_C$ is —CH$_2$O—, (E)-CH=CH—, —(CH$_2$)$_2$—
$R^{1C}$ is 2-fluoro-5-methoxy-phenyl or 5-fluoro-2-methoxy-4-pyridyl;
$R^{2C}$ is cyclopropyl;
$R^{4C}$ is hydrogen or chloro;
$G_C$ is hydrogen, bromo, methyl, isobutyl, isopropyloxy, piperidin-1-yl, cyclopropyl, cyclopentyloxy, cyclohexyloxy, 5-methyl-thien-2-yl, 5-t-butyl-thien-2-yl, 2-methyl-prop-1-enyl, 2,4-difluorophenyl, 3,5-dimethylphenyl, and a substituent selected from g1, g7, or g9;

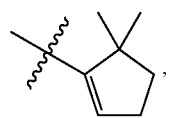
g1

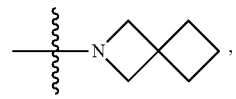
g7

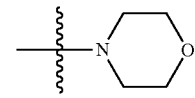
g9 or an enantiomer, diastereomer, or pharmaceutically acceptable salt form thereof.

In one embodiment of the present invention, the compound of Formula (III) is an S-enantiomer

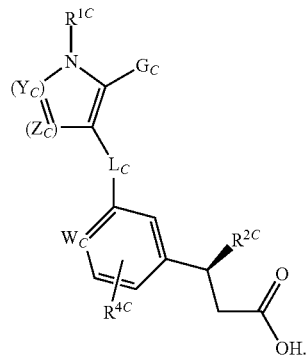

Additional embodiments of the present invention include compounds of Formula (III) as herein defined, or an enantiomer, diastereomer, solvate, or a pharmaceutically acceptable salt form thereof, wherein the substituents selected from one or more of the variables defined herein (e.g. $Y_C$, $Z_C$, $W_C$, $L_C$, $R^{1C}$, $R^{2C}$, $R^{4C}$, and $G_C$) are independently selected to be any individual substituent or any subset of substituents from those exemplified in the listing in Table 1, below.

TABLE 1

(III)

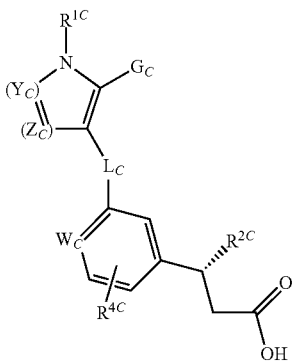

| Cpd | $Y_C$ | $Z_C$ | $W_C$ | $L_C$ | $R^{1C}$ | $R^{2C}$ | $R^{4C}$ | $G_C$ |
|---|---|---|---|---|---|---|---|---|
| 44 | N | N | CH | —CH$_2$O— | 2-fluoro-5-methoxy-phenyl | (3S)-cyclopropyl | H | piperidin-1-yl |

TABLE 1-continued

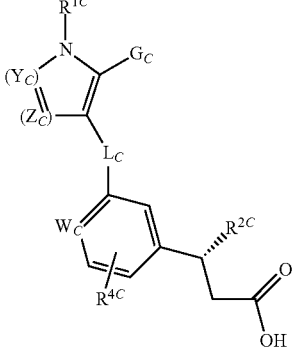

(III)

| Cpd | $Y_C$ | $Z_C$ | $W_C$ | $L_C$ | $R^{1C}$ | $R^{2C}$ | $R^{4C}$ | $G_C$ |
|---|---|---|---|---|---|---|---|---|
| 63 | N | N | N | —CH$_2$O— | 2-fluoro-5-methoxy-phenyl | cyclopropyl | H | g1 |
| 64 | N | N | N | —CH$_2$O— | 2-fluoro-5-methoxy-phenyl | (3S)-cyclopropyl | H | g1 |
| 65 | N | CH | N | —CH$_2$O— | 2-fluoro-5-methoxy-phenyl | cyclopropyl | H | g1 |
| 66 | N | CH | CH | —CH$_2$O— | 2-fluoro-5-methoxy-phenyl | (3S)-cyclopropyl | H | g1 |
| 67 | N | N | CH | —CH$_2$O— | 2-fluoro-5-methoxy-phenyl | (3S)-cyclopropyl | H | cyclopentyloxy |
| 68 | N | N | CH | —CH$_2$O— | 2-fluoro-5-methoxy-phenyl | (3S)-cyclopropyl | H | g7 |
| 69 | N | CH | CH | —CH$_2$O— | 2-fluoro-5-methoxy-phenyl | (3S)-cyclopropyl | H | cyclopropyl |
| 70 | N | CH | CH | —CH$_2$O— | 5-fluoro-2-methoxy-4-pyridyl | (3S)-cyclopropyl | H | cyclopropyl |
| 71 | N | CH | N | —CH$_2$O— | 2-fluoro-5-methoxy-phenyl | cyclopropyl | 5-Cl | g1 |
| 72 | N | CH | CH | —CH$_2$O— | 2-fluoro-5-methoxy-phenyl | (3S)-cyclopropyl | H | H |
| 73 | N | CH | CH | —CH$_2$O— | 2-fluoro-5-methoxy-phenyl | (3S)-cyclopropyl | H | g9 |
| 74 | N | N | CH | (E) —CH=CH— | 2-fluoro-5-methoxy-phenyl | (3S)-cyclopropyl | H | cyclopropyl |
| 75 | N | N | N | —CH$_2$O— | 2-fluoro-5-methoxy-phenyl | (3R)-cyclopropyl | H | g1 |
| 76 | N | CH | CH | (E) —CH=CH— | 2-fluoro-5-methoxy-phenyl | cyclopropyl | H | cyclopropyl |
| 77 | N | CH | CH | —(CH$_2$)$_2$— | 2-fluoro-5-methoxy-phenyl | cyclopropyl | H | cyclopropyl |
| 78 | N | N | N | —CH$_2$O— | 2-fluoro-5-methoxy-phenyl | cyclopropyl | 5-Cl | g1 |
| 79 | N | N | CH | —(CH$_2$)$_2$— | 2-fluoro-5-methoxy-phenyl | (3S)-cyclopropyl | H | cyclopropyl |
| 80 | N | N | CH | —CH$_2$O— | 2-fluoro-5-methoxy-phenyl | (3S)-cyclopropyl | H | g9 |
| 81 | N | CH | CH | —CH$_2$O— | 5-fluoro-2-methoxy-4-pyridyl | (3S)-cyclopropyl | H | H |
| 82 | N | N | CH | —CH$_2$O— | 2-fluoro-5-methoxy-phenyl | (3S)-cyclopropyl | H | methyl |
| 83 | N | N | CH | —CH$_2$O— | 2-fluoro-5-methoxy-phenyl | (3S)-cyclopropyl | H | isobutyl |
| 84 | N | N | CH | —CH$_2$O— | 2-fluoro-5-methoxy-phenyl | (3S)-cyclopropyl | H | 2-methyl-prop-1-enyl |
| 85 | N | N | CH | —CH$_2$O— | 2-fluoro-5-methoxy-phenyl | (3S)-cyclopropyl | H | cyclopropyl |
| 86 | N | N | CH | —CH$_2$O— | 2-fluoro-5-methoxy-phenyl | (3S)-cyclopropyl | H | g1 |
| 87 | CH | N | CH | —CH$_2$O— | 2-fluoro-5-methoxy-phenyl | (3S)-cyclopropyl | H | g1 |
| 88 | N | N | CH | —CH$_2$O— | 2-fluoro-5-methoxy-phenyl | (3S)-cyclopropyl | H | 5-(Me)thien-2-yl |
| 89 | N | CH | CH | —CH$_2$O— | 2-fluoro-5-methoxy-phenyl | (3S)-cyclopropyl | H | 2-methyl-prop-1-enyl |
| 90 | N | CH | CH | —CH$_2$O— | 2-fluoro-5-methoxy-phenyl | (3S)-cyclopropyl | H | Br |
| 91 | CH | N | CH | —CH$_2$O— | 2-fluoro-5-methoxy-phenyl | (3S)-cyclopropyl | H | 2-methyl-prop-1-enyl |

TABLE 1-continued (III)

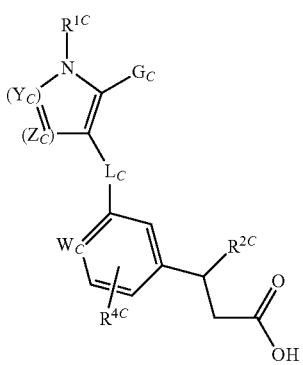

| Cpd | $Y_C$ | $Z_C$ | $W_C$ | $L_C$ | $R^{1C}$ | $R^{2C}$ | $R^{4C}$ | $G_C$ |
|---|---|---|---|---|---|---|---|---|
| 92 | N | N | CH | —CH$_2$O— | 2-fluoro-5-methoxy-phenyl | (3S)-cyclopropyl | H | 5-(t-Bu)thien-2-yl |
| 93 | CH | N | CH | —CH$_2$O— | 2-fluoro-5-methoxy-phenyl | (3S)-cyclopropyl | H | isobutyl |
| 94 | N | CH | CH | —CH$_2$O— | 2-fluoro-5-methoxy-phenyl | (3S)-cyclopropyl | H | 5-(Me)thien-2-yl |
| 95 | N | CH | CH | —CH$_2$O— | 2-fluoro-5-methoxy-phenyl | (3S)-cyclopropyl | H | 2,4-difluorophenyl |
| 96 | N | CH | CH | —CH$_2$O— | 2-fluoro-5-methoxy-phenyl | (3S)-cyclopropyl | H | 3,5-dimethylphenyl |
| 97 | N | N | CH | —CH$_2$O— | 2-fluoro-5-methoxy-phenyl | (3S)-cyclopropyl | H | cyclohexyloxy |
| 98 | N | N | CH | —CH$_2$O— | 2-fluoro-5-methoxy-phenyl | (3S)-cyclopropyl | H | isopropyloxy |

A further embodiment of the present invention includes a compound of Formula (III)

Formula (III)

selected from the group consisting of

Cpd 44, (3S)-3-cyclopropyl-3-[3-[[1-(2-fluoro-5-methoxy-phenyl)-5-(1-piperidyl)triazol-4-yl]methoxy]phenyl]propanoic acid;

Cpd 63, 3-cyclopropyl-3-[2-[[5-(5,5-dimethylcyclopenten-1-yl)-1-(2-fluoro-5-methoxy-phenyl)triazol-4-yl]methoxy]-4-pyridyl]propanoic acid;

Cpd 64, (3S)-3-cyclopropyl-3-[2-[[5-(5,5-dimethylcyclopenten-1-yl)-1-(2-fluoro-5-methoxy-phenyl)triazol-4-yl]methoxy]-4-pyridyl]propanoic acid;

Cpd 65, 3-cyclopropyl-3-[2-[[5-(5,5-dimethylcyclopenten-1-yl)-1-(2-fluoro-5-methoxy-phenyl)pyrazol-4-yl]methoxy]-4-pyridyl]propanoic acid;

Cpd 66, (3S)-3-cyclopropyl-3-[3-[[5-(5,5-dimethylcyclopenten-1-yl)-1-(2-fluoro-5-methoxy-phenyl)pyrazol-4-yl]methoxy]phenyl]propanoic acid;

Cpd 67, (3S)-3-[3-[[5-(cyclopentoxy)-1-(2-fluoro-5-methoxy-phenyl)triazol-4-yl]methoxy]phenyl]-3-cyclopropyl-propanoic acid;

Cpd 68, (3S)-3-[3-[[5-(6-azaspiro[3.3]heptan-6-yl)-1-(2-fluoro-5-methoxy-phenyl)triazol-4-yl]methoxy]phenyl]-3-cyclopropyl-propanoic acid;

Cpd 69, (3S)-3-cyclopropyl-3-[3-[[5-cyclopropyl-1-(2-fluoro-5-methoxy-phenyl)pyrazol-4-yl]methoxy]phenyl]propanoic acid;

Cpd 70, (3S)-3-cyclopropyl-3-[3-[[5-cyclopropyl-1-(5-fluoro-2-methoxy-4-pyridyl)pyrazol-4-yl]methoxy]phenyl]propanoic acid;

Cpd 71, 3-[5-chloro-2-[[5-(5,5-dimethylcyclopenten-1-yl)-1-(2-fluoro-5-methoxy-phenyl)pyrazol-4-yl]methoxy]-4-pyridyl]-3-cyclopropyl-propanoic acid;

Cpd 72, (3S)-3-cyclopropyl-3-[3-[[1-(2-fluoro-5-methoxy-phenyl)pyrazol-4-yl]methoxy]phenyl]propanoic acid;

Cpd 73, (3S)-3-cyclopropyl-3-[3-[[1-(2-fluoro-5-methoxy-phenyl)-5-morpholino-pyrazol-4-yl]methoxy]phenyl]propanoic acid;

Cpd 74, (3S)-3-cyclopropyl-3-[3-[(E)-2-[5-cyclopropyl-1-(2-fluoro-5-methoxy-phenyl)triazol-4-yl]vinyl]phenyl]propanoic acid;

Cpd 75, (3R)-3-cyclopropyl-3-[2-[[5-(5,5-dimethylcyclopenten-1-yl)-1-(2-fluoro-5-methoxy-phenyl)triazol-4-yl]methoxy]-4-pyridyl]propanoic acid;

Cpd 76, 3-cyclopropyl-3-[3-[(E)-2-[5-cyclopropyl-1-(2-fluoro-5-methoxy-phenyl)pyrazol-4-yl]vinyl]phenyl]propanoic acid;

Cpd 77, 3-cyclopropyl-3-[3-[2-[5-cyclopropyl-1-(2-fluoro-5-methoxy-phenyl)pyrazol-4-yl]ethyl]phenyl]propanoic acid;

Cpd 78, 3-[5-chloro-2-[[5-(5,5-dimethylcyclopenten-1-yl)-1-(2-fluoro-5-methoxy-phenyl)triazol-4-yl]methoxy]-4-pyridyl]-3-cyclopropyl-propanoic acid;

Cpd 79, (3S)-3-cyclopropyl-3-[3-[2-[5-cyclopropyl-1-(2-fluoro-5-methoxy-phenyl)triazol-4-yl]ethyl]phenyl]propanoic acid;

Cpd 80, (3S)-3-cyclopropyl-3-[3-[[1-(2-fluoro-5-methoxy-phenyl)-5-morpholino-triazol-4-yl]methoxy]phenyl]propanoic acid;

Cpd 81, (3S)-3-cyclopropyl-3-[3-[[1-(5-fluoro-2-methoxy-4-pyridyl)pyrazol-4-yl]methoxy]phenyl]propanoic acid;

Cpd 82, (3S)-3-cyclopropyl-3-[3-[[1-(2-fluoro-5-methoxy-phenyl)-5-methyl-triazol-4-yl]methoxy]phenyl]propanoic acid;

Cpd 83, (3S)-3-cyclopropyl-3-[3-[[1-(2-fluoro-5-methoxy-phenyl)-5-isobutyl-triazol-4-yl]methoxy]phenyl]propanoic acid;

Cpd 84, (3S)-3-cyclopropyl-3-[3-[[1-(2-fluoro-5-methoxy-phenyl)-5-(2-methylprop-1-enyl)triazol-4-yl]methoxy]phenyl]propanoic acid;

Cpd 85, (3S)-3-cyclopropyl-3-[3-[[5-cyclopropyl-1-(2-fluoro-5-methoxy-phenyl)triazol-4-yl]methoxy]phenyl]propanoic acid;

Cpd 86, (3S)-3-cyclopropyl-3-[3-[[5-(5,5-dimethylcyclopenten-1-yl)-1-(2-fluoro-5-methoxy-phenyl)triazol-4-yl]methoxy]phenyl]propanoic acid;

Cpd 87, (3S)-3-cyclopropyl-3-[3-[[5-(5,5-dimethylcyclopenten-1-yl)-1-(2-fluoro-5-methoxy-phenyl)imidazol-4-yl]methoxy]phenyl]propanoic acid;

Cpd 88, (3S)-3-cyclopropyl-3-[3-[[1-(2-fluoro-5-methoxy-phenyl)-5-(5-methyl-2-thienyl)triazol-4-yl]methoxy]phenyl]propanoic acid;

Cpd 89, (3S)-3-cyclopropyl-3-[3-[[1-(2-fluoro-5-methoxy-phenyl)-5-(2-methylprop-1-enyl)pyrazol-4-yl]methoxy]phenyl]propanoic acid;

Cpd 90, (3S)-3-[3-[[5-bromo-1-(2-fluoro-5-methoxy-phenyl)pyrazol-4-yl]methoxy]phenyl]-3-cyclopropyl-propanoic acid;

Cpd 91, (3S)-3-cyclopropyl-3-[3-[[1-(2-fluoro-5-methoxy-phenyl)-5-(2-methylprop-1-enyl)imidazol-4-yl]methoxy]phenyl]propanoic acid;

Cpd 92, (3S)-3-[3-[[5-(5-tert-butyl-2-thienyl)-1-(2-fluoro-5-methoxy-phenyl)triazol-4-yl]methoxy]phenyl]-3-cyclopropyl-propanoic acid;

Cpd 93, (3S)-3-cyclopropyl-3-[3-[[1-(2-fluoro-5-methoxy-phenyl)-5-isobutyl-imidazol-4-yl]methoxy]phenyl]propanoic acid;

Cpd 94, (3S)-3-cyclopropyl-3-[3-[[1-(2-fluoro-5-methoxy-phenyl)-5-(5-methyl-2-thienyl)pyrazol-4-yl]methoxy]phenyl]propanoic acid;

Cpd 95, (3S)-3-cyclopropyl-3-[3-[[5-(2,4-difluorophenyl)-1-(2-fluoro-5-methoxy-phenyl)pyrazol-4-yl]methoxy]phenyl]propanoic acid;

Cpd 96, (3S)-3-cyclopropyl-3-[3-[[5-(3,5-dimethylphenyl)-1-(2-fluoro-5-methoxy-phenyl)pyrazol-4-yl]methoxy]phenyl]propanoic acid;

Cpd 97, (3S)-3-[3-[[5-(cyclohexoxy)-1-(2-fluoro-5-methoxy-phenyl)triazol-4-yl]methoxy]phenyl]-3-cyclopropyl-propanoic acid; and Cpd 98, (3S)-3-cyclopropyl-3-[3-[[1-(2-fluoro-5-methoxy-phenyl)-5-isopropoxy-triazol-4-yl]methoxy]phenyl]propanoic acid;

or a pharmaceutically acceptable salt form thereof.

For use in medicine, salts of a compound of Formula (III) refer to non-toxic "pharmaceutically acceptable salts." Other salts may, however, be useful in the preparation of a compound of Formula (III) or of a pharmaceutically acceptable salt form thereof. Suitable pharmaceutically acceptable salts of a compound of Formula (III) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compound of Formula (III) carries an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of a compound of Formula (III). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include a solvated compound of Formula (III).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (III) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-}enantiomer = \frac{(mass(+)\text{-}enantiomer)}{(mass(+)\text{-}enantiomer) + (mass(-)\text{-}enantiomer)} \times 100.$$

Another embodiment of the present invention is a composition, including a pharmaceutical composition, comprising, consisting of, and consisting essentially of the (−)-enantiomer of a compound of Formula (III) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-}enantiomer = \frac{(mass(-)\text{-}enantiomer)}{(mass(+)\text{-}enantiomer) + (mass(-)\text{-}enantiomer)} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising one or more compounds of Formula (III) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (III) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (III) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (III) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (III) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I), (II), or (III) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (III).

Advantageously, a compound of Formula (III) may be administered in a single daily dose, or the total daily dosage may be administered in divided doses of two, three and four times daily.

Optimal dosages of a compound of Formula (III) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (III) may be administered in any of the foregoing compositions and dosage regimens or by means of those compositions and dosage regimens established in the art whenever use of a compound of Formula (III) is required for a subject in need thereof.

As GPR40 receptor agonists, the compounds of Formula (III) are useful in methods for treating or preventing a disease, a syndrome, a condition or a disorder in a subject, including an animal, a mammal and a human in which the disease, the syndrome, the condition or the disorder is affected by the modulation, including agonism, of the GPR40 receptor. Such methods comprise, consist of and/or consist essentially of administering to a subject, including an animal, a mammal, and a human, in need of such treatment or prevention, a therapeutically effective amount of a compound, salt or solvate of Formula (III).

In another embodiment, the present invention is directed to a compound of Formula (III) for use in the treatment of a disorder affected by the agonism of GPR40 receptor selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus, dyslipidemia or metabolic syndrome X; more preferably, Type II diabetes mellitus or dyslipidemia.

Additional embodiments of the present invention include compounds 44, and 63-98 of Formula (III) as herein defined, or an enantiomer, diastereomer, solvate, or a pharmaceutically acceptable salt form thereof, exemplified in the listing in Table 2.

TABLE 2

| Cpd No. | Structure |
|---|---|
| 44 | 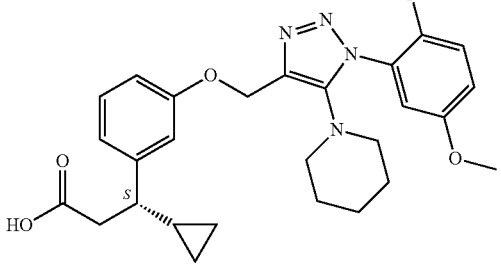 |
| 63 | 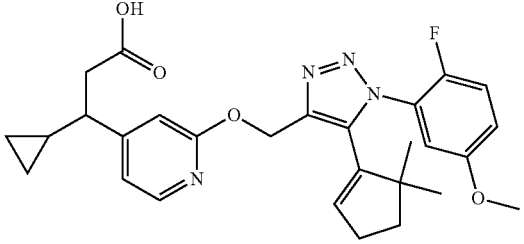 [SMILES: COc1ccc(F)c(-n2nnc(COc3cc(C(CC(=O)O)C4CC4)ccn3)c2C2=CCCC2(C)C)c1] |

TABLE 2-continued

| Cpd No. | Structure |
|---|---|
| 64 | 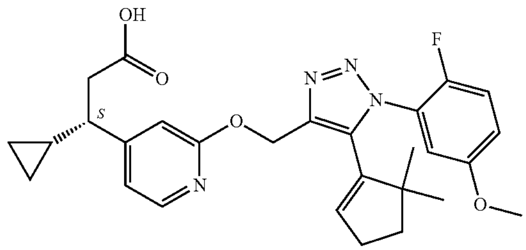 |
| 65 | 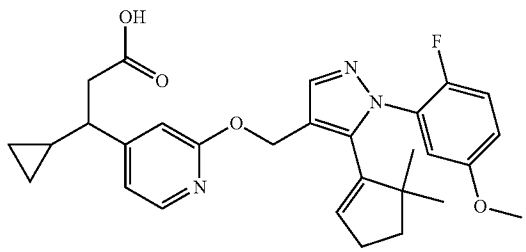 [SMILES: COc1ccc(F)c(-n2ncc(COc3cc(C(CC(=O)O)C4CC4)ccn3)c2C2=CCCC2(C)C)c1] |
| 66 | 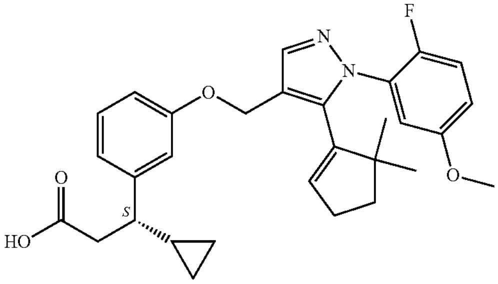 |
| 67 | 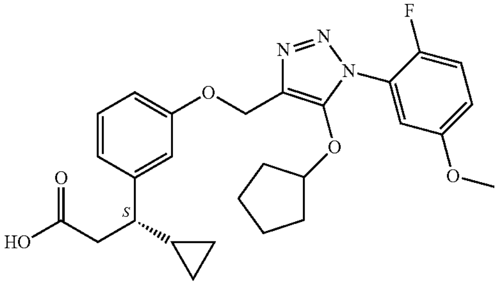 |
| 68 | 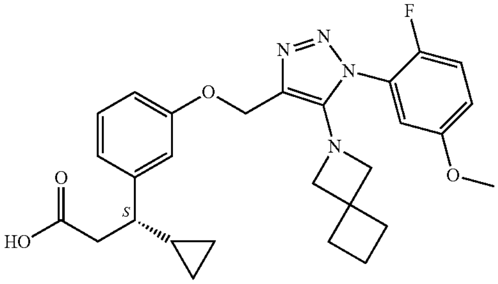 |
| 69 | |
| 70 | |
| 71 | |
| 72 | |
| 73 | |

TABLE 2-continued
| Cpd No. | Structure |
|---|---|
| 74 | 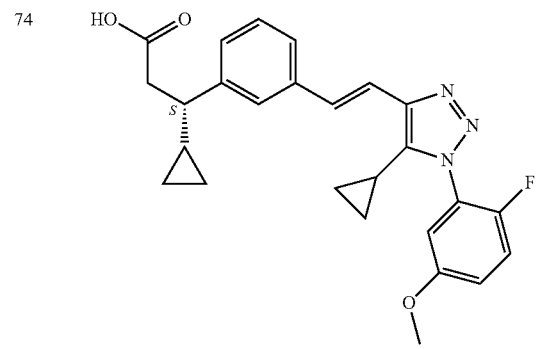 |
| 75 | 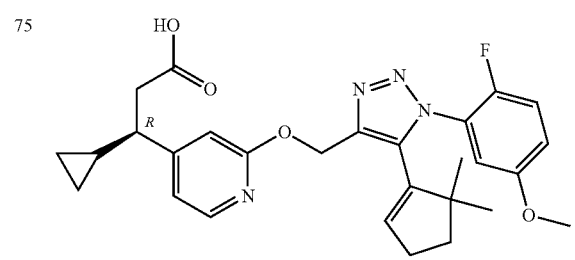 |
| 76 | 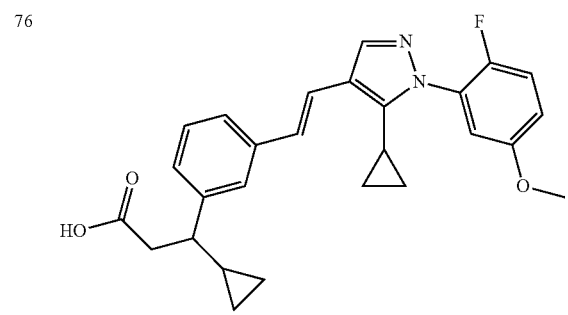 |
| 77 | 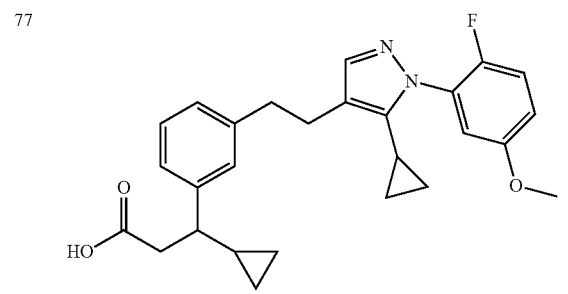 |
| 78 | 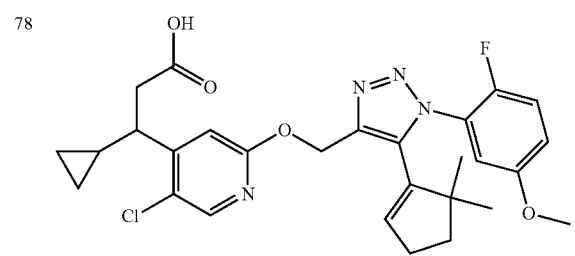 |
| 79 | 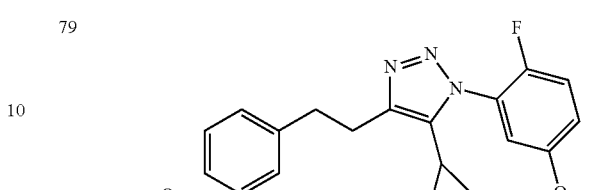 |
| 80 | 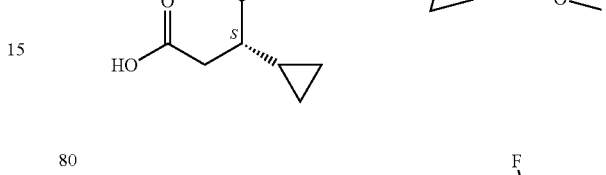 |
| 81 | 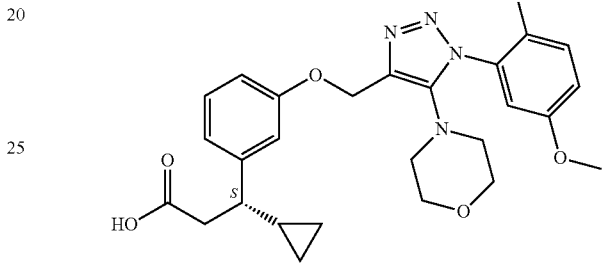 |
| 82 | 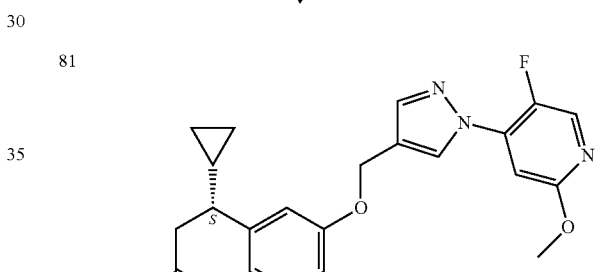 |
| 83 | 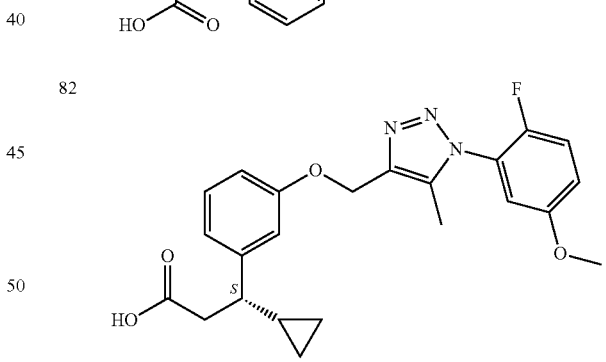 |

TABLE 2-continued
| Cpd No. | Structure |
|---|---|
| 84 | 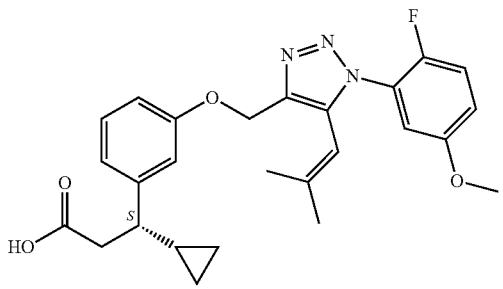 |
| 85 | 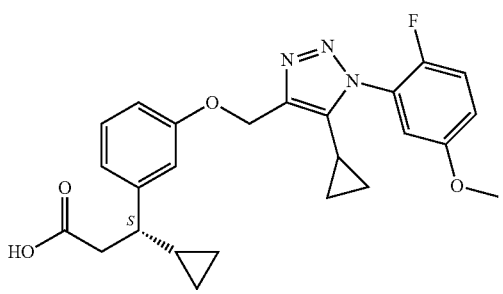 |
| 86 | 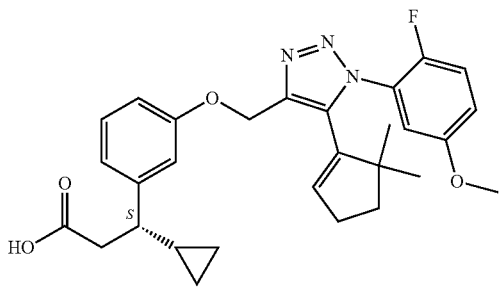 |
| 87 | 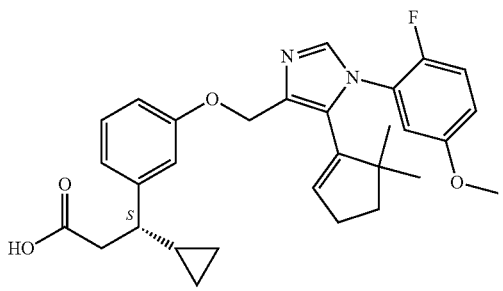 |
| 88 | 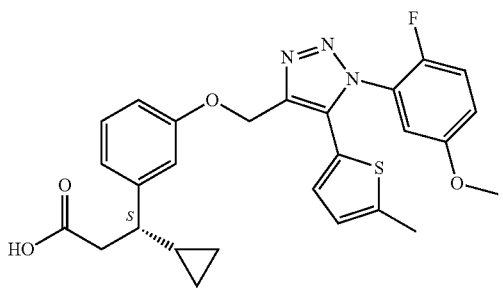 |
TABLE 2-continued
| Cpd No. | Structure |
|---|---|
| 89 | 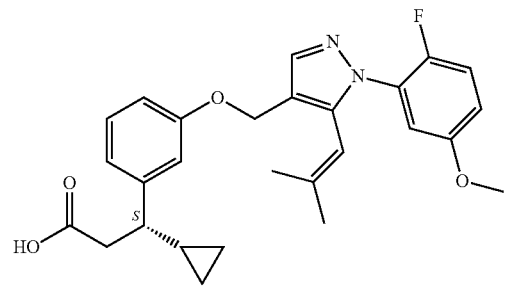 |
| 90 | 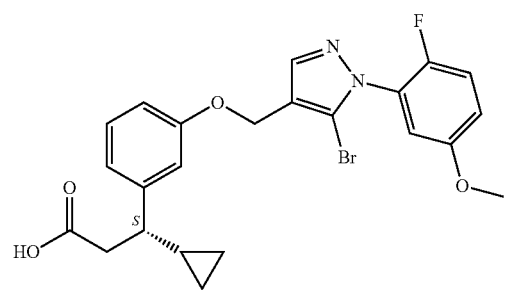 |
| 91 | 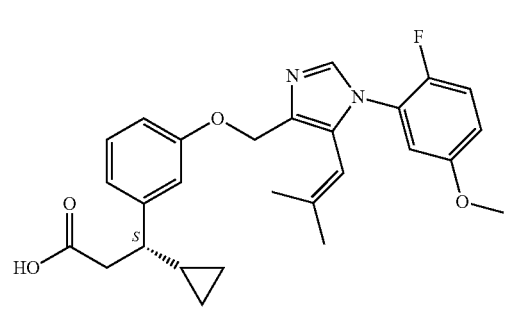 |
| 92 | 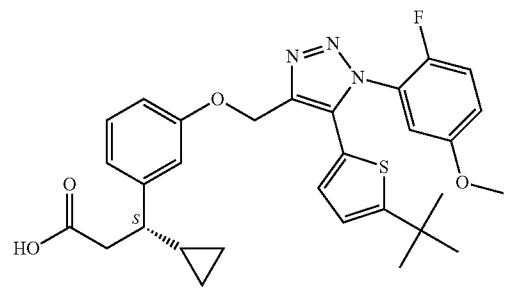 |
| 93 | 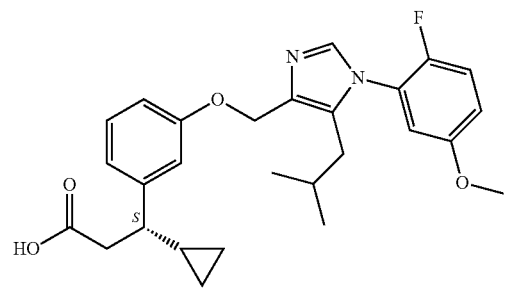 |

TABLE 2-continued

| Cpd No. | Structure |
|---|---|
| 94 | (structure) |
| 95 | (structure) |
| 96 | (structure) |
| 97 | (structure) |
| 98 | (structure) |

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
ADDP 1,1'-(azodicarbonyl)-dipiperidine
AIBN azobisisobutyronitrile
aq. aqueous
$B_2Pin_2$ bis(pinacolato)diboron
Bn or Bzl benzyl
BINAP 2,2'-bis(diphenylphosphino)-1,1'-binaphthyl
Boc tert-butyloxycarbonyl
conc. concentrated
dba dibenzylideneacetone
DBU 1,8-diazabicyclo[5.4.0]undec-7-ene
DCE 1,2-dichloroethane
DCM dichloromethane
DEAD diethylazodicarboxylate
DIBALH or DIBAL diisobutylaluminum hydride
DIPEA or DIEA diisopropyl-ethyl amine
DMA dimethylaniline
DMAP 4-dimethylaminopyridine
DME dimethoxyethane or dimethyl ether
DMF N,N-dimethylformamide
DMSO dimethylsulfoxide
DPPA diphenylphosphoryl azide
dppf 1,1'-bis(diphenylphosphino)ferrocene
dppp 1,3-bis(diphenylphosphino)propane
EA ethyl acetate
ESI electrospray ionization
EtOAc or EA ethyl acetate
EtOH ethanol
GCMS gas chromatography mass spectrometry
h or hr(s) hour or hours
HPLC high performance liquid chromatography
IBX 2-iodoxybenzoic acid
LAH lithium aluminum hydride
LDA lithium diisopropylamide
LHMDS lithium bis(trimethylsilyl)amide
MEK methyl ethyl ketone
MeOH methanol
MHz megahertz
min minute or minutes
MS mass spectrometry
Ms methanesulfonyl
NBS N-bromosuccinimide
NMR nuclear magnetic resonance
PPTS pyridinium p-toluenesulfonate
RP reverse-phase
rt or RT room temperature
$R_t$ retention time
RuPhos bis(2',6'-diisopropoxybiphenyl) cyclohexylphosphine
sec second or seconds
SPhos 2-dicyclohexylphosphino-2',6'-dimethoxybiphenyl
TBAF tetrabutylammonium fluoride
TBDMS t-butyldimethylsilyl
TBP tributylphosphate
TEA or $Et_3N$ triethylamine
TFA trifluoroacetic acid THF tetrahydrofuran
TLC thin layer chromatography
TMS tetramethylsilane
Tf trifluoromethanesulfonyl
Ts 4-toluenesulfonyl
XPhos 2-dicyclohexylphosphino-2',4',6'-triisopropylbiphenyl General Schemes Compounds of formula (I) may be prepared according to the process as described in the Scheme A, below.

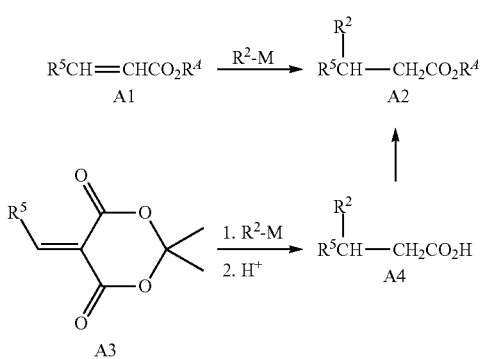

A compound of formula A2 may be prepared as shown in Scheme A. An acrylic ester of formula A1, wherein $R^5$ is 3-hydroxyphenyl, may be used as a substrate for a conjugate addition reaction with a compound of formula $R^2$-M, wherein M is a metal, to obtain a compound of formula A2. The starting acrylate of formula A1 is either commercially available or may be prepared according to the methods described in the scientific literature. A compound of formula $R^2$-M may be (a) a boronic acid to form a compound of formula $R^2$—$B(OH)_2$; (b) a suitably selected boronic ester such as pinacolatoboryl, neopentylglycolatoboryl, and the like; (c) a suitably selected copper reagent or (d) a suitably selected Grignard reagent. One of ordinary skill in the art will understand that a catalyst, optionally in the presence of a ligand, may be required with the use of certain available reagents. In addition, with the use of certain other organometallic reagents, such as a Grignard reagent or a cuprate, the free hydroxyl group may need to be protected with an appropriate hydroxyl protecting group, which may be removed at a later stage in the synthetic sequence. A preferred method for this transformation includes treatment of a compound of formula A1 with a compound of $R^2$-M wherein M is a boronic acid; in the presence of an Rh catalyst; with a suitable ligand such as BINAP. When optically pure BINAP is employed, an enantiomerically enriched compound of formula A2 may be prepared. A compound of formula A2 may be subjected to chiral separation to obtain an optically pure enantiomer. When a compound of formula A3 is employed in place of the acrylate starting material of formula A1, it is necessary to esterify the resultant carboxylic acid of formula A4 to obtain the desired compound of formula A2. One of ordinary skill in the art will recognize that in certain instances, substituent $R^5$ may be interchanged with substituent $R^2$.

Scheme B illustrates a method for the preparation of certain compounds of formula (Ia) of the present invention wherein X is O, Y is N.

Scheme B
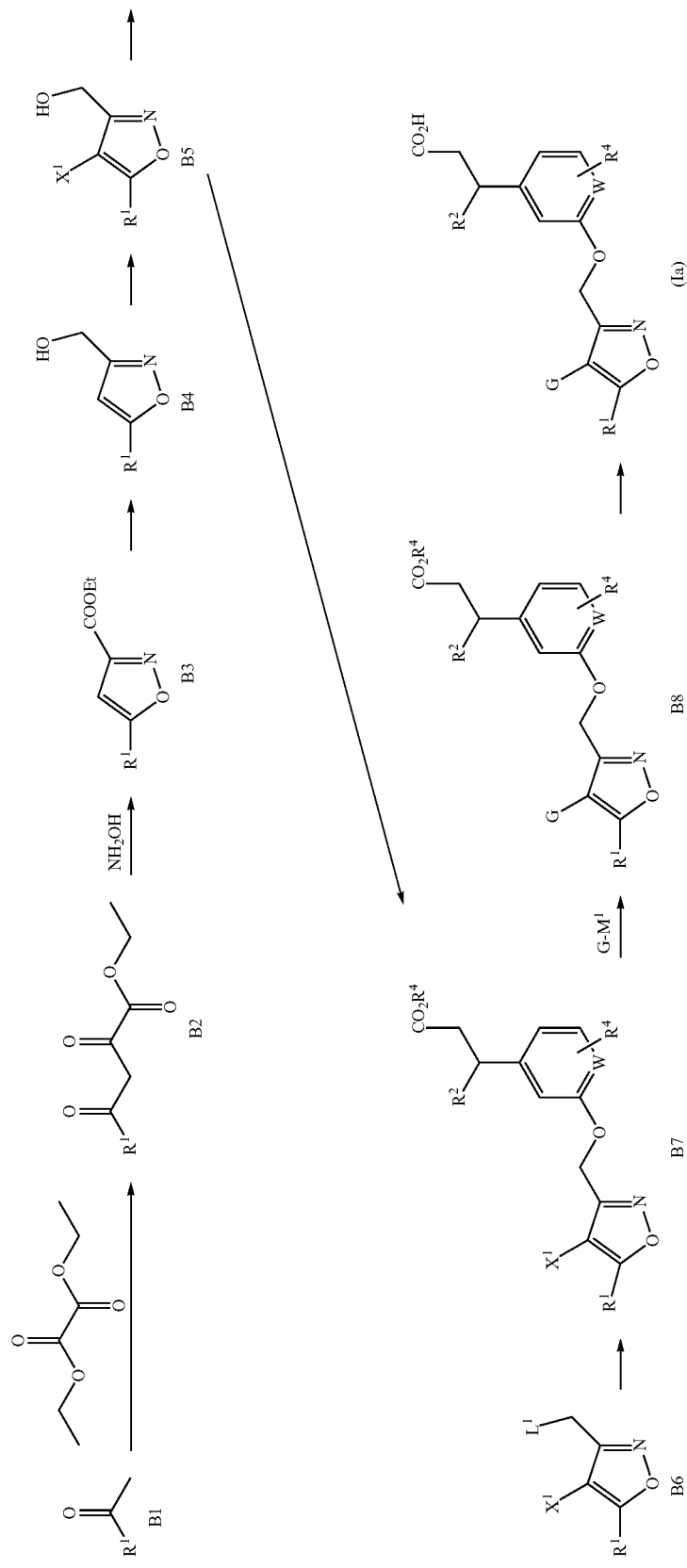

The ring closure of an R¹-substituted dioxobutanoate of formula B2 with NH₂OH is the key step in the construction of the desired isoxazole core structure of the present invention. A solution of a compound of formula B2 may be stirred with a source of NH₂OH such as its hydrochloride salt; in a suitable solvent such as EtOH; under reflux conditions; to effect the cyclo-condensation reaction to obtain a compound of formula B3. The required dioxobutanoate of formula B2 may be obtained by the alkylation of the enolate derived from a ketone of a compound of formula B1 with a reagent such as diethyl oxalate and the like. For example, a ketone of formula B1 may be treated with a base such as NaH, LDA, LiHMDS, LiTMP, or the like; at a temperature ranging from about −78° C. to about room temperature; in suitable solvent such as THF, Et₂O, or DME; to generate the corresponding metal-enolate which may then be reacted with diethyl oxalate. The method of choice for this transformation involves treatment of a ketone of formula B2 with NaH; in DMF solvent; at about room temperature, followed by interception of the resulting sodium enolate with diethyl oxalate. For ketones of formula B1 that are not commercially available, one of ordinary skill in the art may use conventional, known methods described in the scientific literature. The ester group of a compound of formula B3 may be reduced to its corresponding primary alcohol with a suitable reducing agent such as LAH, DIBAL-H, B₂H₆, and the like; in a suitable solvent such as DCM, DCE, THF or diethyl ether; at a temperature ranging from about −78° C. to about 50° C.; to obtain a compound of formula B4. A preferred method for this reduction includes the treatment of a compound of formula B3 with a reducing agent such as DIBALH; in THF; at a temperature of about −78° C. The compound of formula B4 may then be halogenated to obtain a compound of formula B5 wherein X¹ is a halogen, preferably bromo. A preferred method for carrying out this transformation includes, but is not limited to, the bromination of a compound of formula B4 with a brominating agent such as NBS or the like; in a solvent such as DMF or the like; at a temperature ranging from about room temperature to about 60° C. The compound of formula B7 may be obtained from the coupling of a compound of formula B5 with a compound of formula A2. This transformation may be achieved by first converting the hydroxymethyl group of a compound of formula B5 to a suitable leaving group (L¹) such as a halide, tosylate, mesylate, and the like, to obtain a compound of formula B6, followed by reaction with a compound of formula A2. A preferred method for this transformation includes the reaction of a compound of formula B5 with a halogenating agent such as SOCl₂ or the like; in a solvent such as DCM or DCE; to obtain a compound of formula B6 wherein L¹ is chloro. A compound of formula B6 may then be reacted with a compound of formula A2 in the presence of a suitable base such as Na₂CO₃, K₂CO₃ or Cs₂CO₃; in a suitable solvent such as THF, DMF or DMSO; at a suitable temperature. Alternatively, a compound of formula B6 may be directly coupled with a compound of formula A2 under Mitsunobu reaction conditions to obtain a compound of formula B7. A preferred coupling method may includes, but is not limited to, the treatment of a mixture of a compound of formula B6 and a compound of formula A2 with a phosphine source such as PPh₃ or the like; in the presence of a coupling agent such as DEAD or the like; in a suitable solvent such as THF, DCM, or the like; at a suitable temperature ranging from about 0° C. to about room temperature.

A compound of formula B7 may be reacted with a suitably substituted compound of formula G-M¹, wherein G is a suitably selected group, under suitable coupling conditions, to yield the corresponding compound of formula B8. A compound of formula G-M¹ may be (a) a boronic acid to form a compound of formula G-B(OH)₂; (b) a suitably selected boronic ester such as pinacolatoboryl, neopentylglycolatoboryl, and the like; (c) a suitably selected trialkylstannyl such as tri(n-butyl)tin, and the like; (d) a suitably selected trialkylsilyl such as triallylsilyl, and the like; or (e) a suitably selected aryldialkylsilyl such as 2-(hydroxymethyl)phenyl-dimethylsilyl, and the like; or (f) a suitably selected organo zinc reagent such as G-ZnX wherein X is a halide such as chloro, bromo, or iodo.

For example, a compound of formula G-M¹, wherein M¹ is preferably —B(OH)₂ or a boronic ester, may be reacted with a compound of formula B8 under Suzuki coupling conditions, more particularly in the presence of a suitably selected palladium catalyst such as palladium (II) acetate, palladium (II) chloride, bis(acetonitrile)-dichloro-palladium (II), allylpalladium (II) chloride dimer, tris(dibenzylidineacetone) dipalladium (0) (Pd₂(dba)₃), 2-(di-tert-butylphosphino)biphenyl, dichloro-bis(di-tert-butylphenylphosphine)-palladium (II), [1,1'-bis-(diphenylphosphino)-ferrocene]-palladium (II) dichloride dichloromethane adduct ((dppf)PdCl₂.DCM), tetrakis(triphenylphosphine) palladium(0) (Pd(PPh₃)₄), (1,1'-bis(di-tert-butylphosphino)ferrocene palladium (II) chloride, and the like; optionally in the presence of a suitably selected ligand such as triphenylphosphine, tri-o-tolylphosphine, tri(tert-butyl)-phosphine, tricyclohexylphosphine, 1,1'-bis(diphenylphosphino)-ferrocene, 2-(dicyclohexylphosphino)-2',4',6'-tri-i-propyl-1,1'-biphenyl, S-Phos, RuPhos, bis[2-(diphenyl-phosphino)phenyl] ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate, potassium phosphate, or preferably sodium carbonate; in a suitably selected solvent such as ethanol, THF, DMF, toluene, benzene, DME, H₂O, 1,4-dioxane, and the like, or a combination thereof; at a temperature in the range of from about room temperature to about 180° C.

In the final step, the ester functionality of a compound of formula B8 may undergo a conventional saponification to obtain a compound of formula (Ia). One of ordinary skill in the art will recognize that there are a variety of reagents and reaction conditions available for this conversion. A preferred method for this transformation includes treatment of a compound of formula B7 with an aqueous base such as NaOH, LiOH, and the like; in a mixed solvent such as THF/MeOH, and the like; at about room temperature.

It is also understood that it is possible to alter the sequence of some of the synthetic transformations described above without affecting the final outcome of the synthesis.

Scheme C illustrates a method for the preparation of certain compounds of Formula (IIa) of the present invention where in $X_B$ is O, $Y_B$ is N.

Scheme C

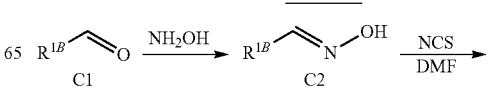

-continued

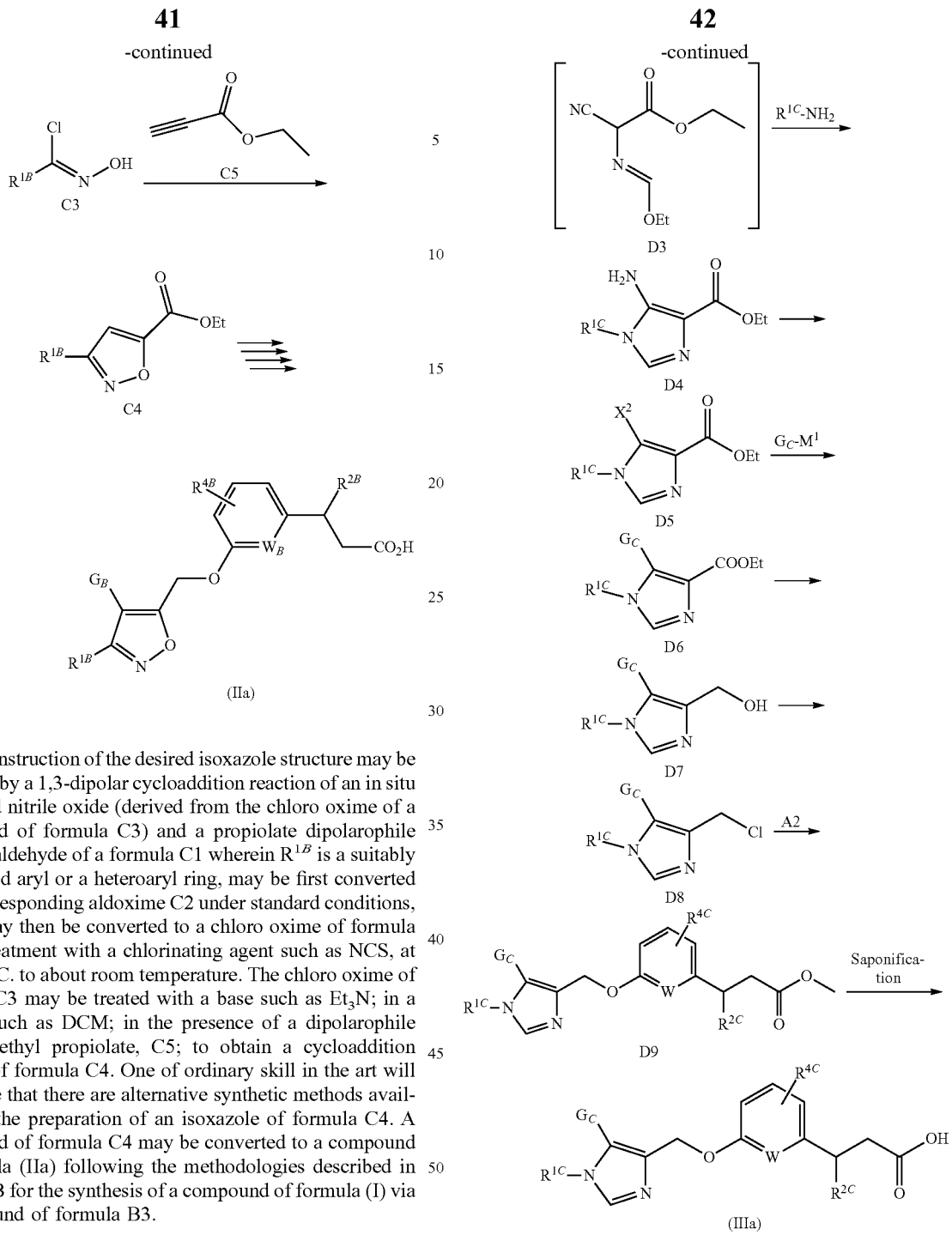

The construction of the desired isoxazole structure may be achieved by a 1,3-dipolar cycloaddition reaction of an in situ generated nitrile oxide (derived from the chloro oxime of a compound of formula C3) and a propiolate dipolarophile C5. The aldehyde of a formula C1 wherein $R^{1B}$ is a suitably substituted aryl or a heteroaryl ring, may be first converted to its corresponding aldoxime C2 under standard conditions, which may then be converted to a chloro oxime of formula C3 by treatment with a chlorinating agent such as NCS, at about 0° C. to about room temperature. The chloro oxime of formula C3 may be treated with a base such as $Et_3N$; in a solvent such as DCM; in the presence of a dipolarophile such as ethyl propiolate, C5; to obtain a cycloaddition product of formula C4. One of ordinary skill in the art will recognize that there are alternative synthetic methods available for the preparation of an isoxazole of formula C4. A compound of formula C4 may be converted to a compound of formula (IIa) following the methodologies described in Scheme B for the synthesis of a compound of formula (I) via a compound of formula B3.

Scheme D illustrates a method for the preparation of certain compounds of formula (IIIa) of the present invention wherein $Y_C$ is CH, $Z_C$ is N.

Scheme D

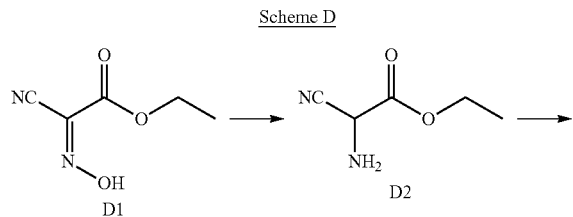

The cyanoglyoxylate oxime of formula D1 may be reduced to an amino-cyanoacetate of formula D2 using one of a variety of available reagents and conditions, for example: (1) $H_2$/Pd, $H_2$/Pt, or Al amalgam in an alcoholic solvent such as MeOH or EtOH; and (2) $Na_2S_2O_4$ or $Na_2S_2O_3$ as a reducing agent. A preferred method for this transformation includes treatment of a compound of formula D1 with $Na_2S_2O_4$; in aqueous $NaHCO_3$; at about room temperature. The amino-cyanoacetate of formula D2 may then be reacted with an orthoester, such as ethyl orthoformate, to generate an intermediate such as D3 in-situ. This intermediate may react with an aniline of formula $R^{1C}$—$NH_2$ to obtain a compound of formula D4. Alternatively, the aniline of formula $R^{1C}$—$NH_2$ may be converted to an N-aryl formimidate of formula $R^{1C}N$=CHOEt, for example, which may then be reacted with a compound of formula D2 to obtain a compound of formula D4.

A compound of formula D4 may be converted to a compound of formula D5 wherein $X^2$ is a halogen. A preferred method for this transformation includes, but is not limited to, the non-aqueous diazotization of the amino group of a compound of formula D4 using a reagent such as tert-butyl nitrite or isoamyl nitrite, followed by the interception of the resulting diazonium salt with an appropriate halogen source such as $I_2/CH_2I_2$, $Cu_2Br_2$, $Cu_2Cl_2$, and the like, to give a compound of formula D5 wherein $X^2$ is iodo, bromo or chloro respectively. It is also understood that this transformation may be effected using standard aqueous Sandmeyer conditions.

A compound of formula D5 may be reacted with a suitably substituted compound of formula $G_C$-$M^1$, wherein $G_C$ is a suitably selected group, under suitable coupling conditions, to yield the corresponding compound of formula D6 using the methods described for the preparation of a compound of formula B8 from a compound of formula B7 (Scheme B).

The ester group of a compound of formula D6 may then be reduced to its corresponding hydroxymethyl group to obtain a compound of formula D7. One of ordinary skill in the art will recognize that there are a variety of reagents and reaction conditions available for this transformation. A preferred set of reaction conditions for this conversion includes treatment of a compound of formula D6 in a suitable solvent such as diethyl ether, THF or DCM; with a hydride source such as LAH or DIBAL-H, or the like; at a temperature at about −78° C. to about room temperature.

The alcohol of formula D7 may be coupled with a compound of formula A2 under standard Mitsunobu conditions to obtain a compound of formula D9. A preferred method for this transformation includes, but is not limited to, the coupling of a compound of formula D7 with a compound of formula A2; using $PPh_3$ and a coupling agent such as DEAD; in a suitable aprotic solvent such as THF; at a suitable temperature ranging from about 0° C. to about room temperature. Alternatively, the hydroxymethyl functionality of a compound of formula D7 may be converted to a leaving group such as a chloride to obtain a compound of formula D8, which may then be reacted with a compound of formula A2 in the presence of a suitable base such as $Na_2CO_3$, $K_2CO_3$, or $Cs_2CO_3$; in a suitable solvent such as THF, DMF or DMSO; at a suitable temperature. A preferred method for this transformation includes, but is not limited to, treatment of a compound of formula D7 with $SOCl_2$; in DCM solvent; at room temperature; to obtain the corresponding benzyl chloride of formula D8. The compound of formula D8 may then be reacted with a compound of formula A2 in the presence of $Cs_2CO_3$ as a base; in a solvent such as DMF; at room temperature; to yield a compound of formula D9.

In the final step, the ester functionality of a compound of formula D9 may undergo a conventional saponification to obtain a compound of formula (IIIa). One of ordinary skill in the art will recognize that there are a variety of reagents and reaction conditions available for this conversion. A preferred method for this transformation includes treatment of a compound of formula D9 with an aqueous base such as NaOH, LiOH, and the like; in a mixed solvent such as THF/MeOH, and the like; at about room temperature.

Scheme E illustrates a method for the preparation of certain compounds of formula (Ib) of the present invention where in X is S, Y is N.

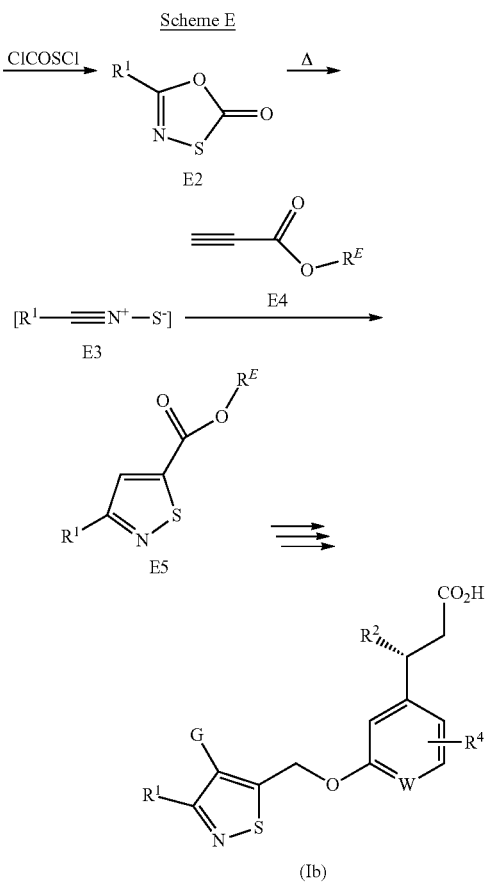

Scheme E

The key step in this synthetic sequence is the 1,3-dipolar cycloaddition of in-situ generated nitrilesulfide of formula E3 with an appropriate dipolarophile of formula E4 to obtain a compound of formula E5. The amide of formula E1 is either commercially available or can be prepared according to the methods described in the scientific literature. The amide E1 can be reacted with ClCOSCl in an inert solvent such as THF, DCE, benzene, toluene, dioxane and the like at about 50-200° C. to obtain a compound of formula E2. The preferred method for this transformation includes the reaction of the amide E1 with ClCOSCl in toluene at 100° C. for about 12 h. The nitrilesulfide intermediate E3 can be generated and trapped in-situ with a dipolarophile by either the thermal or microwave assisted decarboxylation of the 1,3, 4-oxathiazol-2-one E2 in the presence of a compound of formula F4. The preferred method for this transformation includes the heating of a mixture of a compound of formula E2 and E4 where in $R^E$ is a alkyl group in an inert solvent such as THF, DCE, benzene, toluene, dioxane and the like, preferably 1,3-dichlorobenzene at about 150° C. for about 5 h. Compound E5 can be converted to a compound of formula (Ib) following the methodologies described in Scheme B for the synthesis of compounds of formula (Ia) from a compound of formula B3.

Scheme F illustrates a method for the preparation of certain compounds of formula (IIIb) of the present invention where in $Y_C$ and $Z_C$ are each N and $L_C$ is an ether.

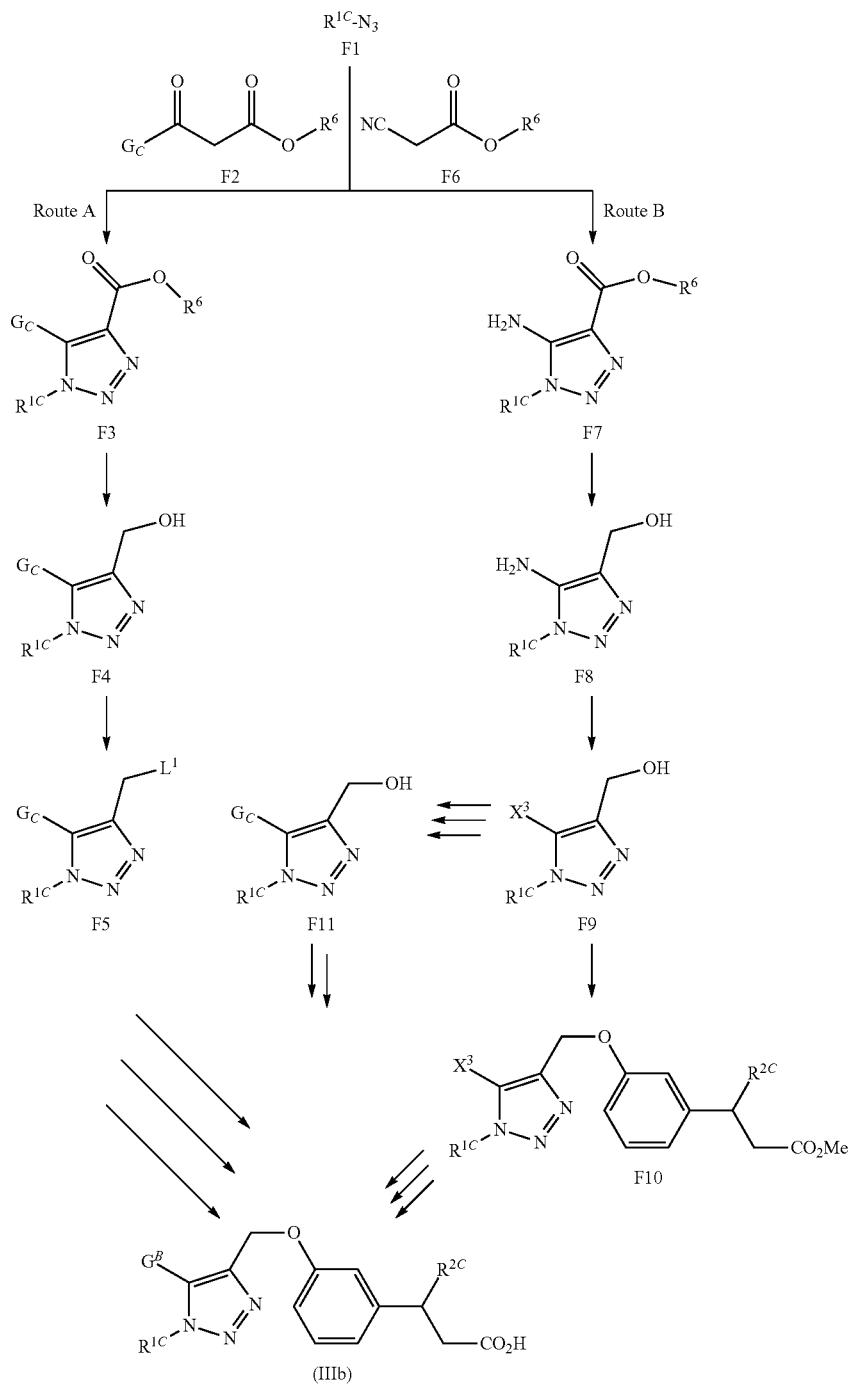

Scheme F

The key step in this synthetic sequence is a 1,3-dipolar cycloaddition of an azide $R^{1C}$—$N_3$ of (F1) with an appropriate β-ketoester of formula F2, in the presence of an organic base, to obtain a compound of formula F3. The azide of formula F1 and β-ketoester of formula F2 are either commercially available or may be prepared according to the methods described in the scientific literature. For instance, a compound of formula F1 may be reacted with a compound of formula F2 wherein $G_C$ is $C_{1-6}$alkyl, or preferably isopropyl, and $R^6$ is ethyl; in a polar solvent such as DMSO; in the presence of an organic base such as $Et_2NH$, $Et_3N$, pyrrolidine, and the like; at about room temperature to about 150° C., preferably at 80° C.; to obtain a compound of formula F3 wherein $G_C$ is $C_{1-6}$alkyl, or preferably isopropyl, and $R^6$ is ethyl. The ester group of a compound of formula F3 may then be reduced to its corresponding alcohol as described hereinbelow. The alcohol may be converted to a compound of formula (IIIb) either by the direct coupling with a compound of formula A2 or via a compound of formula F5 wherein $L^2$ is a leaving group, preferably chloro, using the methods as previously described in Scheme B. The resulting product may be saponified to obtain a compound of formula (IIIb).

An alternate route for the preparation of a compound of formula (IIIb) is shown in Route B. This route utilizes the cycloaddition of an azide of formula F1 with a nitrile of formula F6, such as ethylcyanoacetate, to yield a compound of formula F7. The compound of formula F7 may be reduced with suitable reducing agent such as DIBAL-H; in a suitable solvent such as DCM, diethyl ether, THF, and the like; to obtain a compound of formula F8. The amino functionality of a compound of formula F8 may be converted to a suitable functional group such as a halide, preferably chloro, bromo, or iodo, for the introduction of substituent $G_C$. For example, a compound of formula F8 may be diazotized with an appropriate reagent such as tert-BuNO$_2$; in the presence of a reagent such as CuBr$_2$; to obtain a compound of formula F9 wherein $X^3$ is bromo. It is understood that these two steps may be reversed without affecting the final outcome of the two steps. As previously described, the compound of formula F9 may be carried through the synthesis to yield a compound of formula (IIIb) using an adaptation to the methods described in Scheme B for the conversion of a compound of formula B5 to B7 to a compound of formula (Ia). Alternatively, a compound of formula F9 may be converted to a compound of formula F11 and carried through to furnish a compound of formula (IIIb), as described in the transformation of a compound of formula B5 to a compound of formula (Ia), with or without the protection of the hydroxyl function of the compound of formula F9.

Scheme G illustrates another method for the preparation of certain compounds of formula (Ib) of the present invention where in X is S and Y is N.

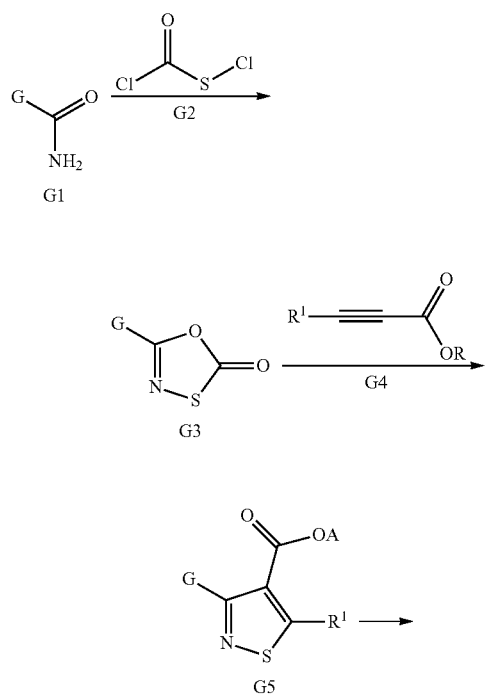

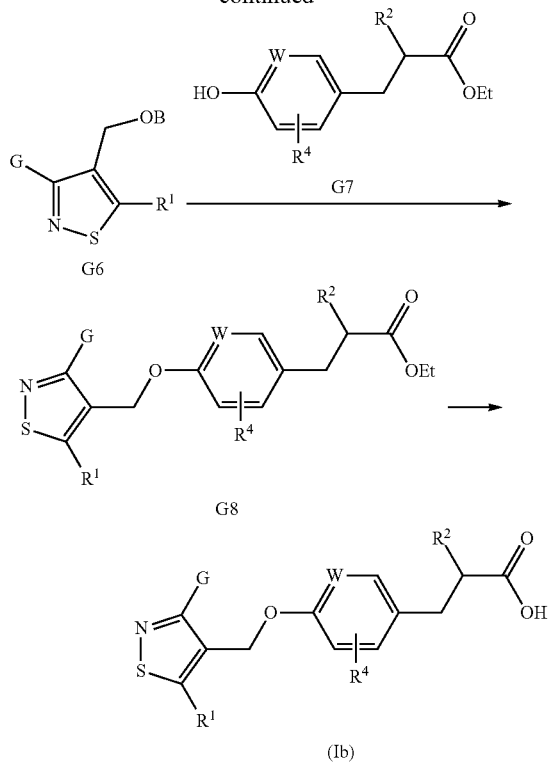

Accordingly, a suitably substituted amide compound of formula G1, a commercially available compound or compound prepared from a corresponding acid through known methods, may be reacted with a commercially available reagent of formula G2, in an organic solvent such as toluene, xylene, chlorobenzene and the like, at a temperature in the range from 100° C. to about 160° C., to yield the corresponding compound of formula G3.

The compound of formula G3 may be reacted with a suitably substituted compound of formula G4, a commercially available compound or compound prepared by known methods, in an organic solvent such as toluene, chlorobenzene, 1,3-dichlorobenzene, and the like, at a temperature in the range from 150° C. to about 200° C., to yield the corresponding compound of formula G5.

The compound of formula G5 may be reacted with a commercially available reducing agent such as LAH, DIBAL, borane/THF complex and the like, in an organic solvent such as THF, ether, dioxane and the like, at a temperature in the range from about −20° C. to about room temperature, to yield the corresponding compound of formula G6 wherein B is hydrogen.

The compound of formula G6 wherein B is hydrogen may be reacted with a suitably substituted compound of formula G7, a compound prepared by known methods, with a commercially available coupling agent such as DEAD/Ph$_3$P, ADDP/TBP, and the like, in an organic solvent such as toluene, THF, dioxane and the like, at a temperature in the range from 0° C. to about 80° C., to yield the corresponding compound of formula G8.

Alternatively, the compound of formula G6, wherein B is hydrogen, may be reacted with a commercially available reagent such as TsCl, MsCl, CCl$_4$/Ph$_3$P, NBS/Ph$_3$P and the like, either in the presence or in the absence of an organic base such as TEA, DIPEA and the like, in an organic solvent such as THF, DCM, ether, and the like, at a temperature in the range of from 0° C. to room temperature, to yield the corresponding compound of formula G6, wherein —OB is a suitable leaving group such as OTs, OMs, Cl, Br, and the like, which is then reacted with a suitably substituted compound of formula G7, a compound prepared by known methods, in the presence of an inorganic base such as $Cs_2CO_3$, $K_2CO_3$, NaH and the like, in an organic solvent such as THF, acetone, DMF and the like, at a temperature in the range from room temperature to 100° C., to yield the corresponding compound of formula G8.

The compound of formula G8 may be reacted with a commercially available inorganic base such as LiOH, NaOH, KOH and the like in a mixed solvent of THF, MeOH and water and the like, at a temperature in the range from 0° C. to about 50° C., to yield the corresponding compound of formula (Ib).

Compounds of formula (Ic) wherein X is S and Y is $C(R^3)$ may alternatively be prepared according to the process outlined in Scheme H, below.

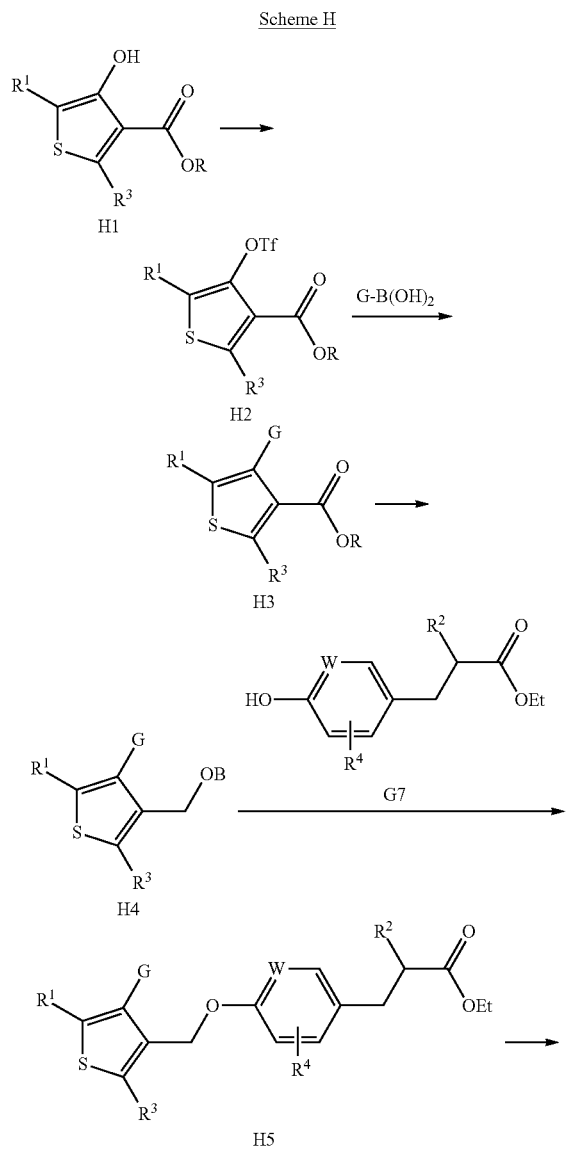

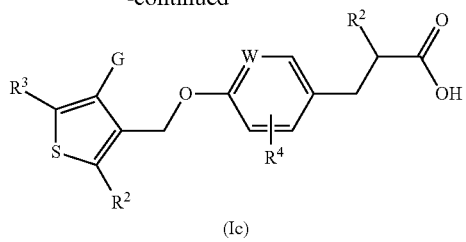

Accordingly, a commercially available or a compound prepared by known methods of formula H1 may be reacted with a commercially available trifluoromethanesulfonic anhydride, in the presence of an organic base such as pyridine, TEA, DIPEA and the like, in an organic solvent such as DCM, 1,2-dichloroethane, THF and the like, at a temperature in the range of from 0° C. to room temperature, to yield the corresponding compound of formula H2.

The suitably substituted compound of formula H2 may be reacted with a suitably substituted compound of formula H3, a commercially available compound or compound prepared by known methods, in the presence of an inorganic base such as $Na_2CO_3$, $K_2CO_3$, $K_3PO_4$, and the like, in the presence of a suitably selected an Pd containing reagent such $Pd(OAc)_2$, $Pd(Ph_3P)_4$, $Pd(Ph_3P)_2Cl_2$, and the like, in the presence of a suitably selected ligand such as $Ph_3P$, BINAP, dppf, and the like, in a mixture of a suitably selected organic solvent such as toluene, ethanol, 1,4-dioxane, and the like, and water, to yield the corresponding compound of formula H3.

The suitably substituted compound of formula H3 may be reacted an inorganic reducing reagent such as borane, LAH, DIBAL and the like, in an organic solvent such as THF, dioxane, ether and the like, at a temperature in the range from −20° C. to room temperature, to yield the corresponding compound of formula H4 wherein B is hydrogen.

The compound of formula H4 wherein B is hydrogen may be reacted with a suitably substituted compound of formula G7, a compound prepared by known methods, with a commercially available coupling agents such as DEAD/$Ph_3P$, ADDP/TBP and the like, in an organic solvent such as toluene, THF, dioxane and the like, at a temperature in the range from 0° C. to about 80° C., to yield the corresponding compound of formula I5.

Alternatively, the compound of formula H4, wherein B is hydrogen, may be reacted with a commercially available reagent such as TsCl, MsCl, $CCl_4/Ph_3P$, $NBS/Ph_3P$ and the like, either in the presence or in the absence of an organic base such as TEA, DIPEA and the like, in an organic solvent such as THF, DCM, diethyl ether and the like, at a temperature in the range from 0° C. to room temperature, to yield the corresponding compound of formula H4, wherein OB is a suitably leaving group such as OTs, OMs or Cl, Br, and the like, which is then reacted with a suitably substituted compound of formula G7, a compound prepared by known methods, in the presence of an inorganic base such as $Cs_2CO_3$, $K_2CO_3$, NaH and the like, in an organic solvent such as THF, acetone, DMF and the like, at a temperature in the range from room temperature to 100° C., to yield the corresponding compound of formula H15.

The compound of formula H5 may be reacted with a commercially available inorganic base such as LiOH, NaOH, KOH and the like in a mixed solvent of THF, MeOH and water and the like, at a temperature in the range from 0° C. to about 50° C., to yield the corresponding compound of formula (Ic).

Compounds of formula (I), (II) or (III) of the present invention wherein L, $L_b$, or $L_c$, respectively, are either —CH=CH— or —(CH$_2$)$_2$— may be prepared according to the process outlined in Scheme I, below.

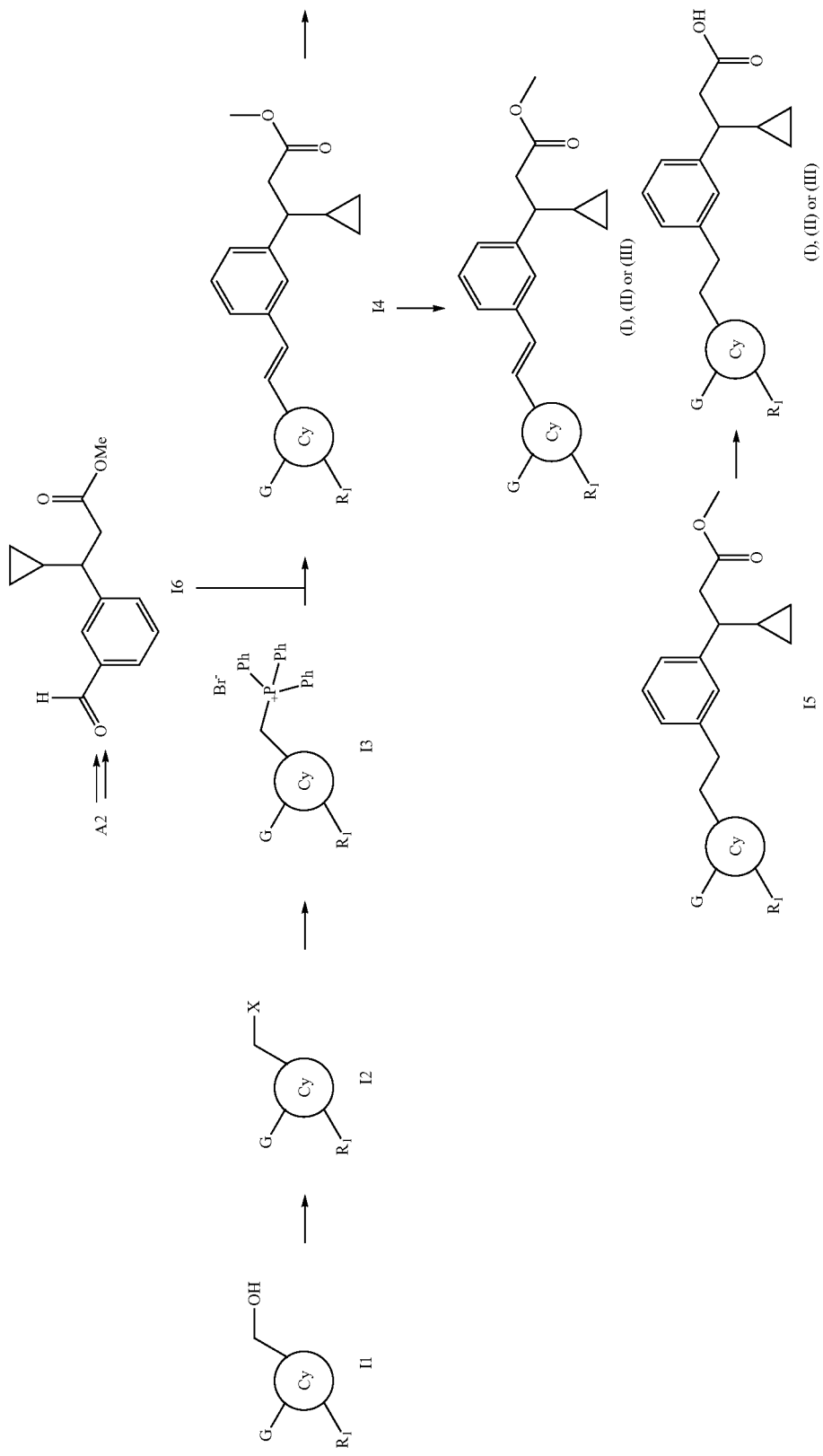

A compound of formula I1 where in Cy represents one of the 5-membered heterocyles described in schemes B-H, can be converted to the compound of formula I2 where in X is a halide, preferably Br. A preferred synthetic method for this conversion includes, but is not limited to, the treatment of the compound I1 with $PBr_3$ in DCM at about 25° C. for 2 h. The halide I2 can then be converted to the Wittig reagent I3 by known methods. The Wittig reagent of formula I3 can be employed in an olefination reaction with the aldehyde of formula I6 using standard Wittig olefination protocol. For example, a compound of formula I3 may be reacted with I6 in the presence of a suitable base such as NaH, in a suitable solvent such as THF, at a suitable temperature in the range of from about 0° C. to 30° C. It is understood that there are many other ways to convert the compound of formula I2 to I4. For example the compound I2 can be converted to Horner-Emmons reagent which can then be employed in an olefination reaction with the aldehyde I6 to obtain the compound of formula I4. Compound I6 may be prepared from compound A2. The preferred method of this transformation includes the conversion of the phenolic function of the A2 to corresponding triflate followed by the Pd catalyzed hydroformylation reaction with high pressure CO gas, preferably around 5 atm, under reductive conditions in the presence of an organic base such as triethyl amine and a reducing agent such as triethylsilane in a solvent such as DMF at a about 80° C. The ethenyl functionality in compounds of formula I4 may be reduced using an appropriate reducing agent, such as $NiCl_2/NaBH_4$ or $H_2/Pd/C$, in a solvent such as ethyl acetate, MeOH, EtOH, to obtain a compound of formula I5. Preferred reaction conditions for this transformation include the hydrogenation of the compound of formula I4 in MeOH at room temperature over 10% Pd/C at about 3 atm of $H_2$ pressure. In the final step, the ester functionality of a compound of formula I4 or I5 may undergo a conventional saponification to obtain a compound of formula (I), (II) or (III). One of ordinary skill in the art will recognize that there are a variety of reagents and reaction conditions available for this conversion. A preferred method for this transformation includes treatment of a compound of formula I4 or I5 with an aqueous base such as NaOH, LiOH, and the like; in a mixed solvent such as THF/MeOH, and the like; at about room temperature.

SPECIFIC EXAMPLES

Example 1

(S)-3-Cyclopropyl-3-(3-((5-(5,5-dimethylcyclopent-1-en-1-yl)-1-(2-fluoro-5-methoxyphenyl)-1H-pyrazol-4-yl)methoxy)phenyl)propanoic acid (Cpd 66)

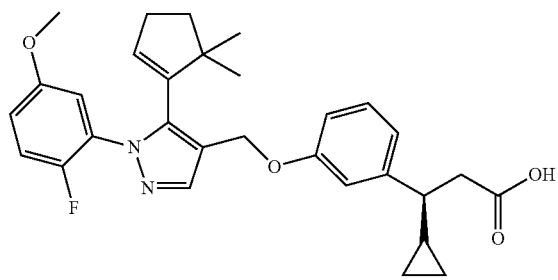 [SMILES: COc1ccc(F)c(-n2ncc(COc3cccc([C@@H](CC(=O)O)C4CC4)c3)c2C2=CCCC2(C)C)c1]

A. (2-Fluoro-5-methoxyphenyl)hydrazine, 1a

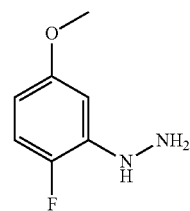

To a mixture of 2-fluoro-5-methoxyphenylboronic acid (2.00 g, 11.8 mmol) and di-t-butyl azodicarboxylate (2.85 g, 12.4 mmol) in MeOH was added $Cu(OAc)_2$ (214 mg, 1.18 mmol) under argon. The mixture was stirred at 45° C. for 6 h and concentrated. The residue obtained was dissolved in DCM (100 mL) and washed with water, satd. $NaHCO_3$, and brine. The organic layer was dried over $Na_2SO_4$, filtered and concentrated. The crude residue was purified by column chromatography on silica gel (0-30% EtOAc/heptane). The resulting yellow oil was dissolved in 1,4-dioxane (5 mL) and treated with 4M HCl in 1,4-dioxane (18 mL, 64 mmol). The resulting mixture was stirred at 50° C. for 2 h, and at RT for 4 h. The precipitate formed was collected by filtration, washed with 1,4-dioxane and ether, and dried under high vacuum to obtain compound 1a as a white solid. $^1$H-NMR (400 MHz, DMSO-$d_6$) δ (ppm): 10.21 (br. s., 2H), 8.28 (br. s., 1H), 7.13 (dd, J=11.1, 8.6 Hz, 1H), 6.77 (dd, J=7.1, 3.0 Hz, 1H), 6.50 (dt, J=9.0, 3.1 Hz, 1H), 3.73 (s, 3H).

B. Ethyl 5-amino-1-(2-fluoro-5-methoxyphenyl)-1H-pyrazole-4-carboxylate, 1b

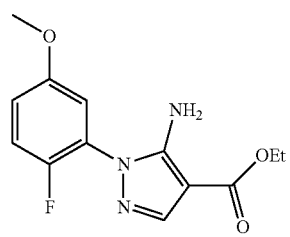

To a stirring solution of compound 1a (1.54 g, 8.00 mmol) and triethylamine (1.11 mL, 8.00 mmol) in EtOH (15 mL) was added ethyl (ethoxymethylene)cyanoacetate (1.49 g, 8.79 mmol) portion wise. The reaction was stirred at rt for 16 h. Water (100 mL) was added, and the mixture was extracted with EtOAc (2×100 mL). The combined organic layers were washed with brine, dried over $Na_2SO_4$, filtered and concentrated. The crude material was purified by column chromatography on silica gel (0-50% EtOAc/heptane). The resulting solid was suspended in AcOH (5 mL) and water (1.6 mL) and stirred at 100° C. for 1 h. The reaction mixture was allowed to cool to RT and poured over ice. The resulting precipitate was extracted with EtOAc (2×100 mL). The combined organic layers were washed with brine, dried over $Na_2SO_4$, filtered and concentrated to give compound 1b as a brown oil. Mass Spectrum (LCMS, ESI pos.): Calcd. for $C_{13}H_{14}FN_3O_3$: 280.1 (M+H). found: 280.1.

C. Ethyl 5-bromo-1-(2-fluoro-5-methoxyphenyl)-1H-pyrazole-4-carboxylate, 1c

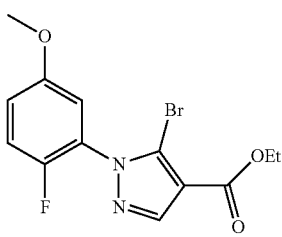

To a solution of compound 1b (133 mg, 0.476 mmol) and CuBr$_2$ (128 mg, 0.571 mmol) in acetonitrile (2 mL), cooled in an ice-water bath, was added t-butyl nitrite (68.0 mL, 0.571 mmol) dropwise under argon. The reaction mixture was warmed to rt over 2 h, and stirred at rt overnight. EtOAc (50 mL) was then added and the organic layer was washed with water, 1N HCl, and brine. After drying over Na$_2$SO$_4$, the organic layer was filtered and concentrated. The resulting crude material was purified by flash chromatography (0-20% EtOAc/heptane). Compound 1c was obtained as a white solid. Mass Spectrum (LCMS, ESI pos.): Calcd. for C$_{13}$H$_{12}$BrFN$_2$O$_3$: 343.0 (M+H). found: 343.0.

D. Ethyl 5-(5,5-dimethylcyclopent-1-en-1-yl)-1-(2-fluoro-5-methoxyphenyl)-1H-pyrazole-4-carboxylate, 1d

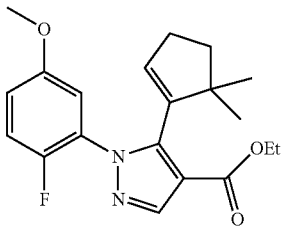

A mixture of compound 1c (104 mg, 0.303 mmol), 2-(5,5-dimethylcyclopent-1-en-1-yl)-4,4,5,5-tetramethyl-1,3,2-dioxaborolane (101 mg, 0.455 mmol) and K$_3$PO$_4$ (257 mg, 1.21 mmol) in 1,4-dioxane (2 mL) and water (0.5 mL) was purged with argon. Dichloro(diphenylphosphinoferrocene)palladium (25 mg, 0.034 mmol) was then added and the mixture was stirred at 80° C. for 24 h. Upon cooling, EtOAc (50 mL) was added. The organic layer was washed with water (50 mL) and brine (50 mL), dried over Na$_2$SO$_4$, filtered and concentrated. The resulting crude material was purified by flash chromatography (0-20% EtOAc/heptane). Compound 1d was obtained as a white solid. Mass Spectrum (LCMS, ESI pos.): Calcd. for C$_{20}$H$_{23}$FN$_2$O$_3$: 359.2 (M+H). found: 359.2.

E. (5-(5,5-Dimethylcyclopent-1-en-1-yl)-1-(2-fluoro-5-methoxyphenyl)-1H-pyrazol-4-yl)methanol, 1e

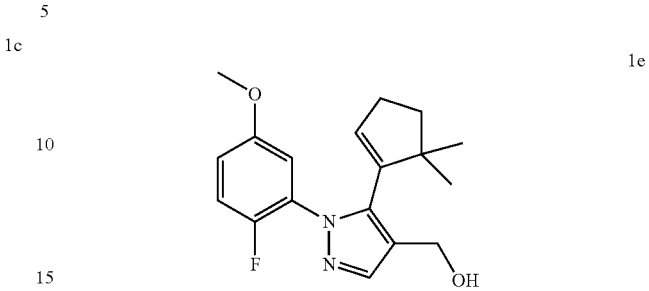

A solution of compound 1d (91.0 mg, 0.254 mmol) in toluene (4 mL) was cooled in a dry ice-acetone bath (−78° C.). DIBAL-H (1M solution in toluene, 1.52 mL, 1.52 mmol) was added dropwise while under argon. The mixture was warmed to rt and stirred for 30 min. The mixture was cooled to −78° C. again, and disodium tartrate (1M, 20 mL) solution was added slowly to quench the reaction. EtOAc (20 mL) was added, and the mixture was stirred at rt for 1 h until the layers were separated. The organic layer was washed with brine, dried over Na$_2$SO$_4$, filtered, and concentrated to obtain Compound 1e as a colorless oil, which was used in the next step without further purification. Mass Spectrum (LCMS, ESI pos.): Calcd. for C$_{18}$H$_{21}$FN$_2$O$_2$: 317.2 (M+H). found: 317.2.

F. (S)-Ethyl 3-cyclopropyl-3-(3-hydroxyphenyl)propanoate, 1f-S

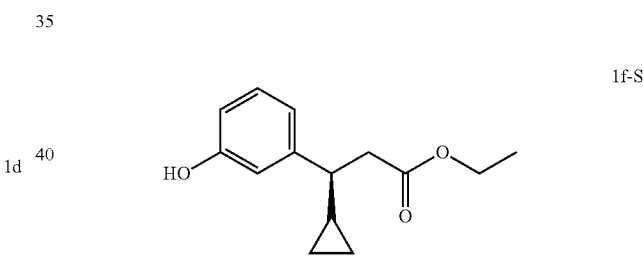

a. Ethyl 3-cyclopropylacrylate, 1f-A

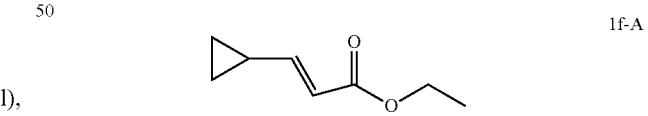

To a solution of cyclopropanecarbaldehyde (20.4 g, 285 mmol) in THF (230 mL) at 0° C. under argon was added ethyl 2-(triphenylphosphoranylidene)acetate (107 g, 292 mmol) portion wise. The mixture was stirred at rt for 16 h before removal of the solvent. The crude solid material obtained was suspended in heptane, sonicated and filtered. The filtrate was concentrated and purified by distillation under reduced pressure to afford compound 1g as a colorless oil. $^1$H-NMR (400 MHz, CDCl$_3$) δ (ppm): 6.42 (dd, J=15.7, 10.1 Hz, 1H), 5.89 (d, J=15.7 Hz, 1H), 4.17 (q, J=7.1 Hz, 2H), 1.51-1.67 (m, 1H), 1.29 (t, J=7.1 Hz, 3H), 0.90-1.02 (m, 2H), 0.59-0.72 (m, 2H).

b. Ethyl 3-cyclopropyl-3-(3-hydroxyphenyl)propanoate, 1f-B

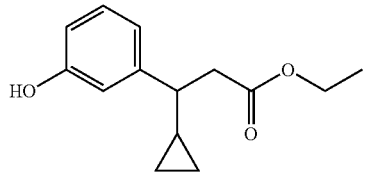

(1f-B)

To a mixture of chloro(1,5-cyclooctadiene)rhodium (I) dimer (1.79 g, 3.63 mmol) in 1,4-dioxane (50 mL) under argon was added 1 N aq. NaOH (109 mL, 109 mmol), (3-hydroxyphenyl)boronic acid (20.0 g, 145 mmol) and a solution of compound 1f-A (10.2 g, 72.5 mmol) in 1,4-dioxane (50 mL) at rt. The mixture obtained was stirred at 50° C. for 16 h. The reaction mixture was allowed to cool to RT, then poured into 1:1 EtOAc/$H_2O$ (100 mL), and acidified with 2 N HCl (aq.) until the pH of the aqueous layer was ~4. The aqueous layer was extracted with EtOAc (2×50 mL). The combined organic layers were dried ($Na_2SO_4$) and filtered. After the removal of the solvents, the crude material was purified by flash chromatography (0-30% EtOAc/heptane) to give racemic compound 1f-B as a yellow oil. $^1$H-NMR (400 MHz, $CDCl_3$) δ (ppm): 7.16 (t, J=7.8 Hz, 1H), 6.80 (d, J=8.1 Hz, 1H), 6.65-6.75 (m, 2H), 4.87 (s, 1H), 3.99-4.14 (m, 2H), 2.63-2.80 (m, 2H), 2.26-2.37 (m, 1H), 1.17 (t, J=7.1 Hz, 3H), 0.93-1.08 (m, 1H), 0.51-0.63 (m, 1H), 0.37-0.49 (m, 1H), 0.27 (dq, J=9.5, 4.9 Hz, 1H), 0.15 (dq, J=9.5, 4.9 Hz, 1H).

c. (S)-Ethyl 3-cyclopropyl-3-(3-hydroxyphenyl) propanoate (1f-S) and (R)-Ethyl 3-cyclopropyl-3-(3-hydroxyphenyl)propanoate (1f-R)

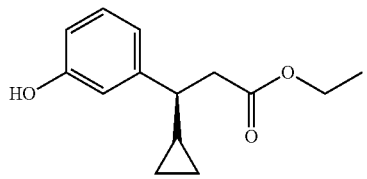

(1f-S)

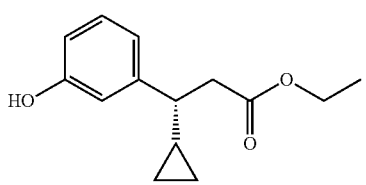

(1f-R)

The racemic mixture of compound 1f-B (29.4 g) was purified by chiral SFC (Stationary phase: Chiraplpak AD 5 µm 250*30 mm), Mobile phase: 90% $CO_2$, 10% i-PrOH), yielding (S)-ethyl 3-cyclopropyl-3-(3-hydroxyphenyl)propanoate (1f-S) (12.9 g, $[\alpha]_D^{20}$=+35.7 c 0.5 $CHCl_3$) and (R)-ethyl 3-cyclopropyl-3-(3-hydroxyphenyl)propanoate (1f-R) (13.5 g).

G. (S)-Ethyl 3-cyclopropyl-3-(3-((5-(5,5-dimethyl-cyclopent-1-en-1-yl)-1-(2-fluoro-5-meth oxyphenyl)-1H-pyrazol-4-yl)methoxy)phenyl)propanoate, 1g

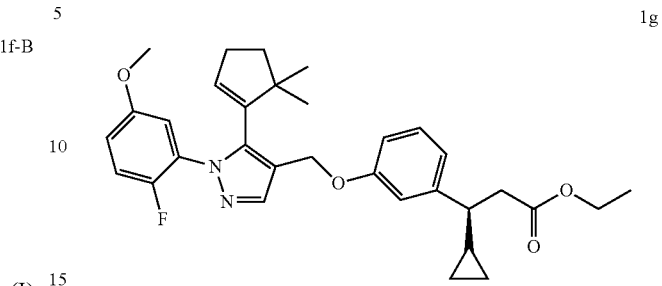

1g

To a solution of compound 1e (40.0 mg, 0.126 mmol), compound 1f-S (44.4 mg, 0.190 mmol) and $PPh_3$ (66.3 mg, 0.253 mmol) in THF (2 mL) was added a solution of di-t-butyl azodicarboxylate (58.2 mg, 0.253 mmol) in THF (1 mL) dropwise under argon. The resulting mixture was stirred at rt for 16 h and concentrated. The residue obtained was purified by flash chromatography (0-30% EtOAc/heptane). Compound 1g was obtained as a colorless oil. Mass Spectrum (LCMS, ESI pos.): Calcd. for $C_{32}H_{37}FN_2O_4$: 533.3 (M+H). found: 533.3.

H. (S)-3-Cyclopropyl-3-(3-((5-(5,5-dimethylcyclopent-1-en-1-yl)-1-(2-fluoro-5-methoxyphenyl)-1H-pyrazol-4-yl)methoxy)phenyl)propanoic acid, Cpd 66

To a solution of compound 1g (55.0 mg, 0.103 mmol) in THF (3 mL) and EtOH (3 mL) was added 1N NaOH (3 mL, 3 mmol) solution. The reaction mixture was stirred at rt for 16 h, and then water (20 mL) was added. The pH of the mixture was adjusted to pH~4 using citric acid (2M solution). The milky solution was extracted with DCM (2×20 mL). The combined organic layers were washed with brine, dried ($Na_2SO_4$), filtered and concentrated. The crude material obtained was purified by flash chromatography (0-70% EtOAc/heptane). Compound 66 was obtained as a white solid. $^1$H-NMR (400 MHz, $CDCl_3$) δ (ppm): 7.87 (s, 1H), 7.20-7.28 (m, 1H), 7.08 (t, J=9.1 Hz, 1H), 6.81-6.94 (m, 5H), 5.96 (s, 1H), 4.83 (s, 2H), 3.76 (s, 3H), 2.71-2.83 (m, 2H), 2.32-2.43 (m, 3H), 1.69 (t, J=7.1 Hz, 2H), 0.95-1.09 (m, 1H), 0.76 (s, 6H), 0.57 (td, J=8.6, 4.0 Hz, 1H), 0.38-0.49 (m, 1H), 0.29 (dq, J=9.5, 4.7 Hz, 1H), 0.16 (dq, J=9.6, 4.9 Hz, 1H). Mass Spectrum (LCMS, ESI pos.): Calcd. for $C_{30}H_{33}FN_2O_4$: 505.2 (M+H). found: 505.3.

Example 2

(S)-3-Cyclopropyl-3-(3-((1-(2-fluoro-5-methoxyphenyl)-5-(2-methylprop-1-en-1-yl)-1H-pyrazol-4-yl)methoxy)phenyl)propanoic acid (Cpd 89)

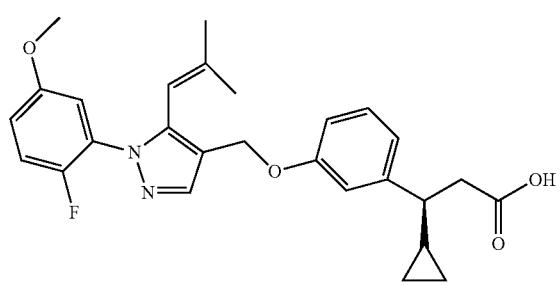 [SMILES: COc1ccc(F)c(-n2ncc(COc3cccc([C@@H](CC(=O)O)C4CC4)c3)c2C=C(C)C)c1]

A. (5-Bromo-1-(2-fluoro-5-methoxyphenyl)-1H-pyrazol-4-yl)methanol, 2a

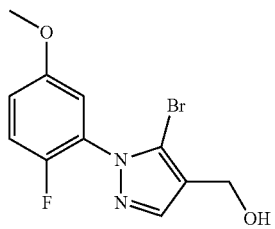

2a

The title compound was obtained using the method described in Example 1, Step E, from compound 1c (350 mg, 1.02 mmol, Example 1, Step C). Compound 2a was isolated as a colorless oil. Mass Spectrum (LCMS, ESI pos.): Calcd. for $C_{11}H_{10}BrFN_2O_2$: 301.1 (M). found: 301.0.

B. 5-Bromo-4-(chloromethyl)-1-(2-fluoro-5-methoxyphenyl)-1H-pyrazole, 2b

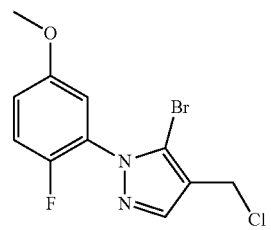

2b

To a solution of compound 2a (291 mg, 0.966 mmol) in DCM (10 mL) cooled in an ice-water bath was added thionyl chloride (0.140 mL, 1.93 mmol) drop wise. The mixture was stirred at 0° C. for 2 h. DCM (50 mL) was added, and the organic layer was washed with water, satd. NaHCO₃, and brine. The organic layer was dried over Na₂SO₄, filtered and concentrated to yield compound 2b as a colorless oil. Mass Spectrum (LCMS, ESI pos.): Calcd. for $C_{11}H_9BrClFN_2O$: 319.5 (M). found: 319.0.

C. (S)-Methyl 3-(3-((5-bromo-1-(2-fluoro-5-methoxyphenyl)-1H-pyrazol-4-yl) methoxy)phenyl)-3-cyclopropylpropanoate, 2c

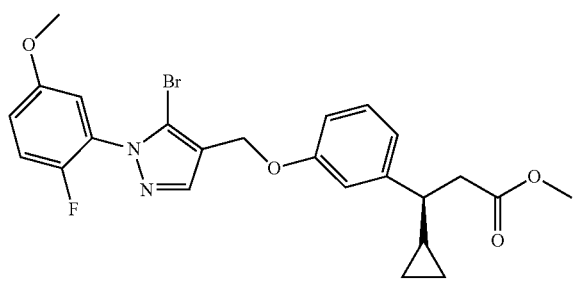

2c

To the solution of compound 2b (300 mg, 0.939 mmol) and (S)-methyl 3-cyclopropyl-3-(3-hydroxyphenyl)propanoate (248 mg, 1.13 mmol, prepared using the similar methods as described in Example 1, step F) in ACN (15 mL) was added Cs₂CO₃ (459 mg, 1.41 mmol). The mixture was stirred at rt for 16 h. EtOAc (50 mL) was added, and the organic layer was washed with water and brine, and dried over Na₂SO₄, filtered and concentrated. The crude material was purified by flash chromatography (0-30% EtOAc/heptane). Compound 2c was obtained as a colorless oil. Mass Spectrum (LCMS, ESI pos.): Calcd. for $C_{24}H_{24}BrFN_2O_4$: 503.3 (M). found: 503.3.

D. (S)-Methyl 3-cyclopropyl-3-(3-((1-(2-fluoro-5-methoxyphenyl)-5-(2-methylprop-1-en-1-yl)-1H-pyrazol-4-yl)methoxy)phenyl)propanoate, 2d

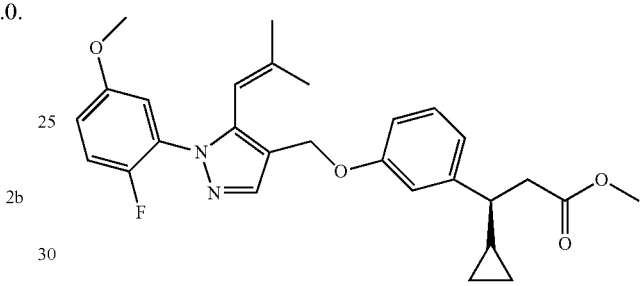

2d

A mixture of compound 2c (23.0 mg, 0.0457 mmol), 2,2-dimethylethenylboronic acid pinacol ester (12.5 mg, 0.0685 mmol), and K₃PO₄ (38.8 mg, 0.183 mmol) in 1,4-dioxane (0.5 mL) and water (0.1 mL) was purged with argon. Dichloro(diphenylphosphinoferrocene)palladium (3.74 mg, 0.00457 mmol) was then added. The resulting mixture was stirred at 80° C. for 4 h. The reaction mixture was allowed to cool to RT and treated with EtOAc (50 mL). The organic layer was washed with water and brine, then dried over Na₂SO₄, filtered and concentrated. The crude material was purified by column chromatography on silica gel (0-30% EtOAc/heptane). Compound 2d was obtained as a colorless oil. Mass Spectrum (LCMS, ESI pos.): Calcd. for $C_{28}H_{31}FN_2O_4$: 479.5 (M+H). found: 479.2.

E. (S)-3-Cyclopropyl-3-(3-((1-(2-fluoro-5-methoxyphenyl)-5-(2-methylprop-1-en-1-yl)-1H-pyrazol-4-yl)methoxy)phenyl)propanoic acid, Cpd 89

Using the method described in Example 1, Step H, the title compound 89 was obtained from compound 2d as a white solid (16 mg, 97% yield). ¹H-NMR (400 MHz, CDCl₃) δ (ppm): 7.82 (s, 1H), 7.20-7.25 (m, 1H), 7.08 (t, J=9.3 Hz, 1H), 6.87-6.97 (m, 2H), 6.80-6.87 (m, 3H), 5.84 (s, 1H), 4.86 (s, 2H), 3.79 (s, 3H), 2.69-2.84 (m, 2H), 2.29-2.41 (m, 1H), 1.80 (s, 3H), 1.57 (s, 3H), 0.96-1.09 (m, 1H), 0.58 (tt, J=8.7, 4.7 Hz, 1H), 0.37-0.48 (m, 1H), 0.29 (dq, J=9.5, 4.9 Hz, 1H), 0.16 (dq, J=9.5, 4.9 Hz, 1H). Mass Spectrum (LCMS, ESI pos.): Calcd. for $C_{27}H_{29}FN_2O_4$: 465.5 (M+H). found: 465.3.

Following the procedures described in Example 2 above, and substituting suitably selected and substituted reagents, starting materials and conditions as would be readily apparent to those skilled in the art, the following representative compounds of the present invention were prepared.

| Cpd No. | Characterization |
|---|---|
| 69 | (S)-3-Cyclopropyl-3-(3-((5-cyclopropyl-1-(2-fluoro-5-methoxyphenyl)-1H-pyrazol-4-yl)methoxy)phenyl)propanoic acid<br>$^1$H-NMR (400 MHz, CDCl$_3$) δ (ppm): 7.73 (s, 1H), 7.22-7.29 (m, 1H), 7.13 (t, J = 9.3 Hz, 1H), 6.90-7.01 (m, 2H), 6.84-6.90 (m, 3H), 4.98 (s, 2H), 3.81 (s, 3H), 2.70-2.85 (m, 2H), 2.31-2.42 (m, 1H), 1.74-1.83 (m, 1H), 0.97-1.09 (m, 1H), 0.70-0.78 (m, 2H), 0.53-0.63 (m, 3H), 0.39-0.49 (m, 1H), 0.30 (dq, J = 9.4, 4.8 Hz, 1H), 0.17 (dq, J = 9.6, 4.9 Hz, 1H). Mass Spectrum (LCMS, ESI pos.) Calcd. For C$_{26}$H$_{27}$FN$_2$O$_4$: 451.5 (M + H); found: 451.3. |
| 90 | (S)-3-(3-((5-Bromo-1-(2-fluoro-5-methoxyphenyl)-1H-pyrazol-4-yl)methoxy)phenyl)-3-cyclopropylpropanoic acid<br>$^1$H-NMR (400 MHz, CDCl$_3$) δ (ppm): 7.87 (s, 1H), 7.22-7.29 (m, 1H), 7.17 (t, J = 9.1 Hz, 1H), 6.97-7.03 (m, 1H), 6.95 (dd, J = 5.6, 3.0 Hz, 1H), 6.88 (s, 2H), 6.86 (s, 1H), 4.96 (s, 2H), 3.81 (s, 3H), 2.69-2.86 (m, 2H), 2.30-2.42 (m, 1H), 0.97-1.10 (m, 1H), 0.58 (tt, J = 8.7, 4.7 Hz, 1H), 0.39-0.49 (m, 1H), 0.29 (dq, J = 9.5, 4.7 Hz, 1H), 0.17 (dq, J = 9.7, 5.0 Hz 1H). Mass Spectrum (LCMS, ESI pos.): Calcd. for C$_{23}$H$_{22}$BrFN$_2$O$_4$: 489.1 (M + H); found: 489.1. |
| 94 | (S)-3-Cyclopropyl-3-(3-((1-(2-fluoro-5-methoxyphenyl)-5-(5-methylthiophen-2-yl)-1H-pyrazol-4-yl)methoxy)phenyl)propanoic acid<br>$^1$H-NMR (400 MHz, CDCl$_3$) δ (ppm): 7.87 (s, 1H), 7.20-7.25 (m, 1H), 7.01-7.08 (m, 1H), 6.90-6.99 (m, 2H), 6.84-6.89 (m, 3H), 6.83 (d, J = 3.5 Hz, 1H), 6.64 (d, J = 2.5 Hz, 1H), 4.98 (s, 2H), 3.77 (s, 3H), 2.70-2.84 (m, 2H), 2.41 (s, 3H), 2.31-2.39 (m, 1H), 0.96-1.09 (m, 1H), 0.53-0.64 (m, 1H), 0.43 (tt, J = 8.7, 4.7 Hz, 1H), 0.29 (dq, J = 9.6, 4.9 Hz, 1H), 0.16 (dq, J = 9.7, 4.9 Hz, 1H). Mass Spectrum (LCMS, ESI pos.) Calcd. For C$_{28}$H$_{27}$FN$_2$O$_4$S: 507.6 (M + H); found: 507.3. |
| 95 | (S)-3-Cyclopropyl-3-(3-((5-(2,4-difluorophenyl)-1-(2-fluoro-5-methoxyphenyl)-1H-pyrazol-4-yl)methoxy)phenyl)propanoic acid<br>$^1$H-NMR (400 MHz, CDCl$_3$) δ (ppm): 7.94 (s, 1H), 7.13-7.28 (m, 2H), 6.88-7.00 (m, 2H), 6.79-6.88 (m, 4H), 6.71-6.79 (m, 2H), 4.88 (s, 2H), 3.76 (s, 3H), 2.67-2.82 (m, 2H), 2.25-2.37 (m, 1H), 0.92-1.05 (m, 1H), 0.51-0.62 (m, 1H), 0.36-0.47 (m, 1H), 0.22-0.32 (m, 1H), 0.13 (dq, J = 9.5, 4.9 Hz, 1H). Mass Spectrum (LCMS, ESI pos.) Calcd. For C$_{29}$H$_{25}$F$_3$N$_2$O$_4$: 523.5 (M + H); found: 523.3. |
| 96 | (S)-3-Cyclopropyl-3-(3-((5-(3,5-dimethylphenyl)-1-(2-fluoro-5-methoxyphenyl)-1H-pyrazol-4-yl)methoxy)phenyl)propanoic acid<br>$^1$H-NMR (400 MHz, CDCl$_3$) δ (ppm): 7.91 (s, 1H), 7.21 (t, J = 7.8 Hz, 1H), 6.90-7.01 (m, 3H), 6.76-6.88 (m, 6H), 4.90 (s, 2H), 3.73 (s, 3H), 2.66-2.82 (m, 2H), 2.26-2.38 (m, 1H), 2.18 (s, 6H), 0.92-1.06 (m, 1H), 0.49-0.63 (m, 1H), 0.36-0.47 (m, 1H), 0.28 (dq, J = 9.4, 4.8 Hz, 1H), 0.14 (dq, J = 9.6, 4.9 Hz, 1H). Mass Spectrum (LCMS, ESI pos.) Calcd. For C$_{31}$H$_{31}$FN$_2$O$_4$: 515.6 (M + H); found: 515.0. |

Example 3

(3S)-3-Cyclopropyl-3-(3-((5-(5,5-dimethylcyclopent-1-enyl)-1-(2-fluoro-5-methoxyphenyl)-1H-imidazol-4-yl)methoxy)phenyl)propanoic acid (Cpd 87)

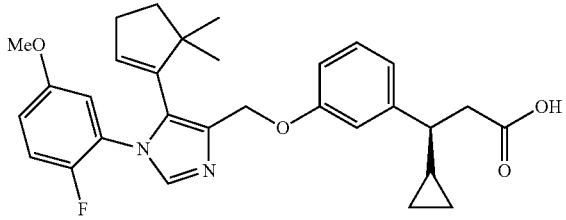 [SMILES: COc1ccc(F)c(-n2cnc(COc3cccc([C@@H](CC(=O)O)C4CC4)c3)c2C2=CCCC2(C)C)c1]

A. Ethyl 2-amino-2-cyanoacetate, 3a

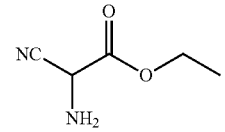

To a mixture of ethyl cyano(hydroxyimino)formate (36.0 g, 253 mmol) in water (960 mL) was added satd. sodium bicarbonate solution (240 mL) followed by addition of Na$_2$S$_2$O$_4$ (44.0 g, 253 mmol). After 1 h, the stirred reaction mixture was treated with another equivalent of Na$_2$S$_2$O$_4$ (44.0 g, 253 mmol), and this was repeated two more times every 2 h. The reaction mixture was stirred for 6 h at RT and extracted with DCM (3×500 mL). The separated organic layers were combined and dried over Na$_2$SO$_4$ and concentrated under vacuum to give compound 3a as a yellow oil. Mass Spectrum (LCMS, ESI pos.): Calcd. for C$_5$H$_8$N$_2$O$_2$: 129.1 (M+H). found: 129.1.

B. Ethyl 5-amino-1-(2-fluoro-5-methoxyphenyl)-1H-imidazole-4-carboxylate, 3b

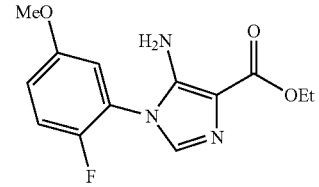

A solution of compound 3a (4.5 g, 35 mmol) and (diethoxymethoxy)ethane (6.3 g, 42 mmol) in CH$_3$CN (50 mL) was stirred at 80° C. for 1 h. The reaction mixture was allowed to cool to RT and treated with 2-fluoro-5-methoxyaniline (3.0 g, 21 mmol). The resulting solution was stirred overnight at RT and concentrated. The residue obtained was purified by flash chromatography (0-25% EtOAc/petroleum ether) on silica gel to obtain compound 3b as a light yellow solid. Mass Spectrum (LCMS, ESI pos.): Calcd. for C$_{13}$H$_{14}$FN$_3$O$_3$: 280.1 (M+H). found: 280.0.

C. Ethyl 1-(2-fluoro-5-methoxyphenyl)-5-iodo-1H-imidazole-4-carboxylate, 3c

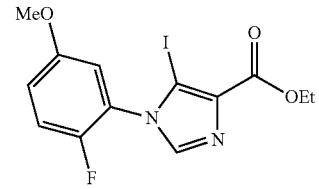

A solution of compound 3b (500 mg, 1.79 mmol) in CH$_2$I$_2$ (3 mL) was treated with 3-methylbutyl nitrite (2.097 g, 17.90 mmol) at 0 to 5° C. during 30 min under N$_2$. The resulting solution was stirred for 45 min at 100° C. in a sealed tube. The reaction mixture was allowed to cool to RT and treated with 10 mL Na$_2$SO$_3$ (satd., aq). The resulting solution was extracted with DCM (3×10 mL). The organic layers were combined and concentrated. The residue obtained was purified by flash chromatography on silica gel (0-40% EtOAc/petroleum ether) to obtain the compound 3c as a red solid. Mass Spectrum (LCMS, ESI pos.): Calcd. for C$_{13}$H$_{12}$FIN$_2$O$_3$: 391.0 (M+H). found: 391.0.

D. Ethyl 5-(5,5-dimethylcyclopent-1-enyl)-1-(2-fluoro-5-methoxyphenyl)-1H-imidazole-4-carboxylate, 3d

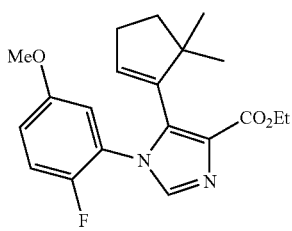

3d

A mixture of compound 3c (230 mg, 0.59 mmol), 2-(5,5-dimethylcyclopent-1-en-1-yl)-4,4,5,5-tetramethyl-1,3,2-dioxaborolane (262 mg, 1.18 mmol), Pd(dppf)Cl$_2$ (24 mg, 0.03 mmol) and Cs$_2$CO$_3$ (577 mg, 1.77 mmol), in dioxane (2 mL) and water (0.5 mL) was stirred overnight at 95° C. under N$_2$. The reaction mixture was allowed to cool to RT and treated with NH$_4$Cl (5 mL, satd., aq). The resulting solution was extracted with EtOAc (3×10 mL). The organic layers were combined and concentrated. The residue obtained was purified by flash chromatography (0-40% EtOAc/petroleum ether) on silica gel to obtain compound 3d as a light yellow oil. Mass Spectrum (LCMS, ESI pos.): Calcd. for C$_{20}$H$_{23}$FN$_2$O$_3$: 359.2 (M+H). found: 359.1.

E. (5-(5,5-Dimethylcyclopent-1-enyl)-1-(2-fluoro-5-methoxyphenyl)-1H-imidazol-4-yl)methanol, 3e

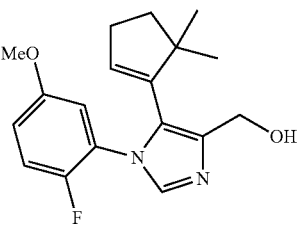

3e

To a solution of compound 3d (110 mg, 0.31 mmol) in THF (5 mL) was added LAH (23 mg, 0.61 mmol) at 0° C. The resulting solution was stirred for 30 min at 0° C. and then treated with Na$_2$SO$_4$.10H$_2$O (2 g). The solids were removed by filtration and the filtrate was concentrated. The residue obtained was purified by flash chromatography (0-50% EtOAc/petroleum ether) on silica gel to obtain compound 3e as a light yellow oil. Mass Spectrum (LCMS, ESI pos.): Calcd. for C$_{18}$H$_{21}$FN$_2$O$_2$: 317.2 (M+H). found: 317.1.

F. 4-(Chloromethyl)-5-(5,5-dimethylcyclopent-1-enyl)-1-(2-fluoro-5-methoxyphenyl)-1H-imidazole, 3f

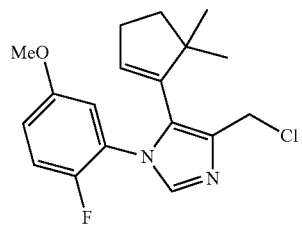

3f

A solution of compound 3e (100 mg, 0.320 mmol) in DCM (2 mL) and DMF (0.05 mL) was treated with thionyl chloride (75 mg, 0.64 mmol). The resulting solution was stirred for 1 h at RT and quenched with water (5 mL). The mixture was extracted with DCM (3×10 mL). The organic layers were combined and concentrated to obtain compound 3f as a yellow solid.

G. Methyl (3S)-3-cyclopropyl-3-(3-((5-(5,5-dimethylcyclopent-1-enyl)-1-(2-fluoro-5-methoxyphenyl)-1H-imidazol-4-yl)methoxy)phenyl)propanoate, 3g

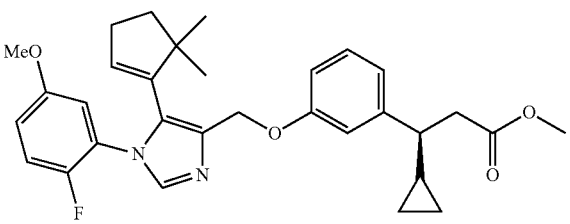

3g

A mixture of compound 3f (106 mg, 0.320 mmol), methyl (3S)-3-cyclopropyl-3-(3-hydroxyphenyl)propanoate (73.0 mg, 0.330 mmol, commercially available, Synnovator Inc., Catalog # PB05716) and Cs$_2$CO$_3$ (207 mg, 0.640 mmol) in CH$_3$CN (3 mL) was stirred overnight at 50° C. The reaction mixture was allowed to cool to RT and treated with water (10 mL). The resulting solution was extracted with EtOAc (3×10 mL). The organic layers were combined and concentrated. The residue obtained was purified by flash chromatography (0-20% EtOAc/petroleum ether) on silica gel to give compound 3g as a light yellow oil. Mass Spectrum (LCMS, ESI pos.): Calcd. for C$_{31}$H$_{35}$FN$_2$O$_4$: 519.3 (M+H). found: 519.3.

H. (3S)-3-Cyclopropyl-3-(3-((5-(5,5-dimethylcyclopent-1-enyl)-1-(2-fluoro-5-methoxyphenyl)-1H-imidazol-4-yl)methoxy)phenyl)propanoic acid, Cpd 87

A mixture of compound 3g (90 mg, 0.17 mmol) and LiOH.H$_2$O (73 mg, 1.7 mmol) in THF (2 mL), water (1 mL) and methanol (0.5 mL) was stirred overnight at RT. The resulting mixture was concentrated to remove organic solvents. The resulting solution was diluted with H$_2$O (5 mL). The pH of the solution was adjusted to 6 with 1N HCl. The solids formed were collected by filtration to give compound 87 as a white solid. $^1$H-NMR (400 MHz, CDCl$_3$) δ (ppm):

7.91 (s, 1H), 7.34-7.39 (m, 1H), 7.19 (t, J=7.6 Hz, 1H), 7.04-7.07 (m, 2H), 6.82-6.89 (m, 3H), 6.00 (s, 1H), 4.79 (s, 2H), 2.59-2.68 (m, 2H), 2.25-2.33 (m, 3H), 1.60 (t, J=6.8 Hz, 2H), 0.98-1.01 (m, 1H), 0.65 (s, 6H), 0.49-0.51 (m, 1H), 0.22-0.33 (m, 2H), 0.12-0.15 (m, 1H). Mass Spectrum (LCMS, ESI pos.): Calcd. for $C_{30}H_{33}FN_2O_4$: 505.2 (M+H). found: 505.1.

Following the procedures described in Example 3 above, and substituting suitably selected and substituted reagents, starting materials and conditions as would be readily apparent to those skilled in the art, the following representative compound of the present invention was prepared.

| Cpd No. | Characterization |
|---|---|
| 91 | (S)-3-Cyclopropyl-3-(3-((1-(2-fluoro-5-methoxyphenyl)-5-(2-methylprop-1-en-1-yl)-1H-imidazol-4-yl)methoxy)phenyl)propanoic acid<br>$^1$H-NMR (300 MHz, DMSO-$d_6$) δ (ppm): 11.52-12.33 (brs, 1H), 8.12 (s, 1H), 7.48-7.43 (m, 1H), 7.07-7.22 (m, 3H), 6.82-6.88 (m, 3H), 5.79 (s, 1H), 4.84 (s, 2H), 3.78 (s, 3H), 2.62-2.66 (m, 2H), 2.24-2.29 (m, 1H), 1.77 (s, 3H), 1.56 (s, 3H), 0.98-1.03 (m, 1H), 0.47-0.51 (m, 1H), 0.22-0.34 (m, 2H), 0.10-0.15 (m, 1H).<br>Mass Spectrum (LCMS, ESI pos.): Calcd. for $C_{27}H_{29}FN_2O_4$: 465.2 (M + H); found: 465.2. |

Example 4

(3S)-3-Cyclopropyl-3-(3-((4-cyclopropyl-5-(2-fluoro-5-methoxyphenyl)isoxazol-3-yl)methoxy)phenyl)propanoic acid (Cpd 37)

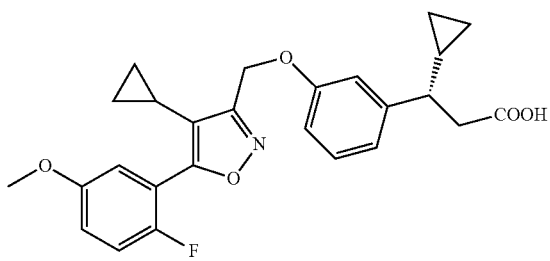 [SMILES: COc1ccc(F)c(-c2onc(COc3cccc([C@@H](CC(=O)O)C4CC4)c3)c2C2CC2)c1]

A. 1-(2-Fluoro-5-methoxyphenyl)ethanone, 4a

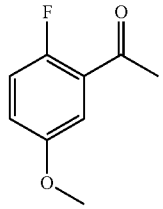

A mixture of 2-bromo-1-fluoro-4-methoxybenzene (5.0 g, 24 mmol), (ethenyloxy)methanol (9.0 g, 122 mmol), Pd(OAc)$_2$ (110 mg, 0.49 mmol), DPPP (480 mg, 1.16 mmol) and potassium carbonate (10 g, 72 mmol) in water (50 mL) was stirred overnight at 90° C. under N$_2$. The reaction mixture was allowed to cool to RT and then concentrated HCl (10 mL) was added. The resulting mixture was stirred for 30 min, and then was extracted with EtOAc (3×50 mL). The organic layers were combined and washed with H$_2$O (2×100 mL), dried over Na$_2$SO$_4$ and concentrated. The residue obtained was purified by flash column chromatography (0-10% EtOAc/petroleum ether) on silica gel to obtain compound 5a as a colorless oil. $^1$H-NMR (300 MHz, DMSO-$d_6$) δ (ppm): 7.18-7.33 (m, 3H), 3.79 (s, 3H), 2.58 (d, J=4.5 Hz, 3H). Mass Spectrum (GCMS, EI): Calcd. for $C_9H_9FO_2$: 168.1 (M). found: 168.2.

B. Ethyl 4-(2-fluoro-5-methoxyphenyl)-2,4-dioxobutanoate, 4b

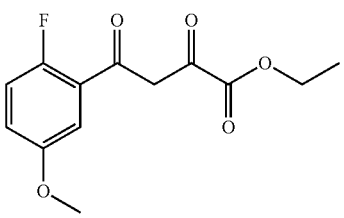

A mixture of 1-(2-fluoro-5-methoxyphenyl)ethan-1-one (4a) (2.6 g, 15 mmol), diethyl oxalate (2.7 g, 18 mmol) and sodium hydride (60% in mineral oil, 1.2 g, 30 mmol) in DMF (5 mL) was stirred overnight at RT. The reaction was then quenched by the addition of satd. NH$_4$Cl (aq., 5 mL). The resulting solution was extracted with EtOAc (3×50 mL). The organic layers were combined and washed with H$_2$O (2×10 mL), dried over Na$_2$SO$_4$ and concentrated. The residue obtained was purified by flash column chromatography (EtOAc/petroleum ether 1:6) on silica gel to obtain compound 4b as a white solid. Mass Spectrum (LCMS, ESI pos.): Calcd. for $C_{13}H_{13}FO_5$: 269.1 (M+H). found: 269.1.

C. Ethyl 5-(2-fluoro-5-methoxyphenyl)isoxazole-3-carboxylate, 4c

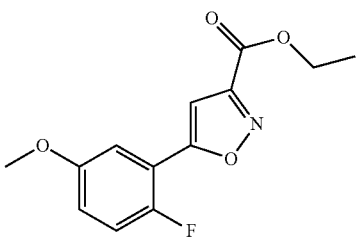

A solution of compound 4b (2.5 g, 9.3 mmol) and NH$_2$OH.HCl (836 mg, 12.1 mmol) in ethanol (15 mL) was heated at reflux for 2 h. The reaction mixture was allowed to cool to RT and treated with satd. NH$_4$Cl (aq., 20 mL). The resulting solution was extracted with EtOAc (3×30 mL). The organic layers were combined and washed with H$_2$O (2×50 mL), dried over Na$_2$SO$_4$ and concentrated. The residue obtained was purified by flash column chromatography (EtOAc/petroleum ether 1:15) on silica gel to obtain compound 4c as a white solid. Mass Spectrum (LCMS, ESI pos.): Calcd. for $C_{13}H_{12}FNO_4$: 266.1 (M+H). found: 266.1.

D. (5-(2-Fluoro-5-methoxyphenyl)isoxazol-3-yl)methanol, 4d

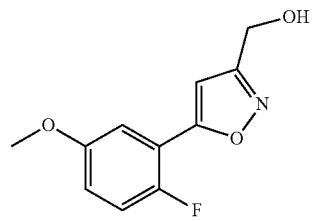

To a solution of compound 4c (2.2 g, 8.3 mmol) in THF (20 mL) was added DIBAL-H (1 M in hexane, 41 mL, 41 mmol) dropwise with stirring at −30° C. The resulting solution was stirred for 1 h at RT. The reaction was then quenched by the addition of satd. sodium potassium tartrate solution (aq., 30 mL). The resulting solution was extracted with EtOAc (3×50 mL). The combined organic layers were washed with $H_2O$ (2×70 mL), dried ($Na_2SO_4$) and concentrated. The residue obtained was purified by flash column chromatography (0-10% EtOAc/DCM) on silica gel to obtain compound 4d as a yellow solid. $^1$H-NMR (300 MHz, DMSO-$d_6$) δ (ppm): 7.34-7.40 (m, 2H), 7.09-7.15 (m, 1H), 6.88 (d, J=3.3 Hz, 1H), 5.59 (t, J=6.3 Hz, 1H), 4.60 (d, J=6.3 Hz, 2H), 3.84 (s, 3H).

E. (4-Bromo-5-(2-fluoro-5-methoxyphenyl)isoxazol-3-yl)methanol, 4e

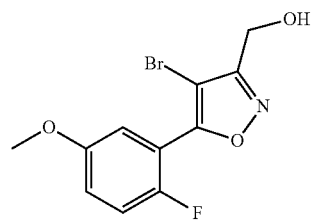

A solution of compound 4d (1.07 g, 4.79 mmol) and NBS (1.02 g, 5.73 mmol) in DMF (10 mL) was stirred overnight at 60° C. The reaction mixture was allowed to cool to RT and treated with satd. $NH_4Cl$ (aq. 20 mL). The resulting solution was extracted with EtOAc (3×20 mL). The combined organic layers were washed with $H_2O$ (2×30 mL), dried over $Na_2SO_4$ and concentrated. The residue obtained was purified by Flash-Prep-HPLC using $CH_3CN$ and water as the mobile phase to give compound 4e as a yellow solid. Mass Spectrum (LCMS, ESI pos.): Calcd. for $C_{11}H_9BrFNO_3$: 302.0 (M+H). found: 302.0.

F. 4-Bromo-3-(chloromethyl)-5-(2-fluoro-5-methoxyphenyl)isoxazole, 4f

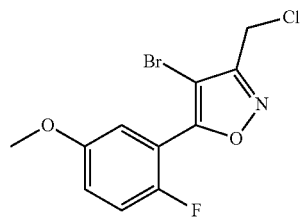

To a solution of compound 4e (710 mg, 2.35 mmol) in DCM (5 mL) and DMF (0.2 mL) was added thionyl chloride (1.32 g, 7.02 mmol) dropwise. The resulting solution was stirred for 1 h at RT. The reaction was then quenched by the addition of satd. $NH_4Cl$ (aq., 5 mL). The resulting solution was extracted with EtOAc (3×5 mL). The combined organic layers were washed with $H_2O$ (2×10 mL), dried over $Na_2SO_4$ and concentrated to give compound 4f as a yellow oil. Mass Spectrum (LCMS, ESI pos.): Calcd. for $C_{11}H_8BrClFNO_2$: 319.9 (M+H). found: 319.8.

G. (3S)-Methyl 3-(3-((4-bromo-5-(2-fluoro-5-methoxyphenyl)isoxazol-3-yl) methoxy)phenyl)-3-cyclopropylpropanoate, 4g

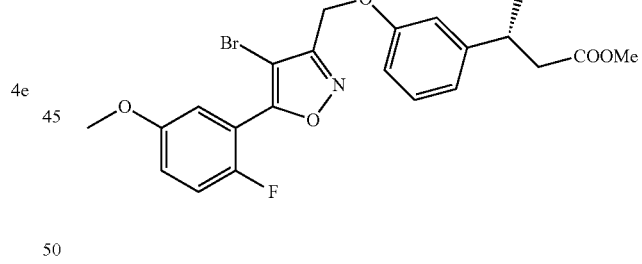

A mixture of 4-bromo-3-(chloromethyl)-5-(2-fluoro-5-methoxyphenyl)isoxazole (cpd 4f, 360 mg, 1.12 mmol), methyl (3S)-3-cyclopropyl-3-(3-hydroxyphenyl)propanoate (271 mg, 1.23 mmol) and $Cs_2CO_3$ (731 mg, 2.24 mmol) in DMF (2 mL) was stirred for 1 h at 80° C. The reaction mixture was allowed to cool to RT and treated with satd. $NH_4Cl$ (aq., 5 mL). The resulting solution was extracted with EtOAc (3×5 mL). The combined organic layers were washed with $H_2O$ (2×10 mL), dried over $Na_2SO_4$ and concentrated. The residue obtained was purified by flash column chromatography (0-10% EtOAc/petroleum ether) on silica gel to obtain compound 4g as a yellow oil. Mass Spectrum (LCMS, ESI pos.): Calcd. for $C_{24}H_{23}BrFNO_5$: 504.1 (M+H). found: 504.1, 506.1.

H. (3S)-Methyl 3-cyclopropyl-3-(3-((4-cyclopropyl-5-(2-fluoro-5-methoxyphenyl)isoxazol-3-yl)methoxy)phenyl)propanoate, 4h

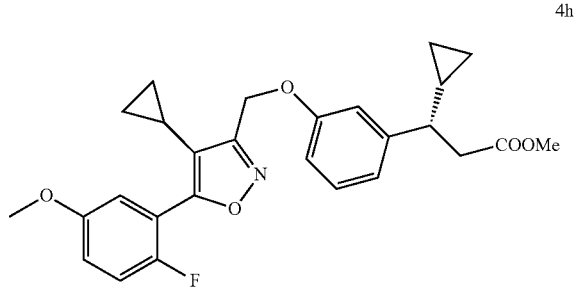 [SMILES: COC(=O)C[C@H](c1cccc(OCc2noc(-c3cc(OC)ccc3F)c2C2CC2)c1)C1CC1]

A mixture of compound 4g (200 mg, 0.40 mmol), cyclopropylboronic acid (36 mg, 0.42 mmol), PdCl$_2$dppf (30 mg, 0.04 mmol) and Cs$_2$CO$_3$ (260 mg, 0.80 mmol) in dioxane (4 mL) and water (1 mL) was stirred at 90° C. for 2 h under N$_2$ in a sealed tube. The reaction mixture was allowed to cool to RT and treated with satd. NH$_4$Cl (aq., 5 mL). The resulting solution was extracted with EtOAc (3×10 mL). The organic layers were combined and washed with water (30 mL) and concentrated. The residue obtained was purified by flash column chromatography (0-10% EtOAc/petroleum ether) on silica gel to obtain compound 4h as a yellow liquid. Mass Spectrum (LCMS, ESI pos.): Calcd. for C$_{27}$H$_{28}$FNO$_5$: 466.2 (M+H). found: 466.2.

I. (3S)-3-Cyclopropyl-3-(3-((4-cyclopropyl-5-(2-fluoro-5-methoxyphenyl)isoxazol-3-yl)methoxy)phenyl)propanoic acid, Cpd 37

The compound 37 was prepared from compound 4h following the procedure described in Example 1, Step H. The solid obtained was purified by Prep-HPLC (eluting with water and CH$_3$CN) gave compound 37 as a white solid. $^1$H-NMR (300 MHz, DMSO-d$_6$) δ (ppm): 7.33-7.39 (m, 1H), 7.15-7.25 (m, 3H), 6.88-6.96 (m, 3H), 5.21 (s, 2H), 3.81 (s, 3H), 2.51-2.60 (m, 2H), 2.29-2.38 (m, 1H), 1.74-1.77 (m, 1H), 0.96-0.99 (m, 1H), 0.74-0.80 (m, 2H), 0.44-0.48 (m, 1H), 0.31-0.39 (m, 2H), 0.20-0.30 (m, 2H), 0.05-0.12 (m, 1H). Mass Spectrum (LCMS, ESI pos.): Calcd. for C$_{26}$H$_{26}$FNO$_5$: 452.2 (M+H). found: 452.1.

Following the procedures described in Example 4 above, and substituting suitably selected and substituted reagents, starting materials and conditions as would be readily apparent to those skilled in the art, the following representative compounds of the present invention were prepared.

| Cpd No. | Characterization |
|---|---|
| 15 | (3S)-3-Cyclopropyl-3-(3-((4-(5,5-dimethylcyclopent-1-enyl)-5-(2-fluoro-5-methoxyphenyl)isoxazol-3-yl)methoxy)phenyl)propanoic acid<br>$^1$H-NMR (300 MHz, DMSO-d$_6$) δ (ppm): 7.29-7.36 (m, 2H), 7.20-7.22 (m, 2H), 7.12-7.15 (m, 2H), 6.85-6.91 (m, 3H), 5.93 (t, J = 5.4 Hz, 1H), 5.06 (s, 2H), 3.76 (s, 3H), 2.63-2.67 (m, 2H), 2.25-2.35 (m, 3H), 1.69 (t, J = 7.2 Hz, 2H), 0.88-1.05 (m, 1H), 0.73 (s, 6H), 0.00-0.52 (m, 4H).<br>Mass Spectrum (LCMS, ESI pos.): Calcd. for C$_{30}$H$_{32}$FNO$_5$: 506.2 (M + H); found: 506.2. |
| 32 | (3S)-3-Cyclopropyl-3-(3-((5-(2-fluoro-5-methoxyphenyl)-4-(5-methylthiophen-2-yl)isoxazol-3-yl)methoxy)phenyl)propanoic acid<br>$^1$H-NMR (300 MHz, DMSO-d$_6$) δ (ppm): 11.45-12.35 (br s, 1H), 6.78-7.34 (m, 9H), 5.22 (s, 2H), 3.76 (s, 3H), 2.64-2.67 (m, 2H), 2.38 (s, 3H), 2.26-2.29 (m, 1H), 0.98-1.01 (m, 1H), 0.14-0.50 (m, 3H).<br>Mass Spectrum (LCMS, ESI pos.): Calcd. for C$_{28}$H$_{26}$FNO$_5$S: 506.1 (M-H); found: 506.1. |
| 33 | (S)-3-Cyclopropyl-3-(3-((5-(2-fluoro-5-methoxyphenyl)-4-(3-methylthiophen-2-yl)isoxazol-3-yl)methoxy)phenyl)propanoic acid<br>$^1$H-NMR (400 MHz, DMSO-d$_6$) δ (ppm): 12.00 (brs, 1H), 7.56-7.58 (m, 1H), 7.31-7.33 (m, 1H), 7.11-7.18 (m, 2H), 6.77-6.98 (m, 5H), 5.09 (s, 2H), 3.65 (s, 3H), 2.61-2.67 (m, 2H), 2.23-2.50 (m, 1H), 1.85 (s, 3H), 0.97-0.98 (m, 1H), 0.31-0.48 (m, 1H), 0.21-0.29 (m, 2H), 0.00-0.12 (m, 2H).<br>Mass Spectrum (LCMS, ESI pos.): Calcd. for C$_{28}$H$_{26}$FNO$_5$S: 508.2 (M + H); found: 508.0. |
| 34 | (S)-3-Cyclopropyl-3-(3-((5-(2-fluoro-5-methoxyphenyl)-4-phenylisoxazol-3-yl)methoxy)phenyl)propanoic acid<br>$^1$H-NMR (300 MHz, DMSO-d$_6$) δ (ppm): 7.29-7.39 (m, 5H), 7.10-7.26 (m, 3H), 7.03-7.09 (m, 1H), 6.79-6.87 (m, 3H), 5.17 (s, 2H), 3.69 (s, 3H), 2.55-2.59 (m, 2H), 2.23-2.32 (m, 1H), 0.94-0.97 (m, 1H), 0.46-0.48 (m, 1H), 0.21-0.30 (m, 2H), 0.07-0.11 (m, 1H).<br>Mass Spectrum (LCMS, ESI pos.): Calcd. for C$_{29}$H$_{26}$FNO$_5$: 488.2 (M + H); found: 488.3. |
| 36 | (3S)-3-Cyclopropyl-3-(3-((5-(2-fluoro-5-methoxyphenyl)-4-(2-methylprop-1-enyl)isoxazol-3-yl)methoxy)phenyl)propanoic acid<br>$^1$H-NMR (300 MHz, DMSO-d$_6$) δ (ppm): 7.30-7.37 (m, 1H), 7.11-7.22 (m, 3H), 6.82-6.88 (m, 3H), 5.99 (s, 1H), 5.11 (s, 2H), 3.77 (s, 3H), 2.43-2.45 (m, 2H), 2.29-2.35(m, 1H), 1.80(s, 3H), 1.30(s, 3H), 0.90-1.05 (m, 1H), 0.44-0.54 (m, 1H), 0.21-0.40 (m, 2H), 0.02-0.18(m, 1H).<br>Mass Spectrum (LCMS, ESI pos.): Calcd. for C$_{27}$H$_{28}$FNO$_5$: 466.2 (M + H); found: 466.2. |
| 45 | (3S)-3-(3-((4-(5-tert-butylthiophen-2-yl)-5-(2-fluoro-5-methoxyphenyl)isoxazol-3-yl)methoxy)phenyl)-3-cyclopropylpropanoic acid<br>$^1$H-NMR (300 MHz, DMSO-d$_6$) δ (ppm): 7.32-7.36 (m, 2H), 7.11-7.29 (m, 2H), 7.04-7.10 (m, 1H), 6.84-6.96 (m, 3H), 6.79 (s, 1H), 5.19 (s, 2H), 3.72 (s, 3H), 2.58-2.60 (m, 2H), 2.26-2.28 (m, 1H), 1.19 (s, 9H), 0.98 (s, 1H), 0.40-0.48 (m, 1H), 0.23-0.27 (m, 2H), 0.11 (s, 1H).<br>Mass Spectrum (LCMS, ESI pos.): Calcd. for C$_{31}$H$_{32}$FNO$_5$S: 550.2 (M + H); found: 550.2. |

Example 5

(3S)-3-Cyclopropyl-3-(3-((5-(5,5-dimethylcyclopent-1-enyl)-1-(2-fluoro-5-methoxyphenyl)-1H-1,2,3-triazol-4-yl)methoxy)phenyl)propanoic acid (Cpd 86)

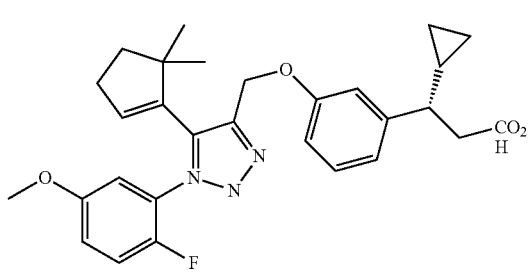

A. 2-Azido-1-fluoro-4-methoxybenzene, 5a

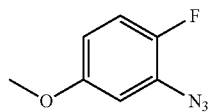

To a mixture of 2-fluoro-5-methoxyaniline (5.0 g, 35 mmol), sulfuric acid (7.5 mL), trifluoroacetic acid (37.5 mL) and water (45 mL) was added $NaNO_2$ (3.7 g, 53 mmol) portionwise at 0° C. The mixture was stirred for 30 min at 0° C. and $NaN_3$ (4.6 g, 71 mmol) was added. The resulting solution was stirred overnight at RT and extracted with EtOAc (2×200 mL). The combined organic layers were dried over $Na_2SO_4$ and concentrated. The residue obtained was purified by column chromatography on silica gel (EtOAc/petroleum ether, 1:100) to give compound 5a as a light yellow oil. $^1$H-NMR (300 MHz, DMSO-$d_6$) δ (ppm): 7.23 (dd, $J_1$=9.0 Hz, $J_2$=10.8 Hz, 1H), 6.72-6.80 (m, 2H), 3.76 (s, 3H). Mass Spectrum (GCMS, EI): Calcd. for $C_7H_6FN_3O$: 167.0 (M). found: 167.2.

B. Ethyl 5-amino-1-(2-fluoro-5-methoxyphenyl)-1H-1,2,3-triazole-4-carboxylate, 5b

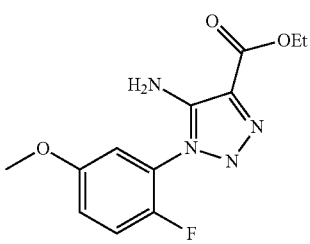

To a solution of EtONa (4.2 g, 62 mmol) in ethanol (30 mL) was added ethyl 2-cyanoacetate (6.5 g, 57 mmol) at 0° C. The resulting mixture was stirred for 30 min and treated with compound 5a (4.8 g, 29 mmol). The resulting solution was stirred for 3 h at RT and quenched with water (100 mL). The mixture was extracted with EtOAc (2×100 mL). The combined organic layers were dried ($Na_2SO_4$) and concentrated. The residue obtained was purified by column chromatography on silica gel (EtOAc/petroleum ether, 1:1) to give compound 5b as a white solid. Mass Spectrum (LCMS, ESI pos.): Calcd. for $C_{12}H_{13}FN_4O_3$: 281.1 (M+H). found: 281.1.

C. (5-Amino-1-(2-fluoro-5-methoxyphenyl)-1H-1,2,3-triazol-4-yl)methanol, 5c

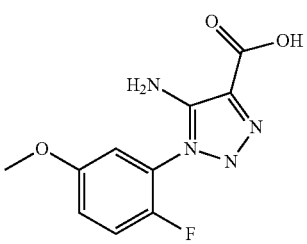

To a solution of compound 5b (4.0 g, 14 mmol) in THF (60 mL) was added DIBAL-H (1 M in hexane, 71 mL, 71 mmol) at −70° C. The resulting solution was stirred for 2 h at −70° C. The reaction was then quenched by satd. sodium potassium tartrate solution (aq., 100 mL). The resulting solution was extracted with EtOAc (2×100 mL). The combined organic layers were dried ($Na_2SO_4$) and concentrated. The residue obtained was purified by column chromatography on silica gel (EtOAc/petroleum ether, 100:1) to give compound 5c as a colorless oil. Mass Spectrum (LCMS, ESI pos.): Calcd. for $C_{10}H_{11}FN_4O_2$: 239.1 (M+H). found: 239.1.

D. (5-Bromo-1-(2-fluoro-5-methoxyphenyl)-1H-1,2,3-triazol-4-yl)methanol, 5d

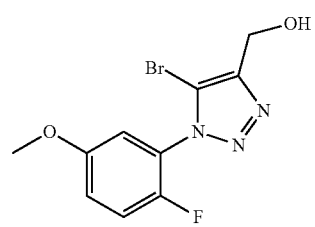

To a stirred mixture of $CuBr_2$ (5.6 g, 25 mmol) and t-BuONO (7.8 g, 76 mmol) in $CH_3CN$ (50 mL) under $N_2$ was added compound 5c (3.0 g, 13 mmol) in $CH_3CN$ (10 mL) dropwise. The resulting solution was stirred for 2 h at 0° C. and treated with satd. $NH_4Cl$ (aq. 100 mL). The mixture was extracted with EtOAc (2×100 mL). The combined organic layers were dried ($Na_2SO_4$) and concentrated. The residue obtained was purified by column chromatography on silica gel (EtOAc/petroleum ether, 1:3) to give compound 5d as a colorless oil. Mass Spectrum (LCMS, ESI pos.): Calcd. for $C_{10}H_9BrFN_3O_2$: 302.0 (M+H). found: 301.9.

E. 5-Bromo-4-(chloromethyl)-1-(2-fluoro-5-methoxyphenyl)-1H-1,2,3-triazole, 5e

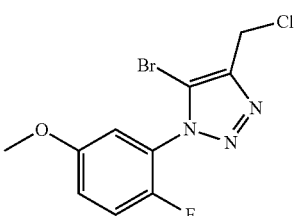

To a solution of compound 5d (600 mg, 1.98 mmol) in DCM (6 mL) and DMF (1 drop) was added thionyl chloride (703 mg, 5.96 mmol) dropwise at 0° C. The resulting solution was stirred for 1 h at RT and concentrated to give compound 5e as a colorless oil.

F. (3S)-Ethyl 3-(3-((5-bromo-1-(2-fluoro-5-methoxyphenyl)-1H-1,2,3-triazol-4-yl) methoxy) phenyl)-3-cyclopropylpropanoate, 5f

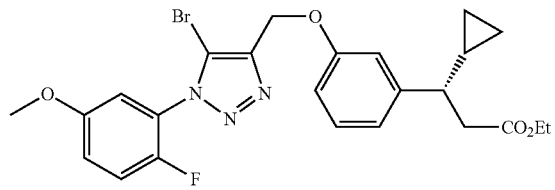

A mixture of compound 5e (170 mg, 0.530 mmol), Cs₂CO₃ (434 mg, 1.33 mmol) and ethyl (3S)-3-cyclopropyl-3-(3-hydroxyphenyl)propanoate (130 mg, 0.550 mmol, as prepared in Example 1, Step F) in DMF (4 mL) was stirred overnight at 60° C. The reaction mixture was allowed to cool to RT and treated with water (10 mL). The resulting mixture was extracted with EtOAc (2×10 mL). The combined organic layers were dried (Na₂SO₄) and concentrated. The residue obtained was purified by column chromatography on silica gel (EtOAc/petroleum ether, 1:3) to give compound 5f as a colorless oil. Mass Spectrum (LCMS, ESI pos.): Calcd. for $C_{24}H_{25}BrFN_3O_4$: 518.1 (M+H). found: 518.1.

G. (3S)-Ethyl 3-cyclopropyl-3-(3-((5-(5,5-dimethylcyclopent-1-enyl)-1-(2-fluoro-5-methoxyphenyl)-1H-1,2,3-triazol-4-yl)methoxy)phenyl)propanoate, 5g

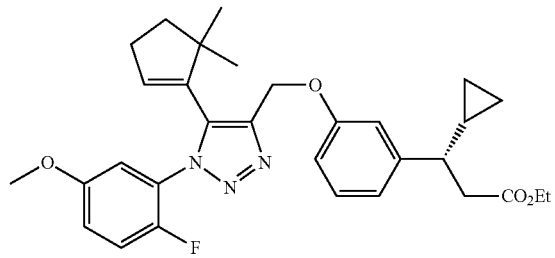

A mixture of compound 5f (120 mg, 0.23 mmol), 2-(5,5-dimethylcyclopent-1-en-1-yl)-4,4,5,5-tetramethyl-1,3,2-dioxaborolane (77 mg, 0.35 mmol), sodium carbonate (61 mg, 0.58 mmol), Pd(dppf)Cl₂ (8.4 mg, 0.01 mmol) in dioxane (4 mL) and water (1 mL) was stirred overnight at 60° C. The reaction mixture was allowed to cool to RT and treated with water (10 mL). The resulting solution was extracted with EtOAc (2×10 mL). The combined organic layers were dried (Na₂SO₄) and concentrated. The residue obtained was purified by column chromatography on silica gel with EtOAc/petroleum ether, 1:3) to give compound 5g as a colorless oil. Mass Spectrum (LCMS, ESI pos.): Calcd. for $C_{31}H_{36}FN_3O_4$: 534.3 (M+H). found: 534.4.

H. (3S)-3Cyclopropyl-3-(3-((5-(5,5-dimethylcyclopent-1-enyl)-1-(2-fluoro-5-methoxyphenyl)-1H-1,2,3-triazol-4-yl)methoxy)phenyl)propanoic acid, Cpd 86

Compound 86 was prepared from compound 5g following the procedure described in Example 3, Step H. ¹H-NMR (300 MHz, DMSO-d₆) δ (ppm): 7.41-7.50 (m, 1H), 7.18-7.31 (m, 3H), 6.75-6.98 (m, 3H), 6.08 (s, 1H), 5.02 (s, 2H), 3.77 (s, 3H), 2.60-2.70 (m, 2H), 2.22-2.41 (m, 3H), 1.61-1.72 (m, 2H), 0.92-1.09 (m, 1H), 0.65-0.80 (s, 6H), 0.41-0.59 (m, 1H), 0.21-0.36 (m, 2H), 0.04-0.13 (m, 1H). Mass Spectrum (LCMS, ESI pos.): Calcd. for $C_{29}H_{32}FN_3O_4$: 506.2 (M+H). found: 506.1.

Following the procedures described in Example 5 above, and substituting suitably selected and substituted reagents, starting materials and conditions as would be readily apparent to those skilled in the art, the following representative compounds of the present invention were prepared.

| Cpd No. | Characterization |
|---|---|
| 84 | (3S)-3-Cyclopropyl-3-(3-((1-(2-fluoro-5-methoxyphenyl)-5-(2-methylprop-1-enyl)-1H-1,2,3-triazol-4-yl)methoxy)phenyl) propanoic acid<br>¹H-NMR (300 MHz, DMSO-d₆) δ (ppm): 11.85-12.21 (s, 1H), 7.41-7.51 (t, 1H), 7.15-7.31 (m, 3H), 6.78-7.01 (m, 3H), 5.88-5.92 (s, 1H), 5.00-5.11 (s, 2H), 4.78-4.88 (s, 3H), 2.61-2.75 (m, 2H), 2.20-2.32 (m, 1H), 1.80-1.85 (s, 3H), 1.50-1.56 (s, 3H), 0.95-1.11 (m, 1H), 0.42-0.58 (m, 1H), 0.22-0.38 (m, 2H), 0.10-0.18 (m, 1H).<br>Mass Spectrum (LCMS, ESI pos.): Calcd. for $C_{26}H_{28}FN_3O_4$: 466.2 (M + H); found: 466.0. |
| 85 | (3S)-3-Cyclopropyl-3-(3-((5-cyclopropyl-1-(2-fluoro-5-methoxyphenyl)-1H-1,2,3-triazol-4-yl)methoxy)phenyl)propanoic acid acid<br>¹H-NMR (300 MHz, DMSO-d₆) δ (ppm): 7.52-7.61 (t, 1H), 7.31-7.35 (m, 1H), 7.20-7.28 (m, 2H), 6.85-7.01 (m, 3H), 5.12-7.19 (s, 2H), 4.78-4.84 (s, 3H), 2.58-2.71 (m, 2H), 2.22-2.33 (m, 1H), 1.71-1.82 (m, 1H), 0.91-1.05 (m, 1H), 0.80-0.88 (m, 2H), 0.69-0.72 (m, 2H), 0.40-0.52 (t, 1H), 0.20-0.31 (m, 2H), 0.11-0.19 (t, 1H).<br>Mass Spectrum (LCMS, ESI pos.) Calcd. for $C_{25}H_{26}FN_3O_4$: 451.2 (M + H); found: 452.0. |
| 88 | (3S)-3-Cyclopropyl-3-(3-((1-(2-fluoro-5-methoxyphenyl)-5-(5-methylthiophen-2-yl)-1H-1,2,3-triazol-4-yl)methoxy)phenyl) propanoic acid<br>¹H-NMR (300 MHz, DMSO-d₆) δ (ppm): 7.26-7.27 (m, 1H), 7.11-7.16 (m, 1H), 6.92-7.12 (m, 5H), 6.87-6.89 (d, J = 2.7 Hz, 1H), 6.69 (s, 1H), 5.24 (s, 2H), 3.81 (s, 3H), 2.78-2.85 (m, 2H), 2.31-2.42 (m, 4H), 1.01-1.11 (m, 1H), 0.55-0.65 (m, 1H), 0.40-0.49 (m, 1H), 0.25-0.33 (m, 1H), 0.14-0.22 (m, 1H).<br>Mass Spectrum (LCMS, ESI pos.): Calcd. for $C_{27}H_{26}FN_3O_4S$: 509.1 (M + H); found: 509.1. |
| 92 | (3S)-3-(3-((5-(5-tert-Butylthiophen-2-yl)-1-(2-fluoro-5-methoxyphenyl)-1H-1,2,3-triazol-4-yl)methoxy)phenyl)-3-cyclopropylpropanoic acid<br>¹H-NMR (300 MHz, DMSO-d₆) δ (ppm): 7.33-7.45 (m, 3H), 7.19-7.24 (m, 2H), 6.86-6.95 (m, 3H), 6.71 (s, 1H), 5.19 (s, 2H), 2.79 (s, 3H), 2.62-2.65 (m, 2H), 2.24-2.27 (m, 1H), 1.20 (s, 9H), 0.96-1.00 (m, 1H), 0.47-0.50(m, 1H), 0.21-0.32 (m, 2H), 0.04-0.11 (m, 1H).<br>Mass Spectrum (LCMS, ESI pos.): Calcd. for $C_{30}H_{32}FN_3O_4S$: 551.7 (M + H); found: 551.7. |

Example 6

(3S)-3-Cyclopropyl-3-(3-((5-(2-fluoro-5-methoxy-phenyl)-4-isobutylisoxazol-3-yl)methoxy)phenyl) propanoic acid (Cpd 35)

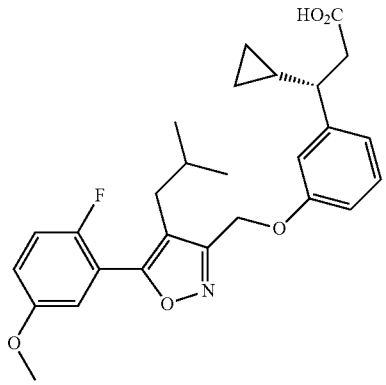 [SMILES: COc1ccc(F)c(-c2onc(COc3cccc([C@@H](CC(=O)O)C4CC4)c3)c2CC(C)C)c1]

A. 4-Bromo-3-(((tert-butyldimethylsilyl)oxy)methyl)-5-(2-fluoro-5-methoxyphenyl) isoxazole, 6a

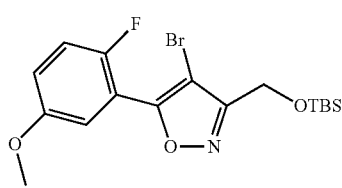

To a solution of [4-bromo-5-(2-fluoro-5-methoxyphenyl)-1,2-oxazol-3-yl]methanol (2 g, 6.6 mmol, as prepared in Example 4, Step E) in DCM (10 mL) was added DMAP (71 mg, 0.58 mmol) and triethylamine (1.34 g, 13.3 mmol), followed by TBSCl (1.33 g, 8.87 mmol). The resulting solution was stirred overnight at RT. The reaction was then quenched by satd. NH$_4$Cl (aq. 10 mL). The resulting solution was extracted with EtOAc (3×10 mL). The organic layers were combined, washed with H$_2$O (2×15 mL), and concentrated. The residue obtained was purified on by column chromatography on silica gel, eluting with petroleum ether, to give compound 6a as a yellow liquid. Mass Spectrum (LCMS, ESI pos.): Calcd. for C$_{17}$H$_{23}$BrFNO$_3$Si: 416.1 (M+H). found: 416.0.

B. 3-((tert-Butyldimethylsilyloxy)methyl)-5-(2-fluoro-5-methoxyphenyl)-4-(2-methylprop-1-enyl) isoxazole, 6b

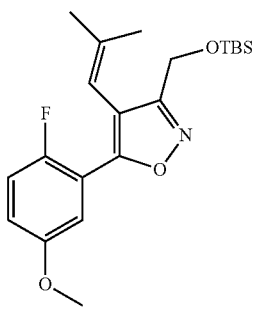

A mixture of compound 6a (250 mg, 0.60 mmol), 4,4,5,5-tetramethyl-2-(2-methylprop-1-en-1-yl)-1,3,2-dioxaborolane (164 mg, 0.90 mmol), Pd(dppf)Cl$_2$ (44 mg, 0.06 mmol) and Cs$_2$CO$_3$ (489 mg, 1.50 mmol) in dioxane (2 mL) and water (0.5 mL) was stirred for 3 h at 95° C. under N$_2$. The reaction mixture was allowed to cool to RT and treated with water (15 mL). The resulting solution was extracted with EtOAc (3×10 mL). The organic layers were combined, dried over anhydrous sodium sulfate and concentrated. The residue obtained was purified by column chromatography on silica gel (EtOAc/petroleum ether, 1:100-1:20) to give compound 6b as a colorless oil. Mass Spectrum (LCMS, ESI pos.): Calcd. for C$_{21}$H$_{30}$FNO$_3$Si: 392.2 (M+H). found: 392.2.

C. 3-((tert-Butyldimethylsilyloxy)methyl)-5-(2-fluoro-5-methoxyphenyl)-4-isobutylisoxazole, 6c

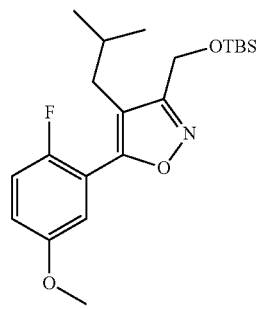

Compound 6b (150 mg, 0.38 mmol) was hydrogenated over 10% Pd/C (150 mg) for 5 h under 1 atm H$_2$ at RT. The reaction mixture was filtered through a pad of diatomaceous earth and the filtrate was concentrated. The residue obtained was purified by column chromatography on silica gel (EtOAc/petroleum ether, 1:100-1:20) to give compound 6c as a colorless oil. Mass Spectrum (LCMS, ESI pos.): Calcd. for C$_{21}$H$_{32}$FNO$_3$Si: 394.2 (M+H). found: 394.1.

D. (5-(2-Fluoro-5-methoxyphenyl)-4-isobutylisoxazol-3-yl)methanol, 6d

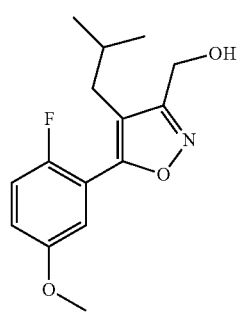

To a solution of compound 6c (120 mg, 0.30 mmol) in THF (5 mL) was added TBAF (1M in THF, 0.82 mL). The resulting solution was stirred for 1 h at RT. The reaction was then poured into water (10 mL). The resulting solution was extracted with EtOAc (3×10 mL). The organic layers were combined, dried over anhydrous sodium sulfate and concentrated. The residue obtained was purified by column chromatography on silica gel (EtOAc/petroleum ether, 1:100-1:10) to give compound 6d as a colorless oil. Mass Spectrum (LCMS, ESI pos.): Calcd. for $C_{15}H_{18}FNO_3$: 280.1 (M+H). found: 280.0.

E. 3-(Chloromethyl)-5-(2-fluoro-5-methoxyphenyl)-4-isobutylisoxazole, 6e

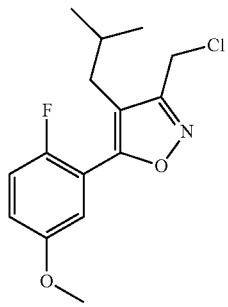

6e

To a stirring solution of compound 6d (90 mg, 0.32 mmol) in DCM (5 mL), and DMF (0.2 mL) was added thionyl chloride (115 mg, 0.98 mmol) dropwise at 0° C. The resulting solution was stirred for 1 h at 0° C. The reaction was then quenched with water (10 mL). The resulting solution was extracted with DCM (3×10 mL). The organic layers were combined, dried over anhydrous sodium sulfate and concentrated to give compound 6e as a colorless oil. Mass Spectrum (LCMS, ESI pos.): Calcd. for $C_{15}H_{17}ClFNO_2$: 298.1 (M+H). found: 298.1.

F. (3S)-Ethyl 3-cyclopropyl-3-(3-((5-(2-fluoro-5-methoxyphenyl)-4-isobutylisoxazol-3-yl)methoxy)phenyl)propanoate, 6f

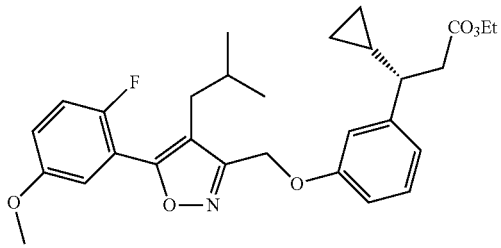

6f

A mixture of compound 6e (85 mg, 0.29 mmol), compound 1f (75 mg, 0.32 mmol) and $Cs_2CO_3$ (168 mg, 0.52 mmol) in $CH_3CN$ (5 mL) was stirred overnight at 50° C. The reaction mixture was allowed to cool to RT and treated with water (10 mL). The resulting solution was extracted with EtOAc (3×10 mL). The organic layers were combined, dried over anhydrous sodium sulfate and concentrated. The residue obtained was purified by column chromatography on silica gel (EtOAc/petroleum ether, 1:100-1:10) to give compound 6f as a colorless oil. Mass Spectrum (LCMS, ESI pos.): Calcd. for $C_{29}H_{34}FNO_5$: 496.2 (M+H). found: 496.3.

G. (3 S)-3-Cyclopropyl-3-(3-((5-(2-fluoro-5-methoxyphenyl)-4-isobutylisoxazol-3-yl)methoxy)phenyl)propanoic acid, Cpd 35

Compound 35 was prepared from compound 6f following the procedure described in Example 3, Step H. $^1$H-NMR (300 MHz, DMSO-d$_6$) δ (ppm): 7.37 (t, J=9.6 Hz, 1H), 7.12-7.25 (m, 3H), 6.87-6.94 (m, 3H), 5.20 (s, 2H), 3.80 (s, 3H), 2.51-2.57 (m, 2H), 2.42-2.49 (m, 2H), 2.28-2.31 (m, 1H), 1.72-1.75 (m, 1H), 0.90-1.05 (m, 1H), 0.74 (s, 3H), 0.71 (s, 3H), 0.44-0.54 (m, 1H), 0.21-0.40 (m, 2H), 0.02-0.18 (m, 1H). Mass Spectrum (LCMS, ESI pos.): Calcd. for $C_{27}H_{30}FNO_5$: 468.2 (M+H). found: 468.2.

Example 7

(3S)-3-Cyclopropyl-3-(3-((4-(5, 5-dimethylcyclopent-1-enyl)-3-(2-fluoro-5-methoxyphenyl)isoxazol-5-yl)methoxy)phenyl)propanoic acid (Cpd 62)

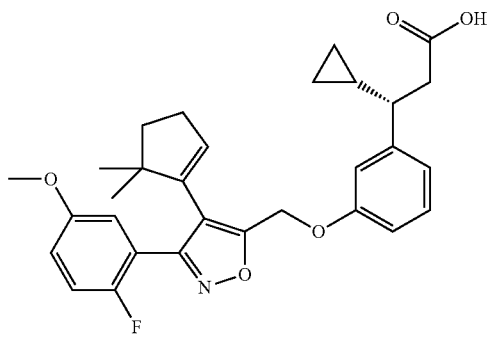 [SMILES: COc1ccc(F)c(-c2noc(COc3cccc([C@@H](CC(=O)O)C4CC4)c3)c2C2=CCCC2(C)C)c1]

A. 2-Fluoro-5-methoxybenzaldehyde, 7a

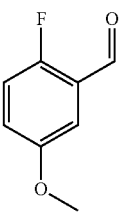

7a

To a stirring solution of 2-bromo-1-fluoro-4-methoxybenzene (6.5 g, 32 mmol) in THF (40 mL) was added n-BuLi (2.5M in THF, 15.2 mL) dropwise at −78° C. under $N_2$. The resulting mixture was stirred for 30 min and treated with DMF (3.7 mL, 48 mmol) dropwise with stirring at −78° C. The resulting solution was stirred for 1 h at RT. The reaction was then quenched by satd. $NH_4Cl$ solution (aq. 30 mL). The resulting solution was extracted with EtOAc (3×30 mL). The organic layers were combined, dried over anhydrous sodium sulfate and concentrated to give compound 7a as a yellow oil. Mass Spectrum (LCMS, ESI pos.): Calcd. for $C_8H_7FO_2$: 155.0 (M+H). found: 155.1.

B. (E)-2-Fluoro-5-methoxybenzaldehyde oxime, 7b

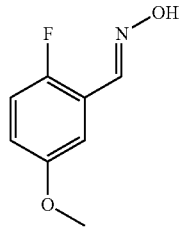

7b

A mixture of compound 7a (6.0 g, 39 mmol), KOAc (7.6 g, 78 mmol) and NH$_2$OH.HCl (4.0 g, 58 mmol) in ethanol (70 mL) was stirred for 2 h at 80° C. The reaction mixture was allowed to cool to RT and treated with water (100 mL). The resulting solution was extracted with EtOAc (3×60 mL). The organic layers were combined, dried over anhydrous sodium sulfate and concentrated. The residue obtained was purified by column chromatography on silica gel (DCM/methanol, 100:1) to give compound 7b as a light yellow solid. Mass Spectrum (LCMS, ESI pos.): Calcd. for C$_8$H$_8$FNO$_2$: 170.0 (M+H). found: 170.1.

C. 2-Fluoro-N-hydroxy-5-methoxybenzimidoyl chloride, 7c

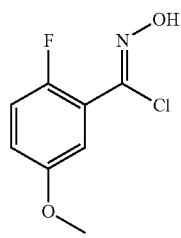

7c

To a stirring solution of compound 7b (5.0 g, 30 mmol) in DMF (20 mL) was added dropwise a solution of NCS (4.3 g, 32 mmol) in DMF (10 mL) at 0° C. The resulting solution was stirred for 2 h at RT and treated with water (100 mL). The mixture was extracted with EtOAc (3×50 mL). The organic layers were combined and washed with water (3×100 mL). The organic layer was dried over anhydrous sodium sulfate and concentrated to give compound 7c as a yellow oil. Mass Spectrum (LCMS, ESI pos.): Calcd. for C$_8$H$_7$ClFNO$_2$: 204.0 (M+H). found: 204.0.

D. Methyl 3-(2-fluoro-5-methoxyphenyl)isoxazole-5-carboxylate, 7d

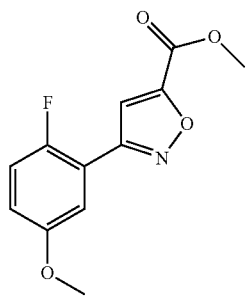

7d

A mixture of compound 7c (4.5 g, 22 mmol) and methyl prop-2-ynoate (2.2 g, 26 mmol) in toluene (70 mL) was treated with TEA (2.7 g, 26 mmol) dropwise with stirring at 0° C. The resulting solution was stirred for 1 h at RT. The reaction was then quenched by water (100 mL). The resulting solution was extracted with EtOAc (3×50 mL). The organic layers were combined, dried over anhydrous sodium sulfate and concentrated. The residue obtained was purified by column chromatography on silica gel (EtOAc/petroleum ether, 1:100-1:20) to give compound 7d as a light yellow solid. Mass Spectrum (LCMS, ESI pos.): Calcd. for C$_{12}$H$_{10}$FNO$_4$: 252.1 (M+H). found: 252.0.

E. (3-(2-Fluoro-5-methoxyphenyl)isoxazol-5-yl)methanol, 7e

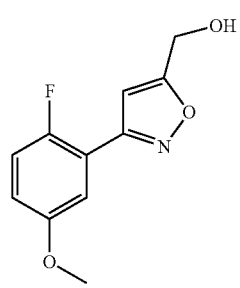

7e

To a solution of compound 7d (1.5 g, 6.0 mmol) in THF (60 mL) was added LiAlH$_4$ (272 mg, 7.17 mmol) in portions at 0° C. The resulting solution was stirred for 20 min at 0° C. The reaction was then quenched by satd. sodium potassium tartrate solution (aq., 30 mL) and stirred vigorously for 30 min. The resulting solution was extracted with EtOAc (3×50 mL). The organic layers were combined, dried over anhydrous sodium sulfate and concentrated. The residue obtained was purified by column chromatography on silica gel (EtOAc/petroleum ether, 1:100-1:10) to give compound 7e as a yellow oil. Mass Spectrum (LCMS, ESI pos.): Calcd. for C$_{11}$H$_{10}$FNO$_3$: 224.1 (M+H). found: 224.0.

F. (4-Bromo-3-(2-fluoro-5-methoxyphenyl)isoxazol-5-yl)methanol, 7f

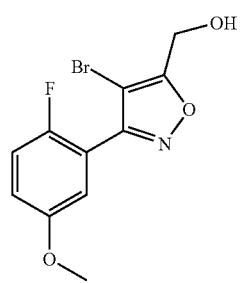

7f

A solution of compound 7e (950 mg, 4.26 mmol), NBS (1.14 g, 6.39 mmol), and PPTS (46 mg, 0.18 mmol) in DCM (20 mL) was stirred overnight at RT. The reaction was then quenched by water (20 mL). The resulting solution was extracted with DCM (3×15 mL). The organic layers were combined, dried over anhydrous sodium sulfate and concentrated. The residue obtained was purified by column chromatography on silica gel (EtOAc/petroleum ether, 1:100-1:10) to give compound 7f as a colorless oil. Mass Spectrum (LCMS, ESI pos.): Calcd. for $C_{11}H_9BrFNO_3$: 302.0 (M+H). found: 301.9.

G. 4-Bromo-5-(chloromethyl)-3-(2-fluoro-5-methoxyphenyl)isoxazole, 7g

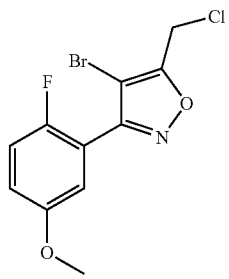

To a stirring solution of compound 7f (300 mg, 0.990 mmol) in DCM (20 mL) and DMF (1 mL) was added thionyl chloride (238 mg, 2.0 mmol) dropwise at 0° C. The resulting solution was stirred for 1 h at RT. The reaction was then quenched by satd. NH$_4$Cl (aq. 10 mL). The resulting solution was extracted with dichloromethane (3×10 mL). The combined organic layers were washed with H$_2$O (2×10 mL), dried over anhydrous sodium sulfate and concentrated to give compound 7g as a yellow oil. Mass Spectrum (LCMS, ESI pos.): Calcd. for $C_{11}H_8BrClFNO_2$: 319.9 (M+H). found: 319.9.

H. (3S)-3-Cyclopropyl-3-(3-((4-(5,5-dimethylcyclopent-1-enyl)-3-(2-fluoro-5-methoxyphenyl)isoxazol-5-yl)methoxy)phenyl)propanoic acid, Cpd 62

The title compound 62 was prepared from compound 7g and methyl (3S)-3-cyclopropyl-3-(3-hydroxyphenyl)propanoate (using an analogous procedure to that described in Example 1, Step F) and then using the methods described in Example 5, Steps F-H. $^1$H-NMR (300 MHz, DMSO-d$_6$) δ (ppm): 7.21-7.32 (m, 2H), 7.02-7.05 (m, 2H), 6.88-6.94 (m, 3H), 5.85 (s, 1H), 5.11 (s, 2H), 3.75 (s, 3H), 2.63-2.68 (m, 2H), 2.27-2.35 (m, 3H), 1.67 (t, J=6.9 Hz, 2H), 0.90-1.05 (m, 1H), 0.67 (s, 6H), 0.44-0.54 (m, 1H), 0.21-0.40 (m, 2H), 0.02-0.18 (m, 1H). Mass Spectrum (LCMS, ESI pos.): Calcd. for $C_{30}H_{32}FNO_5$: 504.2 (M−H). found: 504.2.

Example 8

(3S)-3-Cyclopropyl-3-(3-((1-(2-fluoro-5-methoxyphenyl)-5-isobutyl-1H-1,2,3-triazol-4-yl)methoxy)phenyl)propanoic acid (Cpd 83)

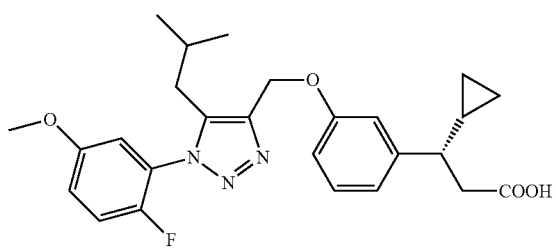 [SMILES: COc1ccc(F)c(-n2nnc(COc3cccc([C@@H](CC(=O)O)C4CC4)c3)c2CC(C)C)c1]

A. Ethyl 5-methyl-3-oxohexanoate, 8a

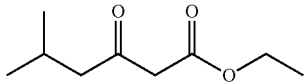

To a stirring solution of 4-methylpentan-2-one (5.0 g, 50 mmol) in THF (50 mL) was added sodium hydride (60% in mineral oil, 4.0 g, 100 mmol) portionwise at 0° C. After 20 min, diethyl carbonate (8.0 g, 68 mmol) was added and the mixture was stirred for 2 h at 80° C. The reaction mixture was allowed to cool to RT and treated with satd. NH$_4$Cl (aq. 100 mL). The resulting mixture was extracted with EtOAc (2×100 mL). The organic layers were combined and concentrated under reduced pressure. The residue obtained was purified by column chromatography on silica gel (EtOAc/petroleum ether, 1:100) to give compound 8a as a light yellow oil. Mass Spectrum (LCMS, ESI pos.): Calcd. for $C_9H_{16}O_3$: 173.1 (M+H). found: 173.1.

B. Ethyl 1-(2-fluoro-5-methoxyphenyl)-5-isobutyl-1H-1,2,3-triazole-4-carboxylate, 8b

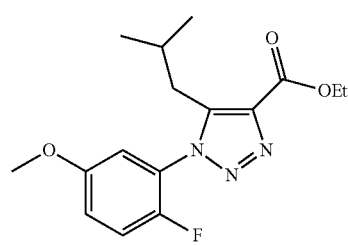

A solution of compound 8a (200 mg, 1.16 mmol), 2-azido-1-fluoro-4-methoxybenzene (210 mg, 1.26 mmol, as prepared in Example 5, Step A) and pyrrolidine (17 mg, 0.24 mmol) in DMSO (1 mL) was stirred overnight at 80° C. The reaction mixture was allowed to cool to RT and treated with water (4 mL). The resulting solution was extracted with EtOAc (2×4 mL). The organic layers were combined and concentrated. The residue obtained was purified by column chromatography on silica gel (EtOAc/petroleum ether, 1:3) to give compound 8b as a colorless oil. Mass Spectrum (LCMS, ESI pos.): Calcd. for $C_{16}H_{20}FN_3O_3$: 322.1 (M+H). found: 322.1.

C. (1-(2-Fluoro-5-methoxyphenyl)-5-isobutyl-1H-1,2,3-triazol-4-yl)methanol, 8c

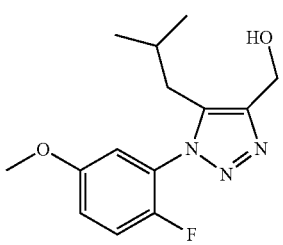

To a solution of compound 8c (180 mg, 0.56 mmol) in THF (5 mL) was added DIBAL-H (1M in hexane, 2.8 mL) at −30° C. The mixture was stirred for 2 h at −30° C. The reaction was then quenched by satd. sodium potassium tartrate solution (aq. 50 mL) and stirred vigorously for 30 min. The resulting solution was extracted with EtOAc (2×50 mL). The organic layers were combined and concentrated. The residue obtained was purified by column chromatography on silica gel (EtOAc/petroleum ether, 1:1) to give compound 8c as a colorless oil. Mass Spectrum (LCMS, ESI pos.): Calcd. for $C_{14}H_{18}FN_3O_2$: 280.1 (M+H). found: 280.1.

D. 4-(Chloromethyl)-1-(2-fluoro-5-methoxyphenyl)-5-isobutyl-1H-1,2,3-triazole, 8d

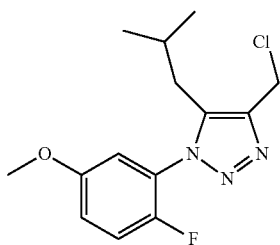

8d

To a stirring solution of compound 8c (110 mg, 0.39 mmol) in DCM (5 mL) and DMF (0.1 mL) was added thionyl chloride (140 mg. 1.2 mmol) at 0° C. The resulting solution was stirred for 1 h at 0° C. and concentrated to give compound 8d as a colorless oil.

E. (3S)-Ethyl 3-cyclopropyl-3-(3-((1-(2-fluoro-5-methoxyphenyl)-5-isobutyl-1H-1,2,3-triazol-4-yl)methoxy)phenyl)propanoate, 8e

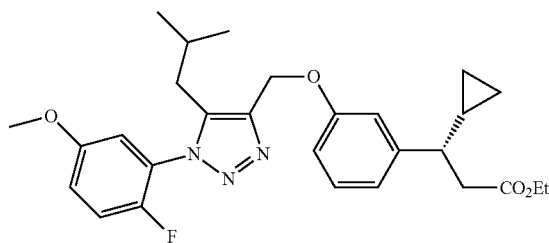

8e

A mixture of compound 1f (113 mg, 0.48 mmol), compound 8d (130 mg, 0.44 mmol) and $Cs_2CO_3$ (356 mg, 1.09 mmol) in $CH_3CN$ (8 mL) was stirred overnight at RT. The resulting mixture was concentrated. The residue was treated with water (20 mL) and extracted with EtOAc (2×20 mL). The organic layers were combined and concentrated. The residue obtained was purified by column chromatography on silica gel (EtOAc/petroleum ether, 1:5) to give compound 8e as a colorless oil. Mass Spectrum (LCMS, ESI pos.): Calcd. for $C_{28}H_{34}FN_3O_4$: 496.3 (M+H); found: 496.3.

F. (3S)-3-Cyclopropyl-3-(3-((1-(2-fluoro-5-methoxyphenyl)-5-isobutyl-1H-1,2,3-triazol-4-yl)methoxy)phenyl)propanoic acid, Cpd 83

Compound 83 was prepared from compound 8e following the procedure described in Example 3, Step H. $^1$H-NMR (400 MHz, DMSO-$d_6$) δ (ppm): 7.51 (t, J=9.2 Hz, 1H), 7.18-7.32 (m, 3H), 6.85-6.92 (m, 3H), 5.16 (s, 2H), 3.81 (s, 3H), 2.59-2.61 (m, 2H), 2.31-2.48 (m, 3H), 1.60-1.63 (m, 1H), 0.95-0.96 (m, 1H), 0.72 (d, J=6.4 Hz, 6H), 0.43-0.45 (m, 1H), 0.23-0.29 (m, 2H), 0.08-0.09 (m, 1H). Mass Spectrum (LCMS, ESI pos.): Calcd. for $C_{26}H_{30}FN_3O_4$: 468.2 (M+H); found: 468.1.

Following the procedures described in Example 8 above, and substituting suitably selected and substituted reagents, starting materials and conditions as would be readily apparent to those skilled in the art, the following representative compound of the present invention was prepared.

| Cpd No. | Characterization |
|---|---|
| 82 | (S)-3-Cyclopropyl-3-(3-((1-(2-fluoro-5-methoxyphenyl)-5-methyl-1H-1,2,3-triazol-4-yl)methoxy)phenyl)propanoic acid<br>$^1$H-NMR (300 MHz, DMSO-$d_6$) δ (ppm): 12.02 (br.m, 1H), 7.51 (t, J = 9.3 Hz, 1H), 7.21-7.29 (m, 3H), 6.81-6.95 (m, 3H), 5.13 (s, 2H), 3.81 (s, 3H), 2.60-2.66 (m, 2H), 2.21-2.30 (m, 4H), 0.95-1.09 (m, 1H), 0.45-0.54 (m, 1H), 0.19-0.39 (m, 2H), 0.09-0.18 (m, 1H).<br>Mass Spectrum (LCMS, ESI pos.): Calcd. for $C_{23}H_{24}FN_3O_4$: 426.2 (M + H); found: 426.2. |

Example 9

(3S)-3-Cyclopropyl-3-(3-((4-(5,5-dimethylcyclopent-1-enyl)-5-(2-fluoro-5-methoxyphenyl)isothiazol-3-yl)methoxy)phenyl)propanoic acid (Cpd 30)

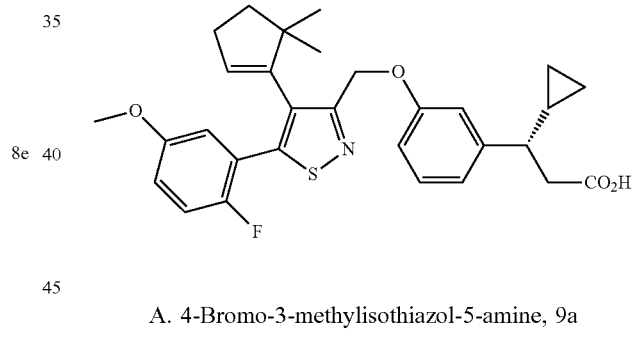

A. 4-Bromo-3-methylisothiazol-5-amine, 9a

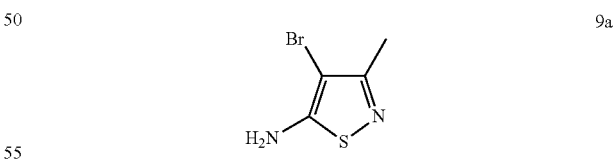

9a

To a solution of 3-methyl-1,2-thiazol-5-amine (2.00 g, 17.5 mmol) and DIEA (3.07 g, 23.7 mmol) in ACN (50 mL) was added NBS (2.35 g, 13.2 mmol). The resulting solution was stirred for 20 min at RT and treated with satd. sodium bicarbonate (aq. 50 mL). The resulting solution was extracted with EtOAc (100 mL). The organic layer was concentrated and the residue obtained was purified by column chromatography on silica gel (EtOAc/petroleum ether, 1:9) to give compound 9a as a brown solid. Mass spectrum (LCMS, ESI pos): Calcd. for $C_4H_5BrN_2S$: 192.9 (M+H); found: 192.9.

B. 4,5-Dibromo-3-methylisothiazole, 9b

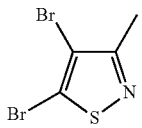

A mixture of CuBr$_2$ (0.58 g, 2.6 mmol) and t-BuONO (0.48 g, 4.7 mmol) in ACN (20 mL) was stirred for 20 min at 0° C. A solution of compound 9a (0.50 g, 2.6 mmol) in ACN (5 mL) was then added dropwise. The resulting solution was stirred for an additional 2 h at RT, treated with satd. NH$_4$Cl solution (aq. 10 mL) and extracted with EtOAc (30 mL). The organic layer was concentrated and the residue obtained was purified on silica gel with EtOAc/petroleum ether (1:100) to give compound 9b as a light yellow solid. $^1$H-NMR (300 MHz, CDCl$_3$) δ (ppm): 2.56 (s, 3H). Mass spectrum (GCMS, EI): Calcd. for C$_4$H$_3$Br$_2$NS: 254.8 (M); found: 254.4, 256.4, 258.4.

C. 4-Bromo-5-(2-fluoro-5-methoxyphenyl)-3-methylisothiazole, 9c

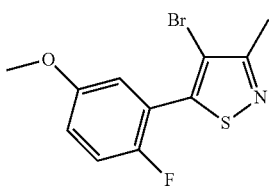

A mixture of (2-fluoro-5-methoxyphenyl)boronic acid (345 mg, 2.03 mmol), Pd(dppf)Cl$_2$ (79 mg, 0.96 mmol), sodium carbonate (509 mg, 4.80 mmol) and compound 9b (480 mg, 1.87 mmol) in 1,4-dioxane (2 mL) and water (0.5 mL) was stirred for 8 h at 60° C. under N$_2$. The reaction mixture was allowed to cool to RT, treated with satd. NH$_4$Cl solution (aq. 10 mL) and extracted with EtOAc (30 mL). The organic layer was concentrated. The residue obtained was purified by column chromatography on silica gel (EtOAc/petroleum ether, 1:100) to give compound 9c as a white solid. Mass spectrum (LCMS, ESI pos): Calcd. for C$_{11}$H$_9$BrFNOS: 302.0 (M+H); found: 301.9.

D. 4-Bromo-3-(bromomethyl)-5-(2-fluoro-5-methoxyphenyl)isothiazole, 9d

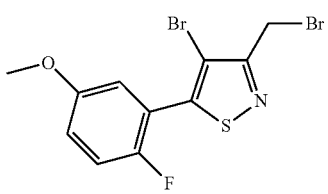

A solution of NBS (213 mg, 1.20 mmol), AIBN (33.4 mg, 0.200 mmol), and compound 11c (300 mg, 0.990 mmol) in CCl$_4$ (6 mL) was stirred overnight at 80° C. under N$_2$. The reaction mixture was allowed to cool to RT and treated with satd. sodium bicarbonate (aq., 20 mL). The resulting solution was extracted with EtOAc (3×30 mL). The organic layers were combined and concentrated. The residue obtained was purified by column chromatography on silica gel (EtOAc/petroleum ether, 1:100) to give compound 9d as a light yellow solid. Mass spectrum (LCMS, ESI pos): Calcd. for C$_{11}$H$_8$Br$_2$FNOS: 380.9 (M+H); found: 379.8, 381.8, 383.8.

E. (3S)-Methyl 3-(3-((4-bromo-5-(2-fluoro-5-methoxyphenyl)isothiazol-3-yl) methoxy)phenyl)-3-cyclopropylpropanoate, 9e

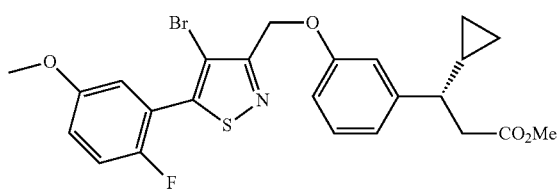

A mixture of compound 9d (220 mg, 0.580 mmol), methyl (3S)-3-cyclopropyl-3-(3-hydroxyphenyl)propanoate (120 mg, 0.54 mmol) and Cs$_2$CO$_3$ (352 mg, 1.08 mmol) in ACN (15 mL) was stirred for 6 h at 60° C. The reaction mixture was allowed to cool to RT and then quenched by satd. NH$_4$Cl (aq., 10 mL). The resulting solution was extracted with EtOAc (3×15 mL). The organic layers were combined and concentrated. The residue obtained was purified by column chromatography on silica gel (EtOAc/petroleum ether, 95:5) to give compound 9e as a light yellow oil. Mass spectrum (LCMS, ESI pos): Calcd. for C$_{24}$H$_{23}$BrFNO$_4$S: 520.1 (M+H); found: 519.9.

F. (3S)-Methyl 3-cyclopropyl-3-(3-((4-(5,5-dimethylcyclopent-1-enyl)-5-(2-fluoro-5-methoxyphenyl)isothiazol-3-yl)methoxy)phenyl)propanoate, 9f

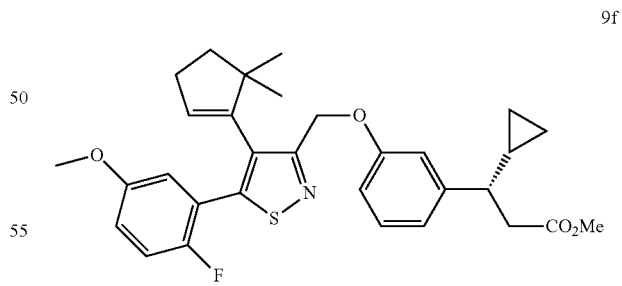

A mixture of Cs$_2$CO$_3$ (11.8 mg, 0.040 mmol), Pd(dppf)Cl$_2$ (263 mg, 0.360 mmol), compound 11e (150 mg, 0.290 mmol), and 2-(5,5-dimethylcyclopent-1-en-1-yl)-4,4,5,5-tetramethyl-1,3,2-dioxaborolane (73.5 mg, 0.330 mmol) in dioxane (2 mL) and water (1 mL) was stirred for 4 h at 90° C. under N$_2$. The mixture was allowed to cool to RT, treated with satd. NH$_4$Cl (aq., 10 mL). The resulting solution was extracted with EtOAc (2×30 mL). The combined organic layers were concentrated and the residue obtained was purified by column chromatography on silica gel (EtOAc/petroleum ether, 90:10) to give compound 9f as a light yellow oil. Mass spectrum (LCMS, ESI pos): Calcd. for $C_{31}H_{34}FNO_4S$: 536.2 (M+H); found: 536.1.

G. (3S)-3-Cyclopropyl-3-(3-((4-(5,5-dimethylcyclopent-1-enyl)-5-(2-fluoro-5-methoxyphenyl)isothiazol-3-yl)methoxy)phenyl)propanoic acid, Cpd 30

Compound 30 was prepared from compound 9f following the procedure described in Example 3, Step H. $^1$H-NMR (300 MHz, DMSO-$d_6$) δ (ppm): 7.12-7.33 (m, 4H), 6.87-6.89 (m, 3H), 5.98 (s, 1H), 5.04 (s, 2H), 3.85 (s, 1H), 2.65-2.70 (m, 2H), 2.28-2.36 (m, 3H), 1.63-1.69 (m, 2H), 0.90-0.98 (m, 1H), 0.49-0.86 (m, 7H), 0.24-0.26 (m, 2H), 0.01-0.12 (m, 1H). Mass Spectrum (LCMS, ESI pos.): Calcd. for $C_{30}H_{32}FNO_4S$: 522.2 (M+H); found: 522.1.

Example 10

(3S)-3-(3-((5-(5-Cyano-2-fluorophenyl)-4-(5,5-dimethylcyclopent-1-enyl)thiophen-3-yl)methoxy)phenyl)-3-cyclopropylpropanoic acid (Cpd 38)

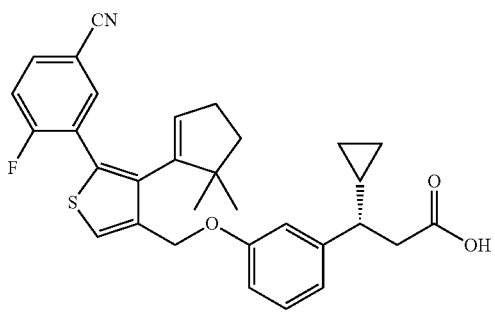 [SMILES: CC1(C)CCC=C1c1c(COc2cccc([C@@H](CC(=O)O)C3CC3)c2)csc1-c1cc(C#N)ccc1F]

A. 4-Bromothiophene-3-carboxylic acid, 10a

10a

To a stirred solution of n-BuLi (2.5M in THF, 90.8 mL, 227 mmol) in THF (500 mL) at −78° C. was added 3,4-dibromothiophene (50.0 g, 207 mmol) dropwise under $N_2$. The resulting mixture was stirred for 30 min at −78° C. and treated with $CO_2$(s) (250 g) and stirred for another 1 h at −78° C. The reaction was then quenched by the addition of 1M sodium hydroxide solution (aq., 300 mL). After the mixture reached RT, the pH of the aqueous solution layer was adjusted to ~3 using 1 N hydrogen chloride solution. The solids formed were collected by filtration and dried to give compound 12a as a white solid. Mass Spectrum (LCMS, ESI neg.): Calcd. for $C_5H_3BrO_2S$: 204.9 (M−H); found: 205.0.

B. 4-Bromo-5-iodothiophene-3-carboxylic acid, 10b

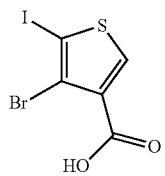

10b

A solution of compound 10a (36.0 g, 174 mmol) in AcOH (850 mL) was stirred for 30 min at 90° C. To this was added a solution of sulfuric acid $H_2SO_4$ (3.5 mL) and $HIO_3$ (7.55 g) in water (25 mL) at 90° C. The reaction mixture was then treated with $I_2$ (17.6 g, 69.3 mmol) in several batches, stirred for an additional 3 h at 90° C. and then at RT overnight. The reaction mixture was cooled in an ice bath and the solids formed were collected by filtration and washed with hexane (3×100 mL) to give compound 12b as a white solid. Mass Spectrum (LCMS, ESI neg.): Calcd. for $C_5H_2BrO_2S$: 330.8 (M−H); found: 330.8, 332.8.

C. (4-Bromo-5-iodothiophen-3-yl)methanol, 10c

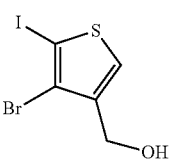

10c

To a stirred solution of compound 10b (12 g, 36 mmol) in THF (200 mL) was added a solution of $BH_3$ (1 M in THF, 72 mL) dropwise at −30° C. under $N_2$. The resulting solution was stirred for 30 min at −30° C. and an additional 2 h at RT. The reaction was then cooled in an ice-water bath and quenched by slow addition of methanol (200 mL) followed by water (200 mL). The resulting solution was extracted with EtOAc (300 mL). The organic layer was concentrated. The resulting residue was purified by flash chromatography (EtOAc/petroleum ether 3:7) on silica gel to yield compound 12c as a white solid). Mass Spectrum (LCMS, ESI pos.): Calcd. for $C_5H_4BrIOS$: 300.8 (M−OH); found: 301.0.

D. 3-Bromo-4-(chloromethyl)-2-iodothiophene, 10d

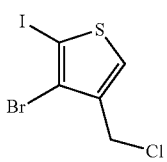

10d

Compound 10d was prepared from compound 10c following a similar procedure as described in Example 5, Step E. $^1$H-NMR (300 MHz, CDCl$_3$) δ (ppm): 7.57 (s, 1H), 4.59 (s, 2H).

E. (S)-Methyl 3-(3-((4-bromo-5-iodothiophen-3-yl)methoxy)phenyl)-3-cyclopropylpropanoate, 10e

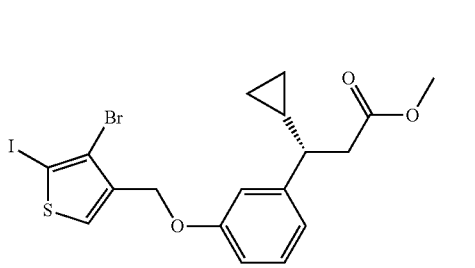

10e

The title compound was prepared from compound 10d and methyl (3S)-3-cyclopropyl-3-(3-hydroxyphenyl)propanoate following a similar procedure to that described in Example 5, Step F. Mass Spectrum (LCMS, ESI pos.): Calcd. for $C_{18}H_{18}BrIO_3S$: 520.9 (M+H). found: 520.8.

F. (3S)-Methyl 3-(3-((4-bromo-5-(5-cyano-2-fluorophenyl)thiophen-3-yl)methoxy)phenyl)-3-cyclopropylpropanoate, 10f

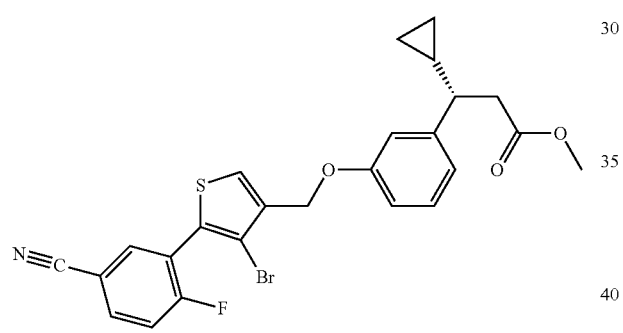

10f

A mixture of compound 10e (120 mg, 0.23 mmol), (5-cyano-2-fluorophenyl)boronic acid (45 mg, 0.27 mmol), XPhos (9 mg, 0.01 mmol), $K_3PO_4$ (97 mg, 0.46 mmol) in THF (0.46 mL) was stirred for 3 h at 50° C. under $N_2$. The reaction mixture was allowed to cool to RT and treated with $H_2O$ (10 mL). The resulting mixture was extracted with EtOAc (2×10 mL). The organic layers were combined, dried over anhydrous sodium sulfate and concentrated. The resulting residue was purified by flash chromatography (0-30% EtOAc/petroleum ether) on silica gel to obtain compound 10f as a colorless oil. Mass Spectrum (LCMS, ESI pos.): Calcd. for $C_{25}H_{21}BrFNO_3S$: 514.0 (M+H); found: 513.9.

G. (3S)-Methyl 3-(3-((5-(5-cyano-2-fluorophenyl)-4-(5,5-dimethylcyclopent-1-enyl)thiophen-3-yl)methoxy)phenyl)-3-cyclopropylpropanoate, 10g

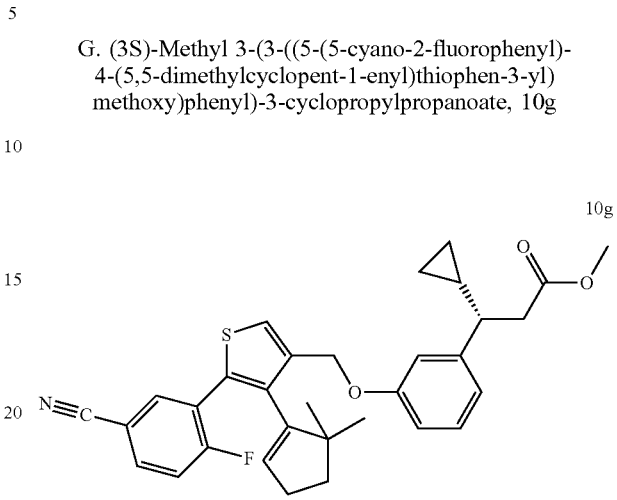

10g

The title compound was prepared from compound 10f and 2-(5,5-dimethylcyclopent-1-en-1-yl)-4,4,5,5-tetramethyl-1,3,2-dioxaborolane following a procedure similar to that described in Example 5, Step G. Mass Spectrum (LCMS, ESI pos.): Calcd. for $C_{32}H_{32}FNO_3S$: 530.2 (M+H); found: 530.0

H. (3S)-3-(3-((5-(5-Cyano-2-fluorophenyl)-4-(5,5-dimethylcyclopent-1-enyl)thiophen-3-yl)methoxy)phenyl)-3-cyclopropylpropanoic acid, Cpd 99

Compound 38 was prepared from compound 10g following a procedure similar to the experimental described in Example 1, Step H. $^1$H-NMR (300 MHz, DMSO-$d_6$) δ (ppm): 11.76 (br, 1H), 7.74-7.76 (m, 2H), 7.62 (s, 1H), 7.32 (t, J=9.0 Hz, 1H), 6.95-7.00 (m, 1H), 6.57-6.64 (m, 3H), 5.67 (s, 1H), 4.65 (s, 2H), 2.37-2.42 (m, 2H), 2.05-2.07 (m, 3H), 1.31-1.48 (m, 2H), 0.70-0.85 (m, 1H), 0.00-0.65 (m, 10H). Mass Spectrum (LCMS, ESI neg.): Calcd. for $C_{31}H_{30}FNO_3S$: 514.2 (M−H), found: 514.1.

Following the procedures described in Example 10, and substituting suitably selected reagents, starting materials and conditions as would be readily apparent to those skilled in the art, the following representative compound of the present invention were prepared.

| Cpd No. | Characterization |
|---|---|
| 13 | (3S)-3-Cyclopropyl-3-(3-((4-(5,5-dimethylcyclopent-1-enyl)-5-(2-fluoro-5-methoxyphenyl)thiophen-3-yl)methoxy)phenyl) propanoic acid<br>$^1$H-NMR: (300 MHz, CD$_3$OD) δ (ppm) : 7.14-7.20 (m, 1H), 7.02-7.06 (m, 2H), 6.79-7.00 (m, 5H), 5.42 (s, 1H), 5.25 (s, 2H), 3.77 (s, 3H), 2.50-2.70 (m, 2H), 2.30-2.45 (m, 1H), 2.20-2.30 (m, 2H), 1.74 (t, J = 6.9 Hz, 2H), 1.03 (s, 6H), 0.90-1.00 (m, 1H), 0.50-0.60 (m, 1H), 0.25-0.40 (m, 2H), 0.00-0.15 (m, 1H).<br>Mass Spectrum (LCMS, ESI pos.): Calcd. for $C_{31}H_{32}FO_4S$: 519.2 (M + H); found: 519.1. |
| 16 | (S)-3-Cyclopropyl-3-(3-((3-(5,5-dimethylcyclopent-1-enyl)-2,3'-bithiophen-4-yl)methoxy)phenyl)propanoic acid<br>$^1$H-NMR(400 MHz, DMSO-$d_6$) δ (ppm): 7.48-7.52(m, 3H), 7.18-7.24 (m, 2H), 6.79-6.84 (m, 3H), 5.79-5.81 (m, 1H), |

| Cpd No. | Characterization |
|---|---|
| | 4.87 (s, 2H), 2.59-2.64 (m, 3H), 2.35-2.39 (m, 3H), 1.69-1.74 (m, 2H), 1.05-1.08 (m, 1H), 0.72 (s, 6H), 0.00-0.60 (m, 4H).<br>Mass Spectrum (LCMS, ESI pos.): Calcd. for $C_{28}H_{30}O_3S_2$: 478.2 (M + H); found: 478.2. |
| 17 | (S)-3-cyclopropyl-3-(3-((5-(3-(dimethylamino)phenyl)-4-(5,5-dimethylcyclopent-1-en-1-yl)thiophen-3-yl)methoxy)phenyl)propanoic acid<br>$^1$H-NMR (400 MHz, DMSO-$d_6$) δ (ppm): 7.50 (s, 1H), 7.13-7.22 (m, 2H), 6.92 (s, 1H), 6.78-6.85 (m, 4H), 6.67-6.71 (m, 1H), 5.83 (s, 1H), 4.88 (s, 2H), 2.88 (s, 6H), 2.50-2.62 (m, 2H), 2.36-2.49 (m, 3H), 1.68 (t, J = 6.9 Hz, 2H), 0.95-1.03 (m, 1H), 0.68 (s, 6H), 0.49-053 (m, 1H), 0.32-0.36 (m, 1H), 0.22-0.26 (m, 1H), 0.08-0.12 (m, 1H).<br>Mass Spectrum (LCMS, ESI pos.): Calcd. for $C_{32}H_{37}NO_3S$: 516.2 (M + H); found: 516.1 |
| 18 | (S)-3-cyclopropyl-3-(3-((4-(5,5-dimethylcyclopent-1-en-1-yl)-5-(2-fluoro-4-methoxyphenyl)thiophen-3-yl)methoxy)phenyl)propanoic acid<br>$^1$H-NMR (400 MHz, DMSO-$d_6$): δ (ppm): 7.69 (s, 1H), 7.34 (t, J = 8.7 Hz, 1H), 7.15 (t, J = 7.8 Hz, 1H), 6.74-6.92 (m, 5H), 5.78 (s, 1H), 4.85 (s, 2H), 3.79 (s, 3H), 2.27-2.50 (m, 5H), 1.55-1.65 (m, 2H), 0.53-0.93 (m, 7H), 0.35-0.50 (m, 1H), 0.20-0.32 (m, 2H), 0.00-0.15 (m, 1H).<br>Mass Spectrum (LCMS, ESI pos.): Calcd. for $C_{31}H_{33}FO_4S$: 519.2 (M + H); found: 519.1. |
| 26 | (S)-3-Cyclopropyl-3-(3-((4-(5,5-dimethylcyclopent-1-enyl)-5-(3-methoxyphenyl)thiophen-3-yl)methoxy)phenyl)propanoic acid<br>$^1$H-NMR (300 MHz, DMSO-$d_6$) δ (ppm): 7.40 (s, 1H), 7.01-7.07 (m, 2H), 6.85-6.86 (m, 2H), 6.57-6.66 (m, 4H), 5.66 (s, 1H), 4.62 (s, 2H), 3.51 (s, 3H), 2.64-2.66 (m, 2H), 2.27-2.45 (m, 3H), 1.42 (s, 2H), 0.81-0.97 (m, 4H), 0.15-0.80 (m, 6H), 0.10 (s, 1H).<br>Mass Spectrum (LCMS, ESI pos.): Calcd. for $C_{30}H_{33}NO_4S$: 503.2 (M + H); found: 504.0. |
| 28 | (S)-3-Cyclopropyl-3-(3-((4-(5,5-dimethylcyclopent-1-enyl)-5-(5-methoxypyridin-3-yl)thiophen-3-yl)methoxy)phenyl)propanoic acid<br>$^1$H-NMR (300 MHz, DMSO-$d_6$) δ (ppm): 11.8-12.1 (m, 1H), 8.21-8.34 (dd, 2H), 7.70-7.75 (s, 1H), 7.45-5.49 (m, 1H), 7.18-7.29 (t, 1H), 6.78-6.91 (m, 3H), 5.92-5.97 (s, 1H), 4.88-4.93 (s, 2H), 3.81-3.88 (s, 3H), 2.61-2.69 (m, 2H), 2.31-2.42 (m, 2H), 2.20-2.30 (m, 1H), 1.60-1.75 (s, 1H), 0.75-1.05 (m, 5H), 0.14-0.52 (m, 5H), 0.08-0.11 (m, 1H).<br>Mass Spectrum (LCMS, ESI pos.): Calcd. for $C_{30}H_{33}NO_4S$: 504.2 (M + H); found: 504.0. |
| 31 | (S)-3-cyclopropyl-3-(3-((4-(5,5-dimethylcyclopent-1-en-1-yl)-5-(2-methoxypyridin-4-yl)thiophen-3-yl)methoxy)phenyl)propanoic acid<br>$^1$H-NMR (400 MHz, DMSO-$d_6$): δ (ppm): 8.16 (d, J = 5.4 Hz, 1H), 7.23 (t, J = 7.8 Hz, 1H), 7.09-7.13 (m, 2H), 6.87-6.96 (m, 4H), 5.60 (t, J = 2.1 Hz, 1H), 5.31 (s, 2H), 3.87 (s, 3H), 2.65-2.69 (m, 2H), 2.26-2.35 (m, 3H), 1.80 (t, J = 6.9 Hz, 2H), 0.99-1.03 (m, 7H), 0.50-0.52 (m, 1H), 0.24-0.34 (m, 2H), 0.12-0.15 (m, 1H).<br>Mass Spectrum (LCMS, ESI pos.): Calcd. for $C_{30}H_{33}NO_4S$: 502.2 (M-H); found: 502.0. |

Example 11

(3S)-3-Cyclopropyl-3-(3-((4-(5,5-dimethylcyclopent-1-enyl)-5-(5-fluoro-2-methoxypyridin-4-yl)thiophen-3-yl)methoxy)phenyl)propanoic acid (Cpd 27)

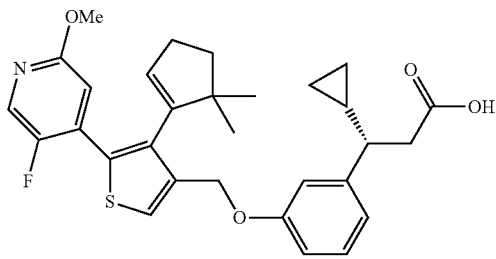 [SMILES: COc1cc(-c2scc(COc3cccc([C@@H](CC(=O)O)C4CC4)c3)c2C2=CCCC2(C)C)c(F)cn1]

A. Methyl 4-bromo-5-iodothiophene-3-carboxylate, 11a

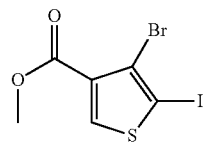

To a stirring solution of compound 10b (2.75 g, 8.26 mmol) in methanol (100 mL) was added thionyl chloride (1.97 g, 16.6 mmol), and the mixture was stirred for 2 h at 60° C. The reaction was allowed to cool to RT and concentrated. The residue was dissolved in EtOAc (50 mL) and washed with satd. sodium bicarbonate (aq., 3×10 mL). The organic layer was separated, dried over sodium sulfate and concentrated to give compound 11a as a white solid. $^1$H-NMR (400 MHz, CDCl$_3$) δ (ppm): 8.29 (s, 1H), 3.89 (s, 3H).

B. Methyl 4-bromo-5-(5-fluoro-2-methoxypyridin-4-yl)thiophene-3-carboxylate, 1b

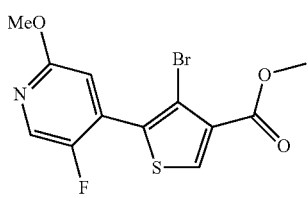

A mixture of compound 11a (600 mg, 1.73 mmol), (5-fluoro-2-methoxypyridin-4-yl) boronic acid (360 mg, 2.11 mmol), XPhos aminobiphenyl palladium chloride precatalyst (64 mg, 0.08 mmol) and 2M K$_3$PO$_4$ (aq., 1.7 mL, 3.4 mmol) in THF (6 mL) was stirred overnight at 40° C. under N$_2$. The resulting mixture was allowed to cool to RT and concentrated. The residue obtained was purified by column chromatography on silica gel (EtOAc/petroleum ether, 1:20) to give compound 11b as a colorless oil. Mass Spectrum (LCMS, ESI pos.): Calcd. for C$_{12}$H$_9$BrFNO$_3$S: 345.9 (M+H); found: 345.9.

C. (3S)-3-Cyclopropyl-3-(3-((4-(5,5-dimethylcyclopent-1-enyl)-5-(5-fluoro-2-methoxypyridin-4-yl)thiophen-3-yl)methoxy)phenyl)propanoic acid, Cpd 27

Compound 27 was prepared from compound 11b and 2-(5,5-dimethylcyclopent-1-en-1-yl)-4,4,5,5-tetramethyl-1,3,2-dioxaborolane following the procedure described in Example 3, Steps D-H. $^1$H-NMR (300 MHz, DMSO-d$_6$) δ (ppm): 8.22 (s, 1H), 7.89 (s, 1H), 7.17 (t, J=7.8 Hz, 1H), 6.94 (d, J=4.8 Hz, 1H), 6.77-6.85 (m, 3H), 5.88 (s, 1H), 4.87 (s, 2H), 3.84 (s, 3H), 2.56-2.58 (m, 2H), 2.28-2.36 (m, 3H), 1.62-1.66 (m, 2H), 0.38-1.00 (m, 8H), 0.14-0.32 (m, 2H), 0.07-0.10 (m, 1H). Mass Spectrum (LCMS, ESI pos.): Calcd. for C$_{30}$H$_{32}$FNO$_4$S: 522.2 (M+H); found: 522.3.

Example 12

(3S)-3-Cyclopropyl-3-(3-((4-(5,5-dimethylcyclopent-1-enyl)-5-(6-methoxybenzo[b]thiophen-4-yl)thiophen-3-yl)methoxy)phenyl)propanoic acid (Cpd 10)

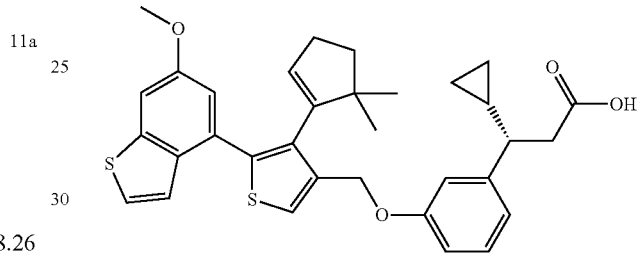

A. 4-Bromo-6-methoxybenzo[b]thiophene-2-carboxylic acid, 12a

A solution of methyl 4-bromo-6-methoxy-1-benzothiophene-2-carboxylate (22 g, 73 mmol) and sodium hydroxide (29 g, 73 mmol) in water (122 mL) and THF (400 mL) was stirred for 12 h at RT. The pH of the solution was adjusted to 4-5 with 1N hydrogen chloride solution. The resulting solution was extracted with EtOAc (3×200 mL). The organic layers were combined, dried over anhydrous sodium sulfate and concentrated under reduced pressure. The crude product obtained was recrystallized from hexane to obtain compound 12a as a yellow solid. $^1$H-NMR (300 MHz, DMSO-d$_6$) δ (ppm): 7.86 (s, 1H), 7.70 (s, 1H), 7.38 (s, 1H), 3.86 (s, 3H).

B. 4-Bromo-6-methoxybenzo[b]thiophene, 12b

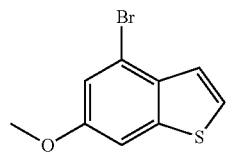

A solution of compound 12a (4.0 g, 14 mmol) and DBU (12 g, 79 mmol) in DMA (20 mL) was heated at 200° C. in a microwave reactor for 40 min. The reaction mixture was treated with water (300 mL) and the pH value of the solution was adjusted to 6-7 with 1N hydrogen chloride solution. The resulting mixture was extracted with EtOAc (3×200 mL). The organic layers were combined, dried over anhydrous sodium sulfate and concentrated. The residue was purified by column chromatography on silica gel (EtOAc/petroleum ether, 1:100-1:30) to give compound 12b as a yellow oil. Mass Spectrum (GCMS, EI): Calcd. for $C_9H_7BrOS$: 241.9 (M); found: 242.0, 244.0.

C. 2-(6-Methoxybenzo[b]thiophen-4-yl)-4,4,5,5-tetramethyl-1,3,2-dioxaborolane, 12c

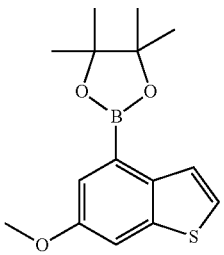

12c

A mixture of compound 12b (600 mg, 2.47 mmol), $B_2Pin_2$ (940 mg, 3.70 mmol), Pd(dppf)Cl$_2$ (90 mg, 0.12 mmol) and KOAc (726 mg, 7.40 mmol) in DMSO (5 mL) was stirred overnight at 80° C. under N$_2$. The reaction mixture was allowed to cool to RT, treated with water (20 mL) and extracted with EtOAc (3×20 mL). The organic layers were combined, dried over anhydrous sodium sulfate and concentrated. The residue obtained was purified by column chromatography on silica gel (EtOAc/petroleum ether, 1:100-1:50) to give compound 12c as a green solid. $^1$H-NMR (300 MHz, CDCl$_3$) δ (ppm): 7.89 (d, J=5.4 Hz, 1H), 7.50 (d, J=2.4 Hz, 1H), 7.46 (d, J=2.4 Hz, 1H), 7.30 (d, J=5.7 Hz, 1H), 3.89 (s, 3H), 1.39 (s, 12H).

D. (3S)-Methyl 3-(3-((4-bromo-5-(6-methoxybenzo[b]thiophen-4-yl)thiophen-3-yl)methoxy)phenyl)-3-cyclopropylpropanoate, 12d

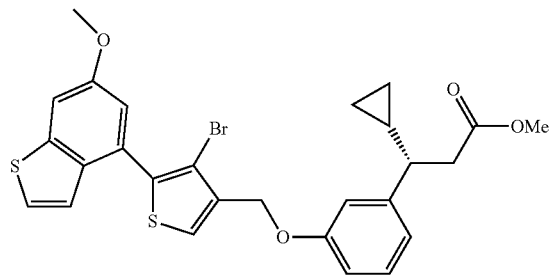

12d

A mixture of compound 10e (400 mg, 0.770 mmol, as prepared in Example 10, Step E), compound 12c (245 mg, 0.840 mmol), Pd(dppf)Cl$_2$ (28 mg, 0.040 mmol), and Na$_2$CO$_3$ (203 mg, 1.92 mmol) in dioxane (8 mL) and water (2 mL) was stirred for 2 h at 50° C. under N$_2$. The reaction mixture was allowed to cool to RT and treated with water (20 mL). The resulting solution was extracted with EtOAc (3×15 mL). The organic layers were combined, dried over anhydrous sodium sulfate and concentrated. The residue obtained was purified by column chromatography on silica gel (EtOAc/petroleum ether, 1:100-1:40) to give compound 12d as a colorless oil. Mass Spectrum (LCMS, ESI pos.): Calcd. for $C_{27}H_{25}BrO_4S_2$: 557.0 (M+H); found: 557.2.

E. (3S)-Methyl 3-cyclopropyl-3-(3-((4-(5,5-dimethylcyclopent-1-enyl)-5-(6-methoxybenzo[b]thiophen-4-yl)thiophen-3-yl)methoxy)phenyl)propanoate, 12e

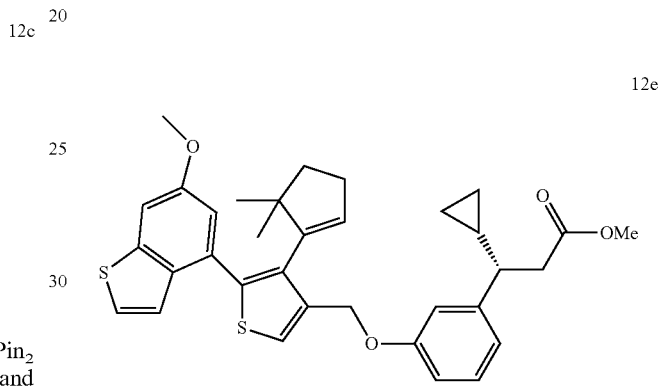

12e

Compound 12e was prepared from compound 12d and 2-(5,5-dimethylcyclopent-1-en-1-yl)-4,4,5,5-tetramethyl-1,3,2-dioxaborolane following a similar procedure to that described in Example 5, Step G. Mass Spectrum (LCMS, ESI pos.): Calcd. for $C_{34}H_{36}O_4S_2$: 573.2 (M+H); found: 573.3.

F. (3S)-3-cyclopropyl-3-(3-((4-(5,5-dimethylcyclopent-1-enyl)-5-(6-methoxybenzo[b]thiophen-4-yl)thiophen-3-yl)methoxy)phenyl)propanoic acid, Cpd 10

Compound 10 was prepared from compound 12e, following a similar procedure to that described in Example 4, Step I. $^1$H-NMR (300 MHz, DMSO-d$_6$) δ (ppm): 11.99 (s, 1H), 7.76 (s, 1H), 7.55-7.59 (m, 2H), 7.36-7.39 (m, 1H), 7.20-7.22 (m, 1H), 7.01 (d, J=2.4 Hz, 1H), 6.88-6.89 (m, 3H), 5.89 (s, 1H), 4.90 (s, 2H), 3.81 (s, 3H), 2.68-2.70 (m, 2H), 2.25-2.27 (m, 3H), 1.44-1.62 (m, 2H), 1.30-1.40 (m, 1H), 0.00-1.10 (m, 10H). Mass Spectrum (LCMS, ESI pos.): Calcd. for $C_{33}H_{34}O_4S_2$: 557.2 [M−H]; found: 557.1.

Following the procedures described in Example 12 above, and substituting suitably selected reagents, starting materials and conditions as would be readily apparent to those skilled in the art, the following representative compound of the present invention were prepared.

| Cpd No. | Characterization |
|---|---|
| 14 | (S)-3-cyclopropyl-3-(3-((4-cyclopropyl-5-(2-fluoro-5-methoxyphenyl)thiophen-3-yl)methoxy)phenyl)propanoic acid<br>$^1$H-NMR: (300 MHz, CDCl$_3$) δ (ppm) 7.16 (t, J = 7.8 Hz, 1H), 6.96 (t, J = 9.1 Hz, 1H), 6.74-6.88 (m, 5H), 5.04 (s, 2H), 3.71 (s, 3H), 3.64-3.70 (m, 1H), 2.63-2.77 (m, 2H), 2.24-2.34 (m, 1H), 1.69-1.82 (m, 2H), 0.88-1.01 (m, 1H), 0.56-0.65 (m, 2H), 0.45-0.55 (m, 1H), 0.30-0.40 (m, 1H), 0.14-0.26 (m, 3H), 0.04-0.13 (m, 1H). Mass Spectrum (LCMS, ESI pos.): Calcd. for C$_{27}$H$_{27}$FO$_4$S: 446.1 (M + H); found: 446.2. |
| 20 | (S)-3-Cyclopropyl-3-(3-((4-(5,5-dimethylcyclopent-1-enyl)-5-phenylthiophen-3-yl)methoxy)phenyl)propanoic acid<br>$^1$H-NMR (300 MHz, DMSO-d6) δ (ppm): 11.89 (s, 1H), 7.65 (s, 1H), 7.48-7.51 (m, 2H),7.32-7.37 (m, 1H), 7.20-7.22 (m, 1H), 6.83-6.87 (m, 3H), 5.88 (s, 1H), 4.87 (s, 2H), 2.64-2.66 (m, 2H), 2.27-2.29 (m, 3H), 1.65 (s, 2H), 1.13 (s, 1H), 0.15-0.90 (m, 6H), 0.10 (s, 2H).<br>Mass Spectrum (LCMS, ESI pos.): Calcd. for C$_{30}$H$_{32}$O$_3$S: 471.6 [M − H]; found: 471.0. |
| 21 | (3S)-3-cyclopropyl-3-(3-((4-(5,5-dimethylcyclopent-1-enyl)-5-(2-fluorophenyl)thiophen-3-yl)methoxy)phenyl)propanoic acid<br>$^1$H-NMR (300 MHz, DMSO-d$_6$) δ (ppm): 11.89 (s, 1H), 7.76 (s, 1H), 7.39-7.45 (m, 2H), 7.20-7.22 (m, 3H), 6.83-6.87 (m, 3H), 5.81 (s, 1H), 4.87 (s, 2H), 2.64-2.66 (m, 2H), 2.27-2.29 (m, 3H), 1.65 (s, 2H), 1.13 (s, 1H), 0.15-0.90 (m, 9H), 0.10 (s, 1H). Mass Spectrum (LCMS, ESI pos.): Calcd. for C$_{30}$H$_{31}$FO$_3$S: 489.6 [M − H]$^-$; found: 489.0. |
| 22 | (3S)-3-Cyclopropyl-3-(3-((4-(5,5-dimethylcyclopent-1-enyl)-5-(2-methoxyphenyl)thiophen-3-yl)methoxy)phenyl)propanoic acid<br>$^1$H-NMR (300 MHz, DMSO-d$_6$) δ (ppm): 11.89 (s, 1H), 7.76 (s, 1H), 7.39-7.45 (m, 2H), 7.20-7.22 (m, 3H), 6.83-6.87 (m, 3H), 5.81 (s, 1H), 4.87 (s, 2H), 2.64-2.66 (m, 2H), 2.27-2.29 (m, 3H), 1.65 (s, 2H), 1.13 (s, 1H), 0.15-0.90 (m, 9H), 0.10 (s, 1H). Mass Spectrum (LCMS, ESI pos.): Calcd. for C$_{31}$H$_{34}$O$_4$S: 501.6 [M − H]$^-$; found: 501.0. |
| 23 | (S)-3-Cyclopropyl-3-(3-((5-(3,5-dimethoxyphenyl)-4-(5,5-dimethylcyclopent-1-enyl)thiophen-3-yl)methoxy)phenyl)propanoic acid<br>$^1$H-NMR (300 MHz, DMSO-d$_6$) δ (ppm): 11.98 (s, 1H), 7.63 (s, 1H), 7.18-7.23 (m, 1H), 6.82-6.87 (m, 3H), 6.68-6.80 (m, 2H), 6.45-6.47 (m, 1H), 5.89 (s, 1H), 4.85 (s, 2H), 3.73 (s, 6H), 2.63-2.66 (m, 2H), 2.49-2.51 (m, 3H), 1.69 (s, 2H), 0.85 (s, 1H), 0.42-0.45 (m, 6H), 0.22-0.32(m, 2H), 0.11-0.13 (d, J = 4.8 Hz, 1H). Mass Spectrum (LCMS, ESI pos.): Calcd. for C$_{32}$H$_{36}$O$_5$S : 531.1 [M − H]$^-$; found: 531.1. |
| 24 | (3S)-3-Cyclopropyl-3-(3-((4-(5,5-dimethylcyclopent-1-enyl)-5-(1H-indol-4-yl)thiophen-3-yl)methoxy)phenyl)propanoic acid<br>$^1$H-NMR (300 MHz, DMSO-d$_6$) δ (ppm): 11.22 (br, 1H), 7.66 (s, 1H), 7.34-7.37 (m, 2H), 7.18-7.23 (m, 1H), 7.05-7.09 (m, 2H), 6.80-6.89 (m, 3H), 6.56-6.57 (m, 1H), 5.85-5.86 (m, 1H), 4.89 (s, 2H), 2.51-2.61 (m, 2H), 2.27-2.31 (m, 3H), 1.52-1.55 (m, 2H), 0.15-1.00 (m, 10H), 0.05-0.12 (m, 1H).<br>Mass Spectrum (LCMS, ESI pos.): Calcd. for C$_{32}$H$_{33}$NO$_3$S: 512.2 (M + H); found: 512.2. |
| 25 | (3S)-3-(3-((5-(Benzofuran-4-yl)-4-(5,5-dimethylcyclopent-1-enyl)thiophen-3-yl)methoxy)phenyl)-3-cyclopropylpropanoic acid<br>$^1$H-NMR (300 MHz, DMSO-d$_6$) δ (ppm): 8.03 (s, 1H), 7.77 (s, 1H), 7.64 (d, J = 8.7 Hz, 1H), 7.39 (d, J = 6.9 Hz, 1H), 7.19-7.27 (m, 2H), 7.01 (s, 1H), 6.82-6.90 (m, 3H), 5.89 (s, 1H), 4.90 (s, 2H), 2.64-2.67 (m, 2H), 2.26-2.31 (m, 3H), 1.45-1.61 (m, 2H), 0.12-1.11 (m, 11H). Mass Spectrum (LCMS, ESI pos.): Calcd. for C$_{32}$H$_{32}$O$_4$S: 512.7 (M + H); found: 512.7. |

Example 13

(3S)-3-(3-(((4-Cyclobutoxy-5-(2-fluoro-5-methoxy-phenyl)isoxazol-3-yl)methoxy)phenyl)-3-cyclopropylpropanoic acid (Cpd 43)

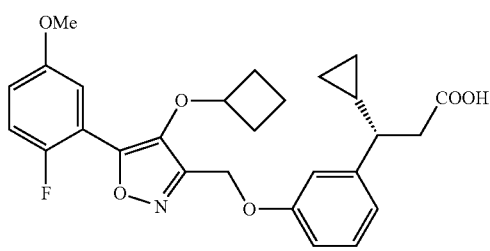 [SMILES: COc1ccc(F)c(-c2onc(COc3cccc([C@@H](CC(=O)O)C4CC4)c3)c2OC2CCC2)c1]

A. Ethyl 4-chloro-2-(hydroxyimino)-3-oxobutanoate, 13a

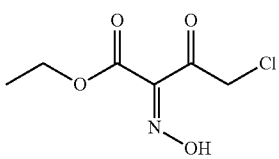

To a stirring solution of ethyl 4-chloro-3-oxobutanoate (44.0 g, 267 mmol), AcOH (250 mL) was added a solution of $NaNO_2$ (23.2 g, 336 mmol) in water (200 mL) dropwise at −10° C. The resulting solution was stirred for 2 h at −4° C. The reaction mixture was then treated with water (50 mL) and extracted with EtOAc (3×30 mL). The organic layers were combined and washed with $H_2O$ (3×30 mL). The organic layer was dried over $Na_2SO_4$ and concentrated to give compound 13a as a colorless oil. $^1$H-NMR (400 MHz, $CDCl_3$) δ (ppm): 4.59 (s, 2H), 4.41 (dd, $J_1$=6.8 Hz, $J_2$=14.4 Hz, 2H), 1.27 (t, J=7.2 Hz, 3H).

B. Ethyl 4-hydroxyisoxazole-3-carboxylate, 13b

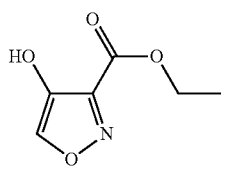

A mixture of compound 13a (44.0 g, 227 mmol) and urea (110 g, 1.83 mol) in DMF (200 mL) was stirred for 20 min at 100° C. The reaction mixture was allowed to cool to RT. The reaction was then quenched with water (50 mL). The resulting solution was extracted with DCM (3×20 mL). The organic layers were combined, washed with $H_2O$ (2×15 mL) and concentrated. The residue obtained was purified by column chromatography (0-20% EtOAc/petroleum ether) on silica gel to obtain compound 13b as a white solid. Mass Spectrum (LCMS, ESI pos.): Calcd. for $C_6H_7NO_4$: 158.0 (M+H); found: 158.0.

C. Ethyl 4-cyclobutoxyisoxazole-3-carboxylate, 13c

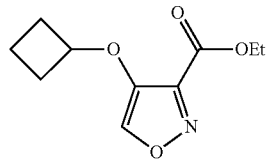

A mixture of compound 13b (500 mg, 3.18 mmol), bromocyclobutane (512 mg, 3.79 mmol) and $Cs_2CO_3$ (2.08 g, 6.38 mmol) in DMF (5 mL) was stirred for 1 h at 60° C. The reaction mixture was allowed to cool to RT and treated with water (20 mL). The resulting solution was extracted with DCM (3×20 mL). The organic layers combined, dried over $Na_2SO_4$ and concentrated. The residue obtained was purified by flash chromatography (0-20% EtOAc/petroleum ether) on silica gel to obtain compound 13c as a yellow solid. Mass Spectrum (LCMS, ESI pos.): Calcd. for $C_{10}H_{13}FNO_4$: 212.1 (M+H); found: 212.1.

D. Ethyl 5-bromo-4-cyclobutoxyisoxazole-3-carboxylate, 13d

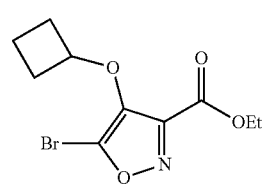

A solution of compound 13c (260 mg, 1.23 mmol) and NBS (262 mg, 1.47 mmol) in DMF (2 mL) was stirred overnight at 60° C. The reaction mixture was allowed to cool to RT. The reaction mixture was treated with water (10 mL) and extracted with DCM (3×10 mL). The separated organic layers were combined, dried over $Na_2SO_4$ and concentrated. The residue obtained was purified by flash chromatography (0-25% EtOAc/petroleum ether) on silica gel to obtain compound 13d as a yellow solid. Mass Spectrum (LCMS, ESI pos.): Calcd. for $C_{10}H_{12}BrNO_4$: 290.0 (M+H); found: 290.0.

E. Ethyl 4-cyclobutoxy-5-(2-fluoro-5-methoxyphenyl)isoxazole-3-carboxylate, 13e

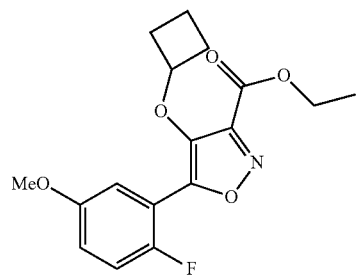

A mixture of compound 13d (293 mg, 1.01 mmol), (2-fluoro-5-methoxyphenyl) boronic acid (250 mg, 1.47 mmol), Pd(dppf)Cl$_2$ (31.6 mg, 0.04 mmol) and Cs$_2$CO$_3$ (562 mg, 1.72 mmol) in dioxane (0.5 mL) and water (2 mL) was stirred for 1 h at 60° C. under N$_2$. The reaction mixture was allowed to cool to RT. The reaction was then quenched with satd. NH$_4$Cl (aq. 5 mL). The resulting solution was extracted with EtOAc (3×5 mL) and the organic layers were combined, washed with H$_2$O (2×10 mL), dried over Na$_2$SO$_4$ and concentrated. The residue obtained was purified by flash chromatography (0-20% EtOAc/petroleum ether) on silica gel to obtain compound 13e as a yellow solid. Mass Spectrum (LCMS, ESI pos.): Calcd. for C$_{17}$H$_{18}$FNO$_5$: 336.1 (M+H); found: 336.1.

F. (4-Cyclobutoxy-5-(2-fluoro-5-methoxyphenyl)isoxazol-3-yl)methanol, 13f

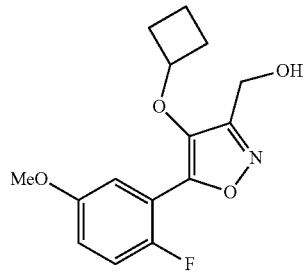

13f

To the stirring solution of compound 13e (160 mg, 0.478 mmol) in THF (4 mL) was added the solution of DIBAL-H in THF (1 M, 2.5 mL, 2.5 mmol) was added at −78° C. The resulting solution was stirred for 1 h at −78° C. and the reaction was then quenched with satd. seignette salt solution (aq. 5 mL). The resulting solution was extracted with EtOAc (3×5 mL). The organic layers were combined, washed with water (2×10 mL) and concentrated. The residue obtained was purified by flash chromatography (0-20% EtOAc/petroleum ether) on silica gel to obtain compound 13f as colorless oil. Mass Spectrum (LCMS, ESI pos.): Calcd. for C$_{15}$H$_{16}$FNO$_4$: 294.1 (M+H); found: 294.2.

G. (3S)-methyl 3-(3-((4-cyclobutoxy-5-(2-fluoro-5-methoxyphenyl)isoxazol-3-yl)methoxy)phenyl)-3-cyclopropylpropanoate, 13g

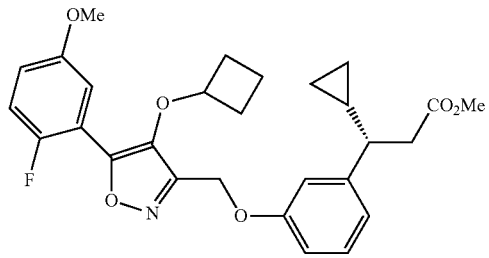

13g

Compound 13g was prepared from compound 13f following the procedures described in Example 14, Steps E and F. Mass Spectrum (LCMS, ESI pos.): Calcd. for C$_{28}$H$_{30}$FNO$_6$: 496.2; found: 496.1.

H. (3S)-3-(3-((4-Cyclobutoxy-5-(2-fluoro-5-methoxyphenyl)isoxazol-3-yl)methoxy)phenyl)-3-cyclopropylpropanoic acid, Cpd 43

Compound 43 was prepared from compound 13g following the procedure described in Example 4, Step I. $^1$H-NMR (300 MHz, DMSO-d$_6$) δ (ppm): 12.00 (brs, 1H), 7.22-7.40 (m, 3H), 7.13-7.18 (m, 1H), 6.89-6.97 (m, 3H), 5.19 (s, 2H), 4.48-4.53 (m, 1H), 3.81 (s, 3H), 2.64-2.68 (m, 2H), 2.26-2.29 (m, 1H), 1.94-2.11 (m, 4H), 1.59-1.62 (m, 1H), 1.35-1.38 (m, 1H), 0.95-1.05 (m, 1H), 0.47-0.51 (m, 1H), 0.24-0.29 (m, 2H), 0.12-0.14 (m, 1H). Mass Spectrum (LCMS, ESI pos.): Calcd. for C$_{27}$H$_{28}$FNO$_6$: 482.2 (M+H). found: 482.2.

Following the procedures described in Example 13 above, and substituting suitably selected reagents, starting materials and conditions as would be readily apparent to those skilled in the art, the following representative compound of the present invention were prepared.

| Cpd No. | Characterization |
|---|---|
| 1 | (3S)-3-(3-[[4-(Cyclopentyloxy)-5-(2-fluoro-5-methoxyphenyl)isoxazol-3-yl]methoxy]phenyl)-3-cyclopropylpropanoic acid<br>$^1$H-NMR (400 MHz, DMSO-d$_6$) δ (ppm): 7.34-7.39 (m, 1H), 7.28-7.29 (m, 1H), 7.20-7.23 (m, 1H), 7.13-7.16 (m, 1H), 6.92-6.96 (m, 1H), 6.88-6.91 (m, 2H), 5.19 (s, 2H), 4.61 (s, 1H), 3.80 (s, 3H), 2.50-2.59 (m, 2H), 2.28-2.33 (m, 1H), 1.69 (m, 2H), 1.56-1.61 (m, 4H), 1.47 (m, 2H), 1.23 (m, 1H), 0.97-0.99 (m, 1H), 0.47-0.48 (m, 2H), 0.29-0.30 (m, 1H), 0.03-0.13 (m, 1H).<br>Mass Spectrum (LCMS, ESI pos.): Calcd. for C$_{28}$H$_{30}$FNO$_6$: 496.2 (M + H); found: 496.2. |
| 39 | (3S)-3-cyclopropyl-3-(3-((5-(2-fluoro-5-methoxyphenyl)-4-isobutoxyisoxazol-3-yl)methoxy)phenyl)propanoic acid<br>$^1$H-NMR (300 MHz, DMSO-d$_6$) δ (ppm): 7.11-7.40 (m, 4H), 6.87-6.96 (m, 3H), 5.22 (s, 2H), 3.80 (s, 3H), 3.74-3.76 (d, J = 6 Hz, 2H), 2.57-2.61 (m, 2H), 2.28-2.34 (m, 1H), 1.84-1.91 (m, 1H), 0.94-0.99 (m, 1H), 0.84-0.86 (d, J = 6 Hz, 6H), 0.47-0.51 (m, 1H), 0.21-0.35 (m, 2H), 0.02-0.18 (m, 1H).<br>Mass Spectrum (LCMS, ESI pos.): Calcd. for C$_{27}$H$_{30}$FNO$_6$: 484.2 (M + H); found: 484.2. |

| Cpd No. | Characterization |
|---|---|
| 40 | (S)-3-(3-((4-(Cyclopentyloxy)-5-(2-fluoro-5-methoxyphenyl)isoxazol-3-yl)methoxy)phenyl)-3-cyclopropylpropanoic acid<br>$^1$H-NMR (400 MHz, DMSO-$d_6$) δ (ppm): 7.35-7.41 (m, 1H), 7.29-7.32 (m, 1H), 7.21-7.25 (m, 1H), 7.14-7.20 (m, 1H), 6.96-7.01(m, 1H), 6.88-6.92 (m, 2H), 5.21 (s, 2H), 4.61 (s, 1H), 3.82 (s, 3H), 2.53-2.68 (m, 2H), 2.23-2.36 (m, 1H), 1.67-1.75 (m, 2H), 1.55-1.67 (m, 4H), 1.41-1.52 (m, 2H), 0.93-1.05 (m, 1H), 0.45-0.53 (m, 1H), 0.22-0.31 (m, 2H), 0.06-0.17(m, 1H).<br>Mass Spectrum (LCMS, ESI pos.): Calcd. for $C_{28}H_{30}FNO_6$: 496.2 (M + H); found: 496.2. |
| 41 | (3S)-3-Cyclopropyl-3-(3-[[4-(cyclopropylmethoxy)-5-(2-fluoro-5-methoxyphenyl)isoxazol-3-yl]methoxy]phenyl)propanoic acid<br>$^1$H-NMR (400 MHz, DMSO-$d_6$) δ (ppm): 7.33-7.41 (m, 2H), 7.12-7.22 (m, 2H), 6.79-6.92 (m, 3H), 5.21 (s, 2H), 3.81-3.83 (m, 5H), 2.27-2.50 (m, 3H), 0.87-1.23 (m, 2H), 0.39-0.45 (m, 3H), 0.16-0.28 (m, 4H), 0.04-0.10 (m, 1H).<br>Mass Spectrum (LCMS, ESI pos.): Calcd. for $C_{27}H_{28}FNO_6$: 482.2(M + H); found: 482.2. |
| 42 | (3S)-3-Cyclopropyl-3-(3-((5-(2-fluoro-5-methoxyphenyl)-4-isopropoxyisoxazol-3-yl)methoxy)phenyl)propanoic acid<br>$^1$H-NMR (300 MHz, DMSO-$d_6$) δ (ppm): 7.23-7.36 (m, 2H), 7.10-7.20 (m, 2H), 6.88-6.96 (m, 3H), 5.19 (s, 2H), 4.19-4.27 (m, 1H), 3.80 (s, 3H), 2.62-2.65 (m, 2H), 2.26-2.32 (m, 1H), 1.14-1.16 (d, J = 6Hz, 6H), 0.98-1.01 (m, 1H), 0.47-0.50 (m, 1H), 0.22-0.32 (m, 2H), 0.06-0.11 (m, 1H).<br>Mass Spectrum (LCMS, ESI pos.): Calcd. for $C_{27}H_{30}FNO_6$: 470.5 (M + H); found: 470.1. |
| 47 | (3S)-3-Cyclopropyl-3-(3-((5-(5-fluoro-2-methoxypyridin-4-yl)-4-isobutoxyisoxazol-3-yl)methoxy)phenyl)propanoic acid<br>$^1$H-NMR (300 MHz, DMSO-$d_6$) δ (ppm): 8.14(s, 1H), 6.98-7.04 (m, 2H), 6.66-6.72 (m, 3H), 5.03 (s, 2H), 3.80(s, 3H), 3.74-3.76 (d, J = 6 Hz, 2H), 2.57-2.61 (m, 2H), 2.28-2.34 (m, 1H), 1.84-1.91 (m, 1H), 0.94-0.99 (m, 1H), 0.84-0.86 (d, J = 6 Hz, 6H),0.47-0.51 (m, 1H), 0.21-0.35 (m, 2H), 0.02-0.18(m, 1H). Mass Spectrum (LCMS, ESI pos.): Calcd. for $C_{26}H_{29}FN_2O_6$: 485.2 (M + H); found: 485.2. |

Example 14

(3S)-3-Cyclopropyl-3-(3-((5-(2-fluoro-5-methoxyphenyl)-4-((2,2,3,3-tetramethylcyclopropyl)methoxy)isoxazol-3-yl)methoxy)phenyl)propanoic acid (Cpd 11)

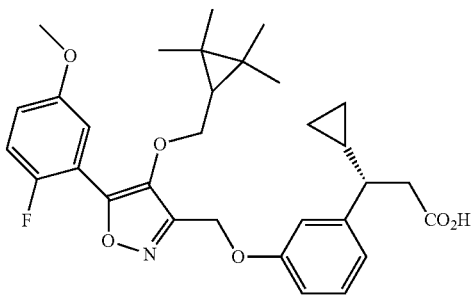 [SMILES: COc1ccc(F)c(-c2onc(COc3cccc([C@@H](CC(=O)O)C4CC4)c3)c2OCC2C(C)(C)C2(C)C)c1]

A. Ethyl 4-(benzyloxy)-5-(2-fluoro-5-methoxyphenyl)isoxazole-3-carboxylate, 14a

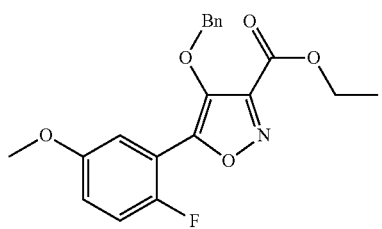

14a

The mixture of ethyl 4-(benzyloxy)-5-bromo-1,2-oxazole-3-carboxylate (3.0 g, 9.2 mmol, as prepared in Example, Step B), (2-fluoro-5-methoxyphenyl)boronic acid (2.35 g, 13.8 mmol), Pd(dppf)Cl$_2$ (340 mg, 0.46 mmol), Cs$_2$CO$_3$ (9 g, 27.6 mmol) in water (12 mL) and dioxane (48 mL) was stirred for 1 h at 90° C. The reaction mixture was allowed to cool to RT and treated with satd. NH$_4$Cl (aq., 60 mL). The resulting solution was extracted with EtOAc (3×60 mL) and the organic layers combined and concentrated under reduced pressure. The residue obtained was purified by flash chromatography (EtOAc/petroleum ether 15:85) on silica gel to obtain compound 14a as a yellow solid. Mass Spectrum (LCMS, ESI pos.): Calcd. for $C_{20}H_{18}FNO_5$: 372.1 (M+H); found: 372.0.

B. Ethyl 5-(2-fluoro-5-methoxyphenyl)-4-hydroxy-isoxazole-3-carboxylate, 14b

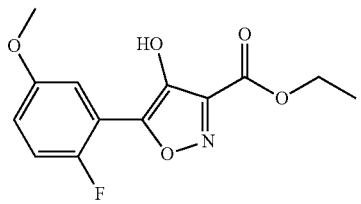

A mixture of compound 14b (2.0 g, 5.4 mmol), Pd on carbon (10%, 0.5 g), methanol (30 mL) was stirred for 0.5 h at RT under $H_2$ (g) (3 atm). The solids were removed by filtration. The filtrate was concentrated under reduced pressure to provide compound 14b as a white solid. Mass Spectrum (LCMS, ESI pos.): Calcd. For $C_{13}H_{12}FNO_5$: 282.1 (M+H); found: 282.0.

C. Ethyl 5-(2-fluoro-5-methoxyphenyl)-4-((2,2,3,3-tetramethylcyclopropyl)methoxy)isoxazole-3-carboxylate, 14c

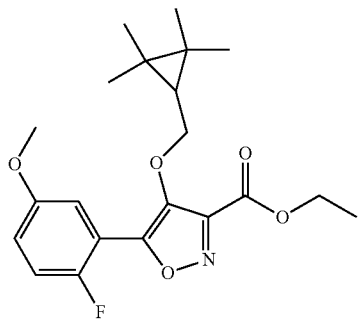

To a solution of compound 14b (400 mg, 1.42 mmol), (2,2,3,3-tetramethylcyclopropyl)methanol (184 mg, 1.44 mmol) and (n-Bu)$_3$P (720 mg, 3.58 mmol) in toluene (20 mL), a solution of ADDP (922 mg, 3.68 mmol) in toluene (20 mL) was added dropwise with stirring. The resulting solution was stirred overnight at 60° C., allowed to cool to RT and then quenched by the addition of satd. NH$_4$Cl (aq. 50 mL). The resulting solution was extracted with EtOAc (3×50 mL). The organic layers were combined and concentrated. The residue obtained was purified by flash chromatography (EtOAc/petroleum ether 1:10) on silica gel to obtain compound 14c as colorless oil. Mass Spectrum (LCMS, ESI pos.): Calcd. for $C_{21}H_{26}FNO_5$: 392.2 (M+H); found: 392.0.

D. (5-(2-Fluoro-5-methoxyphenyl)-4-((2,2,3,3-tetramethylcyclopropyl)methoxy)isoxazol-3-yl)methanol, 14d

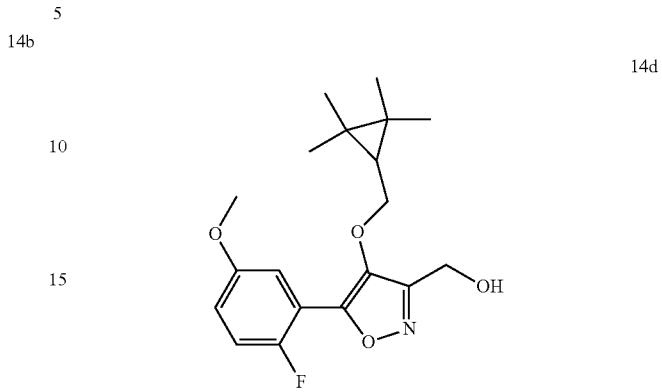

To a stirring solution of compound 14c (324 mg, 0.83 mmol) in THF (10 mL) was added LiAlH$_4$ (63 mg, 1.66 mmol) in portions at 0° C. The resulting solution was stirred for 2 h at RT and quenched by the addition of satd. NH$_4$Cl (aq. 10 mL). The solids were removed by filtration and the resulting solution was washed with EtOAc (3×10 mL). The organic washings were combined and concentrated. The residue obtained was purified by flash chromatography (EtOAc/petroleum ether 1:5-1:3) on silica gel to obtain compound 14d as a colorless oil. Mass Spectrum (LCMS, ESI pos.): Calcd. for $C_{19}H_{24}FNO_4$: 350.2 (M+H). found: 350.0.

E. 3-(Chloromethyl)-5-(2-fluoro-5-methoxyphenyl)-4-((2,2,3,3-tetramethylcyclopropyl)methoxy)isoxazole, 14e

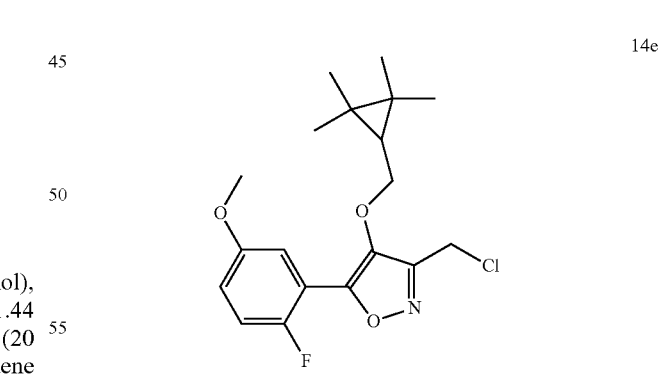

To a stirring solution of compound 14d (152 mg, 0.44 mmol) in DCM (10 mL) and DMF (1 mL) was added thionyl chloride (104 mg, 0.87 mmol) dropwise at 0° C. The resulting solution was stirred for 30 min at 0° C. The reaction was then quenched by the addition of satd. sodium bicarbonate (aq. 50 mL). The resulting solution was extracted with EtOAc (3×50 mL). The organic layers were combined and dried over anhydrous sodium sulfate and concentrated to give the title compound as a yellow oil.

F. (3S)-Methyl 3-cyclopropyl-3-(3-((5-(2-fluoro-5-methoxyphenyl)-4-((2,2,3,3-tetramethylcyclopropyl)methoxy)isoxazol-3-yl)methoxy)phenyl) propanoate, 14f

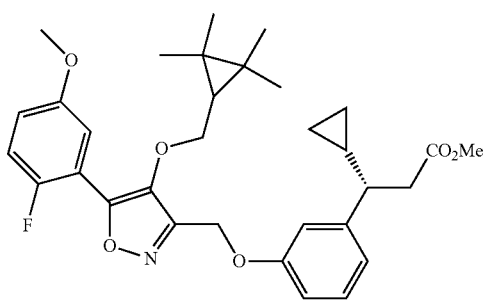

A solution of compound 14e (141 mg, 0.38 mmol), (S)-methyl 3-cyclopropyl-3-(3-hydroxyphenyl)propanoate (101 mg, 0.46 mmol) and $Cs_2CO_3$ (248 mg, 0.76 mmol) in $CH_3CN$ (10 mL) was stirred for 2 h at 50° C. The reaction was allowed to cool to RT and treated with water (50 mL). The resulting solution was extracted with EtOAc (3×50 mL). The organic layers were combined and concentrated. The residue obtained was purified by flash chromatography (EtOAc/petroleum ether) on silica gel to obtain compound 14f as a colorless oil. Mass Spectrum (LCMS, ESI pos.): Calcd. for $C_{32}H_{38}FNO_6$: 552.3 (M+H). found: 552.1.

G. (3S)-3-Cyclopropyl-3-(3-((5-(2-fluoro-5-methoxyphenyl)-4-((2,2,3,3-tetramethylcyclopropyl)methoxy)isoxazol-3-yl)methoxy)phenyl)propanoic acid, Cpd 11

A mixture of compound 14f (110 mg, 0.20 mmol) and LiOH (50 mg, 2.09 mmol) in THF (5 mL), water (2 mL) and methanol (1 mL) was stirred overnight at RT. The resulting mixture was concentrated to remove organic solvents. The pH value of the resulting solution was adjusted to 4-5 with 1 N hydrogen chloride solution. The solids formed were collected by filtration and dried in an oven under reduced pressure to obtain the title compound 11 as a light yellow solid. $^1$H-NMR (300 MHz, DMSO-$d_6$) δ (ppm): 7.32-7.40 (m, 2H), 7.22-7.27 (m, 1H), 7.12-7.17 (m, 1H), 6.89-6.96 (m, 3H), 5.21 (s, 2H), 4.06 (d, J=7.8 Hz, 2H), 3.80 (s, 3H), 2.62-2.76 (m, 2H), 2.26-2.33 (m, 1H), 0.82-1.03 (m, 14H), 0.45-0.50 (m, 2H), 0.22-0.33 (m, 2H), 0.03-0.10 (m, 1H). Mass Spectrum (LCMS, ESI pos.): Calcd. for $C_{31}H_{36}FNO_6$: 538.3 (M+H); found: 538.2.

Following the procedures described in Example 14, and substituting suitably selected reagents, starting materials and conditions as would be readily apparent to those skilled in the art, the following representative compounds of the present invention were prepared.

| Cpd No. | Characterization |
|---|---|
| 2 | (S)-3-Cyclopropyl-3-(3-((5-(5-fluoro-2-methoxypyridin-4-yl)-4-((3,3,5,5-tetramethylcyclohexyl)oxy)isoxazol-3-yl)methoxy)phenyl)propanoic acid<br>$^1$H-NMR (400 MHz, DMSO-$d_6$) δ (ppm): 8.40 (s, 1H), 7.21-7.27 (m, 2H), 6.88-6.94 (m, 3H), 5.20 (s, 2H), 4.32-4.38 (m, 1H), 3.89 (s, 3H), 2.61-2.65 (m, 2H), 2.24-2.30 (m, 1H), 1.74-1.76 (d, J = 8 Hz, 2H), 1.09-1.15 (m, 3H), 0.96-1.03 (m, 2H), 0.83 (s, 6H), 0.73 (s, 6H), 0.46-0.50 (m, 1H), 0.22-0.28 (m, 2H), 0.09-0.11 (m, 1H).<br>Mass Spectrum (LCMS, ESI pos.): Calcd. for $C_{32}H_{39}FN_2O_6$: 567.3 (M + H); found: 567.3. |
| 3 | (S)-3-Cyclopropyl-3-(3-((5-(2-fluoro-5-methoxyphenyl)-4-((3,3,5,5-tetramethylcyclohexyl)oxy)isoxazol-3-yl)methoxy)phenyl)propanoic acid<br>$^1$H-NMR (400 MHz, DMSO-$d_6$): δ (ppm): 7.31-7.35 (m, 1H), 7.25-7.27 (m, 1H), 7.14-7.17 (m, 2H), 6.86-6.91 (m, 3H), 5.14 (s, 2H), 4.21-4.28 (m, 1H), 3.80 (s, 3H), 2.34-2.45 (m, 3H), 1.69-1.71 (d, J = 8 Hz, 2H), 1.05-1.14 (m, 3H), 0.93-1.02 (m, 2H), 0.81 (s, 6H), 0.69 (s, 6H), 0.42-0.46 (m, 1H), 0.24-0.29 (m, 2H), 0.06-0.08 (m, 1H).<br>Mass Spectrum (LCMS, ESI pos.): Calcd. for $C_{33}H_{40}FNO_6$: 566.3 (M + H); found: 566.3. |
| 4 | (S)-3-Cyclopropyl-3-(3-((5-(5-fluoro-2-methoxypyridin-4-yl)-4-((3,3,4,4-tetramethylcyclopentyl)oxy)isoxazol-3-yl)methoxy)phenyl)propanoic acid<br>$^1$H-NMR (300 MHz, DMSO-$d_6$) δ (ppm): 8.39 (s, 1H), 7.18-7.24 (m, 2H), 6.87-6.93 (m, 3H), 5.22 (s, 2H), 4.74-4.77 (m, 1H), 3.89 (s, 3H), 2.51-2.53 (m, 2H), 2.32-2.38 (m, 1H), 1.89-1.97 (m, 2H), 1.68-1.74 (m, 2H), 0.91-0.94 (m, 1H), 0.84 (s, 6H), 0.70 (s, 6H), 0.43-0.45 (m, 1H), 0.23-0.27 (m, 2H), 0.07-0.10 (m, 1H).<br>Mass Spectrum (LCMS, ESI pos.): Calcd. for $C_{31}H_{37}FN_2O_6$: 553.3 (M + H); found: 553.3. |

Example 15

(3S)-3-Cyclopropyl-3-(3-((4-((3,3-dimethylcyclobutyl)methoxy)-5-(2-fluoro-5-methoxyphenyl)isoxazol-3-yl)methoxy)phenyl)propanoic acid (Cpd 5)

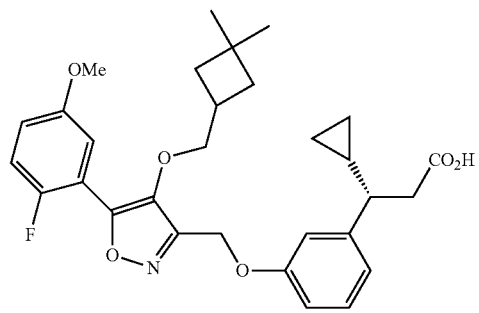 [SMILES: COc1ccc(F)c(-c2onc(COc3cccc([C@@H](CC(=O)O)C4CC4)c3)c2OCC2CC(C)(C)C2)c1]

A. Ethyl 4-((3,3-dimethylcyclobutyl)methoxy)isoxazole-3-carboxylate, 15a

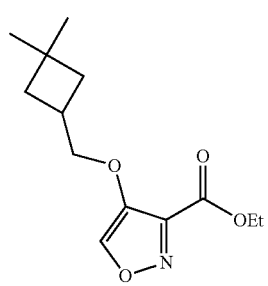

To a stirring solution of ethyl 4-hydroxy-1,2-oxazole-3-carboxylate (551 mg, 3.51 mmol, as prepared in Example 13, Step B), (3,3-dimethylcyclobutyl)methanol (400 mg, 3.50 mmol) and n-Bu₃P (2.13 g, 10.6 mmol) in toluene (10 mL) was added a solution of ADDP (1.78 g, 7.09 mmol) in toluene (10 mL) dropwise at 0° C. The resulting solution was stirred overnight at 60° C. The resulting mixture was allowed to cool to RT and concentrated. The residue obtained was purified by flash chromatography (EtOAc/petroleum ether 1:20) on silica gel to obtain compound 15a as a colorless oil). Mass Spectrum (LCMS, ESI pos.): Calcd. for $C_{13}H_{19}NO_4$: 254.1 (M+H); found: 254.1.

B. (4-((3,3-Dimethylcyclobutyl)methoxy)isoxazol-3-yl)methanol, 15b

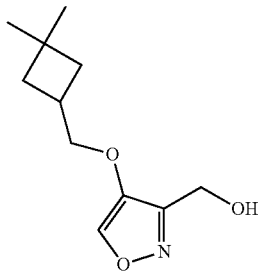

15b

To a stirring solution of compound 15a (670 mg, 2.65 mmol) in THF (20 mL) was added LiAlH₄ (213 mg, 5.61 mmol) in portions at 0° C. The resulting solution was stirred for 2 h at 0° C. and then treated with H₂O (1 mL). The solids formed were removed by filtration. The filter cake was washed with DCM/EtOAc (1:1, 3×30 mL). The organic filtrates were combined and concentrated. The residue obtained was purified by flash chromatography (EtOAc/petroleum ether 1:5) on silica gel to obtain compound 15b as a colorless oil. Mass Spectrum (LCMS, ESI pos.): Calcd. for $C_{11}H_{17}NO_3$: 212.1 (M+H); found: 212.1.

C. (5-Bromo-4-((3,3-dimethylcyclobutyl)methoxy)isoxazol-3-yl)methanol, 15c

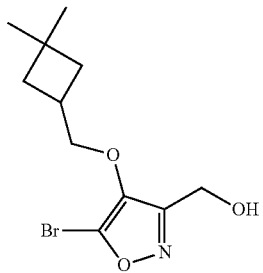

15c

To a stirring solution of compound 15b (430 mg, 2.04 mmol) in DMF (1 mL) was added a solution of NBS (1.09 g, 6.12 mmol) in DMF (5 mL) dropwise. The resulting solution was stirred for 2 h at 50° C. The reaction mixture was allowed to cool to RT, treated with H₂O (50 mL), and extracted with EtOAc (3×100 mL). The organic layers were combined and concentrated. The residue obtained was purified by flash chromatography (EtOAc/petroleum ether 1:5) on silica gel to obtain compound 15c as a colorless oil). Mass Spectrum (LCMS, ESI pos.): Calcd. for $C_{11}H_{16}BrNO_3$: 290.0 (M+H); found: 290.0.

D. 5-Bromo-3-(chloromethyl)-4-((3,3-dimethylcyclobutyl)methoxy)isoxazole, 15d

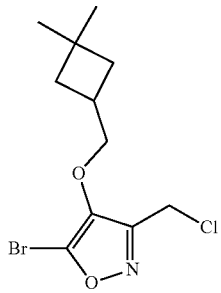

15d

To a stirring solution of compound 15c (310 mg, 1.07 mmol) in DMF (1 mL) and DCM (10 mL) was added a solution of thionyl chloride (383 mg, 3.22 mmol) in DCM (2 mL) dropwise at 0° C. The resulting solution was stirred for 2 h at 0° C. and then quenched with satd. NaHCO₃ (aq. 5 mL). The resulting solution was extracted with EtOAc (3×50 mL). The organic layers were combined and dried over Na₂SO₄ and concentrated to give compound 15d as a colorless oil).

E. (S)-Methyl 3-(3-((5-bromo-4-((3,3-dimethylcyclobutyl)methoxy) isoxazol-3-yl)methoxy)phenyl)-3-cyclopropylpropanoate, 15e

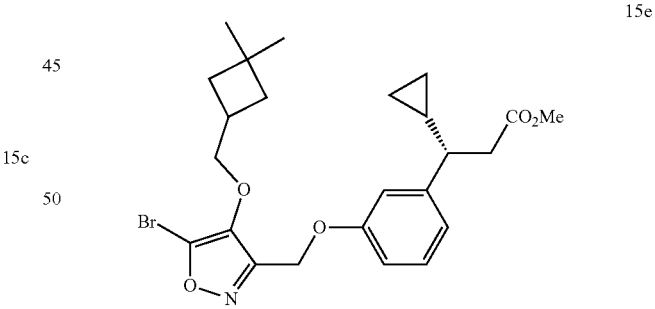

15e

A mixture of compound 15d (287 mg, 0.93 mmol), (S)-methyl 3-cyclopropyl-3-(3-hydroxyphenyl)propanoate (307 mg, 1.39 mmol) and Cs₂CO₃ (757 mg, 2.32 mmol) in CH₃CN (10 mL) was stirred overnight at RT. The reaction was then quenched with water (5 mL). The resulting solution was extracted with EtOAc (3×20 mL). The organic layers were combined and concentrated. The residue obtained was purified by flash chromatography (EtOAc/petroleum ether 1:10) on silica gel to obtain compound 15e as a colorless oil. Mass Spectrum (LCMS, ESI pos.): Calcd. for $C_{24}H_{30}BrNO_5$: 492.1 (M+H); found: 492.1.

F. (3S)-Methyl 3-cyclopropyl-3-(3-((4-((3,3-dimethylcyclobutyl)methoxy)-5-(2-fluoro-5-methoxyphenyl)isoxazol-3-yl)methoxy)phenyl)propanoate, 15f

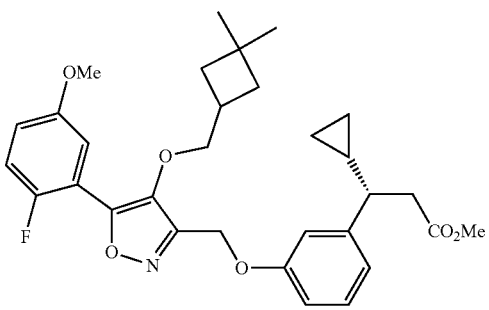

15f

A mixture of compound 15e (100 mg, 0.20 mmol), (2-fluoro-5-methoxyphenyl)boronic acid (75 mg, 0.44 mmol), Pd(dppf)Cl$_2$ (8 mg, 0.01 mmol) and potassium carbonate (75 mg, 0.54 mmol) in DME (0.8 mL) and water (0.2 mL) was stirred overnight at 80° C. under N$_2$. The resulting mixture was concentrated and the residue obtained was purified by flash chromatography (10-20% EtOAc/petroleum ether) on silica gel to obtain compound 15f as a colorless oil. Mass Spectrum (LCMS, ESI pos.): Calcd. for C$_{31}$H$_{36}$FNO$_6$: 538.3 (M+H); found: 538.3.

G. (3S)-3-cyclopropyl-3-(3-((4-((3,3-dimethylcyclobutyl)methoxy)-5-(2-fluoro-5-methoxyphenyl)isoxazol-3-yl)methoxy)phenyl)propanoic acid, Cpd 5

A mixture of compound 15f (52 mg, 0.10 mmol) and LiOH (25 mg, 1.04 mmol) in THF (2 mL), water (1 mL), and methanol (0.5 mL) was stirred overnight at RT. The resulting mixture was concentrated to remove organic solvents and the pH of the resulting solution was adjusted to 3-4 with 1 N HCl solution. The solids formed were collected by filtration and dried in an oven under reduced pressure to obtain the title compound 5 as a yellow solid. $^1$H-NMR (300 MHz, DMSO-d$_6$) δ (ppm): 7.28-7.37 (m, 1H), 7.23-7.28 (m, 2H), 7.13-7.18 (m, 1H), 6.89-6.96 (m, 3H), 5.21 (s, 2H), 3.92 (d, J=6.6 Hz, 2H), 3.80 (s, 3H), 2.64-2.68 (m, 2H), 2.47-2.50 (m, 1H), 2.26-2.29 (m, 1H), 1.67-1.70 (m, 2H), 1.47-1.64 (m, 2H), 0.92-1.05 (m, 7H), 0.40-0.56 (m, 1H), 0.20-0.40 (m, 2H), 0.02-0.11 (m, 1H). Mass Spectrum (LCMS, ESI pos.): Calcd. for C$_{30}$H$_{34}$FNO$_6$: 524.2 (M+H); found: 524.3.

Following the procedures described in Example 15, and substituting suitably selected reagents, starting materials and conditions as would be readily apparent to those skilled in the art, the following representative compound of the present invention was prepared.

| Cpd No. | Characterization |
|---|---|
| 8 | (S)-3-Cyclopropyl-3-(3-((4-((3,3-dimethylcyclobutyl)methoxy)-5-(5-fluoro-2-methoxypyridin-4-yl)isoxazol-3-yl)methoxy)phenyl)propanoic acid<br>$^1$H-NMR (300 MHz, DMSO-d$_6$) δ (ppm): 8.39 (d, J = 2.4 Hz, 1H), 7.17-7.29 (m, 2H), 6.89-6.96 (m, 3H), 5.25 (s, 2H), 4.01 (d, J = 6.9 Hz, 2H), 3.88 (s, 3H), 2.53-2.69 (m, 3H), 2.20-2.32 (m, 1H), 1.64-1.75 (m, 2H), 1.50-1.57 (m, 2H), 0.95-1.10 (m, 7H), 0.45-0.55 (m, 1H), 0.35-0.17 (m, 2H), 0.05-0.11 (m, 1H).<br>Mass Spectrum (LCMS, ESI pos.): Calcd. for C$_{29}$H$_{33}$FN$_2$O$_6$: 525.2 (M + H); found: 525.3. |

Example 16

(3S)-3-cyclopropyl-3-(3-((5-(5-fluoro-2-methoxypyridin-4-yl)-4-(2-methylprop-1-enyl)isoxazol-3-yl)methoxy)phenyl)propanoic acid (Cpd 52)

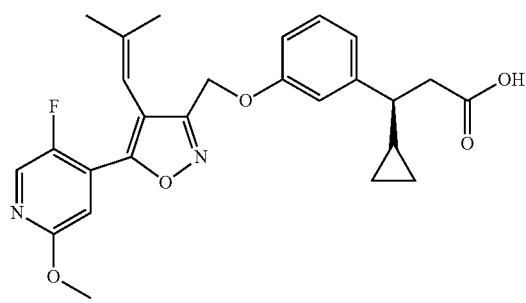 [SMILES: COc1cc(-c2onc(COc3cccc([C@@H](CC(=O)O)C4CC4)c3)c2C=C(C)C)c(F)cn1]

A. Ethyl 4-(benzyloxy)isoxazole-3-carboxylate, 16a

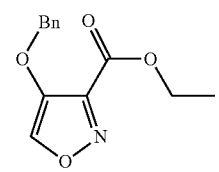

16a

A mixture of ethyl 4-hydroxyisoxazole-3-carboxylate (3.0 g, 19 mmol, as prepared in Example 13, Step B), (bromomethyl)benzene (3.6 g, 21 mmol) and Cs$_2$CO$_3$ (9.4 g, 29 mmol) in DMF (50 mL) was stirred for 2 h at 50° C. The reaction mixture was allowed to cool to RT and treated with H$_2$O (50 mL). The resulting solution was extracted with EtOAc (3×50 mL). The organic layers were combined, dried over Na$_2$SO$_4$ and concentrated. The residue obtained was purified by flash chromatography (0-15% EtOAc/petroleum ether) on silica gel to obtain compound 16a as a white solid. Mass Spectrum (LCMS, ESI pos.): Calcd. for C$_{13}$H$_{13}$NO$_4$: 248.1 (M+H); found: 248.0.

B. Ethyl 4-(benzyloxy)-5-bromoisoxazole-3-carboxylate, 16b

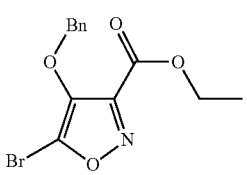

16b

A solution of compound 16a (3.7 g, 15 mmol) and NBS (4 g, 22.5 mmol) in DMF (50 mL) was stirred overnight at 60° C. The reaction mixture was allowed to cool to RT and treated with satd. NH₄Cl (aq. 100 mL). The resulting solution was extracted with EtOAc (3×100 mL). The organic layers were combined, dried over Na₂SO₄ and concentrated. The residue obtained was purified by flash chromatography (0-10% EtOAc/petroleum ether) on silica gel to obtain compound 16b as a yellow oil. Mass Spectrum (LCMS, ESI pos.): Calcd. for $C_{13}H_{12}BrNO_4$: 326.0 (M+H); found: 325.9.

C. Ethyl 4-(benzyloxy)-5-(5-fluoro-2-methoxypyridin-4-yl)isoxazole-3-carboxylate, 16c

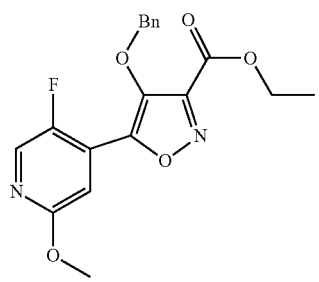

16c

A mixture of compound 16b (550 mg, 1.69 mmol), (5-fluoro-2-methoxypyridin-4-yl)boronic acid (433 mg, 2.53 mmol), Cs₂CO₃ (1.65 g, 5.06 mmol), Pd(dppf)Cl₂ (123 mg, 0.17 mmol) in water (3 mL) and 1,4-dioxane (12 mL) was stirred for 1 h at 80° C. under N₂. The reaction mixture was allowed to cool to RT and treated with satd. NH₄Cl (aq. 15 mL). The resulting solution was extracted with EtOAc (3×15 mL). The organic layers were combined, dried over Na₂SO₄ and concentrated under reduced pressure. The residue obtained was purified by flash chromatography (0-15% EtOAc/petroleum ether) on silica gel to obtain compound 16c as a colorless oil. Mass Spectrum (LCMS, ESI pos.): Calcd. for $C_{19}H_{17}FN_2O_5$: 373.1 (M+H); found: 373.1.

D. Ethyl 5-(5-fluoro-2-methoxypyridin-4-yl)-4-hydroxyisoxazole-3-carboxylate, 16d

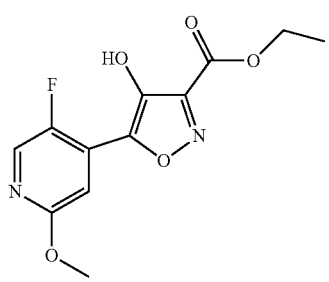

16d

A mixture of compound 18c (450 mg, 1.21 mmol) and Pd/C (10%, wet, 150 mg) in methanol (15 mL) was stirred for 30 min at RT under a H₂ (g) (3 atm). The solids were removed by filtration and the filtrate was concentrated to give compound 16d as a yellow solid. Mass Spectrum (LCMS, ESI pos.): Calcd. for $C_{12}H_{11}FN_2O_5$: 283.1 (M+H); found: 283.0.

E. Ethyl 5-(5-fluoro-2-methoxypyridin-4-yl)-4-(trifluoromethylsulfonyl-oxy)isoxazole-3-carboxylate, 16e

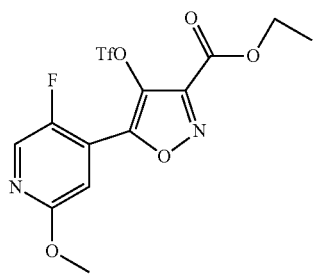

16e

To a stirring solution of compound 16d (320 mg, 1.13 mmol) and 2,6-dimethylpyridine (182 mg, 1.70 mmol) in DCM (10 mL) was added Tf₂O (182 mg, 0.65 mmol) dropwise. The resulting solution was stirred for 1 h at RT. The reaction mixture was treated with satd. NH₄Cl (aq. 10 mL) and extracted with EtOAc (3×10 mL). The organic layers were combined, dried over Na₂SO₄ and concentrated. The residue obtained was purified by flash chromatography (0-10% EtOAc/petroleum ether) on silica gel to obtain compound 16e as a colorless oil. Mass Spectrum (LCMS, ESI pos.): Calcd. for $C_{13}H_{10}F_4N_2O_7S$: 415.0 (M+H); found: 414.9.

F. Ethyl 5-(5-fluoro-2-methoxypyridin-4-yl)-4-(2-methylprop-1-enyl)isoxazole-3-carboxylate, 16f

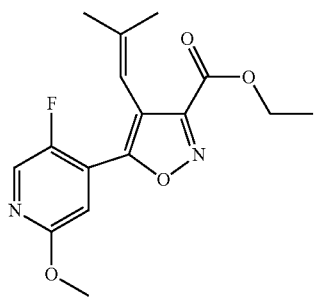

16f

A mixture of compound 16e (450 mg, 1.09 mmol), 4,4,5,5-tetramethyl-2-(2-methylprop-1-en-1-yl)-1,3,2-dioxaborolane (300 mg, 1.65 mmol), Pd(dppf)Cl₂ (80 mg, 0.11 mmol) and Cs₂CO₃ (880 mg, 2.70 mmol) in water (2 mL) and 1,4-dioxane (8 mL) was stirred for 0.5 h at 85° C. under N₂. The reaction mixture was allowed to cool to RT and treated with H₂O (10 mL). The resulting solution was extracted with EtOAc (3×10 mL). The separated organic layers were combined, dried over Na₂SO₄ and concentrated. The residue obtained was purified by flash chromatography (0-10% EtOAc/petroleum ether) on silica gel to obtain compound 16f as a colorless oil. Mass Spectrum (LCMS, ESI pos.): Calcd. for $C_{16}H_{17}FN_2O_4$: 321.1 (M+H); found: 321.0.

G. (3S)-3-cyclopropyl-3-(3-((5-(5-fluoro-2-methoxypyridin-4-yl)-4-(2-methylprop-1-enyl)isoxazol-3-yl)methoxy)phenyl)propanoic acid, Cpd 52

Compound 52 was prepared from compound 16f following the procedures described in Example 3, Steps E-H. $^1$H-NMR (400 MHz, DMSO-d$_6$) δ (ppm): 8.38 (d, J=2.0 Hz, 1H), 7.18 (t, J=8.0 Hz, 1H), 7.09 (d, J=4.8 Hz, 1H), 6.81-6.88 (m, 3H), 6.02 (s, 1H), 5.14 (s, 2H), 3.88 (s, 3H), 2.29-2.48 (m, 3H), 1.87 (s, 3H), 1.31 (s, 3H), 0.88-0.95 (m, 1H), 0.42-0.45 (m, 1H), 0.22-0.34 (m, 2H), 0.04-0.07 (m, 1H). Mass Spectrum (LCMS, ESI pos.): Calcd. for C$_{26}$H$_{27}$FN$_2$O$_5$: 467.2 (M+H); found: 467.2.

Example 17

(3S)-3-Cyclopropyl-3-(3-((5-(5-fluoro-2-methoxypyridin-4-yl)-4-isobutylisoxazol-3-yl)methoxy)phenyl)propanoic acid (Cpd 12)

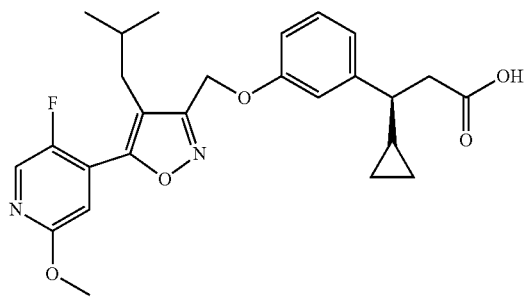 [SMILES: COc1cc(-c2onc(COc3cccc([C@@H](CC(=O)O)C4CC4)c3)c2CC(C)C)c(F)cn1]

A mixture of compound 52 (100 mg, 0.21 mmol, as prepared in Example 16) and 10% palladium on carbon (50 mg) in methanol (10 mL) was stirred 3 h at RT under a H$_2$ (g) (3 atm). The solids were removed by filtration. The filtrate was concentrated and the residue obtained was purified by flash chromatography (0-95% DCM/methanol) on silica gel to obtain compound 12 as a gray solid. $^1$H-NMR (400 MHz, DMSO-d$_6$) δ (ppm): 8.41 (s, 1H), 7.21 (t, J=7.6 Hz, 1H), 7.15 (d, J=4.4 Hz, 1H), 6.86-6.92 (m, 3H), 5.22 (s, 2H), 3.90 (s, 3H), 2.43-2.51 (m, 4H), 2.31-2.33 (m, 1H), 1.75-1.78 (m, 1H), 0.91-0.95 (m, 1H), 0.74 (d, J=6.8 Hz, 6H), 0.43-0.45 (m, 1H), 0.25-0.28 (m, 2H), 0.06-0.07 (m, 1H). Mass Spectrum (LCMS, ESI pos.): Calcd. for C$_{26}$H$_{29}$FN$_2$O$_5$: 469.2 (M+H); found: 469.3.

Example 18

(3S)-3-Cyclopropyl-3-(3-((4-ethoxy-5-(2-fluoro-5-methoxyphenyl)isoxazol-3-yl)methoxy)phenyl)propanoic acid (Cpd 50)

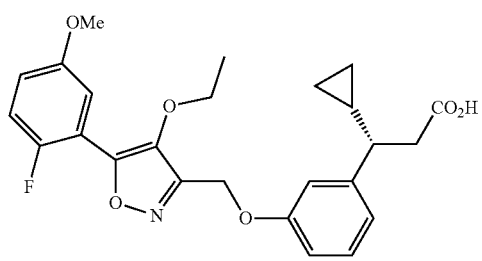 [SMILES: CCOc1c(COc2cccc([C@@H](CC(=O)O)C3CC3)c2)noc1-c1cc(OC)ccc1F]

A. Ethyl 4-(neopentyloxy)isoxazole-3-carboxylate, 18a

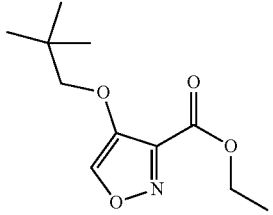

To a stirring solution of ethyl 4-hydroxyisoxazole-3-carboxylate (1.5 g, 9.6 mmol, as prepared in Example 13, Step B), 2,2-dimethylpropan-1-ol (1.26 g, 14.3 mmol) and n-Bu$_3$P (40.4 g, 20 mmol) in toluene (20 mL) was added a solution of ADDP (5.1 g, 20.2 mmol) in toluene (20 mL) dropwise at 0° C. The resulting solution was stirred overnight at 60° C. The reaction mixture was allowed to cool to RT and treated with satd. NH$_4$Cl (aq. 50 mL). The resulting solution was extracted with EtOAc (3×20 mL). The organic layers were combined, dried over Na$_2$SO$_4$ and concentrated. The residue obtained was purified by flash chromatography (0-5% EtOAc/petroleum ether) on silica gel to obtain compound 18a as a light yellow solid. Mass Spectrum (LCMS, ESI pos.): Calcd. for: C$_{11}$H$_{17}$NO$_4$: 228.1 (M+H); found: 228.1.

B. Ethyl 5-bromo-4-(neopentyloxy)isoxazole-3-carboxylate, 18b

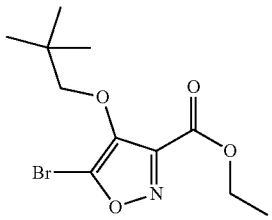

A solution of compound 18a (500 mg, 2.64 mmol) and NBS (941 mg, 5.29 mmol), in DMF (6 mL) was stirred overnight at 80° C. The reaction mixture was allowed to cool to RT and was then quenched with satd. NH$_4$Cl (aq. 20 mL). The resulting solution was extracted with EtOAc (3×10 mL), and the organic layers were combined, dried over Na$_2$SO$_4$ and concentrated. The residue obtained was purified by flash chromatography (0-5% EtOAc/petroleum ether) on silica gel to obtain compound 18b as light yellow oil. Mass Spectrum (LCMS, ESI pos.): Calcd. for C$_{11}$H$_{16}$BrNO$_4$: 306.0 (M+H); found: 305.9.

C. Ethyl 5-(2-fluoro-5-methoxyphenyl)-4-(neopentyloxy)isoxazole-3-carboxylate, 18c

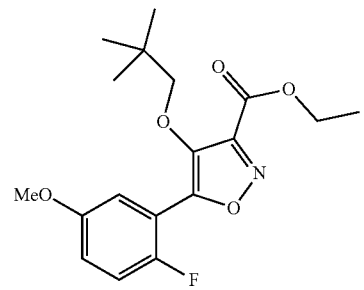

A mixture of compound 18b (150 mg, 0.49 mmol), (2-fluoro-5-methoxyphenyl)boronic acid (167 mg, 0.98 mmol), Pd(dppf)Cl$_2$ (20 mg, 0.02 mmol) and Cs$_2$CO$_3$ (320 mg, 0.98 mmol) in water (0.5 mL) and 1,4-dioxane (2 mL) was stirred for 1 h at 80° C. The reaction mixture was allowed to cool to RT and quenched with satd. NH$_4$Cl (aq. 5 mL). The resulting solution was extracted with EtOAc (3×10 mL). The organic layers were combined, dried over Na$_2$SO$_4$ and concentrated. The residue obtained was purified by flash chromatography (0-5% EtOAc/petroleum ether) on silica gel to obtain compound 18c as a light yellow oil. Mass Spectrum (LCMS, ESI pos.): Calcd. for C$_{18}$H$_{22}$FNO$_5$: 352.1 (M+H); found: 352.0.

D. (4-Ethoxy-5-(2-fluoro-5-methoxyphenyl)isoxazol-3-yl)methanol, 18d

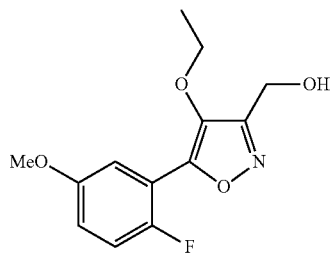

To a stirring solution of compound 18c (120 mg, 0.34 mmol) in THF (3 mL) at 0° C. was added LiAlH$_4$ (26 mg, 0.69 mmol) portionwise. The resulting solution was stirred at 0° C. for 30 min. and quenched by the addition of 2 g of Na$_2$SO$_4$·10H$_2$O. The solids were removed by filtration and the filtrate was concentrated. The residue obtained was purified by flash chromatography (0-20% EtOAc/petroleum ether) on silica gel to obtain compound 18d as a light yellow oil. Mass Spectrum (LCMS, ESI pos.): Calcd. for C$_{13}$H$_{14}$FNO$_4$: 268.1 (M+H); found: 268.0.

D. (3S)-3-cyclopropyl-3-(3-((4-ethoxy-5-(2-fluoro-5-methoxyphenyl)isoxazol-3-yl)methoxy)phenyl) propanoic acid, Cpd 50

Compound 50 was prepared from compound 18d following the procedures described in Example 3, Steps F-H.
$^1$H-NMR (300 MHz, DMSO-d6) δ (ppm): 11.95 (br, 1H), 7.13-7.40 (m, 4H), 6.89-6.97 (m, 3H), 5.22 (s, 2H), 4.03 (q, J$_1$=7.2 Hz, J$_2$=14.1 Hz, 2H), 3.81 (s, 3H), 2.64-2.68 (m, 2H), 2.25-2.28 (m, 1H), 1.21 (t, J=7.2 Hz, 3H), 0.93-1.02 (m, 1H), 0.41-0.49 (m, 1H), 0.24-0.29 (m, 2H), 0.07-0.12 (m, 1H). Mass Spectrum (LCMS, ESI pos.): Calcd. for C$_{25}$H$_{26}$FNO$_6$: 456.2 (M+H); found: 456.1.

Following the procedures described in Example 18, and substituting suitably selected reagents, starting materials and conditions as would be readily apparent to those skilled in the art, the following representative compound of the present invention was prepared.

| Cpd No. | Characterization |
|---|---|
| 51 | (S)-3-Cyclopropyl-3-(3-((4-ethoxy-5-(5-fluoro-2-methoxypyridin-4-yl)isoxazol-3-yl)methoxy)phenyl)propanoic acid<br>$^1$H-NMR (300 MHz, DMSO-d$_6$) δ (ppm): 11.94-12.11 (br.m, 1H), 8.40 (d, J = 2.1 Hz, 1H), 7.21-7.26 (m, 2H), 6.89-6.97 (m, 3H), 5.27 (s, 2H), 4.12 (q, J = 6.9 Hz, 2H), 3.90 (s, 3H), 2.56-2.65 (m, 2H), 2.26-2.31 (m, 1H), 1.25 (t, J = 6.3 Hz, 3H), 0.98-1.02 (m, 1H), 0.48-0.52 (m, 1H), 0.28-0.31 (m, 2H), 0.06-0.11 (m, 1H).<br>Mass Spectrum (LCMS, ESI pos.): Calcd. for C$_{24}$H$_{25}$FN$_2$O$_6$: 457.2 (M + H); found: 457.1. |

Example 19

(3S)-3-Cyclopropyl-3-(3-((5-(2-fluoro-5-methoxyphenyl)-4-(3,3,3-trifluoropropoxy)isoxazol-3-yl)methoxy)phenyl)propanoic acid (Cpd 49)

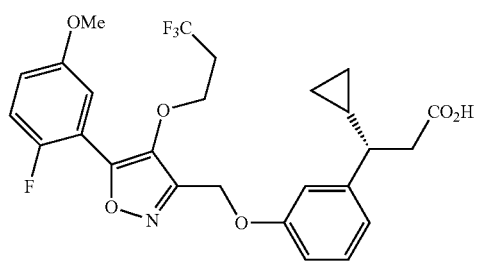 [SMILES: COc1ccc(F)c(-c2onc(COc3cccc([C@@H](CC(=O)O)C4CC4)c3)c2OCCC(F)(F)F)c1]

A. Ethyl 4-(3,3,3-trifluoropropoxy)isoxazole-3-carboxylate, 19a

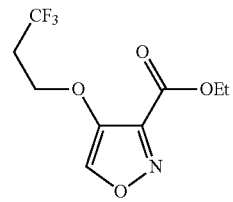

To a stirring solution of ethyl 4-hydroxyisoxazole-3-carboxylate (600 mg, 3.82 mmol, as prepared in Example 13, step B), 3,3,3-trifluoropropan-1-ol (653 mg, 5.72 mmol) and n-Bu$_3$P (1.54 g, 7.62 mmol) in toluene (60 mL) was added ADDP (1.93 g, 7.71 mmol) portionwise at 0° C. The resulting solution was stirred overnight at 60° C. The reaction mixture was allowed to cool to RT and treated with satd. NH$_4$Cl (aq. 100 mL). The resulting solution was extracted with EtOAc (3×100 mL). The organic layers were combined, dried over Na$_2$SO$_4$ and concentrated. The residue obtained was purified by flash chromatography (0-30% EtOAc/petroleum ether) on silica gel to obtain compound 19a as a white solid. Mass Spectrum (LCMS, ESI pos.): Calcd. for C$_9$H$_{10}$F$_3$NO$_4$: 254.1 (M+H); found: 254.0.

B. Ethyl 5-bromo-4-(3,3,3-trifluoropropoxy)isoxazole-3-carboxylate, 19b

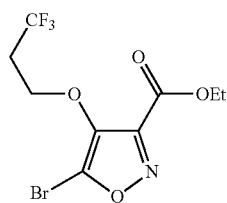

A solution of compound 19a (600 mg, 2.37 mmol) and NBS (2.11 g, 11.9 mmol) in DMF (10 mL) was stirred overnight at 60° C. The reaction mixture was allowed to cool to RT and treated with H$_2$O (10 mL). The resulting solution was extracted with EtOAc (3×10 mL). The organic layers were combined, dried over Na$_2$SO$_4$ and concentrated. The residue obtained was purified by flash chromatography (0-15% EtOAc/petroleum ether) on silica gel to obtain compound 19b as a yellow solid. Mass Spectrum (LCMS, ESI pos.): Calcd. for C$_9$H$_9$BrF$_3$NO$_4$: 332.0 (M+H); found: 332.0.

C. Ethyl 5-(2-fluoro-5-methoxyphenyl)-4-(3,3,3-trifluoropropoxy) isoxazole-3-carboxylate, 19c

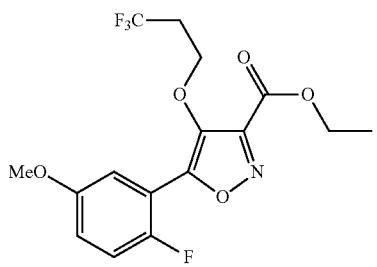

A mixture of compound 19b (450 mg, 1.36 mmol), (2-fluoro-5-methoxyphenyl)boronic acid (350 mg, 2.06 mmol), Pd(dppf)Cl2 (50 mg, 0.07 mmol) and Cs$_2$CO$_3$ (1.1 g, 3.4 mmol) in 1,4-dioxane (8 mL) and water (2 mL) were stirred for 1 h at 85° C. under N$_2$. The reaction mixture was allowed to cool to RT and treated with satd. NH$_4$Cl (aq. 15 mL). The resulting solution was extracted with EtOAc (3×15 mL). The organic layers were combined, dried over Na$_2$SO$_4$ and concentrated. The residue obtained was purified by flash chromatography (0-10% EtOAc/petroleum ether) on silica gel to obtain compound 19c as a yellow oil. Mass Spectrum (LCMS, ESI pos.): Calcd. for C$_{16}$H$_{15}$F4NO$_5$: 378.1 (M+H); found: 378.1.

D. (3S)-3-cyclopropyl-3-(3-((5-(2-fluoro-5-methoxyphenyl)-4-(3,3,3-trifluoropropoxy)isoxazol-3-yl)methoxy)phenyl)propanoic acid, Cpd 49

Compound 49 was prepared from compound 19c following the procedures described in Example 3, Steps E-H.

$^1$H-NMR (300 MHz, DMSO-d$_6$) δ (ppm): 7.27-7.37 (m, 1H), 7.21-7.26 (m, 1H), 7.12-7.19 (m, 2H), 6.85-6.93 (m, 3H), 5.22 (s, 2H), 4.20 (t, J=6.0 Hz, 2H), 3.80 (s, 3H), 2.66-2.73 (m, 2H), 2.32-2.45 (m, 3H), 0.92-0.94 (m, 1H), 0.41-0.43 (m, 1H), 0.22-0.26 (m, 2H), 0.05-0.06 (m, 1H). Mass Spectrum (LCMS, ESI pos.): Calcd. for C$_{26}$H$_{25}$F$_4$NO$_6$: 524.2 (M+H); found: 524.2.

Example 20

(3S)-3-(3-((4-(Cyclohexyloxy)-5-(2-fluoro-5-methoxyphenyl)isoxazol-3-yl)methoxy)phenyl)-3-cyclopropylpropanoic acid (Cpd 46)

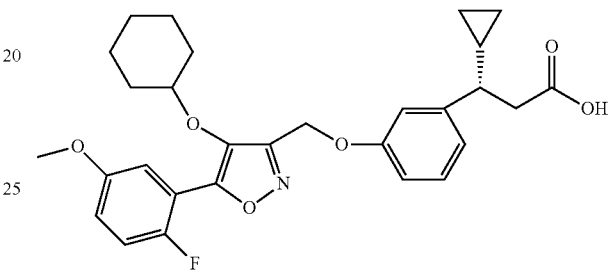

A. Ethyl 4-(cyclohexyloxy)isoxazole-3-carboxylate, 20a

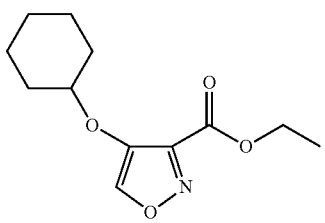

To a solution of ethyl 4-hydroxyisoxazole-3-carboxylate (2.0 g, 12.7 mmol, as prepared in Example 13, Step B), cyclohexanol (2.55 mg, 25.4 mmol), PPh$_3$ (5.0 g, 19 mmol) in THF (20 mL) was added a solution of di-tert-butyl azodicarboxylate (3.51 g, 15.3 mmol) in THF (5 mL) dropwise with stirring. The resulting solution was stirred for 3 h at RT. The reaction was then quenched with water (30 mL). The resulting solution was extracted with EtOAc (3×20 mL). The organic layers were combined, dried over anhydrous Na$_2$SO$_4$ and concentrated. The residue obtained was purified by flash chromatography (EtOAc/petroleum ether 1:100-1:30) on silica gel to obtain compound 20a as a colorless oil. Mass Spectrum (LCMS, ESI pos.): Calcd. for C$_{12}$H$_{17}$NO$_4$: 240.1 (M+H); found: 240.1.

B. Ethyl 5-bromo-4-(cyclohexyloxy)isoxazole-3-carboxylate, 20b

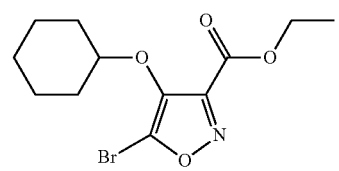

A solution of compound 20a (1.1 g, 4.6 mmol) and NBS (2.05 g, 11.5 mmol) in DMF (10 mL) was stirred for 3 h at 50° C. The reaction mixture was allowed to cool to RT and quenched with water (20 mL). The resulting solution was extracted with EtOAc (3×10 mL). The organic layers were combined, dried over anhydrous $Na_2SO_4$ and concentrated. The residue obtained was purified by flash chromatography (EtOAc/petroleum ether 1:100-1:30) on silica gel to obtain compound 20b as a light yellow oil. Mass Spectrum (LCMS, ESI pos.): Calcd. for $C_{12}H_{16}BrNO_4$: 318.0 (M+H); found: 318.0.

C. (3S)-3-(3-((4-(cyclohexyloxy)-5-(2-fluoro-5-methoxyphenyl)isoxazol-3-yl)methoxy)phenyl)-3-cyclopropylpropanoic acid, Cpd 46

Compound 46 was prepared from compound 20b following the procedures described in Example 13, Steps E-H. $^1$H-NMR (300 MHz, DMSO-$d_6$) δ (ppm): 7.30-7.39 (m, 2H), 7.10-7.23 (m, 2H), 6.86-6.93 (m, 3H), 5.18 (s, 2H), 3.97-4.00 (m, 1H), 3.80 (s, 3H), 2.32-2.45 (m, 3H), 1.73-1.85 (m, 2H), 1.51-1.62 (m, 2H), 1.28-1.35 (m, 3H), 1.07-1.18 (m, 3H), 0.98-1.01 (m, 1H), 0.47-0.51 (m, 1H), 0.21-0.35 (m, 2H), 0.02-0.18 (m, 1H). Mass Spectrum (LCMS, ESI pos.): Calcd. for $C_{29}H_{32}FNO_6$: 510.2 (M+H); found: 510.1.

Example 21

(3S)-3-(3-((4-(Cyclohexyloxy)-5-(5-fluoro-2-methoxypyridin-4-yl)isoxazol-3-yl)methoxy)phenyl)-3-cyclopropylpropanoic acid (Cpd 48)

A. (5-Bromo-4-(cyclohexyloxy)isoxazol-3-yl)methanol, 21a

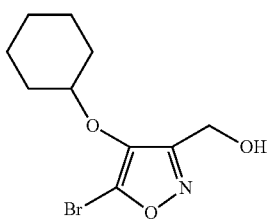

To a stirring solution of compound 20b (500 mg, 1.57 mmol) in THF (10 mL) was added a solution of 1M DIBAL in THF (4.72 mL, 4.72 mmol) dropwise at −78° C. The resulting solution was stirred for 3 h at RT. The reaction was then quenched with seignette salt solution (aq. 15 mL). The resulting solution was stirred vigorously for 1 h, and extracted with EtOAc (3×10 mL). The organic layers were combined, dried over anhydrous $Na_2SO_4$ and concentrated. The residue obtained was purified by flash chromatography (EtOAc/petroleum ether 1:100-1:10) on silica gel to obtain compound 21a as a yellow oil. Mass Spectrum (LCMS, ESI pos.): Calcd. for $C_{10}H_{14}BrNO_3$: 276.0 (M+H); found: 276.1.

B. (3S)-3-(3-((4-(cyclohexyloxy)-5-(5-fluoro-2-methoxypyridin-4-yl)isoxazol-3-yl)methoxy)phenyl)-3-cyclopropylpropanoic acid, Cpd 48

Compound 48 was prepared from compound 21a following the procedures described in Example 15, Steps D-G. $^1$H-NMR (300 MHz, DMSO-$d_6$) δ (ppm): 8.39 (s, 1H), 7.20-7.27 (m, 2H), 6.87-6.95 (m, 3H), 5.23 (s, 2H), 4.06-4.13 (m, 1H), 3.93 (s, 3H), 2.55-2.59 (m, 2H), 2.27-2.34 (m, 1H), 1.73-1.85 (m, 2H), 1.51-1.62 (m, 2H), 1.28-1.35 (m, 3H), 1.07-1.18 (m, 3H), 0.98-1.01 (m, 1H), 0.47-0.51 (m, 1H), 0.21-0.35 (m, 2H), 0.02-0.18 (m, 1H). Mass Spectrum (LCMS, ESI pos.): Calcd. for $C_{28}H_{31}FN_2O_6$: 511.2 (M+H); found: 511.2.

Example 22

(3S)-3-(3-((5-(Cyclopentyloxy)-1-(2-fluoro-5-methoxyphenyl)-1H-1,2,3-triazol-4-yl)methoxy)phenyl)-3-cyclopropylpropanoic acid (Cpd 67)

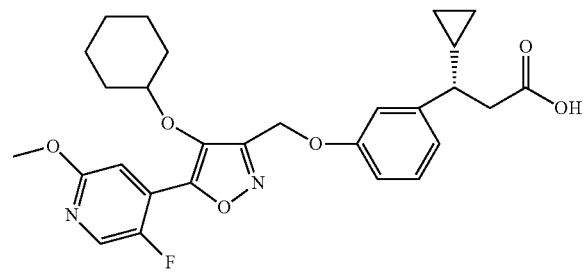 [SMILES: COc1ccc(F)c(-c2onc(COc3cccc([C@@H](CC(=O)O)C4CC4)c3)c2OC2CCCCC2)c1]

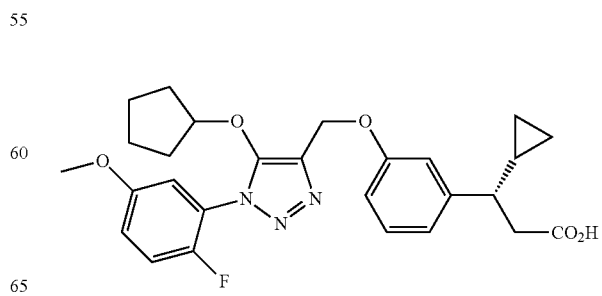

A. (5-Chloro-1-(2-fluoro-5-methoxyphenyl)-1H-1,2,3-triazol-4-yl)methanol, 22a

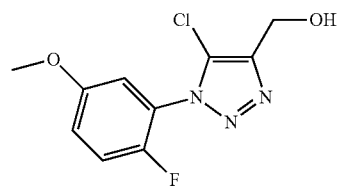

To a mixture of (5-amino-1-(2-fluoro-5-methoxyphenyl)-1H-1,2,3-triazol-4-yl)methanol (1.2 g, 5.0 mmol, as prepared in Example 5, Step C), CuCl (1.04 g, 15.1 mmol) and $CuCl_2$ (2.0 g, 15 mmol) in $CH_3CN$ (15 mL) was added isoamyl nitrite (3.09 g, 26.4 mmol) at 0° C. The resulting solution was stirred overnight at RT. The reaction was then quenched with water (20 mL), and extracted with EtOAc (3×20 mL). The organic layers were combined, dried over $Na_2SO_4$ and concentrated. The residue obtained was purified by flash chromatography (0-35% EtOAc/petroleum ether) on silica gel to obtain compound 22a as a light yellow solid. Mass Spectrum (LCMS, ESI pos.): Calcd. for $C_{10}H_9ClFN_3O_2$: 258.0 (M+H); found: 258.0.

B. (3S)-Methyl 3-(3-((5-chloro-1-(2-fluoro-5-methoxyphenyl)-1H-1,2,3-triazol-4-yl)methoxy)phenyl)-3-cyclopropylpropanoate, 22b

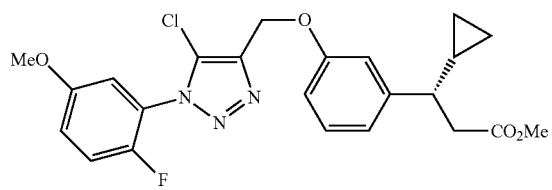

Compound 22b was prepared from compound 22a following the procedures described in Example 3, Steps F-G. Mass Spectrum (LCMS, ESI pos.): Calcd. for $C_{23}H_{23}ClFN_3O_4$: 460.1 (M+H); found: 460.1.

C. (3S)-3-(3-((5-(Cyclopentyloxy)-1-(2-fluoro-5-methoxyphenyl)-1H-1,2,3-triazol-4-yl)methoxy)phenyl)-3-cyclopropylpropanoic acid, Cpd 67

To a solution of cyclopentanol (284 mg, 3.30 mmol) in THF (3 mL) was added NaH (60% in mineral oil, 132 mg, 3.30 mmol). The resulting mixture was stirred for 1 h. To this was added a solution of compound 22b (150 mg, 0.33 mmol) in THF (1 mL). The resulting solution was stirred overnight at 75° C. The reaction mixture was allowed to cool to RT, and water (2 mL) was added. The pH of the solution was adjusted to 4-5 with 1M HCl solution. The resulting solution was extracted with DCM (3×20 mL). The organic layers were combined, dried over $Na_2SO_4$ and concentrated. The residue obtained was purified by Prep-HPLC using water and $CH_3CN$ as the mobile phase to the title compound was obtained as off-white solid. $^1$H-NMR (400 MHz, DMSO-$d_6$) δ (ppm): 7.47 (t, J=9.2 Hz, 1H), 7.20-7.26 (m, 3H), 6.87-6.96 (m, 3H), 5.18 (s, 2H), 4.97-4.99 (m, 1H), 3.80 (s, 3H), 2.65-2.68 (m, 2H), 2.25-2.27 (m, 1H), 1.69-1.72 (m, 4H), 1.44-1.50 (m, 4H), 0.98-1.01 (m, 1H), 0.49-0.52 (m, 1H), 0.24-0.32 (m, 2H), 0.13-0.14 (m, 1H). Mass Spectrum (LCMS, ESI pos.): Calcd. for $C_{27}H_{30}FN_3O_5$: 496.2 (M+H); found: 496.2.

Example 23

(3S)-3-Cyclopropyl-3-(3-((1-(2-fluoro-5-methoxyphenyl)-5-isopropoxy-1H-1,2,3-triazol-4-yl)methoxy)phenyl)propanoic acid (Cpd 98)

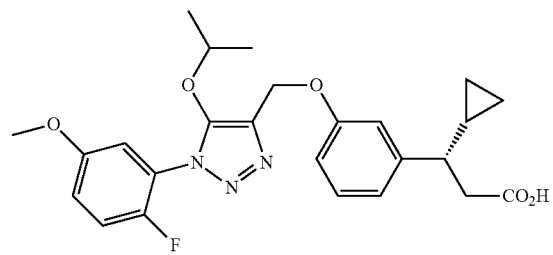 [SMILES: COc1ccc(F)c(-n2nnc(COc3cccc([C@@H](CC(=O)O)C4CC4)c3)c2OC(C)C)c1]

A mixture of Na (322 mg, 14 mmol) in propan-2-ol (3 mL) was stirred for 2 h at 75° C. and was treated with compound 22b (130 mg, 0.28 mmol) in THF (1 mL). The resulting solution was stirred overnight at 75° C. The reaction mixture was allowed to cool to RT and water was added. The pH of the solution was adjusted to 6 with 1N HCl. The resulting solution was extracted with EtOAc (3×5 mL). The combined EtOAc layers were concentrated and the residue obtained was purified by flash chromatography (0-30% EtOAc/petroleum ether) on silica gel to obtain compound 98 as a white solid. $^1$H-NMR (300 MHz, DMSO-$d_6$) δ (ppm): 7.48 (t, J=9.3 Hz, 1H), 7.21-7.26 (m, 3H), 6.86-6.94 (m, 3H), 5.15 (s, 2H), 4.58-4.62 (m, 1H), 3.81 (s, 3H), 2.51-2.57 (m, 2H), 2.28-2.32 (m, 1H), 1.14-1.20 (m, 6H), 0.92-0.98 (m, 1H), 0.42-0.48 (m, 1H), 0.23-0.28 (m, 2H), 0.06-0.11 (m, 1H). Mass Spectrum (LCMS, ESI pos.): Calcd. for $C_{25}H_{28}FN_3O_5$: 470.2 (M+H); found: 470.2.

Example 24

(3S)-3-(3-((5-(Cyclohexyloxy)-1-(2-fluoro-5-methoxyphenyl)-1H-1,2,3-triazol-4-yl)methoxy)phenyl)-3-cyclopropylpropanoic acid (Cpd 97)

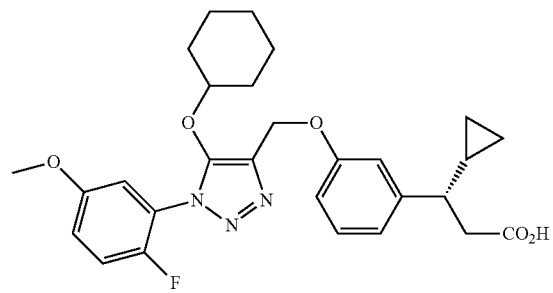 [SMILES: COc1ccc(F)c(-n2nnc(COc3cccc([C@@H](CC(=O)O)C4CC4)c3)c2OC2CCCCC2)c1]

To a solution of cyclohexanol (326 mg, 3.25 mmol) in THF (2 mL) was added NaH (60% in mineral oil, 132 mg, 3.30 mmol). The resulting solution was stirred for 30 min at RT. To this was added a solution of compound 22b (150 mg, 0.33 mmol) in THF (1 mL). The resulting solution was stirred for 2 days at 75° C. After cooling, water was added. The pH of the solution was adjusted to 6 with 1N HCl solution. The resulting solution was extracted with EtOAc (3×10 mL). The combined EtOAc layers were concentrated and the residue obtained was purified by flash chromatography (0-30% EtOAc/petroleum ether) on silica gel to obtain compound 97 as a brown solid. $^1$H-NMR (300 MHz, DMSO-$d_6$) δ (ppm): 11.99 (br, 1H), 7.45 (t, J=9.3 Hz, 1H), 7.21-7.26 (m, 3H), 6.86-6.96 (m, 3H), 5.16 (s, 2H), 4.36-4.42 (m, 1H), 3.80 (s, 3H), 2.63-2.67 (m, 2H), 2.28-2.32 (m, 1H), 1.71-1.81 (m, 2H), 2.45-2.51 (m, 2H), 1.34-1.35 (m, 3H), 1.13-1.16 (m, 3H), 0.92-0.98 (m, 1H), 0.42-0.48 (m, 1H), 0.23-0.28 (m, 2H), 0.06-0.11 (m, 1H). Mass Spectrum (LCMS, ESI pos.): Calcd. for $C_{28}H_{32}FN_3O_5$: 510.2 (M+H); found: 510.2.

Example 25

(3S)-3-Cyclopropyl-3-(3-((1-(2-fluoro-5-methoxyphenyl)-5-(piperidin-1-yl)-1H-1,2,3-triazol-4-yl)methoxy)phenyl)propanoic (Cpd 44)

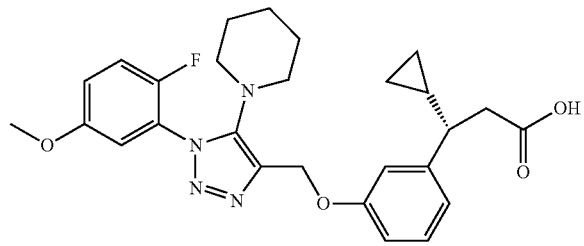 [SMILES: COc1ccc(F)c(-n2nnc(COc3cccc([C@@H](CC(=O)O)C4CC4)c3)c2N2CCCCC2)c1]

A. Ethyl 5-chloro-1-(2-fluoro-5-methoxyphenyl)-1H-1,2,3-triazole-4-carboxylate, 25a

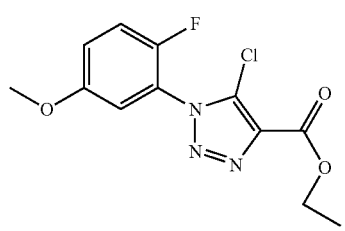

25a

Ethyl 5-amino-1-(2-fluoro-5-methoxyphenyl)-1H-1,2,3-triazole-4-carboxylate (500 mg, 1.78 mmol, as prepared in Example 5, Step B) was added portionwise to a 20% HCl solution (20 mL). The resulting mixture was cooled to 0° C. and treated with a solution of $NaNO_2$ (365 mg, 5.29 mmol) in $H_2O$ (2 mL) dropwise with stirring at 0° C. The resulting mixture was stirred for 30 min to obtain the corresponding diazonium salt solution.

A mixture of CuCl (710 mg, 7.24 mmol) in 20% HCl solution (20 mL) was stirred at 75° C. for 20 min. To the resulting solution, the diazonium salt solution prepared above was added dropwise at 75° C. After the addition, the mixture was stirred for 2 h at 75° C. The resulting solution was allowed to cool to RT and extracted with EtOAc (2×20 mL). The organic layers were combined, washed with satd. sodium carbonate (aq. 20 mL) and concentrated. The residue obtained was purified by flash chromatography (0-30% EtOAc/petroleum ether) on silica gel to obtain compound 25a as a colorless oil. Mass Spectrum (LCMS, ESI pos.): Calcd. for $C_{12}H_{11}ClFN_3O_3$: 300.0 (M+H); found: 300.0.

B. Ethyl 1-(2-fluoro-5-methoxyphenyl)-5-(piperidin-1-yl)-1H-1,2,3-triazole-4-carboxylate, 25b

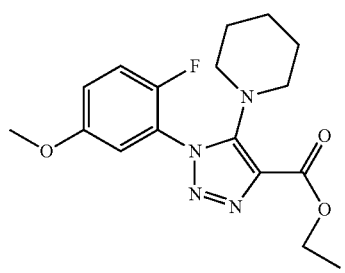

25b

A mixture of BINAP (92 mg, 0.15 mmol), Pd(OAc)$_2$ (16.5 mg, 0.07 mmol), Cs$_2$CO$_3$ (600 mg, 1.84 mmol), compound 25a (220 mg, 0.73 mmol) and piperidine (156 mg, 1.83 mmol) in toluene (8 mL) was stirred overnight at 80° C. under N$_2$. The reaction mixture was allowed to cool to RT and treated with satd. NH$_4$Cl (aq. 10 mL). The resulting solution was extracted with EtOAc (2×10 mL). The organic layers were combined and concentrated. The residue obtained was purified by flash chromatography (EtOAc/petroleum ether 1:3) on silica gel to obtain compound 25b as a colorless oil. Mass Spectrum (LCMS, ESI pos.): Calcd. for $C_{17}H_{21}FN_4O_3$: 349.2 (M+H); found: 349.1.

C. (1-(2-Fluoro-5-methoxyphenyl)-5-(piperidin-1-yl)-1H-1,2,3-triazol-4-yl)methanol, 25c

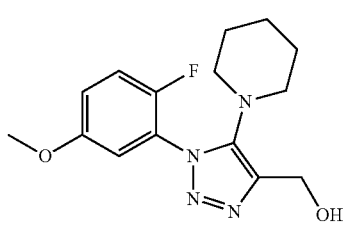

25c

To a solution of compound 25b (110 mg, 0.32 mmol) in THF (4 mL), the solution of DIBAL-H in THF (1 M, 1.5 mL) was added at −70° C. The resulting solution was stirred for 1 h at −70° C. and the reaction was then quenched with satd. seignette salt solution (aq. 10 mL). The resulting solution was extracted with EtOAc (2×10 mL). The organic layers were combined and concentrated. The residue obtained was purified by flash chromatography (0-50% EtOAc/petroleum ether) on silica gel to obtain compound 25c as a colorless oil. Mass Spectrum (LCMS, ESI pos.): Calcd. for $C_{15}H_{19}FN_4O_2$: 307.1 (M+H); found: 307.1.

D. (3S)-methyl 3-cyclopropyl-3-(3-((1-(2-fluoro-5-methoxyphenyl)-5-(piperidin-1-yl)-1H-1,2,3-triazol-4-yl)methoxy)phenyl)propanoate, 25d

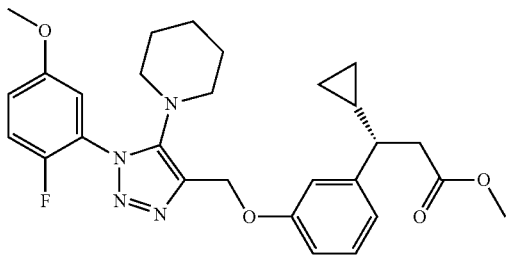

25d

To a stirring solution of compound 25c (60 mg, 0.20 mmol), methyl (3S)-3-cyclopropyl-3-(3-hydroxyphenyl) propanoate (64 mg, 0.29 mmol), Ph$_3$P (154 mg, 0.59 mmol) in THF (2.5 mL) was added a solution of di-tert-butyl azodicarboxylate (113 mg, 0.49 mmol) in THF (1 mL). The resulting solution was stirred for 3 h at RT and concentrated. The residue obtained was purified by flash chromatography (EtOAc/petroleum ether 1:2) on silica gel to obtain compound 25d as a colorless oil. Mass Spectrum (LCMS, ESI pos.): Calcd. for $C_{28}H_{33}FN_4O_4$: 509.2 (M+H); found: 509.3.

E. (3S)-3-Cyclopropyl-3-(3-((1-(2-fluoro-5-methoxyphenyl)-5-(piperidin-1-yl)-1H-1,2,3-triazol-4-yl)methoxy)phenyl)propanoic acid, Cpd 44

Compound 44 was prepared from compound 25d following the procedure described in Example 3, Step H. $^1$H-NMR (300 MHz, DMSO-d$_6$) δ (ppm): 7.47 (t, J=9.3 Hz, 1H), 7.16-7.29 (m, 3H), 6.85-6.95 (m, 3H), 5.15 (s, 2H), 3.80 (s, 3H), 2.80-2.98 (m, 4H), 2.61-2.63 (m, 2H), 2.26-2.32 (m, 1H), 1.35-1.50 (m, 6H), 1.00-1.04 (m, 1H), 0.42-0.48 (m, 1H), 0.21-0.38 (m, 2H), 0.11-0.18 (m, 1H). Mass Spectrum (LCMS, ESI pos.): Calcd. for $C_{27}H_{31}FN_4O_4$: 495.2 (M+H); found: 495.2.

Following the procedures described in Example 25 above, and substituting suitably selected and substituted reagents, starting materials and conditions as would be readily apparent to those skilled in the art, the following representative compounds of the present invention were prepared.

| Cpd No. | Characterization |
|---|---|
| 68 | (3S)-3-[3-[(5-[2-Azaspiro[3.3]heptan-2-yl]-1-(2-fluoro-5-methoxyphenyl)-1H-1,2,3-triazol-4-yl)methoxy]phenyl]-3-cyclopropylpropanoic acid<br>$^1$H-NMR (300 MHz, DMSO-d$_6$) δ (ppm): 2.41-2.44 (m, 1H), 7.18-7.26 (m, 3H), 6.85-6.95 (m, 3H), 5.03 (s, 2H), 3.79-3.81 (m, 7H), 2.62-2.73 (m, 2H), 2.27-2.32 (m, 1H), 2.02-2.07 (m, 4H), 1.63-1.70 (m, 2H), 0.99-1.04 (m, 1H), 0.47-0.51 (m, 1H), 0.24-0.28 (m, 2H), 0.01-0.17 (m, 1H).<br>Mass Spectrum (LCMS, ESI pos.): Calcd. for $C_{28}H_{31}FN_4O_4$: 506.6 (M + H); found: 506.6. |
| 73 | (S)-3-Cyclopropyl-3-(3-((1-(2-fluoro-5-methoxyphenyl)-5-morpholino-1H-pyrazol-4-yl)methoxy)phenyl)propanoic acid<br>$^1$H-NMR (400 MHz, DMSO-d$_6$) δ (ppm): 7.72 (s, 1H), 7.35-7.37 (m, 1H), 7.21-7.23 (m, 1H), 7.06-7.19 (m, 2H), 6.84-6.92 (m, 3H), 4.99 (s, 2H), 3.79 (s, 3H), 3.43-3.44 (m, 4H), 2.91-2.97 (m, 4H), 2.58-2.62 (m, 2H), 2.26-2.28 (m, 1H), 0.99-1.01 (m, 1H), 0.48-0.50 (m, 1H), 0.23-0.31 (m, 2H), 0.09-0.13 (m, 1H).<br>Mass Spectrum (LCMS, ESI pos.): Calcd. for $C_{27}H_{30}FN_3O_5$: 496.2 (M + H); found: 496.3. |
| 80 | (S)-3-Cyclopropyl-3-(3-((1-(2-fluoro-5-methoxyphenyl)-5-morpholino-1H-1,2,3-triazol-4-yl)methoxy)phenyl)propanoic acid<br>$^1$H-NMR (300 MHz, DMSO-d$_6$) δ (ppm): 7.41-7.49 (m, 1H), 7.25-7.33 (m, 1H), 7.21-7.29 (m, 2H), 6.81-6.95 (m, 3H), 5.19 (s, 2H), 3.81 (s, 3H), 3.41-3.52 (m, 4H), 2.91-3.05 (m, 4H), 2.55-2.68 (m, 2H), 2.25-2.41 (m, 1H), 0.91-1.01 (m, 1H), 0.45-0.55 (m, 1H), 0.21-0.38 (m, 2H), 0.05-0.12 (m, 1H).<br>Mass Spectrum (LCMS, ESI pos.): Calcd. for $C_{26}H_{29}FN_4O_5$: 497.2 (M + H); found: 497.3. |

Example 26

(3S)-3-Cyclopropyl-3-(3-((5-(2-fluoro-5-methoxyphenyl)-4-(1,1,1-trifluoropropan-2-yl)thiophen-3-yl)methoxy)phenyl)propanoic acid (Cpd 19)

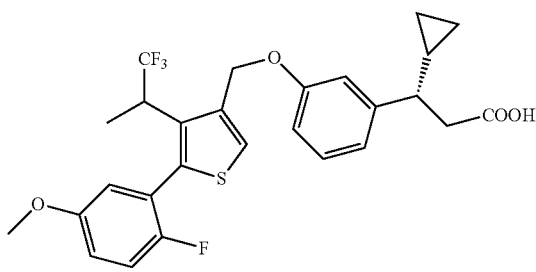 [SMILES: COc1ccc(F)c(-c2scc(COc3cccc([C@@H](CC(=O)O)C4CC4)c3)c2C(C)C(F)(F)F)c1]

A. Methyl (S)-3-(3-((4-bromo-5-(2-fluoro-5-methoxyphenyl)thiophen-3-yl)methoxy)phenyl)-3-cyclopropylpropanoate, 26a

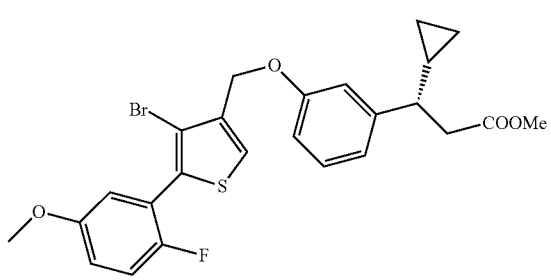

A mixture of compound 10e (600 mg, 1.15 mmol), (2-fluoro-5-methoxyphenyl)boronic acid (215 mg, 1.27 mmol), Pd(dppf)Cl$_2$ (42 mg, 0.06 mmol) and Cs$_2$CO$_3$ (751 mg, 2.30 mmol) in 1,4-dioxane (8 mL) and water (2 mL) was stirred for 2 h at 85° C. under N$_2$ in an oil bath. The reaction mixture was allowed to cool to rt and treated with NH$_4$Cl (aq, 5 mL). The resulting mixture was extracted with EtOAc (3×5 mL). The organic layers were combined, dried over anhydrous sodium sulfate and concentrated. The resulting residue was purified by flash column chromatography (0-10% EtOAc/petroleum ether) on silica gel to obtain compound 26a as a yellow oil. $^1$H NMR (300 MHz, DMSO-d$_6$) δ (ppm): 7.99 (s, 1H), 7.20-7.34 (m, 2H), 7.02-7.10 (m, 2H), 6.85-6.96 (m, 3H), 5.04 (s, 2H), 3.79 (s, 3H), 3.51 (s, 3H), 2.73-2.77 (m, 2H), 2.25-2.83 (m, 1H), 0.98-1.01 (m, 1H), 0.51-0.54 (m, 1H), 0.38-0.41 (m, 1H), 0.12-0.28 (m, 2H).

B. Methyl (S)-3-cyclopropyl-3-(3-((5-(2-fluoro-5-methoxyphenyl)-4-(3,3,3-trifluoroprop-1-en-2-yl)thiophen-3-yl)methoxy)phenyl)propanoate, 26b

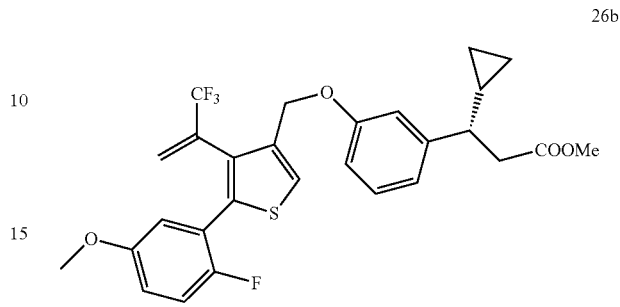

A mixture of compound 26b (280 mg, 0.54 mmol), 6-hydroxyhexyl hydrogen (3,3,3-trifluoroprop-1-en-2-yl)boronate (200 mg, 0.83 mmol), Pd(dppf)Cl$_2$ (20 mg, 0.03 mmol), and Cs$_2$CO$_3$ (438 mg, 1.34 mmol) in 1,4-dioxane (4 mL) and water (1 mL) was stirred for 2 h at 85° C. in an oil bath under N$_2$. The reaction mixture was allowed to cool to rt and treated with water (5 mL). The resulting mixture was extracted with EtOAc (3×5 mL). The organic layers were combined, dried over anhydrous sodium sulfate and concentrated. The resulting residue was purified by flash chromatography (0-15% EtOAc/petroleum ether) on silica gel to obtain compound 26b as a yellow oil. Mass Spectrum (LCMS, ESI pos.): Calcd. for C$_{28}$H$_{26}$F$_4$O$_4$S: 535.2 (M+H); found: 535.0.

C. Methyl (3S)-3-cyclopropyl-3-(3-((5-(2-fluoro-5-methoxyphenyl)-4-(1,1,1-trifluoropropan-2-yl)thiophen-3-yl)methoxy)phenyl)propanoate, 26c

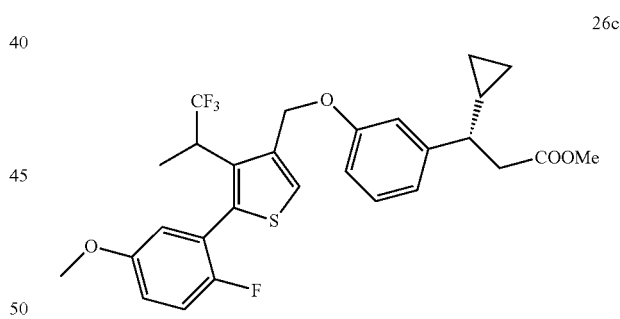

Into a 30-mL pressure tank reactor was placed compound 26b (230 mg, 0.43 mmol), ethyl acetate (10 mL) and Pd/C (10%, 200 mg). The resulting mixture was stirred overnight at 30° C. under a H$_2$ atmosphere (3 atm). The mixture was filtered through a diatomaceous earth pellet and the filtrate was concentrated under reduced pressure. The resulting residue was purified by flash chromatography (0-5% EtOAc/petroleum ether) on silica gel to obtain compound 26c as a yellow oil. Mass Spectrum (LCMS, ESI pos.): Calcd. for C$_{28}$H$_{28}$F$_4$O$_4$S: 537.2 (M+H); found: 537.2.

D. (3S)-3-Cyclopropyl-3-(3-((5-(2-fluoro-5-methoxyphenyl)-4-(1,1,1-trifluoropropan-2-yl)thiophen-3-yl)methoxy)phenyl)propanoic acid, Cpd 19

A mixture of compound 26c (120 mg, 0.22 mmol) and LiOH·H$_2$O (92 mg, 2.19 mmol) in THF (4 mL), water (1 mL) and methanol (1 mL) was stirred overnight at rt. The resulting mixture was concentrated under reduced pressure. The residue was diluted with $H_2O$ (5 mL) and was adjusted to pH~5 with HCl (1 N). The precipitates were collected by filtration. The crude solid (60 mg) were further purified by Prep-HPLC (75% $MeCN/H_2O$ to 95% $MeCN/H_2O$ over 14 min). Compound 19 was obtained as a yellow solid. $^1H$ NMR (300 MHz, DMSO-$d_6$) δ (ppm): 12.01 (brs, 1H), 7.83 (s, 1H), 7.20-7.30 (m, 2H), 7.06-7.11 (m, 1H), 6.86-6.93 (m, 4H), 5.10 (s, 2H), 3.75-3.80 (m, 4H), 2.64-2.68 (m, 2H), 2.26-2.29 (m, 1H), 1.37 (d, J=7.2 Hz, 3H), 0.93-1.02 (m, 1H), 0.43-0.56 (m, 1H), 0.20-0.35 (m, 2H), 0.05-0.15 (m, 1H). Mass Spectrum (LCMS, ESI pos.): Calcd. for $C_{27}H_{26}F_4O_4S$: 545.2 (M+Na); found: 545.0.

Example 27

(3S)-3-(3-((2-Chloro-5-(2-fluoro-5-methoxyphenyl)-4-(1,1,1-trifluoropropan-2-yl)thiophen-3-yl)methoxy)phenyl)-3-cyclopropylpropanoic acid (Cpd 29)

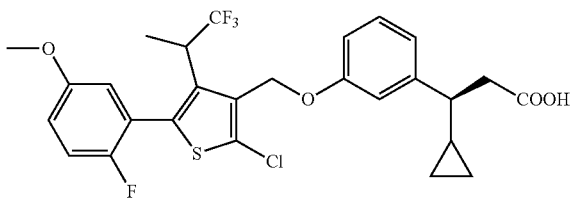 [SMILES: COc1ccc(F)c(-c2sc(Cl)c(COc3cccc([C@@H](CC(=O)O)C4CC4)c3)c2C(C)C(F)(F)F)c1]

A. Methyl (3S)-3-(3-((2-chloro-5-(2-fluoro-5-methoxyphenyl)-4-(1,1,1-trifluoropropan-2-yl)thiophen-3-yl)methoxy)phenyl)-3-cyclopropylpropanoate, 27a

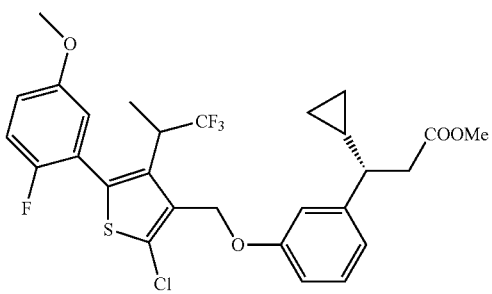

A mixture of compound 26c (60 mg, 0.11 mmol) and NCS (15.8 mg, 0.12 mmol) in DMF (2 mL) was stirred overnight at rt. The reaction was quenched with water (10 mL). The mixture was extracted with DCM (3×5 mL). The organic layers were combined, washed with water (5×3 mL), dried over anhydrous sodium sulfate and concentrated. The resulting residue was purified by flash column chromatography (0-10% EtOAc/petroleum ether) on silica gel to obtain compound 27a as a yellow oil. Mass Spectrum (LCMS, ESI pos.): Calcd. for $C_{28}H_{27}ClF_4O_4S$: 571.1 (M+H); found: 571.0.

B. (3S)-3-(3-((2-Chloro-5-(2-fluoro-5-methoxyphenyl)-4-(1,1,1-trifluoropropan-2-yl)thiophen-3-yl)methoxy)phenyl)-3-cyclopropylpropanoic acid, Cpd 29

Compound 29 was prepared from compound 27a following a similar procedure to that described in Example 26, Step D. $^1H$-NMR (300 MHz, DMSO-$d_6$) δ (ppm): 7.84 (s, 1H), 7.30-7.34 (m, 1H), 7.24-7.27 (m, 1H), 7.15-7.16 (m, 1H), 7.06-7.11 (m, 1H), 6.89-6.95 (m, 2H), 5.13 (s, 2H), 3.77 (s, 3H), 3.30-3.33 (m, 1H), 2.88-2.91 (m, 1H), 2.67-2.69 (m, 2H), 1.35-1.38 (m, 3H), 1.09-1.14 (m, 1H), 0.50-0.52 (m, 1H), 0.23-0.35 (m, 2H), 0.06-0.15 (m, 1H). Mass Spectrum (LCMS, ESI pos.): Calcd. for $C_{27}H_{25}ClF_4O_4S$: 573.1 $[M+NH_4]^+$; found: 573.8.

Example 28

3-(5-Chloro-2-((4-(5,5-dimethylcyclopent-1-en-1-yl)-5-(2-fluoro-5-methoxyphenyl)isoxazol-3-yl)methoxy)pyridin-4-yl)-3-cyclopropylpropanoic acid (Cpd 9)

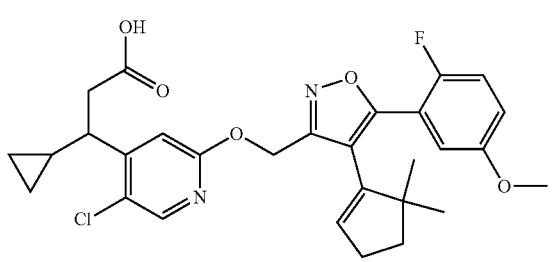 [SMILES: COc1ccc(F)c(-c2onc(COc3cc(C(CC(=O)O)C4CC4)c(Cl)cn3)c2C2=CCCC2(C)C)c1]

A. 5-Chloro-2-methoxyisonicotinic acid, 28a

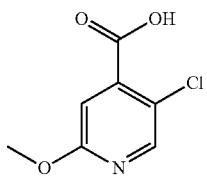

A mixture of 2,5-dichloropyridine-4-carboxylic acid (5 g, 26 mmol) and sodium methylate (4.2 g, 77.8 mmol) in DMSO (20 mL) was stirred for 2 h at 100° C. in an oil bath. The reaction was allowed to cool to rt and treated with water (200 mL), and was adjusted to pH~3-4 with HCl (1 N). The resulting mixture was extracted with EtOAc (3×200 mL). The combined organic layers were washed with water (2×50 mL), dried over anhydrous sodium sulfate and concentrated. This resulted in compound 28a as a light yellow powder. Mass Spectrum (LCMS, ESI pos.): Calcd. for $C_7H_6ClNO_3$: 186.0 (M−H); found: 186.0.

B. 5-Chloro-N,2-dimethoxy-N-methylisonicotinamide, 28b

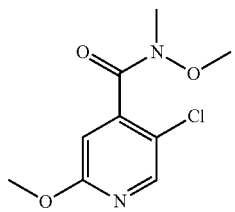

A mixture of compound 28a (1.4 g, 7.46 mmol), methoxy(methyl)amine hydrochloride (876 mg, 8.98 mmol), HATU (4.2 g, 11.05 mmol), and Et₃N (5 mL) in DCM (100 mL) was stirred for 2 h at rt. The reaction was quenched with sodium bicarbonate (aq., 50 mL). The mixture was extracted with EtOAc (3×200 mL). The combined organic layers were washed with water (2×100 mL), dried over anhydrous sodium sulfate and concentrated. The resulting residue was purified by flash column chromatography (0-20% EtOAc/petroleum ether) on silica gel to obtain compound 28b as a light yellow oil. Mass Spectrum (LCMS, ESI pos.): Calcd. for $C_9H_{11}ClN_2O_3$: 231.0 (M+H); found: 231.0.

C. (5-Chloro-2-methoxypyridin-4-yl)(cyclopropyl)methanone, 28c

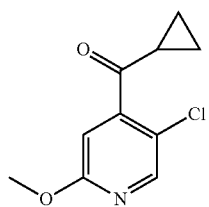

To a solution of compound 28b (3.4 g, 14.74 mmol) in THF (250 mL) was added bromo(cyclopropyl)magnesium (1M in THF, 29 mL, 29.48 mmol) at 0° C. under N₂. The resulting solution was stirred for 2 h at 0° C. The reaction was then quenched with NH₄Cl (satd, 100 mL). The mixture was extracted with EtOAc (3×300 mL). The combined organic layers were washed with water (2×50 mL), dried over anhydrous sodium sulfate and concentrated. The resulting residue was purified by flash column chromatography (0-20% EtOAc/petroleum ether) on silica gel to obtain compound 28c as a yellow oil. Mass Spectrum (LCMS, ESI pos.): Calcd. for $C_{10}H_{10}ClNO_2$: 212.0 (M+H); found: 212.0.

D. Methyl (E)-3-(5-chloro-2-methoxypyridin-4-yl)-3-cyclopropylacrylate, 28d

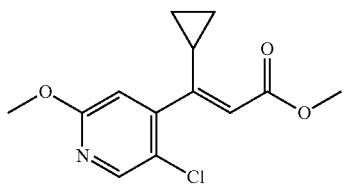

To a solution of methyl 2-(dimethoxyphosphoryl)acetate (10.3 g, 56.6 mmol) in THF (200 mL) was added sodium hydride (2.3 g, 56.6 mmol, 60% w/w in mineral oil) in portions at 0° C. under N₂. The mixture was stirred for 30 min at 0° C. followed by the addition of compound 28c (3.0 g, 14.2 mmol). The resulting solution was stirred for 3 h at 50° C. The reaction was then quenched with NH₄Cl (satd, 100 mL). The mixture was extracted with EtOAc (3×200 mL). The combined organic layers were washed with water (2×100 mL), dried over anhydrous sodium sulfate and concentrated. The resulting residue was purified by flash column chromatography (0-25% EtOAc/petroleum ether) on silica gel to obtain compound 28d as a light yellow oil. Mass Spectrum (LCMS, ESI pos.): Calcd. for $C_{13}H_{14}ClNO_3$: 268.1 (M+H); found: 268.1.

E. Methyl 3-(5-chloro-2-methoxypyridin-4-yl)-3-cyclopropylpropanoate, 28e

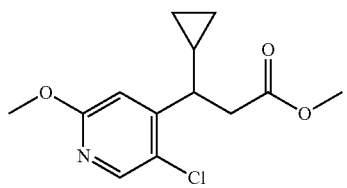

A mixture of compound 28d (1.3 g, 4.85 mmol), NiCl₂·6H₂O (1.0 g, 4.20 mmol) and NaBH₄ (832 mg, 21.9 mmol) in methanol (100 mL) was stirred for 1h at 25° C. The reaction was then quenched NH₄Cl (satd, 50 mL). The mixture was extracted with EtOAc (3×100 mL). The combined organic layers were washed with water (2×50 mL), dried over anhydrous sodium sulfate and concentrated. The resulting residue was purified by flash column chromatography (0-10% EtOAc/petroleum ether) on silica gel to obtain compound 28d as a light yellow oil. Mass Spectrum (LCMS, ESI pos.): Calcd. for $C_{13}H_{16}ClNO_3$: 270.1 (M+H); found: 270.0.

F. 3-(5-Chloro-2-hydroxypyridin-4-yl)-3-cyclopropylpropanoic acid, 28f

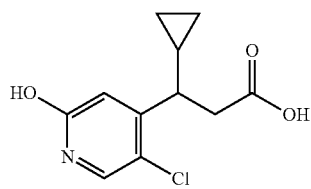

To a solution of compound 28e (1.0 g, 3.71 mmol) in 1,4-dioxane/H₂O (10 mL 1:1 v/v) was added conc. HCl (5 mL). The resulting mixture was stirred overnight at 100° C. After cooling to rt, the mixture was extracted with EtOAc (3×10 mL). The organic layers were combined, dried over anhydrous sodium sulfate and concentrated. Compound 28f was obtained as a yellow oil. Mass Spectrum (LCMS, ESI pos.): Calcd. for $C_{11}H_{12}ClNO_3$: 242.1 (M+H); found: 242.0.

137

G. Ethyl 3-(5-chloro-2-hydroxypyridin-4-yl)-3-cyclopropylpropanoate, 28g

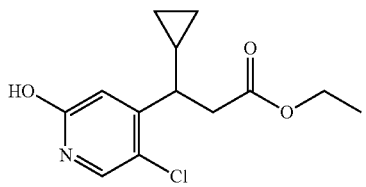

28g

To a solution of compound 28f (1.2 g, 4.97 mmol) in ethanol (15 mL) was added conc. $H_2SO_4$ (1 mL). The resulting mixture was stirred overnight at 80° C. The reaction was allowed to cool to rt and treated with water (20 mL), and the mixture was adjusted to pH-4 with $Na_2HCO_3$ (aq., 1 N). The resulting mixture was extracted with EtOAc (3×50 mL). The organic layers were combined, dried over anhydrous sodium sulfate and concentrated. The resulting residue was purified by flash column chromatography (0-20% EtOAc/petroleum ether) on silica gel to obtain compound 28g as a light yellow oil. Mass Spectrum (LCMS, ESI pos.): Calcd. for $C_{13}H_{16}ClNO_3$: 270.1 (M+H); found: 270.0.

H. (4-(5,5-Dimethylcyclopent-1-en-1-yl)-5-(2-fluoro-5-methoxyphenyl)isoxazol-3-yl)methanol, 28h

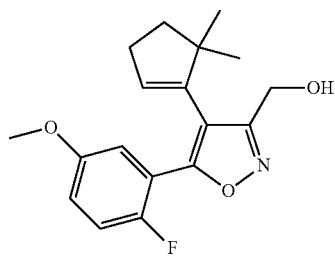

28h

A mixture of compound 4e (1.5 g, 4.97 mmol), 2-(5,5-dimethylcyclopent-1-enyl)-4,4,5,5-tetramethyl-1,3,2-dioxaborolane (2.5 g, 11.3 mmol), Pd(dppf)Cl$_2$ (183 mg, 0.25 mmol) and Cs$_2$CO$_3$ (3.25 g, 9.97 mmol) in 1,4-dioxane (20 mL) and water (5 mL) was stirred overnight at 80° C. in an oil bath. After cooling to rt, the reaction was quenched with water (100 mL). The resulting mixture was extracted with EtOAc (3×100 mL). The organic layers were combined, dried over anhydrous sodium sulfate and concentrated. The resulting residue was purified by flash column chromatography (10-20% EtOAc/petroleum ether) on silica gel to obtain compound 28h as a red oil. Mass Spectrum (LCMS, ESI pos.): Calcd. for $C_{18}H_{20}FNO_3$: 318.1 (M+H); found: 318.1.

138

I. Ethyl 3-(5-chloro-2-((4-(5,5-dimethylcyclopent-1-en-1-yl)-5-(2-fluoro-5-methoxyphenyl)isoxazol-3-yl)methoxy)pyridin-4-yl)-3-cyclopropylpropanoate, 28i

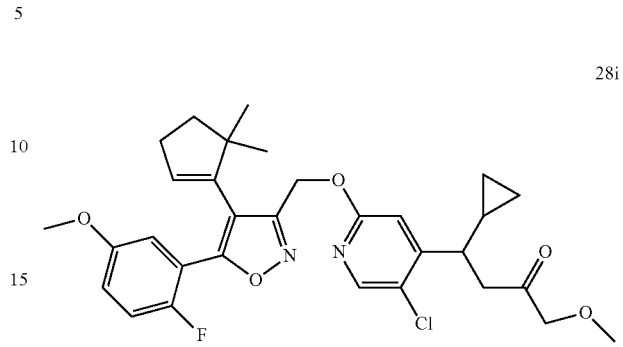

28i

A mixture of compound 28g (129 mg, 0.48 mmol), compound 28h (150 mg, 0.47 mmol), n-Bu$_3$P (10% in hexane w/w, 2.5 g, 1.24 mmol), and ADDP (309 mg, 1.23 mmol) in toluene (5 mL) was stirred overnight at 60° C. The reaction mixture was concentrated under reduced pressure and the resulting residue was purified by flash column chromatography (0-20% EtOAc/petroleum ether) on silica gel to obtain compound 28i as a light yellow oil. Mass Spectrum (LCMS, ESI pos.): Calcd. for $C_{31}H_{34}ClFN_2O_5$: 569.2 (M+H); found: 569.0.

J. 3-(5-Chloro-2-((4-(5,5-dimethylcyclopent-1-en-1-yl)-5-(2-fluoro-5-methoxyphenyl)isoxazol-3-yl)methoxy)pyridin-4-yl)-3-cyclopropylpropanoic acid, Cpd 9

A mixture of compound 28i (100 mg, 0.18 mmol) and LiOH.H$_2$O (17 mg, 0.71 mmol) in THF (4 mL), water (1 mL) and ethanol (1 mL) was stirred overnight at 30° C. The resulting mixture was concentrated under reduced pressure. The residue was diluted with water (5 mL) and the mixture was adjusted to pH-4 with HCl (1 N). The resulting mixture was extracted with EtOAc (3×10 mL). The organic layers were combined, dried over anhydrous sodium sulfate and concentrated. The resulting residue was purified by flash column chromatography (0-50% EtOAc/petroleum ether) on silica gel to obtain compound 9 as a white solid. $^1H$ (400 MHz, DMSO-d$_6$) δ (ppm): 8.17 (s, 1H), 7.29-7.34 (m, 1H), 7.11-7.15 (m, 2H), 7.03 (s, 1H), 5.89 (s, 1H), 5.31-5.39 (m, 2H), 3.75 (s, 3H), 2.62-2.86 (m, 3H), 2.26-2.30 (m, 2H), 1.64-1.67 (m, 2H), 1.06-1.08 (m, 1H), 0.70 (s, 6H), 0.40-0.60 (m, 1H), 0.25-0.35 (m, 2H), 0.10-0.15 (m, 1H). Mass Spectrum (LCMS, ESI pos.): Calcd. for $C_{29}H_{30}ClFN_2O_5$: 541.2 (M+H); found: 541.2.

Following the procedures described in Example 28, and substituting suitably selected reagents, starting materials and conditions as would be readily apparent to those skilled in the art, the following representative compounds of the present invention were prepared.

| Cpd No. | Characterization |
|---|---|
| 53 | 3-Cyclopropyl-3-(2-((4-(5,5-dimethylcyclopent-1-en-1-yl)-3-(2-fluoro-5-methoxyphenyl)isoxazol-5-yl)methoxy)pyridin-4-yl)propanoic acid<br>$^1$H-NMR (300 MHz, DMSO-$d_6$) δ (ppm): 8.07 (s, 1H), 7.25-7.31 (m, 1H), 6.99-7.12 (m, 3H), 6.80 (s, 1H), 5.86 (s, 1H), 5.37 (s, 2H), 3.74 (s, 3H), 3.59-3.61 (m, 2H), 2.22-2.30 (m, 3H), 1.65 (d, J = 7.2 Hz, 2H), 0.98-1.00 (m, 1H), 0.66 (s, 6H), 0.46-0.51 (m, 1H), 0.25-0.34 (m, 2H), 0.16-0.17 (m, 1H).<br>Mass Spectrum (LCMS, ESI pos.): Calcd. for $C_{29}H_{31}FN_2O_5$: 507.2 (M + H); found: 507.2. |
| 55 | 3-(5-Chloro-24(4-(5,5-dimethylcyclopent-1-en-1-yl)-3-(2-fluoro-5-methoxyphenyl)isoxazol-5-yl)methoxy)pyridin-4-yl)-3-cyclopropylpropanoic acid<br>$^1$H-NMR (400 MHz, DMSO-$d_6$) δ (ppm): 8.20 (s, 1H), 7.25-7.28 (m, 1H), 7.11-7.15 (m, 2H), 6.98-7.05 (m, 1H), 5.85 (m, 1H), 5.38 (s, 2H), 3.75 (s, 3H), 2.71-2.83 (m, 2H), 2.60-2.69 (m, 1H), 2.30-2.33 (m, 2H), 1.62-1.67 (m, 2H), 1.01-1.09 (m, 1H), 0.66 (s, 6H), 0.45-0.54 (m, 1H), 0.20-0.38 (m, 2H), 0.11-0.16 (m, 1H).<br>Mass Spectrum (LCMS, ESI pos.): Calcd. for $C_{29}H_{30}ClFN_2O_5$: 541.2 (M + H); found: 541.2. |
| 78 | 3-(5-Chloro-24(5-(5,5-dimethylcyclopent-1-en-1-yl)-1-(2-fluoro-5-methoxyphenyl)-1H-1,2,3-triazol-4-yl)methoxy)pyridin-4-yl)-3-cyclopropylpropanoic acid<br>$^1$H-NMR (400 MHz, DMSO-$d_6$) δ (ppm): 8.17 (s, 1H), 7.15 (t, J = 9.2 Hz, 1H), 7.02-6.98 (m, 1H), 6.93-6.92 (m, 2H), 5.99 (s, 1H), 5.38 (s, 2H), 3.80 (s, 3H), 2.88-2.74 (m, 3H), 2.42-2.34 (m, 2H), 1.73 (t, J = 6.8 Hz, 2H), 1.05-1.09 (m, 1H), 0.78 (s, 6H), 0.68-0.64 (m, 1H), 0.49-0.45 (m, 1H), 0.39-0.36 (m, 1H), 0.21-0.23 (m, 1H).<br>Mass Spectrum (LCMS, ESI pos.): Calcd. for $C_{28}H_{30}ClFN_4O_4$: 541.2 (M + H); found: 541.1. |

Example 29

3-(5-Chloro-2-((5-(5,5-dimethylcyclopent-1-en-1-yl)-1-(2-fluoro-5-methoxyphenyl)-1H-pyrazol-4-yl)methoxy)pyridin-4-yl)-3-cyclopropylpropanoic acid (Cpd 71)

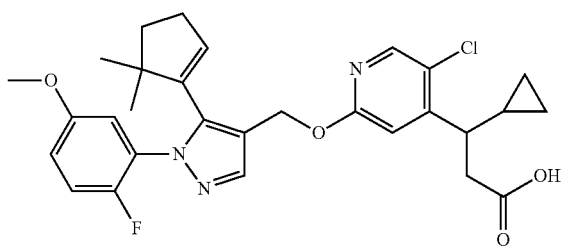

A. 4-(Bromomethyl)-5-(5,5-dimethylcyclopent-1-en-1-yl)-1-(2-fluoro-5-methoxyphenyl)-1H-pyrazole, 29a

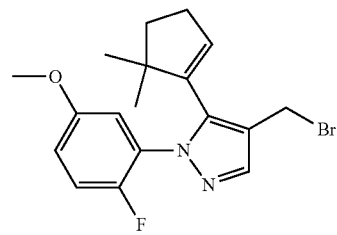

To a solution of compound 1e (90 mg, 0.28 mmol) in DCM (10 mL) was added PBr$_3$ (232 mg, 0.86 mmol) dropwise with stirring at 0° C., followed by dropwise addition of DMF (0.05 mL). The resulting solution was stirred for 1 h at rt. The reaction was quenched with water (10 mL). The resulting mixture was extracted with DCM (3×10 mL), and the organic layers were combined, dried over anhydrous sodium sulfate and concentrated under reduced pressure. This resulted in compound 29a as a yellow oil. Mass Spectrum (LCMS, ESI pos.): Calcd. for $C_{18}H_{20}BrFN_2O$: 379.1 (M+H); found: 379.0.

B. Ethyl 3-(5-chloro-2-((5-(5,5-dimethylcyclopent-1-en-1-yl)-1-(2-fluoro-5-methoxyphenyl)-1H-pyrazol-4-yl)methoxy)pyridin-4-yl)-3-cyclopropylpropanoate, 29b

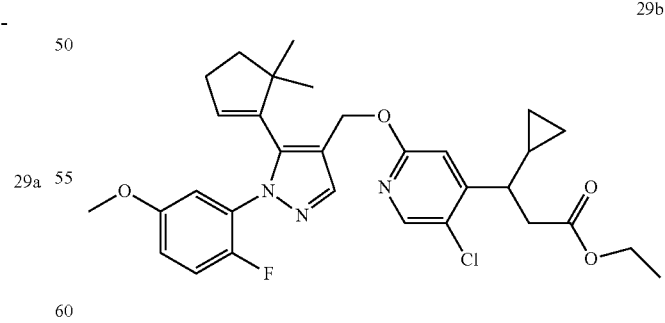

A mixture of compound 29a (100 mg, 0.26 mmol), compound 28g (142 mg, 0.53 mmol), and Ag$_2$CO$_3$ (72 mg) in toluene (5 mL) was stirred for 2 h at 50° C. The reaction was then quenched with water (20 mL). The resulting mixture was extracted with EtOAc (3×10 mL) and the organic layers were combined, dried over anhydrous sodium sulfate and concentrated under reduced pressure. The residue was purified by flash column chromatography (0-10% EtOAc/petroleum ether) on silica gel to obtain compound 29b as a colorless oil. $^1$H-NMR (400 MHz, DMSO-d$_6$) δ (ppm): 8.21 (s, 1H), 7.88 (s, 1H), 7.32 (t, J=9.2 Hz, 1H), 7.00-7.06 (m, 3H), 6.01 (s, 1H), 5.09 (s, 2H), 3.93-3.98 (m, 2H), 3.74 (s, 3H), 2.75-2.87 (m, 3H), 2.30-2.34 (m, 2H), 1.61-1.63 (m, 2H), 1.05-1.15 (m, 4H), 0.66 (s, 6H), 0.55-0.65 (m, 1H), 0.48-0.53 (m, 1H), 0.28-0.35 (m, 1H), 0.15-0.21 (m, 1H).

C. 3-(5-Chloro-2-((5-(5,5-dimethylcyclopent-1-en-1-yl)-1-(2-fluoro-5-methoxyphenyl)-1H-pyrazol-4-yl)methoxy)pyridin-4-yl)-3-cyclopropylpropanoic acid, Cpd 71

A mixture of compound 29b (70 mg, 0.12 mmol) and LiOH.H$_2$O (52 mg, 1.24 mmol) in THF (4 mL), ethanol (1 mL) and water (1 mL) was stirred overnight at rt. The resulting mixture was concentrated under reduced pressure. Water (4 mL) was added, and the mixture was adjusted to pH~5-6 with HCl (2 N). The precipitates were collected by filtration to yield compound 71 as a white solid. $^1$H-NMR (400 MHz, CD$_3$OD) δ (ppm): 8.10 (s, 1H), 7.86 (s, 1H), 7.18 (t, J=7.2 Hz, 1H), 7.01-7.06 (m, 1H), 6.93-6.98 (m, 1H), 6.88 (s, 1H), 6.00 (s, 1H), 5.15 (s, 2H), 3.77 (s, 3H), 2.85-2.95 (m, 1H), 6.68-6.81 (m, 2H), 2.40 (m, 2H), 1.71 (t, J=7.2 Hz, 2H), 1.05-1.15 (m, 1H), 0.76 (s, 6H), 0.55-0.65 (m, 1H), 0.48-0.53 (m, 1H), 0.28-0.35 (m, 1H), 0.15-0.21 (m, 1H). Mass Spectrum (LCMS, ESI pos.): Calcd. for C$_{29}$H$_{31}$ClFN$_2$O$_4$: 538.2 [M−H]$^−$; found: 538.2.

Following the procedures described in Example 29 and substituting suitably selected reagents, starting materials and conditions as would be readily apparent to those skilled in the art, the following representative compound of the present invention were prepared.

| Cpd No. | Characterization |
|---|---|
| 65 | 3-Cyclopropyl-3-(2-((5-(5,5-dimethylcyclopent-1-en-1-yl)-1-(2-fluoro-5-methoxyphenyl)-1H-pyrazol-4-yl)methoxy)pyridin-4-yl)propanoic acid<br>$^1$H-NMR (400 MHz, DMSO-d$_6$) δ (ppm): 8.05 (d, J = 5.2 Hz, 1H), 7.86 (s, 1H), 7.16-7.20 (m, 1H), 6.91-7.04 (m, 3H), 6.70 (s, 1H), 6.00 (s, 1H), 5.15 (s, 2H), 3.77 (s, 3H), 2.68-2.79 (m, 2H), 2.28-2.40 (m, 3H), 1.69 (t, J = 6.8 Hz, 2H), 0.98-1.08 (m, 1H), 0.76 (s, 6H), 0.55-0.65 (m, 1H), 0.48-0.53 (m, 1H), 0.28-0.35 (m, 1H), 0.10-0.20 (m, 1H).<br>Mass Spectrum (LCMS, ESI pos.): Calcd. for C$_{29}$H$_{32}$FN$_3$O$_4$: 504.2 [M − H]$^−$; found: 504.1. |

Example 30

3-Cyclopropyl-3-(2-((5-(5,5-dimethylcyclopent-1-en-1-yl)-1-(2-fluoro-5-methoxyphenyl)-1H-1,2,3-triazol-4-yl)methoxy)pyridin-4-yl)propanoic acid (Cpd 63)

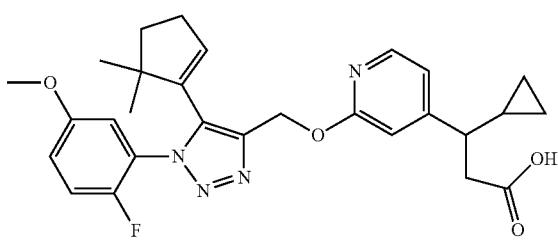

A. (5-(5,5-Dimethylcyclopent-1-en-1-yl)-1-(2-fluoro-5-methoxyphenyl)-1H-1,2,3-triazol-4-yl)methanol, 30a

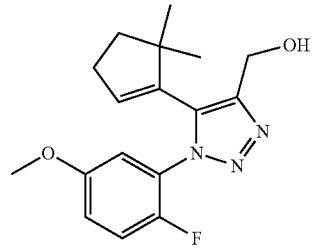

Compound 30a was prepared from compound 5d following similar procedures as described in Example 6, Steps A, B and D. Mass Spectrum (LCMS, ESI pos.): Calcd. for C$_{17}$H$_{20}$FN$_3$O$_2$: 318.1 (M+H); found: 318.0.

B. Ethyl 3-cyclopropyl-3-(2-hydroxypyridin-4-yl)propanoate, 30b

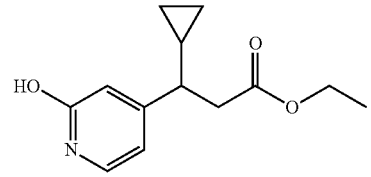

Compound 30b was prepared following similar procedures as described in Example 28, Steps A-F. Mass Spectrum (LCMS, ESI pos.): Calcd. for C$_{13}$H$_{17}$NO$_3$: 236.1 (M+H)$^+$, found: 236.1.

C. 3-Cyclopropyl-3-(2-((5-(5,5-dimethylcyclopent-1-en-1-yl)-1-(2-fluoro-5-methoxyphenyl)-1H-1,2,3-triazol-4-yl)methoxy)pyridin-4-yl)propanoic acid, Cpd 63

Compound 63 was prepared from compound 30a and 30b following procedures similar to those described in Example 29, Steps A-C. $^1$H-NMR (400 MHz, CDCl$_3$) δ (ppm): 8.08 (s, 1H), 7.31 (t, J=9.2 Hz, 1H), 7.16-7.19 (m, 1H), 7.10-7.12 (m, 1H), 6.98 (d, J=1.2 Hz, 1H), 6.75 (s, 1H), 6.07 (s, 1H), 5.34 (s, 2H), 3.83 (s, 3H), 2.76-2.80 (m, 2H), 2.40-2.44 (m, 2H), 2.31-2.34 (m, 1H), 1.75 (t, J=7.2 Hz, 2H), 1.06-1.08 (m, 1H), 0.82 (s, 6H), 0.62-0.66 (m, 1H), 0.45-0.46 (m, 1H), 0.34-0.38 (m, 1H), 0.21 (m, 1H). Mass Spectrum (LCMS, ESI pos.): Calcd. for C$_{28}$H$_{31}$FN$_4$O$_4$: 505.2 [M−H]$^−$; found: 505.2.

143

D. (S)-3-Cyclopropyl-3-(2-((5-(5,5-dimethylcyclopent-1-en-1-yl)-1-(2-fluoro-5-methoxyphenyl)-1H-1,2,3-triazol-4-yl)methoxy)pyridin-4-yl)propanoic acid, Cpd 64 and (R)-3-cyclopropyl-3-(2-((5-(5,5-dimethylcyclopent-1-en-1-yl)-1-(2-fluoro-5-methoxyphenyl)-1H-1,2,3-triazol-4-yl)methoxy)pyridin-4-yl)propanoic acid, Cpd 75

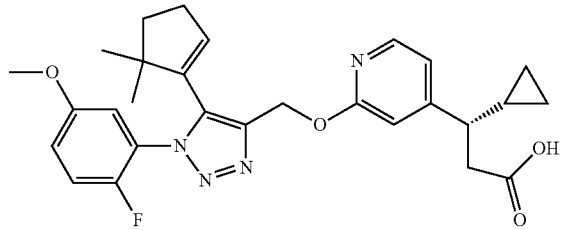 [SMILES: COc1ccc(F)c(-n2nnc(COc3cc(C(CC(=O)O)C4CC4)ccn3)c2C2=CCCC2(C)C)c1]

Cpd 64

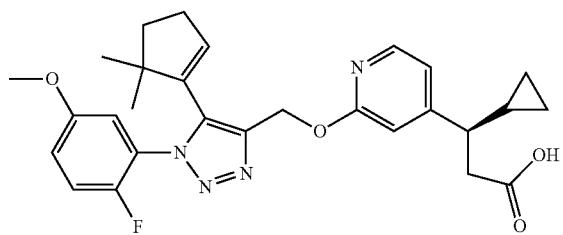

Cpd 75

Compounds 64 and 75 were obtained through a chiral HPLC separation of the racemic compound 63, using the following conditions: column, (R,R)WHELK-01 5/100 Kromasil, 25 cm*21.1 mm; mobile phase, HEX (contained 0.1% HAc) and ethanol (hold 20.0% ethanol in 19 min); detector, UV 254/220 nm.

Compound 64. $^1$H-NMR (400 MHz, DMSO-d$_6$) δ (ppm): 8.08 (d, J=5.2 Hz, 1H), 7.44 (t, J=9.2 Hz, 1H), 7.15-7.25 (m, 2H), 6.97 (d, J=4.8 Hz, 1H), 6.73 (s, 1H), 6.08 (s, 1H), 5.29 (s, 2H), 3.77 (s, 3H), 2.67-2.69 (m, 2H), 2.22-2.38 (m, 3H), 1.64 (t, J=7.2 Hz, 2H), 0.93-1.01 (m, 1H), 0.71 (s, 6H), 0.43-0.51 (m, 1H), 0.21-0.32 (m, 2H), 0.11-0.18 (m, 1H). Mass Spectrum (LCMS, ESI pos.): Calcd. for $C_{28}H_{31}FN_4O_4$: 505.2 [M−H]$^-$; found: 505.2.

Compound 75. $^1$H-NMR (400 MHz, DMSO-d$_6$) δ (ppm): 12.05-12.15 (br.m, 1H), 8.07 (s, 1H), 7.44 (t, J=9.2 Hz, 1H), 7.15-7.25 (m, 2H), 6.97 (m, 1H), 6.72 (s, 1H), 6.08 (s, 1H), 5.29 (s, 2H), 3.77 (s, 3H), 2.67-2.69 (m, 2H), 2.22-2.38 (m, 3H), 1.64 (t, J=7.2 Hz, 2H), 0.93-1.01 (m, 1H), 0.71 (s, 6H), 0.43-0.51 (m, 1H), 0.21-0.32 (m, 2H), 0.11-0.18 (m, 1H). Mass Spectrum (LCMS, ESI pos.): Calcd. for $C_{28}H_{31}FN_4O_4$: 505.2 [M−H]$^-$; found: 505.2.

144

Example 31

(S)-3-Cyclopropyl-3-(3-((1-(2-fluoro-5-methoxyphenyl)-5-isobutyl-1H-imidazol-4-yl)methoxy)phenyl)propanoic acid (Cpd 93)

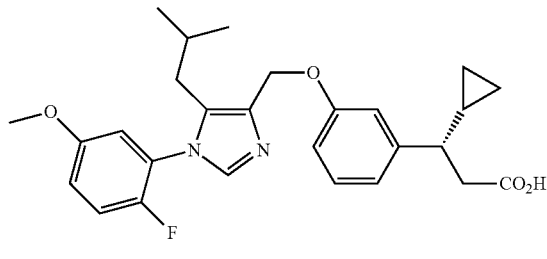 [SMILES: COc1ccc(F)c(-n2cnc(COc3cccc([C@@H](CC(=O)O)C4CC4)c3)c2CC(C)C)c1]

Into a 25-mL pressure tank reactor, was placed compound 91 (60 mg, 0.13 mmol), EtOAc (2 mL) and Pd/C (10%, 70 mg). The resulting mixture was stirred for 1 day at rt under a H$_2$ atmosphere (3.5 atm). The mixture was filtered through a diatomaceous earth pellet and the filtrate was concentrated under reduced pressure. This resulted in compound 93 as a white solid. $^1$H-NMR (400 MHz, DMSO-d$_6$) δ (ppm): 11.42-12.13 (br.m, 1H), 7.74 (s, 1H), 7.42-7.43 (m, 1H), 7.14-7.21 (m, 3H), 6.82-6.92 (m, 3H), 4.93 (s, 2H), 3.79 (s, 3H), 2.61-2.65 (m, 3H), 2.49-2.51 (m, 1H), 2.26-2.31 (m, 1H), 1.32-1.34 (m, 1H), 0.92-1.12 (m, 1H), 0.68 (d, J=3.3 Hz, 6H), 1.41-1.50 (m, 1H), 0.04-0.31 (m, 3H). Mass Spectrum (LCMS, ESI pos.): Calcd. for $C_{27}H_{31}FN_2O_4$: 467.2 [M+H]$^+$; found: 467.2.

Example 32

(S)-3-Cyclopropyl-3-(3-((5-cyclopropyl-1-(5-fluoro-2-methoxypyridin-4-yl)-1H-pyrazol-4-yl)methoxy)phenyl)propanoic acid (Cpd 70) and (S)-3-cyclopropyl-3-(3-((1-(5-fluoro-2-methoxypyridin-4-yl)-1H-pyrazol-4-yl)methoxy)phenyl)propanoic acid (Cpd 81)

Cpd 70

Cpd 81

A. Ethyl 5-cyclopropyl-1-(5-fluoro-2-methoxypyridin-4-yl)-1H-pyrazole-4-carboxylate, 32a, and ethyl 1-(5-fluoro-2-methoxypyridin-4-yl)-1H-pyrazole-4-carboxylate, 32a'

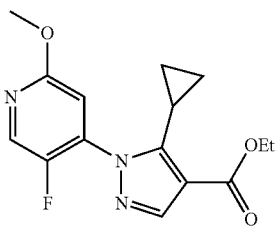

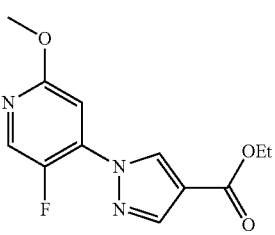

Compound 32a was prepared following procedures similar those described in Example 1, Steps A-D. Mass Spectrum (LCMS, ESI pos.): Calcd. for $C_{15}H_{16}FN_3O_3$: 306.1 (M+H); found: 306.1.

Compound 32a' was the de-bromo bi-product of the Suzuki reaction leading to compound 32a. Mass Spectrum (LCMS, ESI pos.): Calcd. for $C_{12}H_{12}FN_3O_3$: 266.1 (M+H); found: 266.0. Compounds 32a and 32a' were used in the subsequent reaction as a mixture, without further purification.

B. Methyl (S)-3-cyclopropyl-3-(3-((5-cyclopropyl-1-(5-fluoro-2-methoxypyridin-4-yl)-1H-pyrazol-4-yl)methoxy)phenyl)propanoate, 32b, and methyl (S)-3-cyclopropyl-3-(3-((1-(5-fluoro-2-methoxypyridin-4-yl)-1H-pyrazol-4-yl)methoxy)phenyl)propanoate, 32b'

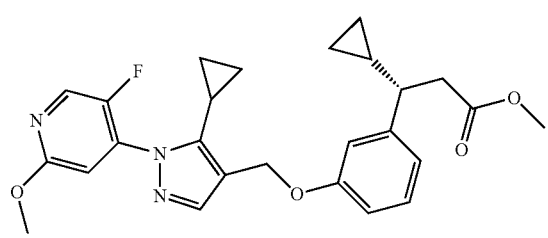

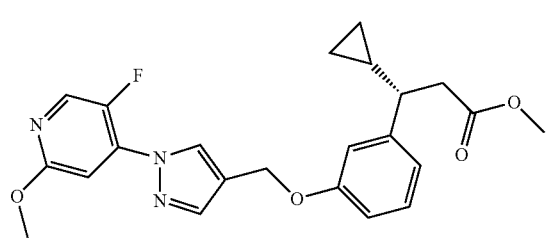

Compounds 32b and 32b' were prepared following procedures similar to those described in Example 3, Steps E-G. The crude mixture was purified by flash column chromatography (0-10% EtOAc/petroleum ether) on silica gel to give compound 32b as a yellow oil and compound 32b' as a yellow oil.

Compound 32b: Mass Spectrum (LCMS, ESI pos.): Calcd. for $C_{26}H_{28}FN_3O_4$: 466.2 (M+H); found: 466.0.

Compound 32b': Mass Spectrum (LCMS, ESI pos.): Calcd. for $C_{23}H_{24}FN_3O_4$: 426.2 (M+H); found: 425.9.

C. (S)-3-Cyclopropyl-3-(3-((5-cyclopropyl-1-(5-fluoro-2-methoxypyridin-4-yl)-1H-pyrazol-4-yl)methoxy)phenyl)propanoic acid, Cpd 70

Compound 70 was prepared from compound 32b following a procedure similar to that described in Example 29, Step C. $^1$H-NMR (300 MHz, DMSO-$d_6$) δ (ppm): 8.42 (s, 1H), 7.83 (s, 1H), 7.12-7.23 (m, 2H), 6.84-6.92 (m, 3H), 4.97 (s, 2H), 3.91 (s, 3H), 2.61-2.62 (m, 2H), 2.26-2.29 (m, 1H), 1.88-1.90 (m, 1H), 0.98-1.01 (m, 1H), 0.75-0.82 (m, 2H), 0.47-0.55 (m, 3H), 0.22-0.32 (m, 2H), 0.11-0.14 (m, 1H). Mass Spectrum (LCMS, ESI pos.): Calcd. for $C_{25}H_{26}FN_3O_4$: 452.2 [M+H]$^+$; found: 452.2.

D. (S)-3-Cyclopropyl-3-(3-((1-(5-fluoro-2-methoxypyridin-4-yl)-1H-pyrazol-4-yl)methoxy)phenyl)propanoic acid, Cpd 81

Compound 81 was prepared from compound 32b' following a procedure similar to that described in Example 29, Step C. $^1$H-NMR (400 MHz, DMSO-$d_6$) δ (ppm): 8.50 (d, J=2.0 Hz, 1H), 8.37 (d, J=3.6 Hz, 1H), 8.01 (s, 1H), 7.26 (d, J=5.6 Hz, 1H), 7.16-7.20 (m, 1H), 6.80-6.90 (m, 3H), 5.05 (s, 2H), 3.89 (s, 3H), 2.44-2.47 (m, 2H), 2.29-2.34 (m, 1H), 0.94-0.96 (m, 1H), 0.44-0.45 (m, 1H), 0.22-0.27 (m, 2H), 0.02-0.08 (m, 1H). Mass Spectrum (LCMS, ESI pos.): Calcd. for $C_{22}H_{22}FN_3O_4$: 412.2 [M+H]$^+$; found: 412.1.

Example 33

(E)-3-Cyclopropyl-3-(3-(2-(5-cyclopropyl-1-(2-fluoro-5-methoxyphenyl)-1H-pyrazol-3-yl)vinyl)phenyl)propanoic acid (Cpd 76)

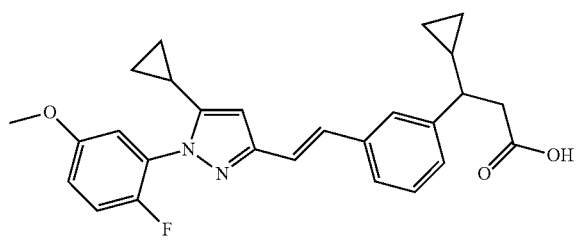 [SMILES: COc1ccc(F)c(-n2nc(/C=C/c3cccc(C(CC(=O)O)C4CC4)c3)cc2C2CC2)c1]

A. (5-Cyclopropyl-1-(2-fluoro-5-methoxyphenyl)-1H-pyrazol-4-yl)methanol, 33a

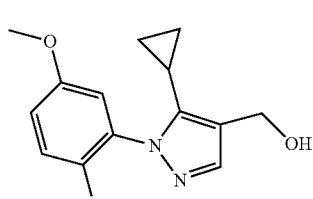

A mixture of compound 2a (3 g, 9.96 mmol), cyclopropylboronic acid (1.72 g, 20.0 mmol), $K_3PO_4$ (6.36 g, 30.0 mmol), $Pd(OAc)_2$ (112 mg, 0.50 mmol) and $PCy_3 \cdot HBF_4$ (368 mg, 1.00 mmol) in toluene (60 mL)/$H_2O$ (10 mL) was stirred for 2 h at 80° C. After cooling to rt, the reaction was quenched with water (100 mL). The resulting mixture was extracted with EtOAc (3×100 mL). The organic layers were combined, dried over anhydrous sodium sulfate and concentrated. The resulting residue was purified by flash column chromatography (0-40% EtOAc/petroleum ether) on silica gel to obtain compound 33a as a yellow solid. Mass Spectrum (LCMS, ESI pos.): Calcd. for $C_{14}H_{15}FN_2O_2$: 263.1 $[M+H]^+$; found: 263.1.

B. 4-(Bromomethyl)-5-cyclopropyl-1-(2-fluoro-5-methoxyphenyl)-1H-pyrazole, 33b

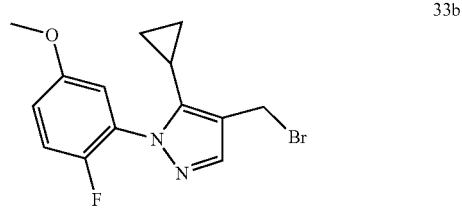 [SMILES: COc1ccc(F)c(-n2ncc(CBr)c2C2CC2)c1]

Compound 33b was prepared from compound 33a following a similar procedure as described in Example 29, Step A. Mass Spectrum (LCMS, ESI pos.): Calcd. for $C_{14}H_{14}BrFN_2O$: 327.0 $[M+H]^+$; found: 327.0.

C. ((5-Cyclopropyl-1-(2-fluoro-5-methoxyphenyl)-1H-pyrazol-4-yl)methyl)triphenylphosphonium, 33c

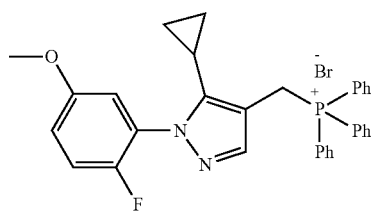

A mixture of compound 33b (1 g, 3.08 mmol) and $PPh_3$ (800 mg, 3.05 mmol) in toluene (20 mL) was stirred for 6 h at 120° C. The resulting mixture was concentrated under reduced pressure. The residue obtained was purified by flash column chromatography (0-5% methanol/DCM) on silica gel to yield compound 33c as a gray solid. Mass Spectrum (LCMS, ESI pos.): Calcd. for $C_{32}H_{29}FN_2OP$: 507.2 $[M]^+$; found: 507.2.

D. Methyl 3-cyclopropyl-3-(3-(((trifluoromethyl)sulfonyl)oxy)phenyl)propanoate, 33d

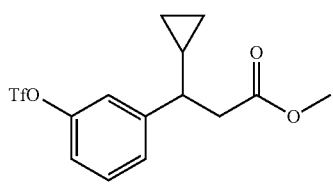

To a solution of methyl 3-cyclopropyl-3-(3-hydroxyphenyl)propanoate (1.5 g, 6.82 mmol, methyl ester of compound 1f-B) and triethylamine (2.83 mL, 20.5 mmol) in DCM (20 mL) was added $Tf_2O$ (2.9 g, 10.3 mmol) dropwise at 0° C. under $N_2$. The resulting solution was stirred for 4 h at 0° C. in a water/ice bath. The reaction was then quenched with brine (50 mL). The resulting solution was extracted with DCM (3×50 mL), and the organic layers were combined, dried over anhydrous sodium sulfate and concentrated under reduced pressure. The resulting residue was purified by flash column chromatography (0-20% EtOAc/petroleum ether) on silica gel to obtain compound 33d as a yellow oil. Mass Spectrum (LCMS, ESI pos.): Calcd. for $C_{14}H_{15}F_3O_5S$: 353.1 $[M+H]^+$; found: 353.1.

E. Methyl 3-cyclopropyl-3-(3-formylphenyl)propanoate, 33e

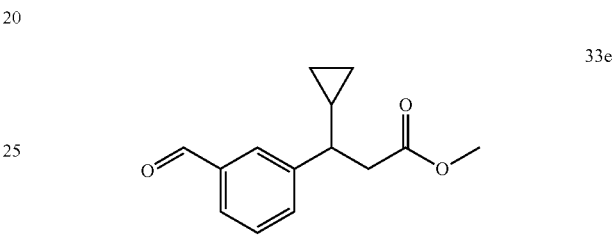

A mixture of compound 33d (1.76 g, 5.00 mmol), triethylamine (1.26 g, 12.5 mmol), triethylsilane (1.16 g, 10.0 mmol), $Pd(OAc)_2$ (56 mg, 0.25 mmol) and DPPP (103 mg, 0.25 mmol) in DMF (25 mL) was stirred for 5 h at 80° C. under a $CO_{(g)}$ atmosphere (5 atm). After cooling to rt, the reaction was quenched with water (25 mL). The resulting mixture was extracted with EtOAc (3×30 mL). The organic layers were combined, dried over anhydrous sodium sulfate and concentrated. The resulting residue was purified by flash column chromatography (0-15% EtOAc/petroleum ether) on silica gel to obtain compound 33e as a yellow oil. Mass Spectrum (LCMS, ESI pos.): Calcd. for $C_{14}H_{16}O_3$: 233.1 $[M+H]^+$; found: 233.0.

F. Methyl (E)-3-cyclopropyl-3-(3-(2-(5-cyclopropyl-1-(2-fluoro-5-methoxyphenyl)-1H-pyrazol-4-yl)vinyl)phenyl)propanoate, 33f

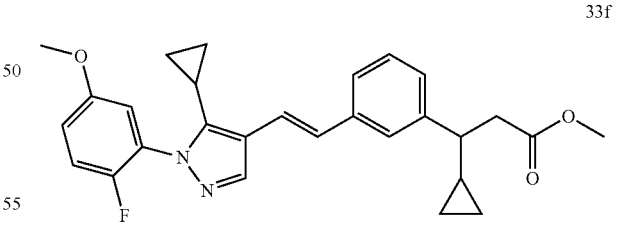

To a stirring solution of compound 33c (587 mg, 1.00 mmol) in THF (14 mL) was added LDA (1 mL, 2M in THF) dropwise at −70° C. under $N_2$. After 30 min at −70° C., a solution of compound 33e (350 mg, 1.51 mmol) in THF (1 mL) was added dropwise. The resulting solution was stirred for 1 h at −70° C. The reaction was then quenched with $NH_4Cl$ (satd 10 mL). The resulting mixture was extracted with EtOAc (3×20 mL). The organic layers were combined, dried over anhydrous sodium sulfate and concentrated. The resulting residue was purified by flash chromatography (0-15% EtOAc/petroleum ether) on silica gel to obtain compound 33f as a yellow oil. Mass Spectrum (LCMS, ESI pos.): Calcd. for $C_{28}H_{29}FN_2O_3$: 461.2 $[M+H]^+$; found: 461.3.

G. (E)-3-Cyclopropyl-3-(3-(2-(5-cyclopropyl-1-(2-fluoro-5-methoxyphenyl)-1H-pyrazol-3-yl)vinyl)phenyl)propanoic acid, Cpd 76

Compound 76 was prepared from compound 33f following a procedure similar to that described in Example 26, Step D. $^1$H-NMR (300 MHz, DMSO-$d_6$) δ (ppm): 8.01 (s, 1H), 6.89-7.50 (m, 9H), 3.80 (s, 3H), 2.59-2.79 (m, 2H), 2.31 (q, J=7.9 Hz, 1H), 1.85-1.96 (m, 1H), 1.01-1.11 (m, 1H), 0.77-0.90 (m, 2H), 0.10-0.60 (m, 6H). Mass Spectrum (LCMS, ESI pos.): Calcd. for $C_{27}H_{27}FN_2O_3$: 447.2 $[M+H]^+$; found: 447.2.

Following the procedures described in Example 33 above, and substituting suitably selected reagents, starting materials and conditions as would be readily apparent to those skilled in the art, the following representative compound of the present invention were prepared.

A. Methyl 3-cyclopropyl-3-(3-(2-(5-cyclopropyl-1-(2-fluoro-5-methoxyphenyl)-1H-pyrazol-4-yl)ethyl)phenyl)propanoate, 34a

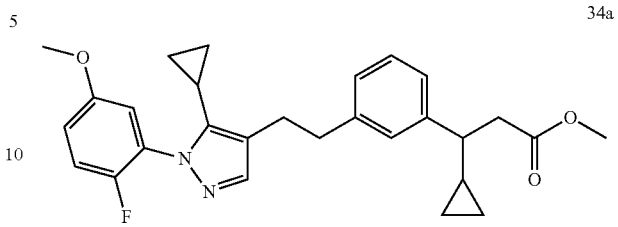

34a

To the solution of compound 33f (120 mg, 0.26 mmol), in methanol (5 mL) was added Pd/C (10%, 30 mg). The resulting mixture was stirred for 2 h at rt under a H$_2$ atmosphere (3 atm). The mixture was filtered through a diatomaceous earth pellet and the filtrate was concentrated under reduced pressure to provide compound 34a as colorless oil. Mass Spectrum (LCMS, ESI pos.): Calcd. for $C_{28}H_{31}FN_2O_3$: 463.2 $[M+H]^+$; found: 463.3.

| Cpd No. | Characterization |
|---|---|
| 6 | (E)-3-Cyclopropyl-3-(3-(2-(4-cyclopropyl-5-(2-fluoro-5-methoxyphenyl)isoxazol-3-yl)vinyl)phenyl)propanoic acid<br>$^1$H-NMR (400 MHz, DMSO-$d_6$) δ (ppm): 7.58-7.69 (m, 2H), 7.53 (d, J = 7.6 Hz, 1H), 7.10-7.43 (m, 6H), 3.82 (s, 3H), 2.66 (d, J = 7.5 Hz, 2H), 2.35 (q, J = 7.8 Hz, 1H), 1.89-1.95 (m, 1H), 1.01-1.07 (m, 1H), 0.87-0.97 (m, 2H), 0.50 (q, J = 7.1 Hz, 1H), 0.12-0.38 (m, 5H).<br>Mass Spectrum (LCMS, ESI pos.): Calcd. for $C_{27}H_{26}FNO_4$: 448.2 $[M + H]^+$; found: 448.1. |
| 58 | (S,E)-3-Cyclopropyl-3-(3-(2-(4-cyclopropyl-3-(2-fluoro-5-methoxyphenyl)isoxazol-5-yl)vinyl)phenyl)propanoic acid<br>$^1$H-NMR (400 MHz, DMSO-$d_6$) δ (ppm): 7.62 (s, 1H), 7.56 (d, J = 7.6 Hz, 1H), 7.20-7.48 (m, 5H), 7.07-7.18 (m, 2H), 3.80 (s, 3H), 2.63-2.70 (m, 2H), 2.29-2.40 (m, 1H), 1.75-1.84 (m, 1H), 1.01-1.12 (m, 1H), 0.76-0.86 (m, 2H), 0.48-0.56 (m, 1H), 0.23-0.37 (m, 4H), 0.12-0.18 (m, 1H).<br>Mass Spectrum (LCMS, ESI pos.): Calcd. for $C_{27}H_{26}FNO_4$: 448.2 $[M + H]^+$; found: 448.1. |
| 74 | (S,E)-3-Cyclopropyl-3-(3-(2-(5-cyclopropyl-1-(2-fluoro-5-methoxyphenyl)-1H-1,2,3-triazol-4-yl)vinyl)phenyl)propanoic acid<br>$^1$H-NMR (300 MHz, DMSO-$d_6$) δ (ppm): 7.16-7.52 (m, 9H), 3.82 (s, 3H), 2.73 (d, J = 7.2 Hz, 2H), 2.31-2.37 (m, 1H), 1.90-1.95 (m, 1H), 1.06-1.09(m, 1H), 0.88-0.95 (m, 2H), 0.54-0.57 (m, 3H), 0.15-0.37 (m, 3H).<br>Mass Spectrum (LCMS, ESI pos.): Calcd. for $C_{26}H_{26}FN_3O_3$: 448.2 $[M + H]^+$; found: 448.3. |

Example 34

3-Cyclopropyl-3-(3-(2-(5-cyclopropyl-1-(2-fluoro-5-methoxyphenyl)-1H-pyrazol-3-yl)ethyl)phenyl)propanoic acid (Cpd 77)

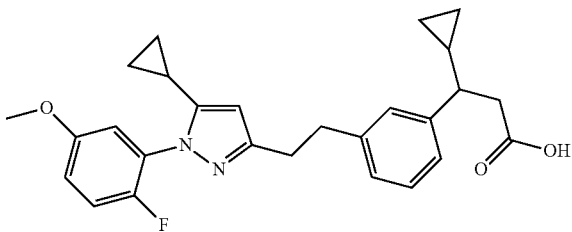 [SMILES: COc1ccc(F)c(-n2nc(CCc3cccc(C(CC(=O)O)C4CC4)c3)cc2C2CC2)c1]

B. 3-Cyclopropyl-3-(3-(2-(5-cyclopropyl-1-(2-fluoro-5-methoxyphenyl)-1H-pyrazol-3-yl)ethyl)phenyl)propanoic acid, Cpd 77

Compound 77 was prepared from compound 34a following a procedure similar to that described in Example 29, Step C. $^1$H-NMR (400 MHz, DMSO-$d_6$) δ (ppm): 7.50 (s, 1H), 7.34 (t, J=9.5 Hz, 1H), 7.20-6.97 (m, 6H), 3.77 (s, 3H), 2.70-2.88 (m, 4H), 2.29-2.55 (m, 3H), 1.55-1.70 (m, 1H), 0.89-0.97 (m, 1H), 0.57-0.70 (m, 2H), 0.41-0.47 (m, 1H), 0.18-0.27 (m, 4H), 0.01-0.09 (m, 1H). Mass Spectrum (LCMS, ESI pos.): Calcd. for $C_{27}H_{29}FN_2O_3$: 449.2 $[M+H]^+$; found: 449.2.

Following the procedures described in Example 34 above, and substituting suitably selected reagents, starting materials and conditions as would be readily apparent to those skilled in the art, the following representative compound of the present invention were prepared.

| Cpd No. | Characterization |
|---|---|
| 7 | 3-Cyclopropyl-3-(3-(2-(4-cyclopropyl-5-(2-fluoro-5-methoxyphenyl)isoxazol-3-yl)ethyl)phenyl)propanoic acid<br>$^1$H-NMR (400 MHz, DMSO-$d_6$) δ (ppm): 7.33 (t, J = 10.0, 1.4 Hz, 1H), 7.05-7.25 (m, 6H), 3.80 (s, 3H), 3.01 (s, 4H), 2.51-2.59 ( m, 2H), 2.31 (q, J = 7.8 Hz, 1H), 1.64 (tt, J = 8.3, 5.3 Hz, 1H), 0.89-0.95 (m, 1H), 0.72-0.85 (m, 2H), 0.39-0.52 (m, 1H), 0.16-0.32 (m, 4H), 0.07-0.12 (m, 1H).<br>Mass Spectrum (LCMS, ESI pos.): Calcd. for $C_{27}H_{28}FNO_4$: 450.2 [M + H]$^+$; found: 450.2. |
| 54 | (3S)-3-Cyclopropyl-3-(3-(2-(4-(2,2-dimethylcyclopentyl)-3-(2-fluoro-5-methoxyphenyl)isoxazol-5-yl)ethyl)phenyl)propanoic acid<br>$^1$H-NMR (300 MHz, CD$_3$OD) δ (ppm): 7.10-7.21 (m, 5H), 6.98-7.08 (m, 1H), 6.86-6.88 (m, 1H), 3.80 (s, 3H), 3.07-3.19 (m, 4H), 2.68-2.74 (m, 2H), 2.32-2.46 (m, 2H), 1.57-1.77(m, 4H), 1.37-1.43 (m, 2H), 1.01-1.09 (m, 1H), 0.59-0.64 (m, 7H), 0.29-0.37 (m, 2H), 0.11-0.13(m, 1H).<br>Mass Spectrum (LCMS, ESI pos.): Calcd. for $C_{31}H_{36}FNO_4$: 506.3 [M + H]$^+$; found: 506.2. |
| 57 | (S)-3-Cyclopropyl-3-(3-(2-(4-cyclopropyl-3-(2-fluoro-5-methoxyphenyl)isoxazol-5-yl)ethyl)phenyl)propanoic acid<br>$^1$H-NMR (400 MHz, DMSO-$d_6$) δ (ppm): 7.30 (t, J = 9.3 Hz, 1H), 7.18 (t, J = 8 Hz, 1H), 6.98-7.12 (m, 5H), 3.78 (s, 3H), 3.10 (t, J = 7.3 Hz, 2H), 2.98 (t, J = 7.5 Hz, 2H), 2.51-2.62 (m, 3H), 2.21-2.38 (m, 1H), 1.36-1.44 (m, 1H), 0.86-0.97 (m, 1H), 0.53-0.63 (m, 2H), 0.41-0.48 (m, 1H), 0.18-0.26 (m, 2H), 0.03-0.09 (m, 2H). Mass Spectrum (LCMS, ESI pos.): Calcd. for $C_{27}H_{28}FNO_4$: 450.2 [M + H]$^+$; found: 450.1. |
| 79 | (S)-3-Cyclopropyl-3-(3-(2-(5-cyclopropyl-1-(2-fluoro-5-methoxyphenyl)-1H-1,2,3-triazol-4-yl)ethyl)phenyl)propanoic acid<br>$^1$H-NMR (300 MHz, DMSO-$d_6$) δ (ppm): 7.46 (t, J = 9.4 Hz, 1H), 6.95-7.26 (m, 6H), 3.80 (s, 3H), 2.97 (d, J = 4.3 Hz, 4H), 2.54-2.69 (m, 2H), 2.20-2.28 (m, 1H), 1.47-1.53 (m, 1H), 0.95-0.99 (m, 1H), 0.64-0.70 (m, 2H), 0.45-0.50 (m, 1H), 0.19-0.29 (m, 4H), 0.05-0.10 (m, 1H). Mass Spectrum (LCMS, ESI pos.): Calcd. for $C_{26}H_{28}FN_3O_3$: 450.2 [M + H]$^+$; found: 450.3. |

Example 35

(S,E)-3-Cyclopropyl-3-(3-(2-(4-(5, 5-dimethylcyclopent-1-en-1-yl)-3-(2-fluoro-5-methoxyphenyl)isoxazol-5-yl)vinyl)phenyl)propanoic acid (Cpd 56) and (S,Z)-3-cyclopropyl-3-(3-(2-(4-(5,5-dimethylcyclopent-1-en-1-yl)-3-(2-fluoro-5-methoxyphenyl)isoxazol-5-yl)vinyl)phenyl)propanoic acid (Cpd 59)

Cpd 56

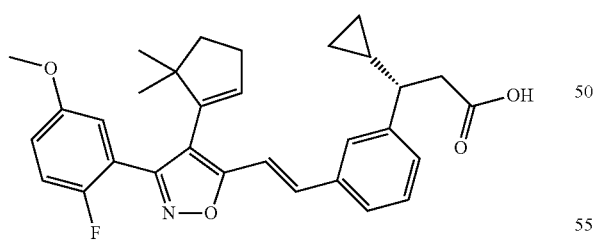

Cpd 59

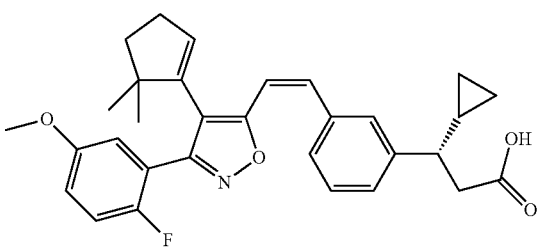

A. 4-Bromo-3-(2-fluoro-5-methoxyphenyl)isoxazole-5-carbaldehyde, 35a

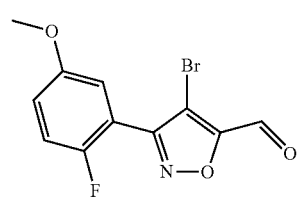

35a

A mixture of compound 7f (400 mg, 1.32 mmol), IBX (500 mg, 1.79 mmol) in DMSO (5 mL) was stirred overnight at 40° C. The reaction was then quenched with NaHCO$_3$ (satd, 5 mL). The resulting solution was extracted with EtOAc (3×5 mL), and the organic layers were combined, washed with water (2×10 mL) and concentrated under reduced pressure. The residue was purified by flash column chromatography (0-20% EtOAc/petroleum ether) on silica gel to obtain compound 35a as a yellow oil. $^1$H-NMR (300 MHz, CDCl$_3$) δ (ppm): 8.54 (s, 1H), 7.12-7.18 (m, 1H), 7.01-7.04 (m, 2H), 3.83 (s, 3H).

B. 4-(5,5-Dimethylcyclopent-1-en-1-yl)-3-(2-fluoro-5-methoxyphenyl)isoxazole-5-carbaldehyde, 35b

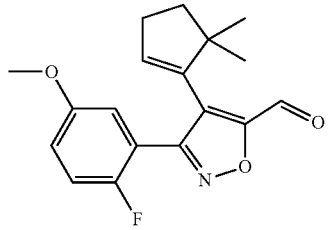

35b

Compound 35b was prepared from compound 35a following a procedure similar to that described in Example 3, Step D. Mass Spectrum (LCMS, ESI pos.): Calcd. for $C_{18}H_{18}FNO_3$: 316.1 (M+H); found: 316.1.

C. Methyl (S)-3-cyclopropyl-3-(3-(((trifluoromethyl)sulfonyl)oxy)phenyl)propanoate, 35c

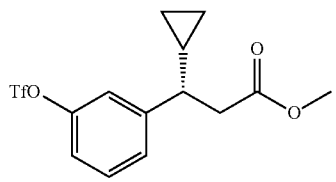

35c

Compound 35c was prepared following a procedure similar to that described in Example 33, Step D. Compound 35c was used in the next step without further purification.

D. Methyl (S)-3-cyclopropyl-3-(3-(hydroxymethyl)phenyl)propanoate, 35d

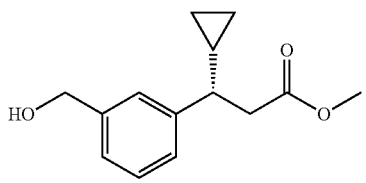

35d

A mixture of compound 35d (500 mg, 1.42 mmol), potassium acetoxymethyl-trifluoroborate (500 mg, 2.79 mmol), $Pd_2(dba)_3$ (100 mg, 0.11 mmol), RuPhos (100 mg, 0.21 mmol) and $Na_2CO_3$ (200 mg, 1.90 mmol) in 1,4-dioxane (15 mL) and $H_2O$ (1.5 mL) was stirred for 3 h at 110° C. under $N_2$. The reaction was then quenched with water (100 mL). The resulting mixture was extracted with EtOAc (2×50 mL). The organic layers were combined, dried over anhydrous sodium sulfate and concentrated. The resulting residue was purified by flash column chromatography (0-50% EtOAc/petroleum ether) on silica gel to obtain compound 35d as a yellow oil. $^1$H-NMR (300 MHz, CDCl$_3$) δ (ppm): 7.15-7.30 (m, 4H), 4.69 (s, 2H), 3.60 (s, 3H), 2.68-2.80 (m, 2H), 2.33-2.41 (m, 1H), 0.96-1.05 (m, 1H), 0.55-0.60 (m, 1H), 0.40-0.45 (m, 1H), 0.24-0.29 (m, 1H), 0.12-0.18 (m, 1H).

E. Ethyl (S)-3-cyclopropyl-3-(3-((diethoxyphosphoryl)methyl)phenyl)propanoate, 35e

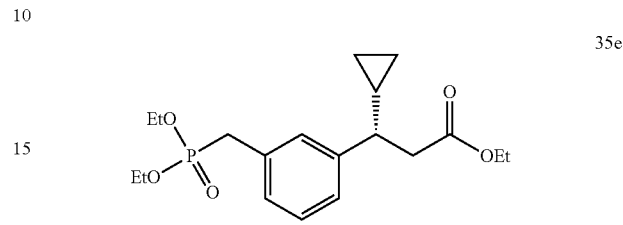

35e

To a solution of compound 35d (1 g, 4.27 mmol) in toluene (30 mL) was added diiodozinc (2.5 g, 7.83 mmol) and triethyl phosphite (5 g, 30.09 mmol). The resulting solution was stirred overnight at 120° C. under $N_2$. After cooling to rt, the reaction was quenched with water/ice (100 mL). The resulting mixture was extracted with EtOAc (2×300 mL). The organic layers were combined, dried over anhydrous sodium sulfate and concentrated. The resulting residue was purified by flash column chromatography (0-50% EtOAc/DCM) on silica gel to obtain compound 35e as a yellow oil. Mass Spectrum (LCMS, ESI pos.): Calcd. for $C_{19}H_{29}O_5P$: 369.2 (M+H); found: 369.2.

F. Ethyl (S)-3-cyclopropyl-3-(3-(2-(4-(5,5-dimethylcyclopent-1-en-1-yl)-3-(2-fluoro-5-methoxyphenyl)isoxazol-5-yl)vinyl)phenyl)propanoate, 35f

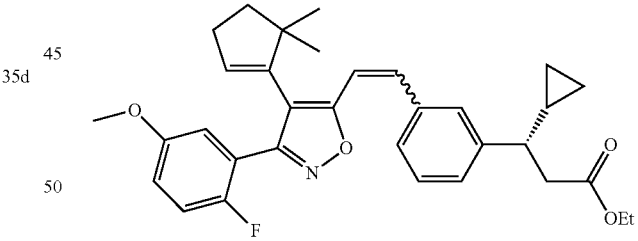

35f

To a mixture of compound 35e (134 mg, 0.36 mmol) and 15-crown-5 (50 mg) in THF (2 mL) was added sodium hydride (16 mg, 0.4 mmol, 60% in mineral oil). After stirring at rt for 15 min, compound 35b (100 mg, 0.32 mmol) was added, and the resulting solution was stirred for 2 h at rt. The reaction was then quenched with NH$_4$Cl (satd, 5 mL). The resulting solution was extracted with EtOAc (3×5 mL), and the organic layers were combined, washed with $H_2O$ (2×10 mL) and concentrated under reduced pressure. The residue was purified by flash column chromatography (0-5% EtOAc/petroleum ether) on silica gel to obtain compound 35f as a yellow oil. Mass Spectrum (LCMS, ESI pos.): Calcd. for $C_{33}H_{36}FNO_4$: 530.3 (M+H); found: 530.2.

G. (S,E)-3-Cyclopropyl-3-(3-(2-(4-(5,5-dimethylcyclopent-1-en-1-yl)-3-(2-fluoro-5-methoxyphenyl)isoxazol-5-yl)vinyl)phenyl)propanoic acid (Cpd 56) and (S,Z)-3-cyclopropyl-3-(3-(2-(4-(5,5-dimethylcyclopent-1-en-1-yl)-3-(2-fluoro-5-methoxyphenyl)isoxazol-5-yl)vinyl)phenyl)propanoic acid (Cpd 59)

A mixture of compound 35f (30 mg, 0.056 mmol) and LiOH.H₂O (24 mg, 0.57 mmol) in THF (4 mL)/water (1 mL)/methanol (1 mL) was stirred overnight at rt. The reaction mixture was concentrated under reduced pressure. The residue was dissolved in water (5 mL), and the pH of the solution was adjusted to ~5 with HCl (1 N). The precipitates were collected by filtration. The crude product was purified by chiral HPLC with the following conditions: column, repaired ADH, 21.2*150 mm, 5 um; mobile phase, hex (0.1% TFA) and IPA (hold 40.0% IPA in 8 min); Detector, UV 254/220 nm to provide compound 56 and compound 59.

Compound 56: $^1$H-NMR (300 MHz, DMSO-$d_6$) δ (ppm): 12.00 (brs, 1H), 7.44-7.54 (m, 2H), 7.37 (s, 1H), 7.25-7.32 (m, 3H), 7.04-7.12 (m, 2H), 6.90-6.95 (m, 1H), 5.94 (s, 1H), 3.75 (s, 3H), 2.69-2.72 (m, 2H), 2.32-2.45 (m, 3H), 1.73 (t, J=6.9 Hz, 2H), 1.03-1.06 (m, 1H), 0.70 (s, 6H), 0.52-0.53 (m, 1H), 0.26-0.34 (m, 2H), 0.15-0.17 (m, 1H). Mass Spectrum (LCMS, ESI pos.): Calcd. for $C_{31}H_{32}FNO_4$: 502.2 [M+H]$^+$. found: 502.2.

Compound 59: $^1$H-NMR (300 MHz, DMSO-$d_6$) δ (ppm): 7.24-7.38 (m, 5H), 6.93-7.11 (m, 3H), 6.36 (d, J=12.6 Hz, 1H), 5.82 (s, 1H), 3.74 (s, 3H), 2.62-2.64 (m, 2H), 2.26-2.36 (m, 3H), 1.70-1.70 (t, J=6.9 Hz, 2H), 0.95-1.07 (m, 1H), 0.70 (s, 6H), 0.52-0.53 (m, 1H), 0.26-0.34 (m, 2H), 0.15-0.17 (m, 1H). Mass Spectrum (LCMS, ESI pos.): Calcd. for $C_{31}H_{32}FNO_4$: 502.2 [M+H]$^+$; found: 502.2.

Example 36

(S)-3-Cyclopropyl-3-(3-((4-(5,5-dimethylcyclopent-1-en-1-yl)-3-(2-fluoro-5-methoxyphenyl)isothiazol-5-yl)methoxy)phenyl)propanoic acid (Cpd 61)

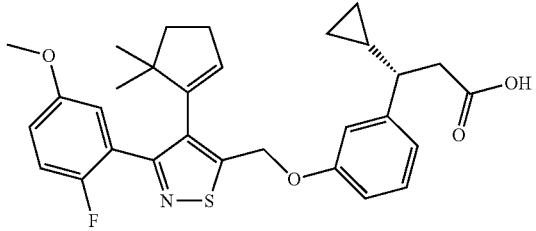 [SMILES: COc1ccc(F)c(-c2nsc(COc3cccc([C@@H](CC(=O)O)C4CC4)c3)c2C2=CCCC2(C)C)c1]

A. 2-Fluoro-5-methoxybenzamide, 36a

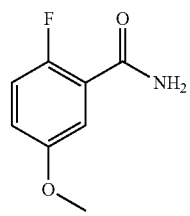

36a

To a solution of 2-fluoro-5-methoxybenzonitrile (2 g, 13.2 mmol) in DMSO (6.6 mL) was added H₂O₂ (1.6 mL) and K₂CO₃ (274 mg, 1.98 mmol). The resulting solution was stirred for 30 min at rt. The reaction was then quenched with NaHCO₃ (satd, 30 mL). The resulting solution was extracted with EtOAc (50 mL), and the organic layers were combined, and concentrated under reduced pressure. The residue was purified by flash column chromatography (0-10% EtOAc/petroleum ether) on silica gel to obtain compound 36a as a white solid. $^1$H-NMR (400 MHz, DMSO-$d_6$) δ (ppm): 7.66-7.70 (m, 2H), 7.04-7.23 (m, 3H), 3.77 (s, 3H).

B. 5-(2-Fluoro-5-methoxyphenyl)-1,3,4-oxathiazol-2-one, 36b

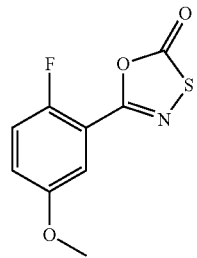

36b

A mixture of 36a (2.86 g, 16.9 mmol) and chloro(chlorosulfanyl)methanone (3.29 g, 25.1 mmol) in toluene (50 mL) was stirred overnight at 100° C. in an oil bath. The resulting mixture was concentrated under reduced pressure. The residue was purified by flash column chromatography (0-20% EtOAc/petroleum ether) on silica gel to obtain compound 36b as a yellow solid. $^1$H-NMR (300 MHz, DMSO-$d_6$) δ (ppm): 7.24-7.49 (m, 3H), 3.80 (s, 3H).

C. Ethyl 3-(2-fluoro-5-methoxyphenyl)isothiazole-5-carboxylate, 36c

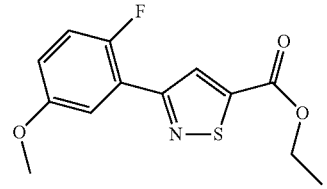

36c

A mixture of compound 36b (2.4 g, 10.6 mmol) and ethyl but-3-ynoate (2.37 g, 21.1 mmol) in 1,3-dichlorobenzene (8 mL) was stirred for 5 h at 150° C. in an oil bath. After cooling to rt, the reaction was quenched with NH₄Cl (satd, 10 mL). The resulting solution was extracted with EtOAc (3×15 mL), and the organic layers were combined and concentrated under reduced pressure. The residue was purified by flash column chromatography (0-10% EtOAc/petroleum ether) on silica gel to obtain compound 36c as a yellow solid. Mass Spectrum (LCMS, ESI pos.): Calcd. for $C_{13}H_{12}FNO_3S$: 282.1 [M+H]$^+$; found: 282.1.

D. (S)-3-Cyclopropyl-3-(3-((4-(5,5-dimethylcyclopent-1-en-1-yl)-3-(2-fluoro-5-methoxyphenyl)isothiazol-5-yl)methoxy)phenyl)propanoic acid, Cpd 61

Compound 61 was prepared from compound 36c following similar procedures as described in Example 7, Steps E-H. $^1$H-NMR (300 MHz, DMSO-$d_6$) δ (ppm): 7.83 (d, J=3.0 Hz, 1H), 7.56 (d, J=6.3 Hz, 1H), 7.17-7.23 (m, 1H), 6.96-7.00 (m, 2H), 6.85-6.89 (m, 2H), 5.60-5.70 (m, 1H), 5.55 (s, 2H), 3.78 (s, 3H), 2.28-2.39 (m, 5H), 1.79-1.84 (m, 2H), 1.23 (s, 6H), 0.96-0.98 (m, 1H), 0.40-0.50 (m, 1H), 0.18-0.30 (m, 2H), 0.01-0.09 (m, 1H). Mass Spectrum (LCMS, ESI pos.): Calcd. for $C_{30}H_{32}FNO_4S$: 522.2 (M+H); found: 522.0.

Example 37

(S)-3-(3-((5-(Tert-butyl)-4-(2-fluoro-5-methoxyphenyl)thiophen-2-yl)methoxy)phenyl)-3-cyclopropylpropanoic acid (Cpd 60)

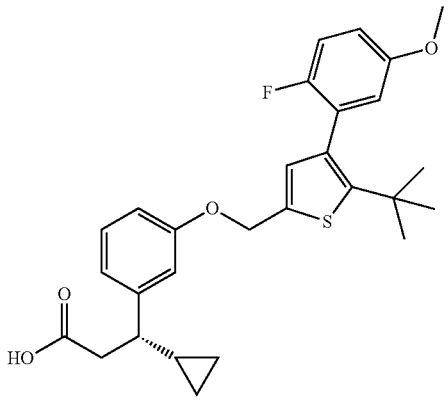 [SMILES: COc1ccc(F)c(-c2cc(COc3cccc([C@@H](CC(=O)O)C4CC4)c3)sc2C(C)(C)C)c1]

A. Methyl 4-bromo-5-(tert-butyl)thiophene-2-carboxylate, 37a

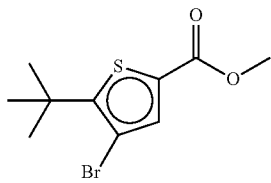

A solution of the methyl 5-(tert-butyl)thiophene-2-carboxylate (1.0 g, 5 mmol) in $CH_2Cl_2$ (5 mL) was added dropwise to a stirred suspension of $AlCl_3$ (1.7 g, 12 mmol) in $CH_2Cl_2$ (5 mL) at 0° C. The reaction mixture was then stirred for an additional 30 min. A solution of $Br_2$ in $CH_2Cl_2$ (2 M, 2.5 mL, 5 mmol) was added at the same temperature and the stirring was continued for 1 h. The reaction mixture was poured onto acidic crushed ice (5 g, conc. aq HCl (2 mL) and extracted with $CH_2Cl_2$ (2×10 mL). The combined organic layers were washed successively with brine (10 mL) and satd aq $NaHCO_3$ (10 mL) and subsequently dried over $MgSO_4$. The solvent was evaporated under reduced pressure and the residue was distilled to give compound 37a. $^1$H-NMR (300 MHz, $CDCl_3$) δ (ppm): 7.62 (s, 1H), 5.30 (s, 1H), 3.86 (s, 3H), 1.51 (s, 9H).

B. Methyl 5-(tert-butyl)-4-(2-fluoro-5-methoxyphenyl)thiophene-2-carboxylate, 37b

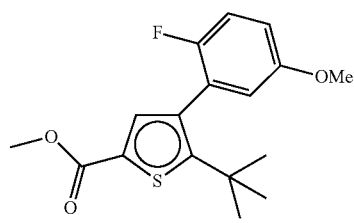

A mixture of compound 37a (459 mg, 1.65 mmol), (2-fluoro-5-methoxyphenyl)boronic acid (338 mg, 1.98 mmol), $Pd(PPh_3)_4$ (191 mg, 0.166 mmol) and $K_2CO_3$ (572 mg, 4.14 mmol) in dioxane (10 mL) was stirred for 48 h at 98° C. under $N_2$. The reaction mixture was allowed to cool to rt and was treated with water (15 mL). The resulting solution was extracted with EtOAc (3×10 mL). The organic layers were combined, dried over anhydrous sodium sulfate and concentrated. The residue obtained was purified by column chromatography on silica gel (EtOAc/petroleum ether, 1:100-1:20) to give compound 37b. $^1$H-NMR (300 MHz, $CDCl_3$) δ: 7.47-7.52 (m, 1H), 6.97-7.04 (m, 1H), 6.82-6.91 (m, 1H), 6.75 (dd, J=6.1, 3.0 Hz, 1H), 3.85 (s, 3H), 3.77 (s, 3H), 1.25-1.33 (m, 9H).

C. (5-(Tert-butyl)-4-(2-fluoro-5-methoxyphenyl)thiophen-2-yl)methanol, 37c

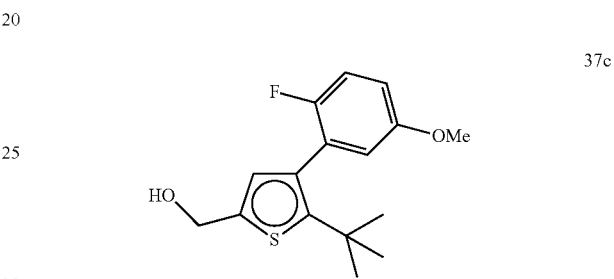

To a solution of compound 37b (258 mg, 0.800 mmol) in THF, LAH (1 M in THF, 0.800 mL, 1.00 mmol) was added at 0° C. The resulting mixture was stirred for 30 min at 0° C. Water (0.1 mL), 3N NaOH (0.1 mL), and water (0.3 mL) were added sequentially with stirring. The mixture was extracted with DCM (3×20 mL). The combined organic phases were dried and then concentrated to give compound 37c. Mass Spectrum (LCMS, ESI pos.): Calcd. for $C_{16}H_{19}FO_2S$: 317.1 (M+Na); found: 317.0.

D. (S)-Methyl 3-(3-((5-(tert-butyl)-4-(2-fluoro-5-methoxyphenyl)thiophen-2-yl)methoxy)phenyl)-3-cyclopropylpropanoate, 37d

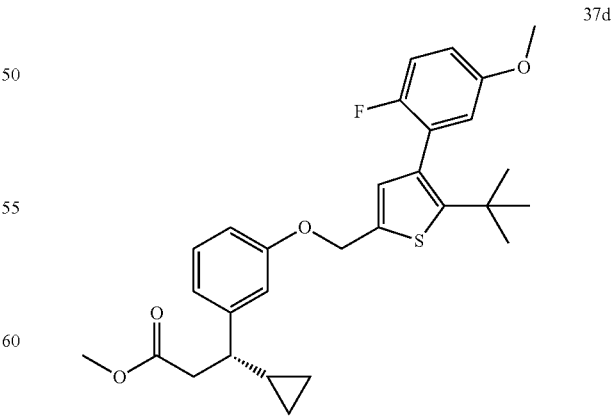

To a mixture of methyl (3S)-3-cyclopropyl-3-(3-hydroxyphenyl)propanoate (75 mg, 0.34 mmol), compound 37c (100 mg, 0.34 mmol) and $Ph_3P$ (0.26 g, 0.51 mmol) in DCM (10 mL), was added DEAD (80.67 µL, 0.51 mmol) dropwise at 0° C. The resulting mixture was allowed to warm to rt with stirring overnight. The reaction mixture was filtered and concentrated. The residue obtained was purified by flash column chromatography on silica gel (0-50% EtOAc/heptane) to give compound 37d. Mass Spectrum (LCMS, ESI pos.): Calcd. for $C_{29}H_{33}FO_4S$: 519.6 (M+Na); found: 519.2.

E. (S)-3-(3-((5-(tert-butyl)-4-(2-fluoro-5-methoxyphenyl)thiophen-2-yl)methoxy)phenyl)-3-cyclopropylpropanoic acid, Cpd 60

The title compound 60 was prepared from compound 37d following the procedure described in Example 3, Step H. $^1$H-NMR (300 MHz, CDCl$_3$) δ: 7.19-7.27 (m, 1H), 6.95-7.03 (m, 1H), 6.74-6.91 (m, 6H), 5.10 (s, 2H), 3.73-3.80 (m, 3H), 2.70-2.83 (m, 2H), 2.30-2.40 (m, 1H), 1.22-1.31 (m, 9H), 0.94-1.07 (m, 1H), 0.52-0.62 (m, 1H), 0.36-0.46 (m, 1H), 0.28 (dq, J=9.5, 4.7 Hz, 1H), 0.15 (dq, J=9.5, 4.9 Hz, 1H). Mass Spectrum (LCMS, ESI pos.): Calcd. for $C_{28}H_{31}FO_4S$: 505.6 (M+Na); found: 505.1.

BIOLOGICAL EXAMPLES

In Vitro Assays

GPR40 Calcium Flux Assay

Compounds were tested in a calcium flux assay using transfected HEK293 cells stably expressing either human GPR40 or rat GPR40. Human GPR40 expressing cells were cultured in DMEM-High Glucose media supplemented with 10% fetal bovine serum, 1× L-Glutamine, 1× Penicillin/Streptomycin and 500 µg/mL G418. Rat GPR40 expressing cells were cultured in DMEM-High Glucose media supplemented with 10% fetal bovine serum and 1 µg/mL puromycin. Cells were plated into poly-D-lysine coated 384-well plates and cultured overnight in a 37° C. humidified tissue culture incubator under 5% CO$_2$/90% O$_2$ atmosphere. On the day of the experiment, the culture media was replaced with assay buffer (HBSS, 20 mM HEPES, 0.1% BSA) and the cells incubated at 37° C. for 1 h. Calcium-sensitive fluorescent dye (Fluo 8 No-Wash Calcium Dye, ABD Bioquest) was then added and the cells incubated for another 30 min at 37° C. followed by 15 min at room temperature while protected from the light. The cell plate and a plate of diluted compounds of Formula (III) were loaded into a fluorescent plate reader that added compounds onto the cells while measuring the fluorescence intensity of each well. The plate reader recorded fluorescence intensity at 1 second intervals for 8 min and provided the data for analysis in an Excel format. EC50 values were calculated using Prism (GraphPad) software. Resultant data are shown in Table 3.

TABLE 3

| Cpd | hGPR40 Ca$^{2+}$ Assay EC50 (µM) | rGPR40 Ca$^{2+}$ Assay EC50 (µM) |
|---|---|---|
| 44 | 0.014, 0.014 | NT* |
| 63 | 0.001 | NT |
| 64 | 0.001 | NT |
| 65 | 0.001 | NT |
| 66 | 0.002, 0.001 | NT |
| 67 | 0.006, 0.010, 0.010 | NT |
| 68 | 0.007, 0.012, 0.011 | NT |
| 69 | 0.015, 0.021, 0.017 | NT |
| 70 | 0.016 | NT |
| 71 | 0.024 | NT |

TABLE 3-continued

| Cpd | hGPR40 Ca$^{2+}$ Assay EC50 (µM) | rGPR40 Ca$^{2+}$ Assay EC50 (µM) |
|---|---|---|
| 72 | 0.024, 0.045, 0.039 | NT |
| 73 | 0.027 | NT |
| 74 | 0.038 | NT |
| 75 | 0.060 | NT |
| 76 | 0.066 | NT |
| 77 | 0.066 | NT |
| 78 | 0.069 | NT |
| 79 | 0.103 | NT |
| 80 | 0.273 | NT |
| 81 | 0.428 | NT |
| 82 | 0.261, 0.248 | NT |
| 83 | 0.007, 0.006 | NT |
| 84 | 0.038, 0.031, 0.037, 0.037 | NT |
| 85 | 0.065, 0.063 | NT |
| 86 | 0.004, 0.002 | NT |
| 87 | 0.085, 0.068 | NT |
| 88 | 0.024, 0.023 | NT |
| 89 | 0.0110, 0.009 | NT |
| 90 | 0.086, 0.083 | NT |
| 91 | 0.477, 0.413 | NT |
| 92 | 0.010, 0.009 | NT |
| 93 | 0.136, 0.132 | NT |
| 94 | 0.121, 0.060 | NT |
| 95 | 0.065, 0.055 | NT |
| 96 | 0.025, 0.023 | NT |
| 97 | 0.013, 0.008 | NT |
| 98 | 0.047, 0.036 | NT |

*The notation "NT" means Not Tested. Where multiple values are displayed for a single compound, these values are representative of values determined upon repeated testing.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (III)

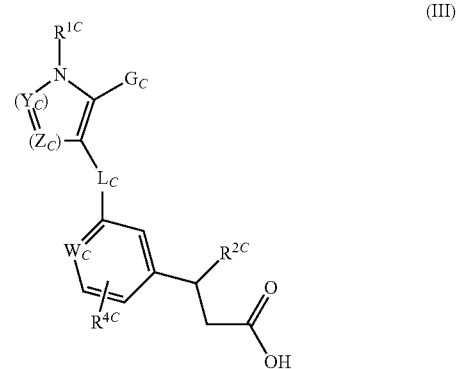

wherein
Y$_C$ is N or CH;
Z$_C$ is N or CH;
W$_C$ is N or CH;
L$_C$ is —CH$_2$O—, —CH=CH—, or —(CH$_2$)$_{1-2}$—;
R$^{1C}$ is selected from the group consisting of phenyl, pyridin-4-yl, thienyl, benzothiophenyl, benzofuranyl, and indolyl; wherein said benzothiophenyl, benzofuranyl, and indolyl are attached to the core (Y$_Z$)-(Z$_C$) containing ring via its benzo ring; and wherein R$^{1C}$ is optionally independently substituted with one or two substituents selected from $C_{1-4}$alkyl, methoxy, fluoro, cyano, di($C_{1-4}$alkyl)amino, or trifluoromethyl;

$R^{2C}$ is $C_{3-5}$cycloalkyl, $C_{1-6}$alkyl, or cyano;

$R^{4C}$ is hydrogen or chloro;

$G_C$ is selected from the group consisting of hydrogen, bromo, $C_{1-6}$alkyl, $C_{1-6}$alkoxy, unsubstituted $C_{3-7}$cycloalkyl, unsubstituted $C_{3-7}$cycloalkoxy, unsubstituted $C_{3-7}$cycloalkyl-methoxy, $C_{2-6}$alk-1-en-1-yl, 3,3,3-trifluoropropoxy, ($C_{1-6}$alkyl)thien-2-yl, difluorophenyl, dimethylphenyl, and a substituent selected from the group consisting of g1 to g9;

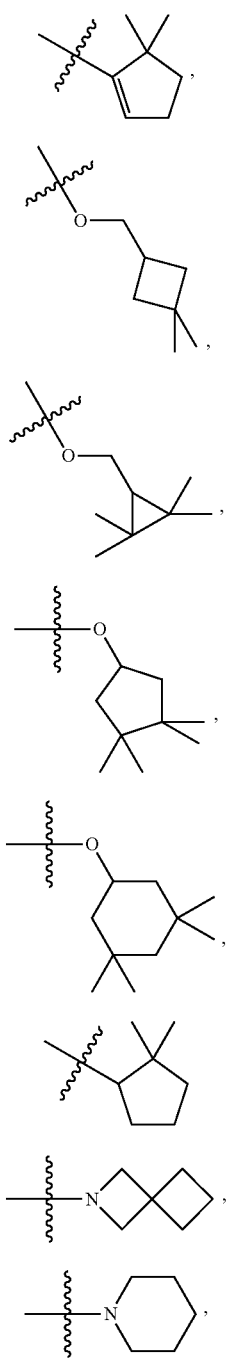

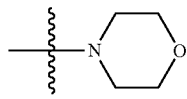

or an enantiomer, diastereomer, or pharmaceutically acceptable salt form thereof.

2. The compound of claim 1 wherein $Y_C$ is N.
3. The compound of claim 1 wherein $L_C$ is —CH$_2$O—, (E)-CH=CH—, or —(CH$_2$)$_2$—.
4. The compound of claim 3 wherein $L_C$ is —CH$_2$O—.
5. The compound of claim 1 wherein $R^{1C}$ is selected from the group consisting of phenyl, pyridin-4-yl, and thienyl; wherein $R^{1C}$ is optionally independently substituted with one or two substituents selected from $C_{1-4}$alkyl, methoxy, or fluoro.
6. The compound of claim 5 wherein $R^{1C}$ is selected from the group consisting of phenyl and pyridin-4-yl; wherein $R^{1C}$ is optionally independently substituted with one or two substituents selected from methoxy or fluoro.
7. The compound of claim 6 wherein $R^{1C}$ is 2-fluoro-5-methoxyphenyl or 5-fluoro-2-methoxy-pyridin-4-yl.
8. The compound of claim 1 wherein $R^{2C}$ is $C_{3-5}$cycloalkyl.
9. The compound of claim 8 wherein $R^{2C}$ is cyclopropyl.
10. The compound of claim 1 wherein $R^{4C}$ is hydrogen.
11. The compound of claim 1 wherein $G_C$ is selected from the group consisting of hydrogen, bromo, $C_{1-4}$alkyl, $C_{1-4}$alkoxy, unsubstituted $C_{3-7}$cycloalkyl, unsubstituted $C_{3-7}$cycloalkoxy, $C_{2-4}$alk-1-en-1-yl, difluorophenyl, dimethylphenyl, ($C_{1-4}$alkyl)thien-2-yl, and a substituent selected from the group consisting of g1 to g9;

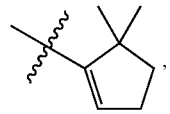

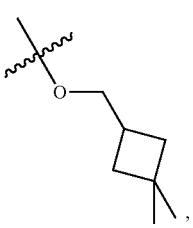

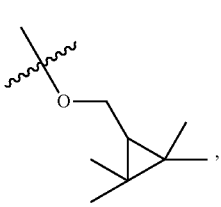

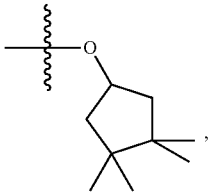

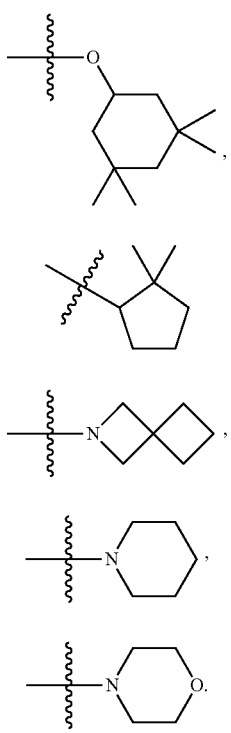

g5 g6 g7 g8 g9

12. The compound of claim 11 wherein $G_C$ is hydrogen, bromo, methyl, isobutyl, isopropyloxy, cyclopropyl, cyclopentyloxy, cyclohexyloxy, 5-methyl-thien-2-yl, 5-t-butyl-thien-2-yl, 2-methyl-prop-1-enyl, or a substituent selected from g1, g7, g8, or g9;

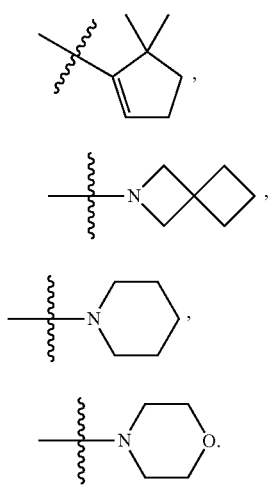

g1 g7 g8 g9

13. The compound of claim 11 wherein $G_C$ is hydrogen, bromo, methyl, isobutyl, isopropyloxy, piperidin-1-yl, cyclopropyl, cyclopentyloxy, cyclohexyloxy, 5-methyl-thien-2-yl, 5-t-butyl-thien-2-yl, 2-methyl-prop-1-enyl, 2,4-difluorophenyl, 3,5-dimethylphenyl, or a substituent selected from g1, g7, or g9;

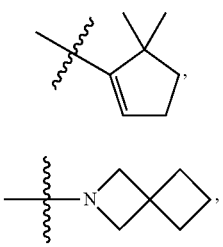

g1 g7 g9

14. A compound of Formula (III)

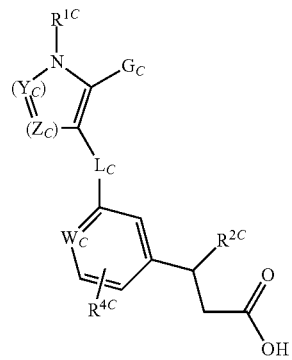

Formula (III)

wherein $Y_C$ is N or CH;

$Z_C$ is N or CH;

$W_C$ is N or CH;

$L_C$ is —CH$_2$O—, —CH=CH—, or —(CH$_2$)$_2$—;

$R^{1C}$ is selected from the group consisting of phenyl, pyridin-4-yl, and thienyl; wherein $R^{1C}$ is optionally independently substituted with one or two substituents selected from $C_{1-4}$alkyl, methoxy, or fluoro;

$R^{2C}$ is $C_{3-5}$cycloalkyl;

$R^{4C}$ is hydrogen or chloro;

$G_C$ is selected from the group consisting of hydrogen, bromo, $C_{1-4}$alkyl, $C_{1-4}$alkoxy, unsubstituted $C_{3-7}$cycloalkyl, unsubstituted $C_{3-7}$cycloalkoxy, $C_{2-4}$alk-1-en-1-yl, difluorophenyl, dimethylphenyl, ($C_{1-4}$alkyl)thien-2-yl, and a substituent selected from the group consisting of g1 to g9;

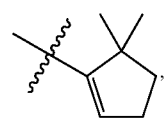

g1

-continued g2
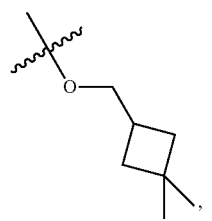

g3
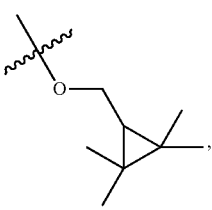

g4
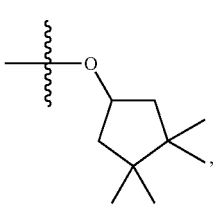

g5
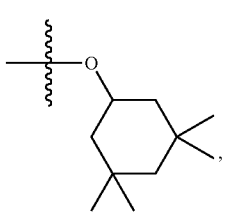

g6
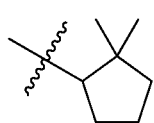

g7
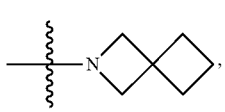

g8
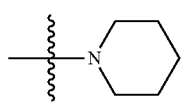

g9
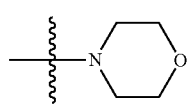

or an enantiomer, diastereomer, or pharmaceutically acceptable salt form thereof.

15. A compound of Formula (III)

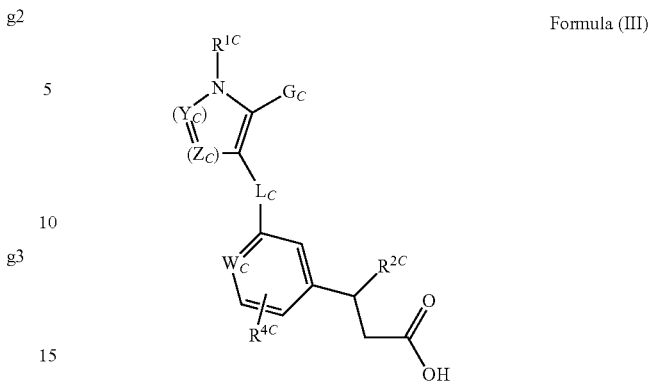

Formula (III)

wherein
 $Y_C$ is N;
 $Z_C$ is N or CH;
 $W_C$ is N or CH;
 $L_C$ is —CH$_2$O—, —CH═CH—, or —(CH$_2$)$_2$—;
 $R^{1C}$ is selected from the group consisting of phenyl and pyridin-4-yl;
wherein $R^{1C}$ is optionally independently substituted with one or two substituents selected from methoxy or fluoro;
 $R^{2C}$ is C$_{3-5}$cycloalkyl;
 $R^{4C}$ is hydrogen or chloro;
 $G_C$ is selected from the group consisting of hydrogen, bromo, C$_{1-4}$alkyl, C$_{1-4}$alkoxy, unsubstituted C$_{3-7}$cycloalkyl, unsubstituted C$_{3-7}$cycloalkoxy, C$_{2-4}$alk-1-en-1-yl, difluorophenyl, dimethylphenyl, (C$_{1-4}$alkyl)thien-2-yl, and a substituent selected from the group consisting of g1 to g9;

g1 g2 g3 g4

-continued

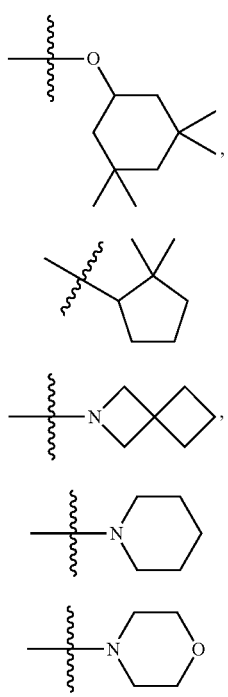

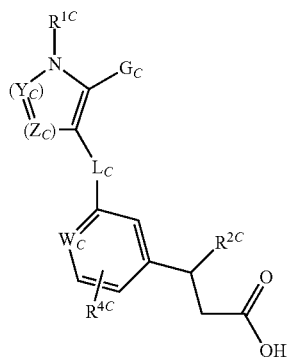

or an enantiomer, diastereomer, or pharmaceutically acceptable salt form thereof.

16. A compound of Formula (III)

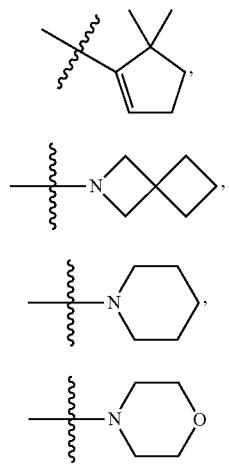

Formula (III)

wherein
- $Y_C$ is N;
- $Z_C$ is N or CH;
- $W_C$ is N or CH;
- $L_C$ is —CH$_2$O—, —CH=CH—, or —(CH$_2$)$_2$—;
- $R^{1C}$ is selected from the group consisting of phenyl and pyridin-4-yl;
- wherein $R^{1C}$ is optionally independently substituted with one or two substituents selected from methoxy or fluoro;
- $R^{2C}$ is C$_{3-5}$cycloalkyl;
- $R^{4C}$ is hydrogen or chloro;
- $G_C$ is selected from the group consisting of hydrogen, bromo, C$_{1-4}$alkyl, C$_{1-4}$alkoxy, unsubstituted C$_{3-7}$cycloalkyl, unsubstituted C$_{3-7}$cycloalkoxy, C$_{2-4}$alk-1-en-1-yl, difluorophenyl, dimethylphenyl, (C$_{1-4}$alkyl)thien-2-yl, and a substituent selected from the group consisting of g1, g7, g8, and g9;

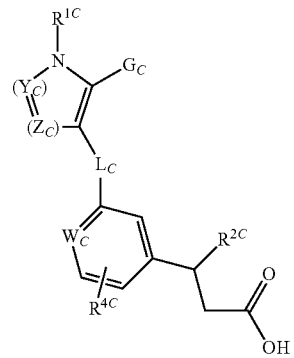

or an enantiomer, diastereomer, or pharmaceutically acceptable salt form thereof.

17. A compound of Formula (III)

Formula (III)

wherein
- $Y_C$ is N or CH;
- $Z_C$ is N or CH;
- $W_C$ is N or CH;
- $L_C$ is —CH$_2$O—;
- $R^{1C}$ is selected from the group consisting of phenyl and pyridin-4-yl;
- wherein $R^{1C}$ is optionally independently substituted with one or two substituents selected from methoxy or fluoro;
- $R^{2C}$ is cyclopropyl;
- $R^{4C}$ is hydrogen or chloro;
- $G_C$ is hydrogen, bromo, methyl, isobutyl, isopropyloxy, cyclopropyl, cyclopentyloxy, cyclohexyloxy, 2-fluoro-5-methoxy-phenyl, 5-methyl-thien-2-yl, 5-t-butyl-thien-2-yl, 2-methyl-prop-1-enyl, and a substituent selected from g1, g7, g8, or g9;

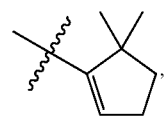

g1

-continued

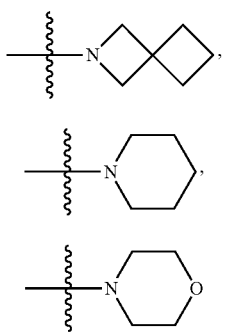

g7

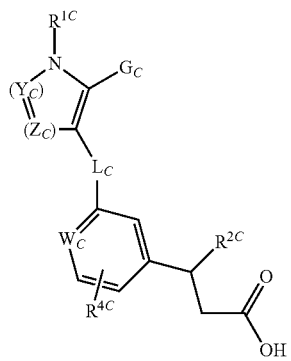

g8 g9 or an enantiomer, diastereomer, or pharmaceutically acceptable salt form thereof.

18. A compound of Formula (III)

Formula (III)

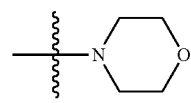

wherein $Y_C$ is N or CH;

$Z_C$ is N or CH;

$W_C$ is N or CH;

$L_C$ is —CH$_2$O—, (E)-CH=CH—, or —(CH$_2$)$_2$—;

$R^{1C}$ is 2-fluoro-5-methoxy-phenyl or 5-fluoro-2-methoxy-4-pyridyl;

$R^{2C}$ is cyclopropyl;

$R^{4C}$ is hydrogen or chloro;

$G_C$ is hydrogen, bromo, methyl, isobutyl, isopropyloxy, piperidin-1-yl, cyclopropyl, cyclopentyloxy, cyclohexyloxy, 5-methyl-thien-2-yl, 5-t-butyl-thien-2-yl, 2-methyl-prop-1-enyl, 2,4-difluorophenyl, 3,5-dimethylphenyl, or a substituent selected from g1, g7, or g9;

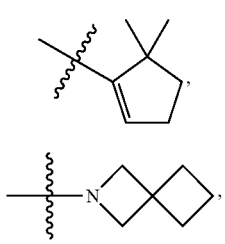

g1 g7

-continued g9 or an enantiomer, diastereomer, or pharmaceutically acceptable salt form thereof.

19. The compound of claim 1 wherein the compound exists as its S-enantiomer

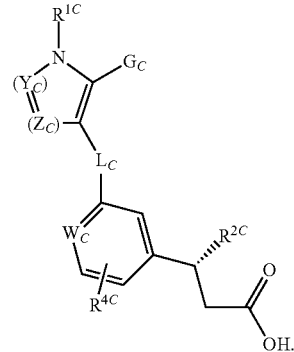

20. The compound of claim 18 wherein the compound exists as its S-enantiomer

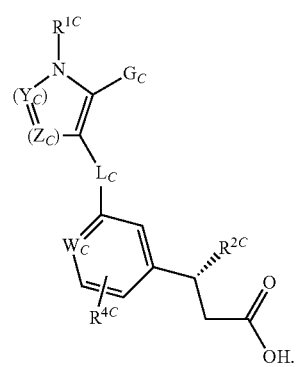

21. A compound according to claim 1 selected from the group consisting of Cpd 44, (3S)-3-cyclopropyl-3-[3-[[1-(2-fluoro-5-methoxy-phenyl)-5-(1-piperidyl)triazol-4-yl]methoxy]phenyl]propanoic acid;

Cpd 63, 3-cyclopropyl-3-[2-[[5-(5,5-dimethylcyclopenten-1-yl)-1-(2-fluoro-5-methoxy-phenyl)triazol-4-yl]methoxy]-4-pyridyl]propanoic acid;

Cpd 64, (3S)-3-cyclopropyl-3-[2-[[5-(5,5-dimethylcyclopenten-1-yl)-1-(2-fluoro-5-methoxy-phenyl)triazol-4-yl]methoxy]-4-pyridyl]propanoic acid;

Cpd 65, 3-cyclopropyl-3-[2-[[5-(5,5-dimethylcyclopenten-1-yl)-1-(2-fluoro-5-methoxy-phenyl)pyrazol-4-yl]methoxy]-4-pyridyl]propanoic acid;

Cpd 66, (3S)-3-cyclopropyl-3-[3-[[5-(5,5-dimethylcyclopenten-1-yl)-1-(2-fluoro-5-methoxy-phenyl)pyrazol-4-yl]methoxy]phenyl]propanoic acid;

Cpd 67, (3S)-3-[3-[[5-(cyclopentoxy)-1-(2-fluoro-5-methoxy-phenyl)triazol-4-yl]methoxy]phenyl]-3-cyclopropyl-propanoic acid;

Cpd 68, (3S)-3-[3-[[5-(6-azaspiro[3.3]heptan-6-yl)-1-(2-fluoro-5-methoxy-phenyl)triazol-4-yl]methoxy]phenyl]-3-cyclopropyl-propanoic acid;

Cpd 69, (3S)-3-cyclopropyl-3-[3-[[5-cyclopropyl-1-(2-fluoro-5-methoxy-phenyl)pyrazol-4-yl]methoxy]phenyl]propanoic acid;

Cpd 70, (3S)-3-cyclopropyl-3-[3-[[5-cyclopropyl-1-(5-fluoro-2-methoxy-4-pyridyl)pyrazol-4-yl]methoxy]phenyl]propanoic acid;

Cpd 71, 3-[5-chloro-2-[[5-(5,5-dimethylcyclopenten-1-yl)-1-(2-fluoro-5-methoxy-phenyl)pyrazol-4-yl]methoxy]-4-pyridyl]-3-cyclopropyl-propanoic acid;

Cpd 72, (3S)-3-cyclopropyl-3-[3-[[1-(2-fluoro-5-methoxy-phenyl)pyrazol-4-yl]methoxy]phenyl]propanoic acid;

Cpd 73, (3S)-3-cyclopropyl-3-[3-[[1-(2-fluoro-5-methoxy-phenyl)-5-morpholino-pyrazol-4-yl]methoxy]phenyl]propanoic acid;

Cpd 74, (3S)-3-cyclopropyl-3-[3-[(E)-2-[5-cyclopropyl-1-(2-fluoro-5-methoxy-phenyl)triazol-4-yl]vinyl]phenyl]propanoic acid;

Cpd 75, (3R)-3-cyclopropyl-3-[2-[[5-(5,5-dimethylcyclopenten-1-yl)-1-(2-fluoro-5-methoxy-phenyl)triazol-4-yl]methoxy]-4-pyridyl]propanoic acid;

Cpd 76, 3-cyclopropyl-3-[3-[(E)-2-[5-cyclopropyl-1-(2-fluoro-5-methoxy-phenyl)pyrazol-4-yl]vinyl]phenyl]propanoic acid;

Cpd 77, 3-cyclopropyl-3-[3-[2-[5-cyclopropyl-1-(2-fluoro-5-methoxy-phenyl)pyrazol-4-yl]ethyl]phenyl]propanoic acid;

Cpd 78, 3-[5-chloro-2-[[5-(5,5-dimethylcyclopenten-1-yl)-1-(2-fluoro-5-methoxy-phenyl)triazol-4-yl]methoxy]-4-pyridyl]-3-cyclopropyl-propanoic acid;

Cpd 79, (3S)-3-cyclopropyl-3-[3-[2-[5-cyclopropyl-1-(2-fluoro-5-methoxy-phenyl)triazol-4-yl]ethyl]phenyl]propanoic acid;

Cpd 80, (3S)-3-cyclopropyl-3-[3-[[1-(2-fluoro-5-methoxy-phenyl)-5-morpholino-triazol-4-yl]methoxy]phenyl]propanoic acid;

Cpd 81, (3S)-3-cyclopropyl-3-[3-[[1-(5-fluoro-2-methoxy-4-pyridyl)pyrazol-4-yl]methoxy]phenyl]propanoic acid;

Cpd 82, (3S)-3-cyclopropyl-3-[3-[[1-(2-fluoro-5-methoxy-phenyl)-5-methyl-triazol-4-yl]methoxy]phenyl]propanoic acid;

Cpd 83, (3S)-3-cyclopropyl-3-[3-[[1-(2-fluoro-5-methoxy-phenyl)-5-isobutyl-triazol-4-yl]methoxy]phenyl]propanoic acid;

Cpd 84, (3S)-3-cyclopropyl-3-[3-[[1-(2-fluoro-5-methoxy-phenyl)-5-(2-methylprop-1-enyl)triazol-4-yl]methoxy]phenyl]propanoic acid;

Cpd 85, (3S)-3-cyclopropyl-3-[3-[[5-cyclopropyl-1-(2-fluoro-5-methoxy-phenyl)triazol-4-yl]methoxy]phenyl]propanoic acid;

Cpd 86, (3S)-3-cyclopropyl-3-[3-[[5-(5,5-dimethylcyclopenten-1-yl)-1-(2-fluoro-5-methoxy-phenyl)triazol-4-yl]methoxy]phenyl]propanoic acid;

Cpd 87, (3S)-3-cyclopropyl-3-[3-[[5-(5,5-dimethylcyclopenten-1-yl)-1-(2-fluoro-5-methoxy-phenyl)imidazol-4-yl]methoxy]phenyl]propanoic acid;

Cpd 88, (3S)-3-cyclopropyl-3-[3-[[1-(2-fluoro-5-methoxy-phenyl)-5-(5-methyl-2-thienyl)triazol-4-yl]methoxy]phenyl]propanoic acid;

Cpd 89, (3S)-3-cyclopropyl-3-[3-[[1-(2-fluoro-5-methoxy-phenyl)-5-(2-methylprop-1-enyl)pyrazol-4-yl]methoxy]phenyl]propanoic acid;

Cpd 90, (3S)-3-[3-[[5-bromo-1-(2-fluoro-5-methoxy-phenyl)pyrazol-4-yl]methoxy]phenyl]-3-cyclopropyl-propanoic acid;

Cpd 91, (3S)-3-cyclopropyl-3-[3-[[1-(2-fluoro-5-methoxy-phenyl)-5-(2-methylprop-1-enyl)imidazol-4-yl]methoxy]phenyl]propanoic acid;

Cpd 92, (3S)-3-[3-[[5-(5-tert-butyl-2-thienyl)-1-(2-fluoro-5-methoxy-phenyl)triazol-4-yl]methoxy]phenyl]-3-cyclopropyl-propanoic acid;

Cpd 93, (3S)-3-cyclopropyl-3-[3-[[1-(2-fluoro-5-methoxy-phenyl)-5-isobutyl-imidazol-4-yl]methoxy]phenyl]propanoic acid;

Cpd 94, (3S)-3-cyclopropyl-3-[3-[[1-(2-fluoro-5-methoxy-phenyl)-5-(5-methyl-2-thienyl)pyrazol-4-yl]methoxy]phenyl]propanoic acid;

Cpd 95, (3S)-3-cyclopropyl-3-[3-[[5-(2,4-difluorophenyl)-1-(2-fluoro-5-methoxy-phenyl)pyrazol-4-yl]methoxy]phenyl]propanoic acid;

Cpd 96, (3S)-3-cyclopropyl-3-[3-[[5-(3,5-dimethylphenyl)-1-(2-fluoro-5-methoxy-phenyl)pyrazol-4-yl]methoxy]phenyl]propanoic acid;

Cpd 97, (3S)-3-[3-[[5-(cyclohexoxy)-1-(2-fluoro-5-methoxy-phenyl)triazol-4-yl]methoxy]phenyl]-3-cyclopropyl-propanoic acid; and Cpd 98, (3S)-3-cyclopropyl-3-[3-[[1-(2-fluoro-5-methoxy-phenyl)-5-isopropoxy-triazol-4-yl]methoxy]phenyl]propanoic acid;

or a pharmaceutically acceptable salt form thereof.

22. A pharmaceutical composition comprising a compound of claim 1 and at least one of a pharmaceutically acceptable carrier, a pharmaceutically acceptable excipient, and a pharmaceutically acceptable diluent.

23. A pharmaceutical composition comprising a compound of claim 21 and at least one of a pharmaceutically acceptable carrier, a pharmaceutically acceptable excipient, and a pharmaceutically acceptable diluent.

24. The pharmaceutical composition of claim 22, wherein the composition is a solid oral dosage form.

25. The pharmaceutical composition of claim 23, wherein the composition is a solid oral dosage form.

26. The pharmaceutical composition of claim 22, wherein the composition is a syrup, an elixir or a suspension.

27. The pharmaceutical composition of claim 23, wherein the composition is a syrup, an elixir or a suspension.

28. A method of treating a disorder modulated by the GPR40 receptor, comprising administering to a subject in need thereof a therapeutically effective amount of the compound of claim 1.

29. A method of treating a disorder, wherein said disorder is affected by the agonism of the GPR40 receptor, comprising administering to a subject in need thereof a therapeutically effective amount of the compound of claim 1.

30. The method of claim 28 wherein said disorder is selected from the group consisting of Type II diabetes mellitus, obesity, obesity-related disorders, impaired glucose tolerance, insulin resistance, metabolic syndrome, hypertension, cardiovascular risk factors related to unmanaged cholesterol and/ or lipid levels, osteoporosis, inflammation, and eczema.

31. A method of treating a disorder selected from the group consisting of Type II diabetes mellitus, obesity, obesity-related disorders, impaired glucose tolerance, insulin resistance, metabolic syndrome, hypertension, cardiovascular risk factors related to unmanaged cholesterol and/or lipid levels, osteoporosis, inflammation, and eczema, comprising administering to a subject in need thereof a therapeutically effective amount of the compound of claim 1.

* * * * *